US008841287B2

(12) United States Patent
Cai et al.

(10) Patent No.: US 8,841,287 B2
(45) Date of Patent: Sep. 23, 2014

(54) DIAMINO-PYRIDINE, PYRIMIDINE, AND PYRAZINE MODULATORS OF THE HISTAMINE H4 RECEPTOR

(75) Inventors: Hui Cai, San Diego, CA (US); Frank Chavez, Camarillo, CA (US); Paul J. Dunford, Solana Beach, CA (US); Andrew J. Greenspan, San Diego, CA (US); Steven P. Meduna, San Diego, CA (US); Jorge A. Quiroz, Princeton, NJ (US); Brad M. Savall, San Diego, CA (US); Kevin L. Tays, Cardiff by the Sea, CA (US); Robin L. Thurmond, San Diego, CA (US); Jianmei Wei, San Diego, CA (US); Ronald L. Wolin, San Diego, CA (US); Xiaohu Zhang, Beijing (CN)

(73) Assignee: Janssen Pharmaceutica N.V., Beerse (BE)

( * ) Notice: Subject to any disclaimer, the term of this patent is extended or adjusted under 35 U.S.C. 154(b) by 244 days.

(21) Appl. No.: 12/997,567

(22) PCT Filed: Jun. 11, 2009

(86) PCT No.: PCT/US2009/047033
§ 371 (c)(1),
(2), (4) Date: Dec. 10, 2010

(87) PCT Pub. No.: WO2009/152325
PCT Pub. Date: Dec. 17, 2009

(65) Prior Publication Data
US 2011/0092474 A1 Apr. 21, 2011

Related U.S. Application Data

(60) Provisional application No. 61/114,425, filed on Nov. 13, 2008, provisional application No. 61/114,416, filed on Nov. 13, 2008, provisional application No. 61/061,039, filed on Jun. 12, 2008.

(51) Int. Cl.
*A01N 43/00* (2006.01)

(52) U.S. Cl.
USPC ........ 514/210.2; 514/343; 514/253; 514/275; 514/252.14; 514/252.2; 514/252.05; 514/218; 514/333; 514/247; 544/360; 544/295; 544/323; 544/324; 544/238; 544/224; 546/256; 546/279.1; 540/575

(58) Field of Classification Search
CPC ............... A61K 31/50; C09K 19/3455; C12N 2501/82; C09B 62/12; C09B 62/442
USPC ................... 514/210.2, 343, 253.01, 252.05, 514/252.14, 252.2, 275, 252.02, 333, 247, 514/218; 544/324, 360, 323, 238, 295, 224; 546/245, 279.1; 540/575
See application file for complete search history.

(56) References Cited

U.S. PATENT DOCUMENTS

| | | | |
|---|---|---|---|
| 3,907,801 A | 9/1975 | Wu et al. | |
| 4,788,196 A | 11/1988 | Cross et al. | |
| 5,147,876 A | 9/1992 | Mizuchi et al. | |
| 5,449,676 A * | 9/1995 | Amschler et al. | 514/247 |
| 6,593,330 B2 | 7/2003 | Nilsson | |
| 6,610,694 B1 * | 8/2003 | Kawano et al. | 514/252.04 |
| 6,803,362 B2 | 10/2004 | Carruthers et al. | |
| 6,825,198 B2 | 11/2004 | Chiang et al. | |
| 7,507,737 B2 | 3/2009 | Edwards et al. | |
| 7,534,798 B2 | 5/2009 | Balan et al. | |
| 7,759,336 B2 | 7/2010 | Habashita et al. | |
| 2005/0182067 A1* | 8/2005 | Balan et al. | 514/252.18 |
| 2007/0185075 A1 | 8/2007 | Bell et al. | |
| 2008/0194577 A1 | 8/2008 | Cai et al. | |

FOREIGN PATENT DOCUMENTS

| | | |
|---|---|---|
| EP | 1437348 A1 | 7/2004 |
| EP | 1505064 A1 | 9/2005 |
| EP | 1767537 A1 | 3/2007 |
| WO | 91/09849 A1 | 7/1991 |
| WO | 01/47921 A1 | 7/2001 |
| WO | 02/22605 A1 | 3/2002 |
| WO | 03/076430 A1 | 9/2003 |
| WO | 03/076438 A1 | 9/2003 |
| WO | 2005/014556 A1 | 2/2005 |
| WO | 2005/054239 A1 | 6/2005 |
| WO | WO2005/054239 A1 | 6/2005 |
| WO | 2006/050965 A1 | 5/2006 |
| WO | 2006/063718 A1 | 6/2006 |
| WO | 2007/031529 A2 | 3/2007 |
| WO | 2007/072163 A3 | 6/2007 |
| WO | WO2007/072163 A2 | 6/2007 |
| WO | 2007/082878 A1 | 7/2007 |
| WO | 2007/090852 A2 | 8/2007 |
| WO | 2007/090853 A1 | 8/2007 |
| WO | 2007/090854 A1 | 8/2007 |
| WO | 2007/141571 | 12/2007 |
| WO | 2008/031566 A2 | 3/2008 |
| WO | 2008/060766 A2 | 5/2008 |

(Continued)

OTHER PUBLICATIONS

Guither et al, J. Heterocyclic Chem., 1965, 2(1), 67-71.*

(Continued)

*Primary Examiner* — Jason Sims
*Assistant Examiner* — Ibrahim D Bori

(57) ABSTRACT

Diamino-pyridine, pyrimidine and pyridazine compounds which may be used as $H_4$ receptor modulators, and in pharmaceutical compositions and methods for the treatment of disease states, disorders, and conditions mediated by $H_4$ receptor activity, such as allergy, asthma, autoimmune diseases, and pruritis.

31 Claims, No Drawings

(56) References Cited

FOREIGN PATENT DOCUMENTS

| | | |
|---|---|---|
| WO | 2008/074445 A1 | 6/2008 |
| WO | 2008/122378 A1 | 10/2008 |
| WO | 2009/068512 A1 | 6/2009 |

OTHER PUBLICATIONS

Barlin et al, (J. Chem. Soc., C, 1967, 2473-2476).*
Amin et al., "Inflammation and Structural Changes in the Airways of Patients with Atopic and Nonatopic Asthma", American Journal of Respiratory and Critical Care Medicine, 2000 162:2295-2301.
Anisman et al., "Interleukin-1β Production in Dysthymia before and after Pharmacotherapy" Biol. Psychiatry, (1999) 1999, 46(2):1649-1655.
Becker, "Preparation of Pyrimidine Derivatives as Potential Medicinal Agents by the Reaction of 2-Amino-4-chloro-6-methylpyrimidine . . . " Journal Heterocyclic Chemistry, 2005 42:1289.
Bell et al., "Involvement of histamine H4 and H1 receptors in scratching induced by histamine receptor agonists in BalbC mice" British Journal of Pharmacology 2004, 142:374-380.
Benoist et al., "Mast cells in autoimmune disease" Nature 2002, 420(6917):875-878.
Buckland et al., "Histamine induces cytoskeletal changes in human eosinophils via the H4 receptor" British Journal of Pharmacology (2003) 140:1117-1127.
Gutzmer et al., "Histamine H4 Receptor Stimulation Suppresses IL-12p70 Production and Mediates Chemotaxis in Human Monocyte-Derived Dendritic Cells" J. Immunol. 2005, 174(9), 5224-5232.
Heinisch et al., "Pyridazines, 89. on the Synthesis of Novel 1,2-Diazine Containing Tricyclic Systems: Preparation of Dipyridazinodiazepinones" Heterocycles 1999, 51(5), 1035-1050.
Hofstra et al., "Histamine H4 Receptor Mediates Chemotaxis and Calcium Mobilization of Mast Cells", J. Pharmacol. Expt. Ther. 2003, 305(3):1212-1221.
Hofstra et al., "Histamine H4 Receptor Mediates Chemotaxis and Calcium Mobilization of Mast Cells", Curr. Opin. Invest. Drugs 2004, 5:1174-1183.
Ikawa et al., "Histamine H4 Receptor Expression in Human Synovial Cells Obtained from Patients Suffering from Rheumatoid Arthritis", Biol. Pharm. Bull, 2005, 28(10):2016-2018.
Jokuti et al., "Histamine H4 Receptor Expression is Elevated in Human Nasal Polyp Tissue", Cell Biology International, 2007, 31:1367-1370.
Kassel et al., "Local increase in the number of mast cells and expression of nerve growth factor . . .", Clinical and Experimental Allergy, 2001, 31:1432-1440.
Kim et al., "Cytokine imbalance in the pathophysiology of major depressive disorder" Progress in Neuro-Psychopharmacology & Biological Psychiatry, 2007, 31:1044-1053.
Kirby et al., "Bronchoaleolar Cell Profiles of Asthmatic and Nonasthmatic Subjects 1-3", American Rev. Respir. Dis., 1987, 136:379-388.
Kling et al., "Sustained Low-Grade Pro-inflammatory State in Unmedicated, Remitted Women with Major Depressive Disorder" Biol. Phychiatry, 2007, 62, 309-313.
Krug et al., "Interleukin 16 and T-cell Chemoattractant Activity in Bronchoalveolar Lavage 24 Hours after Allergen Challenge in Asthma" Am. J. Resp. Crit. Care Med. 2000, 162(1), 105-111.
Lespagnol et al., "Recheresdans la serie des sulfonamides" Chim. Therap. 1965, 1:26-31.
Coge et al., "Structure and Expression of the Human Histamine H4-Receptor Gene" Biochemical and Biophysical Research Communication (2001) 284:301-309.
Cohen, "The immunopathogenesis of sepsis", Nature 2002, 420(6917), 885-891.
Coussens et al., "Inflammation and cancer", Nature, 2002 420:19-26.

Crimi et al., "Increased Numbers of Mast Cells in Bronchial Mucosa after the Late-Phase Asthmatic Response to Allergen" American Rev. Respiratory Diseases, 1991 144(6):1282-1286.
Damaj et al., "Functional Expression of H4 Histamine Receptor in Human Natural Killer Cells, Monocytes, and Dendritic Cells" J. Immunol. 2007, 179:7907-7915.
De Esch et al., "The histamine H4 receptor as a new therapeutic target for inflammation" Trends Pharmacol. Sci., 2005, 26(9):462-469.
Dunford et al., "The Histamine H4 Receptor Mediates Allergic Airway Inflammation by Regulation the Activation of CD4+ T Cells" The Journal of Immunology, 2006, 176:7062-7070.
Dunford et al., "Histamine H4 receptor antagonists are superior to traditional anthistamines in the attentuation of experimental pruitus", J. Allergy Clin. Immunol. 2007, 119(1), 176-183.
Fokkens et al., "Dynamics of mast cells in the nasal mucosa of patients with allergic rhinitis and non-allergic controls: a biopsy study" Clinical and Experimental Allergy, 1992, 22:701-710.
Frommberger et al., "Interleukin-6-(IL-6) plasma levels in depression and schizophrenia: comparison between the acute state and after remission" Eur Arch Psychiatry Ctin Neurosci (1997) 247 : 228-233.
Ganter et al., "Histamine H4 and H2 Receptors Control Histamine-Induced Interleukin-16 Release from Human CD8" J. Pharmacol. Exp. Ther. 2002, 303(1): 300-307.
Gavreau et al., "Increased Numbers of Both Airway Basophils and Mast Cells in Sputum after Allergen Inhalation Challenge of Atopic Asthmatics" Am. J. Resp. Crit. Care Med., 2000, 161(5):1473-1478.
Lespagnol et al., "Recherches dans la serie pyrimidique (*)" Chim. Therap. 1971, 6(2), 105-108.
Libby, "Inflammation in Atherosclerosis", Nature 2002, 420, 868-874.
Ling et al., "Histamine H4 receptor mediates eosinophil chemotaxis with cell shape change and adhesion molecule upregulation" British Journal of Pharmacology,. 2004, 142, 161-171.
Lippert et al., "Human Skin Mast Cells Express H2 and H4, but not H3 Receptors" J. Invest. Dermatol. 2004, 123(1), 116-123.
Liu et al., "Cloning and Pharmacological Characterization of a Fourth Histamine Receptor (H4) Expressed in Bone Marrow" Mol. Pharmacol. 2001, 59(3), 420-426.
Mashikian et al., "Identification of IL-16 as the lymphocyte chemotactic activity in the bronchoalveolar lavage fluid of histamine-challenged asthmatic patients" J. Allergy Clin. Immunol. 1998, 106(6):786-792.
Moorman et al., "In Patients With Heart Failure Elevated Soluble TNF-Receptor 1 Is Associated With Higher Risk of Depression", Journal of Cardiac Failure, 2007, 13(9)738-743.
Morse et al., "Cloning and Characterization of a Novel Human Histamine Receptor", J. Pharmacol. Exp. Ther. 2001, 296(3), 1058-1066.
Nathan, et al., "Points of control in inflammation" Nature 2002, 420(6917), 846-852.
O'Brien et al., "Plasma cytokine profiles in depressed patients who fail to respond to selective serotonin reuptake inhibitor therapy" Journal of Psychiatric Research, 2007, 41, 326-331.
O'Brien et al., "Cytokine profiles in bipolar affective disorder: Focus on acutely ill patients" J. Affective Disorders, 2006, 90, 263-267.
O'Reilly, et al., "Identification of a Histamine H4 Receptor on Human Eosinophils—Role in Eosinophil Chemotaxis" Journal of Receptors and Signal Transduction, 2002, 22(1-4):431-448.
Ortiz-Dominguez et al., "Immune variations in bipolar disorder: phasic differences" Bip. Disporder 9, 2007, p. 596.
Shin et al., "Molecular Modeling and Site-Specific Mutagenesis of the Histamine-Binding Site of the Histamine H4 Receptor" Molecular Pharmacology, 2002, vol. 62(1):38-47 Abstract p. 42, Fig. 2.
Slater, et al., "Increase in epithelial mast cell Numbers in the nasal mucosa of patients with perennial allergic rhinitis" J. Laryngol. Otol. 1996, 110, 929-933.
Sluzewska et al., "Indicators of Immune Activation in Major Depression", Psychiatry Research 64 (1996) 161-167.
Soygur et al., "Interleukin-6 levels and HPA axis activation in breast cancer patients with major depressive disorder" Progress in Neuro-Psychopharmacology & Biolofical Psychiatry, 2007, 31:1242-1247.

(56) References Cited

OTHER PUBLICATIONS

Steinberg et al., "Atherogenesis in perspective: Hypercholesterolemia and inflammation as partners in crime" Nature Med. 2002, 8(11), 1211-1217.

Takeshita et al., "Critical Role of Histamine H4 Receptor in Leukotriene B4 Production and Mast Cell-Dependent Neutrophil Recruitment Induced by Zymosan in Vivo" The Journal of Pharmacology and Experimental Therapeutics, 2003 307:1072-1078.

Thurmond et al. "The role of histamine H1 and H4 receptors in allergic inflammation: the search for new antihistamines" Nat. Rev. Drug Disc. 2008, 7:41-53.

Thurmond et al. "A Potent and Selective Histamine H4 Receptor Antagonist with nti-Inflammatory Properties" J. Pharmacol. Exp. Ther. 2004, 309(1):404-413.

Tracey, "The Inflammatory Reflex" Nature 2002, 420(6917), 853-859.

Varga et al., "Inhibitory effects of histamine H4 receptor antagonists on experimental colitis in the rat" European Journal of Pharmacology, 2005, 522:130-138.

Voehringer, "Type 2 Immunity Reflects Orchestrated Recruitment of Cells Committed to IL-4 Production" Immunity 2004, 20(3): 267-277.

Weiner et al., "Inflammation and therapeutic vaccination in CNS diseases" Nature 2002, 420(6917): 879-884.

Willecomme, "Recheres dans la serie de la Piperazine", Ann. Chim., 1969, T.4:405-428.

Zhang et al., The Histamine H4 receptor in autoimmunie diseases, Expert Opin. Investig. Drugs, 2006, 15 (11):1443-1452.

European Search Report dated Mar. 27, 2012, EP App. No. 09763614.6.

* cited by examiner

DIAMINO-PYRIDINE, PYRIMIDINE, AND PYRAZINE MODULATORS OF THE HISTAMINE H4 RECEPTOR

This application is a national phase application under 35 U.S.C. §371 of International Application PCT/US2009/047033, filed on Jun. 11, 2009, which claims the benefit of U.S. provisional patent application Ser. Nos. 61/061,039, filed Jun. 12, 2008, 61/114,416, filed Nov. 13, 2008, and 61/114,425, filed Nov. 13, 2008, all of which are incorporated herein by reference.

FIELD OF THE INVENTION

The present invention relates to certain diamino-pyridine, pyrimidine, and pyridazine compounds, pharmaceutical compositions containing them, methods of making them, and methods of using them for the modulation of the histamine $H_4$ receptor and for the treatment of disease states, disorders, and conditions mediated by histamine $H_4$ receptor activity.

BACKGROUND OF THE INVENTION

The histamine $H_4$ receptor ($H_4R$), sometimes also referred to simply as "H4" or "$H_4$", is the most recently identified receptor for histamine (for reviews, see: Fung-Leung, W.-P., et al., Curr. Opin. Invest. Drugs 2004, 5(11), 1174-1183; de Esch, I. J. P., et al., Trends Pharmacol. Sci. 2005, 26(9), 462-469; Zhang, M. et al. Pharmacol. Ther. 2007, 113, 594-606; Thurmond, R. L. et al. Nat. Rev. Drug Disc. 2008, 7, 41-53; Zhang, M. et al. Expert Opin. Investig. Drugs 2006, 15(11), 1443-1452). The receptor is found in the bone marrow and spleen and is expressed on eosinophils, basophils, mast cells (Liu, C., et al., Mol. Pharmacol. 2001, 59(3), 420-426; Morse, K. L., et al., J. Pharmacol. Exp. Ther. 2001, 296(3), 1058-1066; Hofstra, C. L., et al., J. Pharmacol. Exp. Ther. 2003, 305(3), 1212-1221; Lippert, U., et al., J. Invest. Dermatol. 2004, 123(1), 116-123; Voehringer, D., et al., Immunity 2004, 20(3), 267-277), CD8+ T cells (Gantner, F., et al., J. Pharmacol. Exp. Ther. 2002, 303(1), 300-307), dendritic cells, and human synovial cells from rheumatoid arthritis patients (Ikawa, Y., et al., Biol. Pharm. Bull. 2005, 28(10), 2016-2018). The histamine $H_4$ receptor is also elevated in human nasal polyp tissue (Jókúti, A. et al. Cell. Biol. Int. 2007, 31, 1367-1370). However, expression in neutrophils and monocytes is less well defined (Ling, P., et al., Br. J. Pharmacol. 2004, 142(1), 161-171; Damaj, B. B. et al. J. Immunol. 2007, 179, 7907-7915). Receptor expression is at least in part controlled by various inflammatory stimuli (Coge, F., et al., Biochem. Biophys. Res. Commun. 2001, 284(2), 301-309; Morse, et al., 2001), thus supporting that $H_4$ receptor activation influences inflammatory responses. Because of its preferential expression on immunocompetent cells, the $H_4$ receptor is closely related with the regulatory functions of histamine during the immune response.

A biological activity of histamine in the context of immunology and autoimmune diseases is closely related with the allergic response and its deleterious effects, such as inflammation. Events that elicit the inflammatory response include physical stimulation (including trauma), chemical stimulation, infection, and invasion by a foreign body. The inflammatory response is characterized by pain, increased temperature, redness, swelling, reduced function, or a combination of these.

Mast cell degranulation (exocytosis) releases histamine and leads to an inflammatory response that may be initially characterized by a histamine-modulated wheal and flare reaction. A wide variety of immunological stimuli (e.g., allergens or antibodies) and non-immunological (e.g., chemical) stimuli may cause the activation, recruitment, and de-granulation of mast cells. Mast cell activation initiates allergic inflammatory responses, which in turn cause the recruitment of other effector cells that further contribute to the inflammatory response. It has been shown that histamine induces chemotaxis of mouse mast cells (Hofstra, et al., 2003). Chemotaxis does not occur using mast cells derived from $H_4$ receptor knockout mice. Furthermore, the response is blocked by an $H_4$-specific antagonist, but not by $H_1$, $H_2$ or $H_3$ receptor antagonists (Hofstra, et al., 2003; Thurmond, R. L., et al., J. Pharmacol. Exp. Ther. 2004, 309(1), 404-413). The in vivo migration of mast cells to histamine has also been investigated and shown to be $H_4$ receptor dependent (Thurmond, et al., 2004). The migration of mast cells may play a role in allergic rhinitis and allergy where increases in mast cell number are found (Kirby, J. G., et al., Am. Rev. Respir. Dis. 1987, 136(2), 379-383; Crimi, E., et al., Am. Rev. Respir. Dis. 1991, 144(6), 1282-1286; Amin, K., et al., Am. J. Resp. Crit. Care Med. 2000, 162(6), 2295-2301; Gauvreau, G. M., et al., Am. J. Resp. Crit. Care Med. 2000, 161(5), 1473-1478; Kassel, O., et al., Clin. Exp. Allergy 2001, 31(9), 1432-1440). In addition, it is known that in response to allergens there is a redistribution of mast cells to the epithelial lining of the nasal mucosa (Fokkens, W. J., et al., Clin. Exp. Allergy 1992, 22(7), 701-710; Slater, A., et al., J. Laryngol. Otol. 1996, 110, 929-933). These results show that the chemotactic response of mast cells to histamine is mediated by histamine $H_4$ receptors.

It has been shown that eosinophils can chemotax towards histamine (O'Reilly, M., et al., J. Recept. Signal Transduction 2002, 22(1-4), 431-448; Buckland, K. F., et al., Br. J. Pharmacol. 2003, 140(6), 1117-1127; Ling et al., 2004). Using $H_4$ selective ligands, it has been shown that histamine-induced chemotaxis of eosinophils is mediated through the $H_4$ receptor (Buckland, et al., 2003; Ling et al., 2004). Cell surface expression of adhesion molecules CD11b/CD18 (LFA-1) and CD54 (ICAM-1) on eosinophils increases after histamine treatment (Ling, et al., 2004). This increase is blocked by $H_4$ receptor antagonists but not by $H_1$, $H_2$, or $H_3$ receptor antagonists.

The $H_4R$ also plays a role in dendritic cells and T cells. In human monocyte-derived dendritic cells, $H_4R$ stimulation suppresses IL-12p70 production and drives histamine-mediated chemotaxis (Gutzmer, R., et al., J. Immunol. 2005, 174 (9), 5224-5232). A role for the $H_4$ receptor in CD8+ T cells has also been reported. Gantner, et al., (2002) showed that both $H_4$ and $H_2$ receptors control histamine-induced IL-16 release from human CD8+ T cells. IL-16 is found in the bronchoalveolar fluid of allergen- or histamine-challenged asthmatics (Mashikian, V. M., et al., J. Allergy Clin. Immunol. 1998, 101 (6, Part 1), 786-792; Krug, N., et al., Am. J. Resp. Crit. Care Med. 2000, 162(1), 105-111) and is considered important in CD4+ cell migration. The activity of the receptor in these cell types indicates an important role in adaptive immune responses such as those active in autoimmune diseases.

In vivo $H_4$ receptor antagonists were able to block neutrophillia in zymosan-induced peritonitis or pleurisy models (Takeshita, K., et al., J. Pharmacol. Exp. Ther. 2003, 307(3), 1072-1078; Thurmond, et al., 2004). In addition, $H_4$ receptor antagonists have activity in a widely used and well-characterized model of colitis (Varga, C., et al., Eur. J. Pharmacol. 2005, 522(1-3), 130-138). These results support the conclusion that $H_4$ receptor antagonists have the capacity to be anti-inflammatory in vivo.

Another physiological role of histamine is as a mediator of itch and $H_1$ receptor antagonists are not completely effective in the clinic. Recently, the $H_4$ receptor has also been implicated in histamine-induced scratching in mice (Bell, J. K., et al., Br. J. Pharmacol. 2004, 142(2), 374-380). The effects of histamine could be blocked by $H_4$ antagonists. These results support the hypothesis that the $H_4$ receptor is involved in histamine-induced itch and that $H_4$ receptor antagonists will therefore have positive effects in treating pruritis. Histamine $H_4$ receptor antagonists have been shown to attenuate experimental pruritis (Dunford, P. J. et al. J. Allergy Clin. Immunol. 2007, 119(1), 176-183).

Modulation of $H_4$ receptors controls the release of inflammatory mediators and inhibits leukocyte recruitment, thus providing the ability to prevent and/or treat $H_4$-mediated diseases and conditions, including the deleterious effects of allergic responses such as inflammation. Compounds according to the present invention have $H_4$ receptor modulating properties. Compounds according to the present invention have leukocyte recruitment inhibiting properties. Compounds according to the present invention have anti-inflammatory properties. Modulation of the histamine $H_4$ receptor has also been implicated in the treatment of pain (Intl. Pat. Appl. Publ. WO 2008/060766 (Abbott).

Numerous pro-inflammatory cytokines have been increasingly reported to be elevated in patients suffering of major depression (Frommberger et al., European Archives of Psychiatry & Clinical Neuroscience. 1997, 247(4), 228-33; Sluzewska A., et al., Psychiatry Research, 1996, 64(3), 161-7; Ortiz-Dominguez, et al., Bip. Disporder 9, 2007; O'Brien, et al., J. Affective Disorders, 2006, 90, 263-267; Anisman H. et al., Biological Psychiatry, 1999, 46(12), 1649-55) (when compared with non-depressed subjects or, in some cases, correlated with symptom severity). These include increased acute-phase proteins (Kling et al., Biol. Phychiatry, 2007, 62, 309-313; Kim et al., Progress in Neuro-Psychopharmacology & Biological Psychiatry, 2007, 31, 1044-1053; (C-reactive protein, α-1-acid glycoprotein, α-1-antichymotrypsin and haptoglobin), increased expression of chemokines and adhesion molecules (including human macrophage chemoattractant protein-1 (MCP-1), soluble intracellular adhesion molecule-1 (sICAM-1) and E-selectin), increased serum and/or plasma concentrations of interleukin (IL-1-β, IL-6, and tumor necrosis factor (TNF)-α, both in the peripheral blood circulation and in the central nervous system (particularly in the cerebrospinal fluid) with a higher level of consistency when measuring TNF-α and IL-6 (O'Brien et al., Journal of Psychiatric Research, 2007, 41, 326-331; Moorman et al., J. of Cardiac Failure, 2007, 13(9), 738-43; Soygur et al., Progress in Neuro-Psychopharmacology & Biolofical Psychiatry, 2007, 31, 1242-1247). Additionally, allelic variants of the genes for IL-1β and TNF-α increase the risk for depression and are associated with reduced responsiveness to antidepressant therapy. Finally, there is available preclinical evidence supporting the involvement of several cytokines in models of depression and some clinical evidence of the involvement of cytokines antagonism in the treatment of depressive symptoms on patients suffering from active inflammatory diseases (Kim et al., Progress in Neuro-Psychopharmacology & Biological Psychiatry, 2007, 31, 1044-1053).

[5-(4,6-dimethyl-1H-benzoimidazol-2-yl)-4-methyl-pyrimidin-2-yl]-[3-(1-methyl-piperidin-4-yl)-propyl]-amine (U.S. Pat. No. 7,507,737, Example 2) is a potent antagonist of the $H_4$ receptor ($H_4R$) with a $K_i$ of 8.4 nM and greater than 25-fold selectivity over other histamine receptors in vitro. It inhibited histamine-induced shape change of eosinophils, chemotaxis of mast cells, and IL-6 production in mast cells. In vivo, [5-(4,6-dimethyl-1H-benzoimidazol-2-yl)-4-methyl-pyrimidin-2-yl]-[3-(1-methyl-piperidin-4-yl)-propyl]-amine reduced inflammation in mouse models of asthma, arthritis and dermatitis. The compound also inhibited lipopolysaccharide (LPS)-induced tumor necrosis factor alpha (TNF-α) production and other cytokines in vivo.

Based on this the evidence and the effects of $H_4R$ antagonism it is proposed that [5-(4,6-dimethyl-1H-benzoimidazol-2-yl)-4-methyl-pyrimidin-2-yl]-[3-(1-methyl-piperidin-4-yl)-propyl]-amine and its chemically related family of compounds has antidepressant and/or anxiolytic properties suitable for the treatment of mood disorders (including but not limited to Major Depressive Disorder, Bipolar Disorder, Treatment Resistant Major Depressive Disorder and Treatment Resistant Bipolar Disorder), anxiety disorders (including but not limited to Generalized Anxiety Disorder, Social Phobia, and post traumatic stress disorder). It is envisaged that $H_4$ antagonists will share such properties suitable for the treatment of such disorders.

Adiposity-associated inflammation and insulin resistance are associated with the development of type II diabetes, fatty liver and atherosclerosis. Macrophages are recruited into adipose tissue and atherosclerotic plaques, and are activated to release inflammatory cytokines and chemokines. High fat diets associated with the development of these conditions may lead to increased gut permeability and dyslipidemia. Consequent toll-ligand receptor, 2 and 4 (TLR2, TLR4) activation of adipocytes and macrophages by bacteria and by high levels of free fatty acids leads to an inflammatory phenotype and insulin resistance. Specifically, insulin signaling pathways may be attenuated by cytokines such as TNFα and IL-6 and activation of kinases including c-jun kinase, NKkB or PKCθ, downstream of TLR2/4 stimulation. Effects on insulin receptor signaling are potentiated by increased infiltration of monocyte/macrophages into the tissue by release of chemokines such as MCP-1.

H4R is a high affinity receptor for histamine expressed on monocyte/macrophage populations and other hematopoietic cells. Antagonism of the H4R has been shown to reduce TLR4 signaling in vitro and to reduce TLR2 and TLR4 mediated inflammatory cytokine production in vitro and in vivo. Levels of pro-inflammatory mediators including TNF-α, IL-6 and LTB4 have been variously shown to be inhibited by H4R antagonism in TLR dependent systems. Data obtained in the context of this invention support the claim that H4R antagonists have beneficial properties towards the treatment of type 2 diabetes and related metabolic disorders through inflammation reduction.

Histamine $H_4$ receptor antagonists have anti-inflammatory and anti-pruritic activity in animal models when given systemically. This invention also relates to the use of topical formulations of $H_4$ receptor antagonists for the topical treatment of dermal inflammation and pruritus. The use of topical therapies for skin conditions such as urticaria and atopic dermatitis may be preferred over systemic administration due to improved safety profiles. The topical application of an $H_4$ receptor antagonist, (5-chloro-1H-indol-2-yl)-(4-methyl-piperazin-1-yl)-methanone (U.S. Pat. No. 6,803,362, Example 1) was tested in the context of this invention in a mouse model of pruritus. The results support the claim that topical treatment with $H_4$ receptor antagonists have beneficial properties towards topical anti-pruritic treatment, and it is envisaged that they also have such properties regarding topical anti-inflammatory treatment. Topical formulation of such antagonists may have utility in both human and veterinary health.

Examples of textbooks on the subject of inflammation include: 1) Gallin, J. I.; Snyderman, R., *Inflammation: Basic Principles and Clinical Correlates*, 3rd ed.; Lippincott Williams & Wilkins: Philadelphia, 1999; 2) Stvrtinova, V., et al., Inflammation and Fever. *Pathophysiology Principles of Diseases* (Textbook for Medical Students); Academic Press: New York, 1995; 3) Cecil; et al. *Textbook Of Medicine*, 18th ed.; W.B. Saunders Co., 1988; and 4) Stedman's Medical Dictionary.

Background and review material on inflammation and conditions related with inflammation can be found in articles such as the following: Nathan, C., Nature 2002, 420(6917), 846-852; Tracey, K. J., Nature 2002, 420(6917), 853-859; Coussens, L. M., et al., Nature 2002, 420(6917), 860-867; Libby, P., Nature 2002, 420, 868-874; Benoist, C., et al., Nature 2002, 420(6917), 875-878; Weiner, H. L., et al., Nature 2002, 420(6917), 879-884; Cohen, J., Nature 2002, 420(6917), 885-891; Steinberg, D., Nature Med. 2002, 8(11), 1211-1217.

Thus, small-molecule histamine $H_4$ receptor modulators according to this invention control the release of inflammatory mediators and inhibit leukocyte recruitment, and may be useful in treating inflammation of various etiologies, including the following conditions and diseases: inflammatory disorders, allergic disorders, dermatological disorders, autoimmune disease, lymphatic disorders, pruritis, and immunodeficiency disorders. Diseases, disorders and medical conditions that are mediated by histamine $H_4$ receptor activity include those referred to herein.

Certain diamine-substituted pyridines are described in the following publications: Intl. Pat. Appl. Publ. WO 2008/122378 (UCB Pharma, Oct. 16, 2008); Intl. Pat. Appl. Publ. WO 1991/09849 (Upjohn, Jul. 11, 1991); Intl. Pat. Appl. Publ. WO 2006/063718 (Hoffmann La Roche, Jun. 22, 2006); U.S. Pat. No. 4,788,196 (Pfizer, Nov. 29, 1988); and U.S. Pat. No. 4,806,536 (Pfizer, Feb. 21, 1989).

Certain amine-substituted 2-aminopyrimidines are disclosed in the following publications: Becker, I. J. Het. Chem. 2005, 42(7), 1289-1295; Eur. Pat. Appl. No. EP 1437348 (Jul. 14, 2004); U.S. Pat. No. 3,907,801 (Sep. 23, 1975); Lespagnol, A. et al. Chim. Therap. 1971, 6(2), 105-108; Willecomme, B. Annales de Chimie 1969, 4(6), 405-428; Lespagnol, A. et al. Chim. Therap. 1965, 1, 26-31; Intl. Pat. Appl. Publ. WO 2001/62233 (Aug. 30, 2007); Intl. Pat. Appl. Publ. WO 2001/47921 (Jul. 5, 2001); U.S. Pat. Appl. Publ. US 2007/0167459 (Ono Pharmaceutical Co., Jul. 19, 2007); U.S. Pat. Appl. Publ. US 2003/0105106 (Pfizer, Jun. 5, 2003); U.S. Pat. Appl. Publ. US 2002/0147200 (Nilsson, Oct. 10, 2002); and U.S. Pat. No. 5,147,876 (Mitsui, Sep. 15, 1992).

Certain amine-substituted 2-aminopyridazines are disclosed in the following publications: Heinisch, G. Heterocycles 1999, 51(5), 1035-1050; U.S. Pat. Appl. Publ. US 2005182067 (Amgen Inc., Aug. 18, 2005) and Intl. Pat. Appl. WO 2002/022605 (Vertex Pharmaceuticals Inc., Mar. 21, 2002). Additionally, (5-piperazin-1-yl-pyridazin-3-yl)-p-tolyl-amine (CAS No. 1092336-93-0) is commercially available.

Certain substituted 2-aminopyrimidines as histamine $H_4$ antagonists are disclosed in Intl. Pat. Appl. Publ. WO 2008/074445 (UCB Pharma, Jun. 26, 2008); WO 2005/054239 (Bayer Healthcare AG; Jun. 16, 2005) and EP 1505064 (Bayer Healthcare AG; Feb. 9, 2005; counterpart of Intl. Pat. Appl. Publ. WO 2005/014556). Substituted pyrimidines are described as histamine $H_4$ ligands in U.S. Pat. Appl. Publ. 2007/0185075 (Pharmacia Corp.; Aug. 9, 2007), Intl. Pat. Appl. Publ. WO 2007/031529 (Palau Pharma S.A.; Mar. 22, 2007), and U.S. patent application Ser. No. 12/070,051 (Feb. 14, 2008). Additional disclosures of amino pyrimidines as histamine $H_4$ ligands include: Intl. Pat. Appl. Publ. Nos. WO 2007/090852, WO 2007/090853, and WO 2007/090854 (Aug. 16, 2007), and EP 1767537 (Mar. 28, 2007), all reported by Cellzome Ltd., Intl. Pat. Appl. Publ. Nos. WO 2008/031556 (UCB Pharma; Mar. 20, 2008), WO 2006/050965 (Argenta; May 18, 2006), and WO 2007/072163 (Pfizer; Jun. 28, 2007).

However, there remains a need for potent histamine $H_4$ receptor modulators with desirable pharmaceutical properties. Certain diamino-pyridine, pyrimidine and pyridazine derivatives have been found in the context of this invention to have histamine $H_4$ receptor-modulating activity.

SUMMARY OF THE INVENTION

One aspect of this invention concerns compounds of Formula (I)

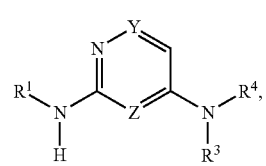

Formula (I)

wherein

Z is CH or N;

Y is CH or N;

Z and Y are defined independently of each other, and the ring containing said Y and Z members does not have more than two nitrogen members; provided that i) when Y is CH and Z is CH or N, then;

$R^1$ is:

a) —$(CH_2)_2OCH_3$, —$(CH_2)_2SCH_3$, or $C_{1-8}$alkyl, each independently unsubstituted or substituted with —OH or —$CF_3$;

b) —$(CH_2)_{0-2}$—$Ar^1$, —$CHR^2$—$Ar^1$, or —$(CH_2)_{0-2}$—$Ar^2$, each of said $Ar^1$ and $Ar^2$ independently unsubstituted or substituted with halo, —$CH_3$, or —$OCH_3$, $Ar^1$ is a 6-membered aromatic carbocyclic ring, $Ar^2$ is a 5 to 6-membered heteroaromatic ring containing N, S or O; or c) cycloalkyl, —$(CH_2)$-(monocyclic cycloalkyl), —$(CH_2)$-(bridged polycyclic cycloalkyl)$_{0-1}$, —$(CHR^2)$-(monocyclic cycloalkyl), —$(CH_2)$-(fused cycloalkyl), —$(CH_2)$-(bridged monocyclic cycloalkyl), —$(CH_2)_{0-1}$-tetrahydrofuranyl, or —$(CH_2)_{0-1}$-tetrahydropyranyl, each of said cycloalkyl independently unsubstituted or substituted with one, two, or three $C_{1-4}$alkyl substituents;

$R^2$ is —$C_{1-4}$alkyl;

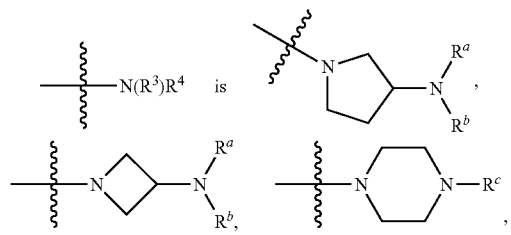

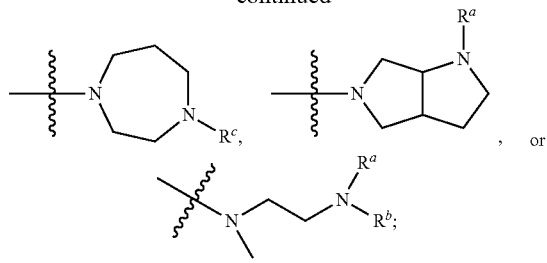

where $R^a$, $R^b$, and $R^c$ are each independently H or $C_{1-3}$alkyl; provided that:
when $R^1$ is isopropyl, then $R^c$ is methyl;
when $R^1$ is 4-methylphenyl, then $R^c$ is methyl;
when Z is N, Y is CH, and $R^1$ is benzyl unsubstituted or substituted with halo, then $R^c$ is methyl;
ii) when Y is N and Z is CH, then;
$R^1$ is:
 a) —$(CH_2)_2OCH_3$, —$(CH_2)_2SCH_3$, or $C_{1-8}$alkyl, each independently unsubstituted or substituted with —OH or —$CF_3$;
 b) —$(CH_2)_{0-2}$—$Ar^1$, —$CHR^2$—$Ar^1$, —$(CH_2)_{0-2}$—$Ar^2$, each of said $Ar^1$ and $Ar^2$ independently unsubstituted or substituted with halo, —$CH_3$, —$OCH_3$,
 $Ar^1$ is a 6-membered aromatic carbocyclic ring,
 $Ar^2$ is a 5 to 6-membered heteroaromatic ring containing N, S or O; or
 c) cycloalkyl, —$(CH_2)$-(monocyclic cycloalkyl), —$(CH_2)$-(bridged polycyclic cycloalkyl)$_{0-1}$, —$(CHR^2)$-(monocyclic cycloalkyl), —$(CH_2)$-(fused cycloalkyl), —$(CH_2)$-(bridged monocyclic cycloalkyl), —$(CH_2)_{0-1}$-tetrahydrofuranyl, —$(CH_2)_{0-1}$-tetrahydropyranyl, each independently unsubstituted or substituted with one, two, or three $C_{1-4}$alkyl substituents;
$R^2$ is —$C_{1-4}$alkyl;

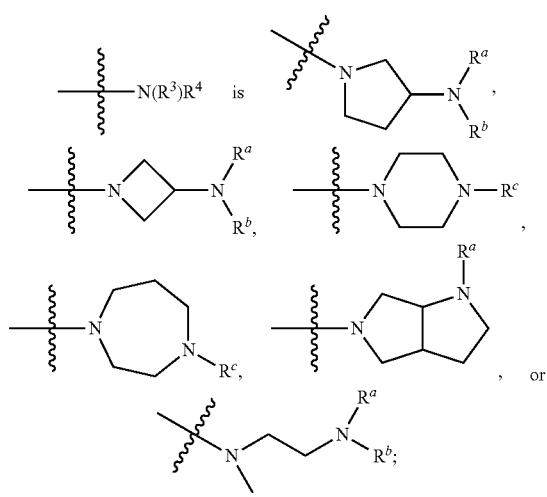

where $R^a$, $R^b$, and $R^c$ are each independently H or $C_{1-3}$alkyl.

Other embodiments concern chemical entities of Formula (I) where Y is CH, and Z is CH or N.

Further embodiments concern chemical entities of Formula (I) where Y is N and Z is CH.

Further embodiments are provided by pharmaceutically acceptable salts of compounds of Formula (I), pharmaceutically acceptable prodrugs of compounds of Formula (I), and pharmaceutically active metabolites of compounds of Formula (I).

In certain embodiments, the compound of Formula (I) is a compound selected from those species described or exemplified in the detailed description below.

In a further aspect, the invention relates to pharmaceutical compositions for treating a disease, disorder, or medical condition mediated by histamine $H_4$ receptor activity, comprising an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of Formula (I).

Pharmaceutical compositions according to the invention may further comprise a pharmaceutically acceptable excipient.

In another aspect, the invention is directed to a method of treating a subject suffering from or diagnosed with a disease, disorder, or medical condition mediated by histamine $H_4$ receptor activity, comprising administering to the subject in need of such treatment an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In certain preferred embodiments of the inventive method, the disease, disorder, or medical condition is inflammation. Inflammation herein refers to the response that develops as a consequence of histamine release, which in turn is caused by at least one stimulus. Examples of such stimuli are immunological stimuli and non-immunological stimuli.

In another aspect, the chemical embodiments of the present invention are useful as histamine $H_4$ receptor modulators. Thus, the invention is directed to a method for modulating histamine $H_4$ receptor activity, including when such receptor is in a subject, comprising exposing histamine $H_4$ receptor to an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I).

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION OF INVENTION AND ITS PREFERRED EMBODIMENTS

The disclosures of the publications, including but not limited to patents and patent applications, cited anywhere in any part of this specification are incorporated herein by reference in their entirety.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "cycloalkyl" refers to a saturated or partially saturated carbocycle, such as monocyclic, fused polycyclic, bridged monocyclic, bridged polycyclic, or spiro polycyclic carbocycle having from 3 to 12 ring atoms per carbocycle. Where the term cycloalkyl is qualified by a specific characterization, such as monocyclic, fused polycyclic, bridged polycyclic, and spiro polycyclic, then such term cycloalkyl refers only to the carbocycle so characterized. Illustrative examples of cycloalkyl groups include the following entities, in the form of properly bonded moieties:

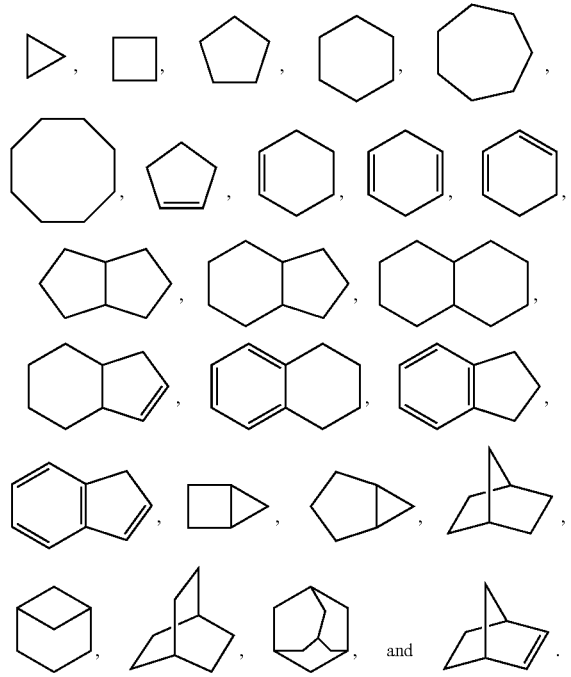

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

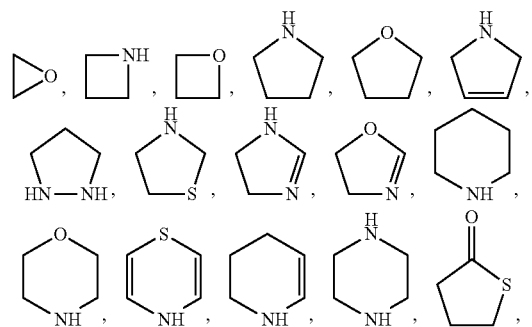

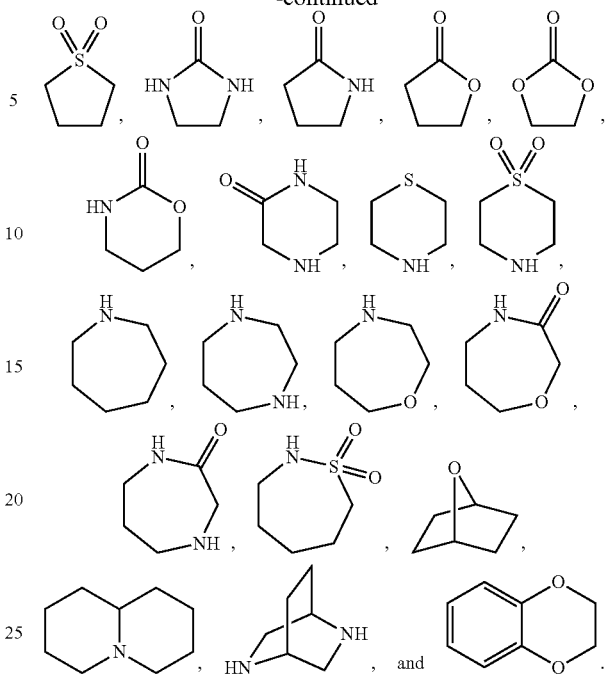

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

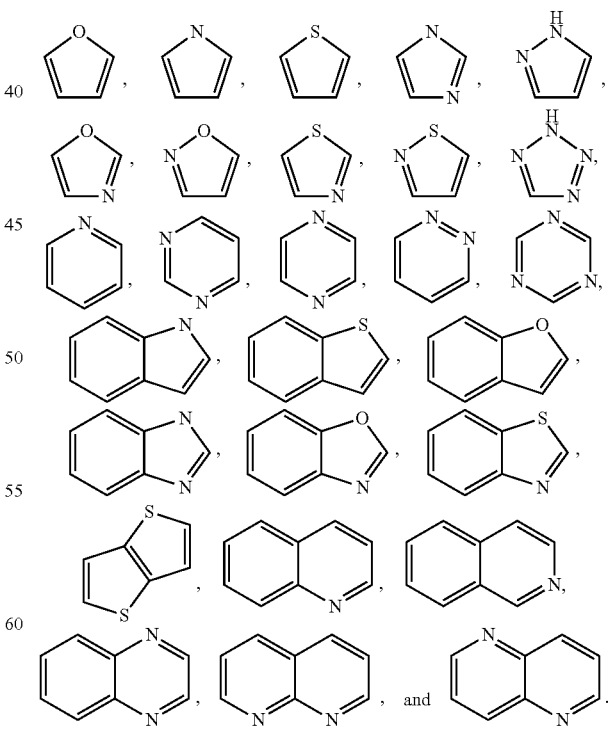

Those skilled in the art will recognize that the species of heteroaryl, cycloalkyl, and heterocycloalkyl groups listed or illustrated above are not exhaustive, and that additional species within the scope of these defined terms may also be selected.

The term "halogen" represents chlorine, fluorine, bromine, or iodine. The term "halo" represents chloro, fluoro, bromo, or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to refer also to any one of hydrates, solvates, and polymorphs of such compounds, and mixtures thereof, even if such forms are not listed explicitly. In some embodiments, the solvent is water and the solvates are hydrates.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Reference to a chemical entity herein stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{125}$I, respectively. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^{1-4}$, $R^{a-c}$, and Z, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^{1-4}$, $R^{a-c}$, and Z, and any other generic substituent symbol used herein.

The nomenclature "$C_{1-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n.

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

Some embodiments are given by compounds of Formula (I) where Y is CH, Z is CH or N, and $R^1$ is $C_{1-8}$alkyl (unsubstituted or substituted with —OH or —CF$_3$), phenyl, pyridyl, benzyl, pyridin-2-ylmethyl, phenylethyl, 1-phenyl-ethyl (each independently unsubstituted or substituted with halo, —CH$_3$, —OCH$_3$), cycloalkyl, —(CH$_2$)-(monocyclic cycloalkyl), —(CHR$^2$)-(monocyclic cycloalkyl), —(CH$_2$)-(fused cycloalkyl), —(CH$_2$)-(bridged polycyclic cycloalkyl), —(CH$_2$)$_{0-1}$-tetrahydrofuranyl, or —(CH$_2$)$_{0-1}$-tetrahydropyranyl (each independently unsubstituted or substituted with one, two, or three $C_{1-4}$alkyl substituents). In some of these embodiments, $R^1$ is 2,2-dimethylpropanol, 2,2-dimethylpropan-1-ol, 2,2-dimethylpropyl, 2-methyl-1-propan-2-ol, 2-methylpropan-2-ol, 3-propanol, (1-methylethyl), 2,2-dimethylpropyl, 2-methoxyethyl, 2-methylpropyl, 4,4,4-trifluorobutyl, propyl, butyl, tert-butyl, propan-1-ol, 2-(methylsulfanyl)ethyl, 2-phenylethyl, furan-3-ylmethyl, pyridin-2-ylmethyl, (1R)-1-phenylethyl, benzyl, phenyl, 4-fluorobenzyl, 4-methoxybenzyl, 4-methylbenzyl, bicyclo[2.2.1]hept-2-ylmethyl, tetrahydro-2H-pyran-4-yl, tetrahydrofuran-2-ylmethyl, (1R,2R,3R,5S)-2,6,6-trimethylbicyclo[3.1.1]hept-3-yl, (1R,2S,4R)-1,7,7-trimethylbicyclo[2.2.1]hept-2-yl, (1S,2S,3S,5R)-2,6,6-trimethylbicyclo[3.1.1]hept-3-yl, (1S,2S,4R)-bicyclo[2.2.1]hept-2-yl, (1S,5R)-2,6,6-trimethylbicyclo[3.1.1]hept-3-yl, (2R)-tetrahydrofuran-2-ylmethyl, (2S)-bicyclo[2.2.1]hept-2-yl], [(2S)-tetrahydrofuran-2-ylmethyl, (3R)-tetrahydrofuran-3-yl, (6,6-dimethylbicyclo[3.1.1]hept-2-yl)methyl, bicyclo[2.2.1]hept-2-yl, cyclobutyl, cyclohexyl, cyclopentyl, cyclopropyl, cyclohexylmethyl, cyclopentylmethyl, cyclopropylmethyl, adamantan-1-yl, 2-adamantyl, bicyclo[2.2.1]hept-2-yl, or (6,6-dimethyl-bicyclo[3.1.1]hept-2-yl)-methyl.

In some embodiments, where Y is CH and Z is CH or N, $R^1$ is

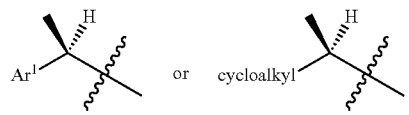

In some embodiments, where Y is CH and Z is CH or N,

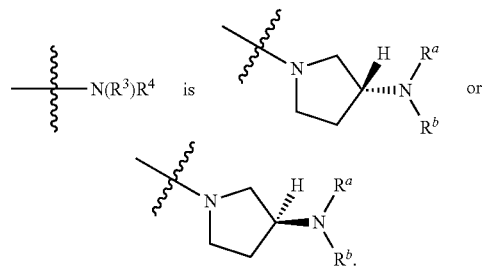

In some embodiments, where Y is CH and Z is CH or N,

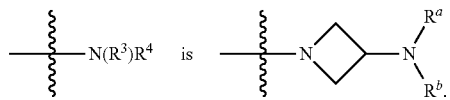

In some embodiments, where Y is CH and Z is CH or N,

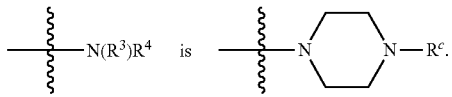

In some embodiments, where Y is CH and Z is CH or N,

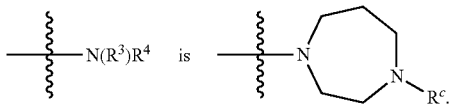

In some embodiments, where Y is CH and Z is CH or N,

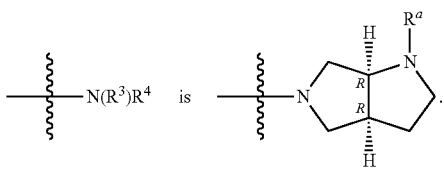

In some embodiments, where Y is CH and Z is CH or N,

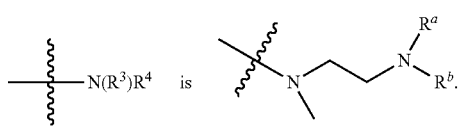

In some embodiments, where Y is CH and Z is CH or N, $R^a$ is H.

In some embodiments, where Y is CH and Z is CH or N, $R^b$ is H or methyl.

In some embodiments, where Y is CH and Z is CH or N, $R^c$ is H or methyl. In some embodiments, where Y is CH and Z is CH or N, $R^2$ is —$CH_3$.

In some embodiments Y and Z are CH.

In some embodiments Y and Z is N.

Some further embodiments are given by compounds of Formula (I) where Y is N, Z is CH, and $R^1$ is $C_{1-8}$alkyl (unsubstituted or substituted with —OH or —$CF_3$), phenyl, pyridyl, benzyl, pyridin-2-ylmethyl, phenylethyl, 1-phenylethyl (each independently unsubstituted or substituted with halo, —$CH_3$, —$OCH_3$), cycloalkyl, —($CH_2$)-(monocyclic cycloalkyl), —($CHR^2$)-(monocyclic cycloalkyl), —($CH_2$)-(fused cycloalkyl), —($CH_2$)-(bridged polycyclic cycloalkyl), —($CH_2$)$_{0-1}$-tetrahydrofuranyl, or —($CH_2$)$_{0-1}$-tetrahydropyranyl (each independently unsubstituted or substituted with one, two, or three $C_{1-4}$alkyl substituents). In some of these embodiments, $R^1$ is 2,2-dimethylpropanol, 2,2-dimethylpropan-1-ol, 2,2-dimethylpropyl, 2-methyl-1-propan-2-ol, 2-methylpropan-2-ol, 3-propanol, (1-methylethyl), 2,2-dimethylpropyl, 2-methoxyethyl, 2-methylpropyl, 4,4,4-trifluorobutyl, propyl, butyl, tert-butyl, propan-1-ol, 2-(methylsulfanyl)ethyl, 2-phenylethyl, furan-3-ylmethyl, pyridin-2-ylmethyl, (1R)-1-phenylethyl, benzyl, phenyl, 4-fluorobenzyl, 4-methoxybenzyl, 4-methylbenzyl, bicyclo[2.2.1]hept-2-ylmethyl, tetrahydro-2H-pyran-4-yl, tetrahydrofuran-2-ylmethyl, (1R,2R,3R,5S)-2,6,6-trimethylbicyclo[3.1.1]hept-3-yl, (1R,2S,4R)-1,7,7-trimethylbicyclo[2.2.1]hept-2-yl, (1S,2S,3S,5R)-2,6,6-trimethylbicyclo[3.1.1]hept-3-yl, (1S,2S,4R)-bicyclo[2.2.1]hept-2-yl, (1S,5R)-2,6,6-trimethylbicyclo[3.1.1]hept-3-yl, (2R)-tetrahydrofuran-2-ylmethyl, (2S)-bicyclo[2.2.1]hept-2-yl], [(2S)-tetrahydrofuran-2-ylmethyl, (3R)-tetrahydrofuran-3-yl, (6,6-dimethylbicyclo[3.1.1]hept-2-yl)methyl, bicyclo[2.2.1]hept-2-yl, cyclobutyl, cyclohexyl, cyclopentyl, cyclopropyl, cyclohexylmethyl, cyclopentylmethyl, cyclopropylmethyl, adamantan-1-yl, 2-adamantyl, bicyclo[2.2.1]hept-2-yl, or (6,6-dimethyl-bicyclo[3.1.1]hept-2-yl)-methyl.

In some embodiments, where Y is N and Z is CH, $R^1$ is

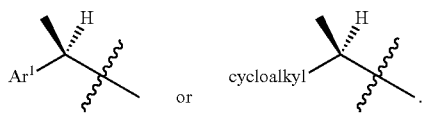

In some embodiments, where Y is N and Z is CH,

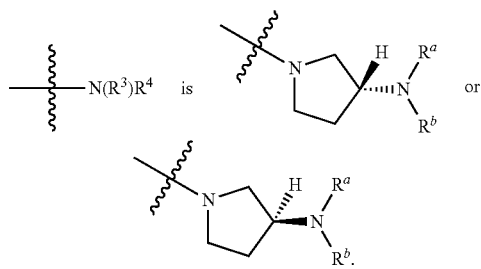

In some embodiments, where Y is N and Z is CH,

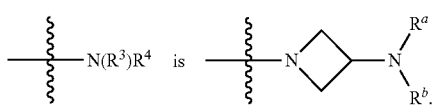

In some embodiments, where Y is N and Z is CH,

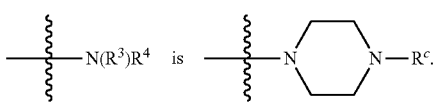

In some embodiments, where Y is N and Z is CH,

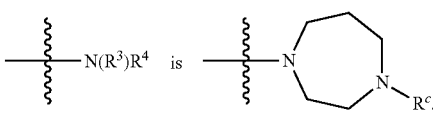

In some embodiments, where Y is N and Z is CH,

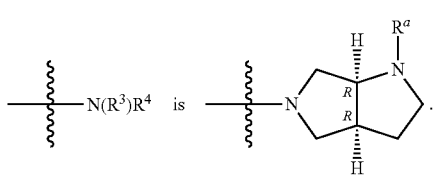

In some embodiments, where Y is N and Z is CH,

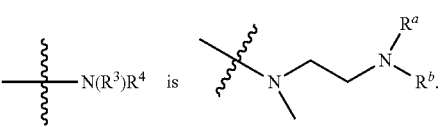

In some embodiments, where Y is N and Z is CH, and $R^a$ is H.

In some embodiments, where Y is N and Z is CH, $R^b$ is H or methyl.

In some embodiments, where Y is N and Z is CH, $R^c$ is H or methyl.

In some embodiments, where Y is N and Z is CH, $R^2$ is —CH$_3$.

In some embodiments, where Y is N and Z is CH.

The invention includes also pharmaceutically acceptable salts of the compounds represented by Formula (I), preferably of those described above and of the specific compounds exemplified herein, and methods using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

Where the compound of Formula (I) contains a plurality of basic nitrogens, one skilled in the art will recognize that suitable salts include salts formed with one or more equivalents of an inorganic or organic acid. In preferred embodiments of Formula (I), such salts include bis hydrochloride salts.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl ($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J. Med. Chem.* 1996, 39, 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of compounds of Formula (I), and uses of such metabolites in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

The compounds of Formula (I) and their pharmaceutically acceptable salts, pharmaceutically acceptable prodrugs, and pharmaceutically active metabolites, whether alone or in combination, (collectively, "active agents") of the present invention are useful as histamine $H_4$ receptor modulators in the methods of the invention. Such methods for modulating histamine $H_4$ receptor activity comprise exposing histamine $H_4$ receptor to an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I). Embodiments of this invention inhibit histamine $H_4$ receptor activity.

In some embodiments, the histamine $H_4$ receptor is in a subject diagnosed with or suffering from a disease, disorder, or medical condition mediated through histamine $H_4$ receptor activity, such as those described herein. Symptoms or disease states are intended to be included within the scope of "medical conditions, disorders, or diseases."

Accordingly, the invention relates to methods of using the active agents described herein to treat subjects diagnosed with or suffering from a disease, disorder, or condition mediated through histamine $H_4$ receptor activity, such as inflammation. Active agents according to the invention may therefore be used as anti-inflammatory agents. Active agents according to the invention may also be used for the treatment of pain.

In some embodiments, an active agent of the present invention is administered to treat inflammation. Inflammation may be associated with various diseases, disorders, or conditions, such as inflammatory disorders, allergic disorders, dermatological disorders, autoimmune disease, lymphatic disorders, and immunodeficiency disorders, including the more specific conditions and diseases given below. Regarding the onset and evolution of inflammation, inflammatory diseases or inflammation-mediated diseases or conditions include, but are not limited to, acute inflammation, allergic inflammation, and chronic inflammation.

Treatment of inflammation according to this invention includes topical treatments. For example, topical treatments of conditions such as pruritus, urticaria, and atopic dermatitis.

Illustrative types of inflammation treatable with a histamine $H_4$ receptor-modulating agent according to the invention include inflammation due to any one of a plurality of conditions such as allergy, asthma, dry eye, chronic obstructed pulmonary disease (COPD), atherosclerosis, rheumatoid arthritis (see: Ohki, E. et al. Biol. Pharm. Bull. 2007, 30(11), 2217-2220), multiple sclerosis, inflammatory bowel diseases (including colitis, Crohn's disease, and ulcerative colitis), psoriasis, pruritus, itchy skin, atopic dermatitis, urticaria (hives), ocular inflammation (e.g., post-surgical ocular inflammation), conjunctivitis, dry eye, nasal polyps, allergic rhinitis, nasal itch, scleroderma, autoimmune thyroid diseases, post-operative adhesion (See: U.S. Pat. Appl. Publ. 2007/0185163), and immune-mediated (also known as type 1) diabetes mellitus and lupus, which are characterized by excessive or prolonged inflammation at some stage of the disease. Treatment of metabolic disorders, such as type 2 diabetes, is also envisaged within the scope of this invention. Treatment of other metabolic disorders envisaged within the scope of this invention include chronic renal failure, hepatic cholestasis, and diabetes mellitus.

Other autoimmune diseases that lead to inflammation include Myasthenia gravis, autoimmune neuropathies, such as Guillain-Barré, autoimmune uveitis, autoimmune hemolytic anemia, pernicious anemia, autoimmune thrombocytopenia, temporal arteritis, anti-phospholipid syndrome, vasculitides, such as Wegener's granulomatosis, Behcet's disease, dermatitis herpetiformis, pemphigus vulgaris, vitiligio, primary biliary cirrhosis, autoimmune hepatitis, autoimmune oophoritis and orchitis, autoimmune disease of the adrenal gland, polymyositis, dermatomyositis, spondyloarthropathies, such as ankylosing spondylitis, and Sjogren's syndrome.

Pruritis treatable with a histamine $H_4$ receptor-modulating agent according to the invention includes that which is a symptom of allergic cutaneous diseases (such as atopic dermatitis and hives).

Treatment of mood and anxiety disorders is also envisaged within the scope of this invention. Examples of such mood disorders include major depression disorder, bipolar disorder, treatment-resistant major depression disorder, and treatment-resistant bipolar disorder. Examples of such anxiety disorders include generalized anxiety disorder, social phobia, and post traumatic stress disorder.

In other embodiments, an active agent of the present invention is administered to treat allergy, rheumatoid arthritis, asthma, autoimmune diseases, or pruritis.

Thus, the active agents may be used to treat subjects diagnosed with or suffering from a disease, disorder, or condition mediated through histamine $H_4$ receptor activity. The term "treat" or "treating" as used herein is intended to refer to administration of an active agent or composition of the invention to a subject for the purpose of effecting a therapeutic or prophylactic benefit through modulation of histamine $H_4$ receptor activity. Treating includes reversing, ameliorating, alleviating, inhibiting the progress of, lessening the severity of, or preventing a disease, disorder, or condition, or one or more symptoms of such disease, disorder or condition mediated through modulation of histamine $H_4$ receptor activity. The term "subject" refers to a mammalian patient in need of such treatment, such as a human. Some embodiments of this invention are envisaged for veterinary use. "Modulators" include both inhibitors and activators, where "inhibitors" refer to compounds that decrease, prevent, inactivate, desensitize or down-regulate histamine $H_4$ receptor expression or activity, and "activators" are compounds that increase, activate, facilitate, sensitize, or up-regulate histamine $H_4$ receptor expression or activity.

In treatment methods according to the invention, an effective amount of at least one active agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.001 to about 200 mg of active agent per kg of subject's body weight per day, preferably about 0.05 to 100 mg/kg/day, or about 1 to 35 mg/kg/day, or about 0.1 to 10 mg/kg daily in single or divided dosage units (e.g., BID, TID, QID). For a 70-kg human, an illustrative range for a suitable dosage amount is from about 1 to 200 mg/day, or about 5 to 50 mg/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of Formula (I) or included with such an agent in a pharmaceutical composition according to the invention. In an exemplary embodiment, additional active ingredients are those that are known or discovered to be effective in the treatment of conditions, disorders, or diseases mediated by histamine $H_4$ receptor activity, such as another histamine $H_4$ receptor modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the active agent according to the invention.

When referring to modulating the target receptor, an "effective amount" means an amount sufficient to affect the activity of such receptor. Measuring the activity of the target receptor may be performed by routine analytical methods. Target receptor modulation is useful in a variety of settings, including assays.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and optionally (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the active agents of the invention can be provided in the form of tablets or capsules, or as a solution, emulsion, or suspension. To prepare the oral compositions, the active agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Each of the reactions depicted in Scheme A is preferably run at a temperature from about room temperature to the reflux temperature of the organic solvent used. Unless otherwise specified, the variables are as defined above in reference to Formula (I)

SCHEME A

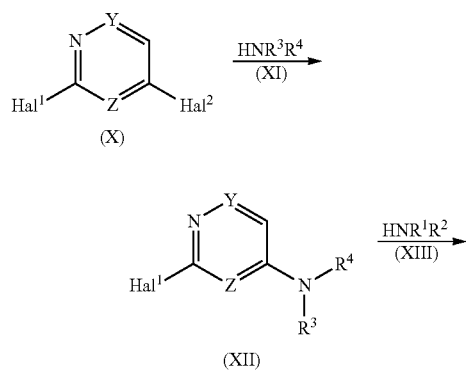

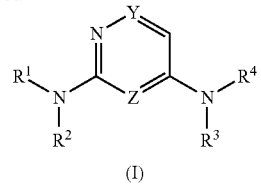

(I)

As shown in Scheme A, compounds of Formula (I) are prepared by sequential reaction of compounds (X) with amines (XI) and amines (XIII). Where Y and Z are CH, Hal$^1$ is chloro, and Hal$^2$ is chloro, bromo, or iodo, addition of amines (XI) by palladium-catalyzed amination gives compounds (XII). Amination reactions are performed in the presence of a palladium(0) catalyst such as tris(dibenzylideneacetone)dipalladium(0) (Pd$_2$(dba)$_3$), or tetrakis(triphenylphosphine)palladium, a ligand such as 4,5-bis(diphenylphosphino)-9,9-dimethylxanthene (Xantphos), 2-dicyclohexylphosphino-2',4',6'-triisopropylbiphenyl (X-Phos), 1,1'-bis(diphenylphosphino)ferrocene (dppf), 2,2'-bis(diphenylphosphino)-1,1'-bihaphthyl (BINAP), Cy-MAP [(2'-dicyclohexylphosphanylbiphen-2-yl)dimethylamine], Cy$_2$P(Ph-Ph) (dicyclohexyl-2-biphenylphosphane), tBu$_2$P(Ph-Ph) (di-tert-butyl-2-biphenylphosphane), tBu$_3$P, or lPr.HCl (lPr=1,4-bis(2,6-diisopropyl)imidazol-2-ylidene), and a base such as sodium tert-butoxide, potassium tert-butoxide, lithium or sodium bis(trimethylsilyl)amide, or Cs$_2$CO$_3$, in a solvent such as toluene, tetrahydrofuran (THF), dimethylacetamide (DMA), dimethoxyethane (DME), or tert-butanol, or a mixture thereof, at a temperature from about 50° C. to about 140° C. (Ji et al. *J. Org. Chem.* 2003, 24, 4611-4614). Preferably, reactions are performed using Pd$_2$(dba)$_3$, Xantphos, and sodium tert-butoxide, in toluene, at a temperature of about 70° C. to about 110° C.

Compounds (XII) where Y and Z are CH and Hal$^1$ is chloro are subsequently converted to pyridines of Formula (I) by palladium-catalyzed amination with amines (XIII), as described above. Preferably, reactions are performed using palladium(II) acetate (Pd(OAc)$_2$), BINAP, and sodium tert-butoxide, in toluene, DMA, or tert-butanol (or a mixture thereof), at a temperature of about 50° C. to about 110° C.

Where Y is CH and Z is N, Hal$^1$ is chloro, and Hal$^2$ is chloro, bromo, or iodo, compounds (X) are reacted by displacement with amines (XI), with or without the presence of a tertiary amine base (such as diisopropylethylamine or triethylamine), in an organic solvent such as methanol, ethanol, isopropanol, tert-amyl alcohol, pentan-1-ol, THF, or acetonitrile, or a mixture thereof, at a temperature of about 0° C. to about 180° C., either by traditional heating or under microwave conditions to provide compounds of formula (XII). Compounds (XII) where Y is CH and Z is N and Hal$^1$ is chloro are subsequently reacted with amines (XIII) using displacement conditions as described to provide pyrimidines of Formula (I).

Additionally, compounds of Formula (I) are prepared by sequential reaction of compounds (X) with amines (XI) and amines (XIII). Compounds (X) where Y is N and Z is CH, Hal$^1$ and Hal$^2$ are chloro, are reacted with amines), with or without the presence of a tertiary amine base (such as diisopropylethylamine or triethylamine), in a solvent such as THF or DMF and the like, at a temperature of about 23° C. to about 110° C., to provide compounds (XII). Addition of amines (XIII) either by palladium-catalyzed amination, as described, or by displacement of the chlorine with the amine (XIII) neat or in a polar solvent such as DME, with or without the presence of a tertiary amine base (such as diisopropylethylamine or triethylamine) at temperatures ranging from 100° C. to 250° C. under conventional heating or microwave conditions, provides pyridazines of Formula (I)

SCHEME B

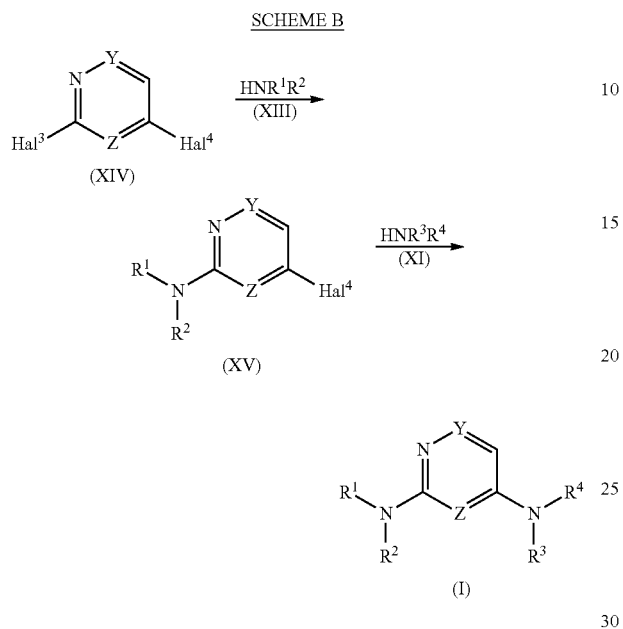

As shown in Scheme B, compounds of Formula (I) are prepared by sequential reaction of compounds (XIV) with amines (XIII) and amines (XI). Compounds (XIV) where Y and Z are CH, $Hal^3$ is fluoro and $Hal^4$ is iodo or bromo, are reacted with amines (XIII) in a polar solvent such as N-methylpyrrolidinone (NMP), N,N-dimethylformamide, DMA, dimethylsulfoxide, or a mixture thereof, at a temperature of about 50° C. to about 110° C., either by traditional heating or under microwave conditions to provide compounds (XV). Addition of amines (XI) either by palladium-catalyzed amination (as described for Scheme A) or by nucleophilic aromatic substitution in the presence of a Lewis acid such as ytterbium trifluormethanesulfonate (Yb(OTf)$_3$), in a polar solvent such as DMA or NMP, at a temperature of about 150° C. to about 250° C. under conventional heating or microwave conditions, provides pyridines of Formula (I).

Compounds (XIV) where Y is CH and Z is N, $Hal^3$ is chloro, and $Hal^4$ is chloro, are reacted by displacement with amines (XIII) to give compounds (XV) and then with amines (XI) to give pyrimidines of Formula (I). Displacement reactions are performed as described for Scheme A

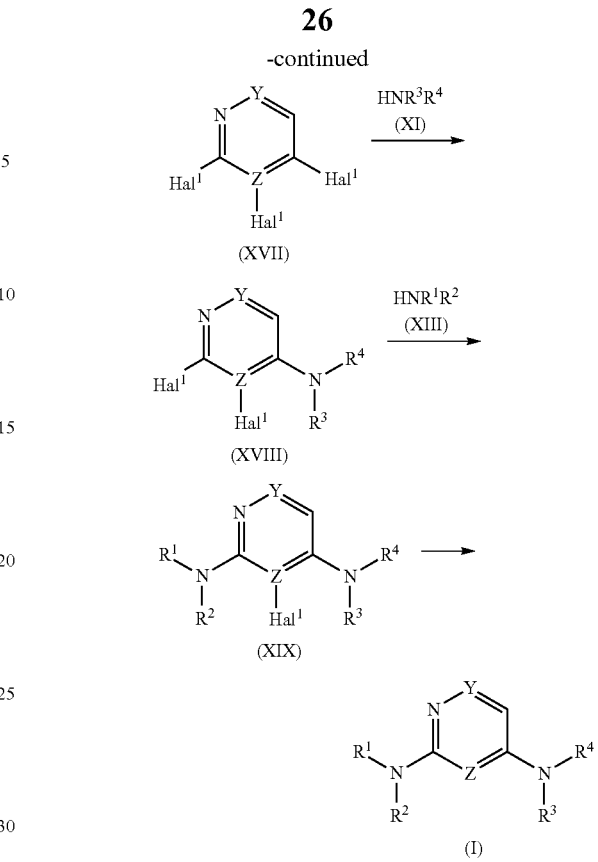

As shown in Scheme C, compounds (XVII), where Y is N, Z is C, and $Hal^1$ is chloro, are prepared by chlorination of compounds (XVI) using conditions know to one skilled in the art, for example, by reaction with phosphoryl chloride, at temperatures ranging from 65° C. to about 120° C. afford compounds (XVII). Compounds (XVII) are reacted by displacement with amines (XI), with a tertiary amine base (such as diisopropylethylamine or triethylamine), in an organic solvent such as methanol, ethanol, isopropanol, tert-amyl alcohol, pentan-1-ol, THF, or acetonitrile, or a mixture thereof, at a temperature of about 23° C. to 180° C., either by traditional heating or under microwave conditions. Compounds (XVIII) are subsequently reacted with amines (XIII) using displacement conditions as described to provide pyridazines (XIX). Reaction of halo-pyridazines (XIX) with a reducing agent such as 10% palladium on carbon, in the presence of ammonium formate, in a polar solvent such as methanol, at temperatures ranging from 65° C. to 85° C. provides compounds of Formula (I)

SCHEME C

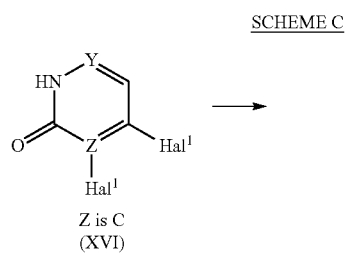

SCHEME D

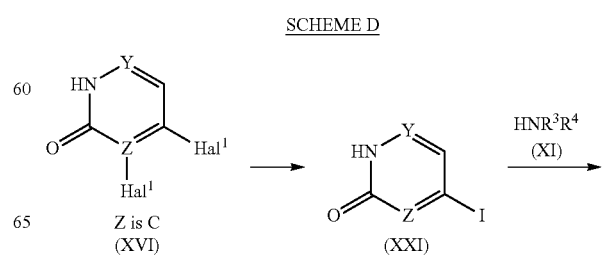

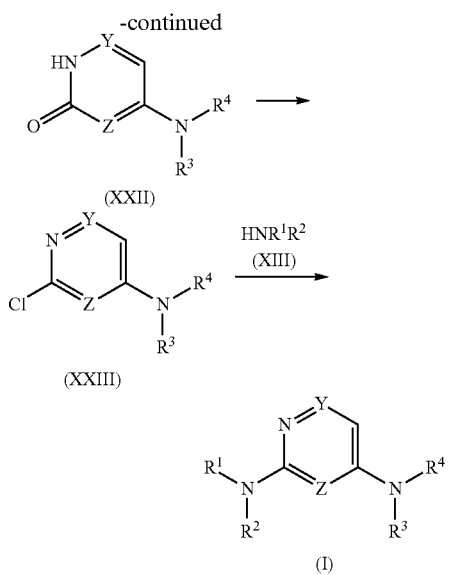

As shown in Scheme D, compounds (XVI), where Y is N, Z is C, and Hal$^1$ is chloro, are reacted with hydrogen iodide acid (57%), at temperatures ranging from 100° C. to 150° C. to provide 5-iodo-4H-pyridazin-3-one intermediate (XXI). Subsequent reaction of intermediate (XXI) with amines (XI) in a displacement fashion, in an organic solvent such as methanol, ethanol, isopropanol, tert-amyl alcohol, pentan-1-ol, THF, or acetonitrile, or a mixture thereof, at a temperatures ranging from 23° C. to 180° C., either by traditional heating or under microwave heating provide compounds of formula (XXII). Chlorination of compounds (XXII) using conditions known to one skilled in the art, for example, by reaction with phosphoryl chloride, at temperatures ranging from 65° C. to about 120° C. afford compounds (XXIII). Compounds (XXIII) are reacted with amines (XIII) in a displacement reaction, in an organic solvent such as methanol, ethanol, isopropanol, tert-amyl alcohol, pentan-1-ol, THF, or acetonitrile, or a mixture thereof, at a temperature of about 23° C. to 200° C., either by traditional heating or under microwave heating provide compounds of Formula (I).

In the above Schemes, where the diamine HNR$^3$R$^4$ (XIII) contains a nitrogen protecting group (PG), such as a tert-butoxycarbonyl (Boc) group or benzyl group, in place of the R$^a$ or R$^c$ substituent, the protecting group is removed by deprotection conditions known to one skilled in the art, to provide compounds where R$^a$ or R$^c$ is H. For example, a tert-butoxycarbonyl group is removed using an organic acid such as TFA (neat or in a solvent such as CH$_2$Cl$_2$) or an inorganic acid such as HCl (in a solvent such as 1,4-dioxane, ether, methanol, isopropanol, or formic acid, or a mixture thereof). Reductive amination or alkylation procedures may be used to convert compounds where R$^c$ is H to compounds where R$^c$ is C$_{1-3}$alkyl.

Compounds of Formula (I) may be converted to their corresponding salts using methods described in the art. For example, an amine of Formula (I) is treated with trifluoroacetic acid, HCl, or citric acid in a solvent such as Et$_2$O, CH$_2$Cl$_2$, THF, MeOH, chloroform, or isopropanol to provide the corresponding salt form. Alternately, trifluoroacetic acid or formic acid salts are obtained as a result of reverse phase HPLC purification conditions. Cyrstalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions are "dried," they are generally dried over a drying agent such as Na$_2$SO$_4$ or MgSO$_4$. Where mixtures, solutions, and extracts were "concentrated", they were typically concentrated on a rotary evaporator under reduced pressure. Silica gel (SiO$_2$) was used for flash chromatographic purification (FCC) and the eluent used is listed in parentheses.

Microwave heating was performed on a Personal Chemistry Emrys™ Optimizer using Biotage microwave vials.

Analytical reversed-phase high-performance liquid chromatography (HPLC) was performed on a Hewlett Packard HPLC Series 1100, with a Phenomenex ONYX® monolithic C18 (5 μm, 4.6×100 mm) column. Detection was done at λ=230, 254 and 280 nm. The flow rate was 1 mL/min. The gradient was 10 to 90% acetonitrile/water (20 mM NH$_4$OH) over 5.0 min. Preparative reversed-phase HPLC was performed on a Dionex instrument equipped with a YMC Pack ODS 250×30 mm column with a gradient of 10 to 50% NH$_4$OH in acetonitrile (0.05% water) over 15 min at a flow rate of 70 mL/min. Alternatively, compounds were purified on a Waters LC/MS equipped with a Waters XBridge C18 column (100×30 mm) with a gradient of 1 to 25% acetonitrile/water (0.05% trifluoroacetic acid (TFA)) over 15 min at a flow rate of 44 mL/min. Analytical reversed-phase HPLC was performed on Agilent HPLC with C18 (5 μm, 4.6×150 mm) column. Detection was done at λ=214 and 254 nm. The flow rate was 1 mL/min. The gradient was 10 to 90% acetonitrile/water (0.1% formic Acid) over 10 min.

Preparative thin-layer chromatography (TLC) was performed using 20×20 cm silica gel 60 F$_{254}$ plates, with a 0.5 mm thickness.

Preparative reversed-phase HPLC was performed on Gemini column C18 (150×21.2 mm) with a gradient of 5 to 60% acetonitrile and water (0.1% trifluoroacetic acid or 0.1% formic acid) over 14 min at a flow rate 20 mL/min monitored at 214 nm.

Compounds were analyzed in a free-base, hydrochloride or trifluoroacetate salt form. Hydrochloride salts were obtained either: 1) during the removal of the tert-butylcarbamoyl (Boc) group; or 2) by treatment of a solution of the purified free base in THF, CHCl₃ or CH₂Cl₂ (DCM) with at least two equivalents of a solution of HCl in 1,4-dioxane or ether followed by concentration. TFA salts were obtained directly from HPLC purification.

Nuclear magnetic resonance (NMR) spectra were obtained on Bruker model DRX spectrometers (400 MHz or 500 MHz) or Varian (300 MHz) spectrometer. The format of the ¹H NMR data below is: chemical shift in ppm downfield of the tetramethylsilane reference (multiplicity, coupling constant J in Hz, integration).

Mass spectra were obtained on an Agilent series 1100 MSD or 1200 MSD using electrospray ionization (ESI) in either positive or negative modes as indicated. The MS data presented is the m/z found (typically [M+H]⁺) for the molecular ion.

Chemical names were generated using ACD/Name Version 10 (Advanced Chemistry Development, Toronto, Ontario, Canada) or ChemDraw Version 6.0.2 (CambridgeSoft, Cambridge, Mass.).

Example 1

Bicyclo[2.2.1]hept-2-yl-[4-((3R)-3-methylamino-pyrrolidin-1-yl)-pyridin-2-yl]-amine dihydrochloride

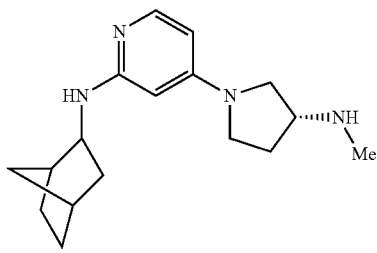 [SMILES: CN[C@@H]1CCN(c2ccnc(NC3CC4CCC3C4)c2)C1]

(3R)-[1-(2-Chloro-pyridin-4-yl)-pyrrolidin-3-yl]-methylamine. To a stirring solution of 2-chloro-4-bromopyridine (4.3 g, 22.1 mmol) in toluene (100 mL) was added (R)-methyl-pyrrolidin-3-yl-amine (1.7 g, 17.0 mmol) and sodium tert-butoxide (2.5 g, 26.0 mmol). The flask was evacuated and flushed with $N_{2(g)}$ twice. A mixture of 4,5-bis(diphenylphosphino)-9,9-dimethylxanthene (Xantphos; 590 mg, 1.0 mmol) and tris(dibenzylideneacetone)-dipalladium(0) (Pd₂(dba)₃; 310 mg, 0.34 mmol) was added in one portion and the mixture was heated at 85° C. for 20 h. The mixture was cooled to room temperature (rt), diluted with H₂O (75 mL), and extracted with ethyl acetate (EtOAc; 3×). The combined organic layers were dried and concentrated to give a clear brown oil. The oil was purified by FCC (0 to 5% 2 M NH₃ in MeOH/CH₂Cl₂) to give the title compound as a brown solid (1.1 g, 30%). MS (ESI): mass calcd. for $C_{10}H_{14}ClN_3$, 211.09 m/z found, 212.1 [M+H]. ¹H NMR (DMSO-d₆): 7.86 (d, J=5.9, 1H), 6.47-6.38 (m, 2H), 3.45-3.17 (m, 4H), 3.11-3.01 (m, 1H), 2.29 (s, 3H), 2.15-2.00 (m, 1H), 1.82 (br s, 1H), 1.79-1.65 (m, 1H). Bicyclo[2.2.1]hept-2-yl-[(3R)-4-(3-methylamino-pyrrolidin-1-yl)-pyridin-2-yl]-amine. To a stirring mixture of [(3R)-1-(2-chloro-pyridin-4-yl)-pyrrolidin-3-yl]-methyl-amine (97 mg, 0.46 mmol), exo-2-aminonorbornane (164 μL, 1.4 mmol) in ethylene glycol dimethyl ether (DME; 4 mL) in a scintillation vial was added sodium tert-butoxide (245 mg, 2.6 mmol). To the stirring mixture was added in one portion Pd(OAc)₂ (16 mg, 0.024 mmol) and racemic 2,2'-bis(diphenylphosphino)-1,1'-bihaphthyl (BINAP; 19 mg, 0.031 mmol). The mixture was heated at 65° C. for 20 h, then was cooled to rt and filtered through a plug of diatomaceous earth. The plug was washed with MeOH (2 mL) and the filtrate was purified directly by FCC (5% 2 M NH₃ in MeOH/CH₂Cl₂) to give a clear light golden oil (70 mg, 54%). Bicyclo[2.2.1]hept-2-yl-[(3R)-4-(3-methylamino-pyrrolidin-1-yl)-pyridin-2-yl]-amine. To a stirring solution of bicyclo[2.2.1]hept-2-yl-[(3R)-4-(3-methylamino-pyrrolidin-1-yl)-pyridin-2-yl]-amine in 1:1 Et₂O/CH₂Cl₂ (8 mL) was added 1 N HCl in Et₂O (1 mL). The organic layers was separated and concentrated to give the desired product (89 mg, 100%) as a beige solid. MS (ESI): mass calcd. for $C_{17}H_{26}N_4$, 286.2; m/z found, 287.3 [M+H]⁺. ¹H NMR (DMSO-d₆): 12.07 (s, 1H), 9.57 (br s, 1H), 9.46 (br s, 1H), 7.81 (d, J=5.1, 1H), 7.66 (d, J=4.6, 1H), 6.28 (d, J=7.4, 1H), 5.64 (s, 1H), 3.89 (br s, 1H), 3.85-3.61 (m, 3H), 3.49 (br s, 2H), 2.60 (s, 3H), 2.35-2.20 (m, 3H), 2.18 (s, 1H), 1.95-1.85 (m, 1H), 1.55-1.46 (m, 3H), 1.37-1.25 (m, 2H), 1.21-1.09 (m, 2H).

The compounds in Example 2 through Example 15 were prepared using methods analogous to those described for Example 1.

Example 2

N-Cyclopentyl-4-[(3R)-3-(methylamino)pyrrolidin-1-yl]pyridin-2-amine

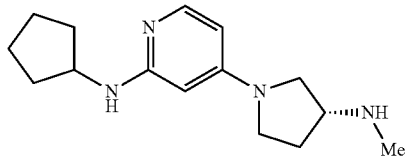

MS (ESI): mass calcd. for $C_{15}H_{24}N_4$, 260.2; m/z found, 261.3 [M+H]⁺. ¹H NMR (DMSO-d₆): 7.57 (d, J=5.9, 1H), 5.77 (dd, J=5.9, 2.1, 1H), 5.72 (d, J=7.1, 1H), 5.42 (s, 1H), 4.05-3.96 (m, 1H), 3.36-3.29 (m, 2H), 3.28-3.15 (m, 2H), 2.99-2.91 (m, 1H), 2.29 (s, 3H), 2.06-1.98 (m, 1H), 1.90-1.81 (m, 2H), 1.81-1.72 (m, 2H), 1.71-1.62 (m, 2H), 1.55-1.46 (m, 2H), 1.45-1.35 (m, 2H).

Example 3

4-[(3R)-3-(Methylamino)pyrrolidin-1-yl]-N-propylpyridin-2-amine dihydrochloride

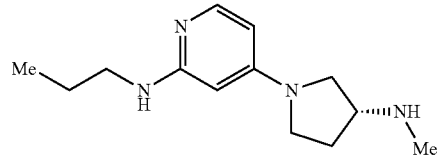 [SMILES: CCCNc1cc(N2CC[C@@H](NC)C2)ccn1]

MS (ESI): mass calcd. for $C_{13}H_{22}N_4$, 260.2; m/z found, 235.2 [M+H]⁺. ¹H NMR (DMSO-d₆): 12.12 (s, 1H), 9.46-9.26 (m, 2H), 7.71 (d, J=5.2, 1H), 7.65 (d, J=6.9, 1H), 6.29 (d, J=7.4, 1H), 5.68 (s, 1H), 3.90 (br s, 1H), 3.78-3.61 (m, 3H), 3.37 (br s, 1H), 3.28-3.16 (m, 2H), 2.61 (s, 3H), 2.46-2.21 (m, 2H), 1.58 (q, J=7.3, 2H), 0.95 (t, J=7.4, 3H).

Example 4

N-(Cyclopropylmethyl)-4-[(3R)-3-(methylamino) pyrrolidin-1-yl]pyridin-2-amine ditrifluoroacetate

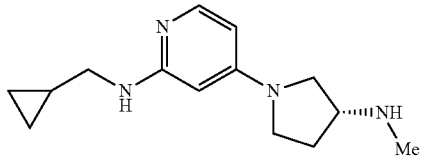 [SMILES: CN[C@@H]1CCN(c2ccnc(NCC3CC3)c2)C1]

MS (ESI): mass calcd. for $C_{14}H_{22}N_4$, 246.2; m/z found, 247.2 [M+H]$^+$. $^1$H NMR (DMSO-$d_6$): 12.00 (s, 1H), 8.96 (s, 2H), 7.74 (d, J=5.1, 1H), 7.66 (d, J=4.3, 1H), 6.30 (d, J=7.4, 1H), 5.71 (s, 1H), 3.94 (br s, 2H), 3.60 (br s, 2H), 3.12 (d, J=6.8, 2H), 2.67 (s, 3H), 2.51-2.42 (m, 2H), 2.42-2.36 (m, 1H), 1.58-1.46 (m, 1H), 0.53 (d, J=8.0, 2H), 0.27 (d, J=6.1, 2H).

Example 5

4-[(3R)-3-(Methylamino)pyrrolidin-1-yl]-N-[(3R)-tetrahydrofuran-3-yl]pyridin-2-amine dihydrochloride

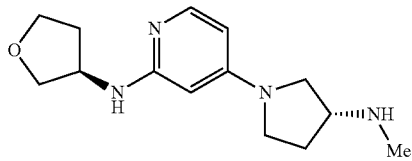 [SMILES: CN[C@@H]1CCN(c2ccnc(N[C@@H]3CCOC3)c2)C1]

MS (ESI): mass calcd. for $C_{14}H_{22}N_4O$, 262.2; m/z found, 263.2 [M+H]$^+$. $^1$H NMR (DMSO-$d_6$): 12.14 (s, 1H), 9.55 (br s, 1H), 9.48 (s, 1H), 7.99 (d, J=7.1, 1H), 7.68 (d, J=7.1, 1H), 7.48 (s, J=8.0, 0.5H), 7.12 (d, J=8.4, 0.5H), 6.32 (d, J=7.4, 1H), 5.73 (s, 1H), 4.35-4.21 (m, 1H), 3.95-3.79 (m, 3H), 3.82-3.70 (m, 2H), 3.66-3.50 (m, 2H), 2.61 (t, J=5.1, 3H), 2.45-2.21 (m, 4H), 1.88-1.74 (m, 1H).

Example 6

4-[(3R)-3-(Methylamino)pyrrolidin-1-yl]-N-[tetrahydrofuran-2-ylmethyl]pyridin-2-amine dihydrochloride

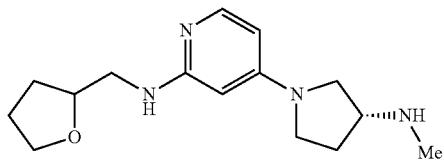 [SMILES: CN[C@@H]1CCN(c2ccnc(NCC3CCCO3)c2)C1]

The title compound was prepared as a mixture of diastereomers. MS (ESI): mass calcd. for $C_{15}H_{24}N_4O$, 276.2; m/z found, 277.2 [M+H]$^+$. $^1$H NMR (DMSO-$d_6$): 12.34 (s, 1H), 9.63 (br s, 1H), 9.60 (s, 1H), 7.75-7.61 (m, 2H), 6.27 (d, J=7.4, 1H), 5.77 (s, 1H), 4.05-3.96 (m, 1H), 3.96-3.83 (m, 1H), 3.82-3.61 (m, 6H), 3.38-3.30 (m, 2H), 2.58 (s, 3H), 2.48-2.38 (m, 2H), 2.04-1.85 (m, 3H), 1.78-1.72 (m, 1H).

Example 7

N-(4-Fluorobenzyl)-4-[(3R)-3-(methylamino)pyrrolidin-1-yl]pyridin-2-amine dihydrochloride

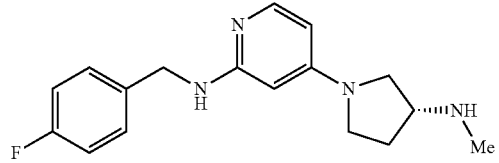

MS (ESI): mass calcd. for $C_{17}H_{21}FN_4$, 300.2; m/z found, 301.2 [M+H]$^+$. $^1$H NMR (DMSO-$d_6$): 12.39 (s, 1H), 9.38 (br s, 2H), 8.15 (t, J=6.0, 1H), 7.68 (d, J=7.1, 1H), 7.48-7.38 (m, 2H), 7.25-7.13 (m, 2H), 6.29 (d, J=7.4, 1H), 5.73 (s, 1H), 4.52 (d, J=6.0, 2H), 3.96 (br s, 1H), 3.92-3.38 (m, 4H), 2.59 (s, 3H), 2.42-2.21 (m, 2H).

Example 8

N-Cyclopropyl-4-[(3R)-3-(methylamino)pyrrolidin-1-yl]pyridin-2-amine dihydrochloride

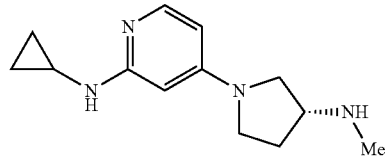 [SMILES: CN[C@@H]1CCN(c2ccnc(NC3CC3)c2)C1]

MS (ESI): mass calcd. for $C_{13}H_{20}N_4$, 232.2; m/z found, 233.2 [M+H]$^+$. $^1$H NMR (DMSO-$d_6$): 12.21 (s, 1H), 9.58 (br s, 2H), 8.28 (d, J=5.4, 0.35H), 8.19 (s, 1H), 7.70 (s, 0.65H), 6.90 (d, J=7.4, 0.65H), 6.35 (d, J=7.4, 0.65H), 5.78 (s, 1H), 4.02-3.33 (m, 6H), 2.60 (s, 3H), 2.43-2.25 (m, 2H), 0.88-0.86 (m, 2H), 0.56-0.50 (m, 2H).

Example 9

4-[(3R)-3-(Methylamino)pyrrolidin-1-yl]-N-[(1R,1S,2S,3S,5R)-2,6,6-trimethylbicyclo[3.1.1]hept-3-yl]pyridin-2-amine

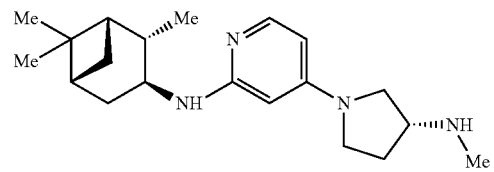 [SMILES: CN[C@@H]1CCN(c2ccnc(N[C@H]3C[C@H]4C[C@@H]([C@@H]3C)C4(C)C)c2)C1]

MS (ESI): mass calcd. for $C_{20}H_{32}N_4$, 328.5; m/z found, 329.3 [M+H]$^+$. $^1$H NMR (CD$_3$OD): 7.56 (d, J=6.2, 1H), 5.93 (dd, J=6.2, 2.2, 1H), 5.56 (d, J=2.1, 1H), 4.80 (s, 4H), 3.99 (dt, J=9.4, 6.3, 1H), 3.52 (dd, J=10.0, 6.4, 1H), 3.49-3.40 (m, 1H), 3.38-3.27 (m, 4H), 3.11 (dd, J=10.0, 5.2, 1H), 2.71-2.61 (m, 1H), 2.46-2.37 (m, 1H), 2.23 (td, J=13.6, 5.9, 1H), 2.01-1.77 (m, 4H), 1.58 (ddd, J=13.8, 5.6, 2.4, 1H), 1.24 (d, J=8.9, 3H), 1.13 (t, J=7.4, 3H), 1.10 (s, 3H), 1.03 (d, J=9.7, 1H).

Example 10

4-[(3R)-3-(Methylamino)pyrrolidin-1-yl]-N-[(1R,2R,3R,5S)-2,6,6-trimethylbicyclo[3.1.1]hept-3-yl]pyridin-2-amine

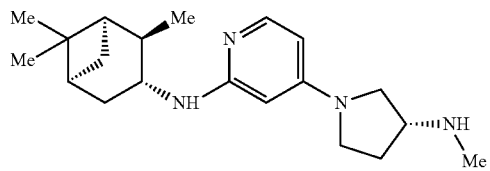 [SMILES: CN[C@@H]1CCN(c2ccnc(N[C@@H]3C[C@@H]4C[C@H]([C@H]3C)C4(C)C)c2)C1]

MS (ESI): mass calcd. for C$_{20}$H$_{32}$N$_4$, 328.5; m/z found, 329.3 [M+H]$^+$. $^1$H NMR (CD$_3$OD): 7.56 (d, J=6.2, 1H), 5.95 (dd, J=6.3, 2.2, 1H), 5.57 (d, J=2.1, 1H), 3.99 (dt, J=9.4, 6.3, 1H), 3.52 (dd, J=10.0, 6.3, 1H), 3.46 (dd, J=14.7, 8.9, 1H), 3.39-3.28 (m, 6H), 3.13 (dd, J=10.0, 5.1, 1H), 2.67 (t, J=11.6, 1H), 2.47-2.37 (m, 1H), 2.23 (td, J=13.7, 5.9, 1H), 2.02-1.78 (m, 4H), 1.58 (ddd, J=13.8, 5.6, 2.4, 1H), 1.26 (s, 3H), 1.14 (d, J=7.2, 3H), 1.10 (s, 3H), 1.03 (d, J=9.7, 1H).

Example 11

N-Benzyl-4-[(3R)-3-(methylamino)pyrrolidin-1-yl]pyridin-2-amine

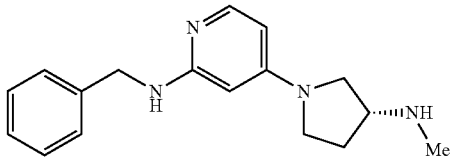 [SMILES: CN[C@@H]1CCN(c2ccnc(NCc3ccccc3)c2)C1]

MS (ESI): mass calcd. for C$_{17}$H$_{22}$N$_4$, 282.4; m/z found, 283.3 [M+H]$^+$. $^1$H NMR (CD$_3$OD): 7.57 (d, J=6.1, 1H), 7.36-7.32 (m, 2H), 7.31-7.26 (m, 2H), 7.20 (t, J=7.2, 1H), 5.93 (dd, J=6.2, 2.2, 1H), 5.51 (d, J=2.1, 1H), 4.41 (s, 2H), 3.44 (dd, J=10.0, 6.4, 1H), 3.41-3.32 (m, 1H), 3.28-3.19 (m, 1H), 3.04 (dd, J=10.0, 5.1, 1H), 2.27-2.10 (m, 1H), 1.93-1.76 (m, 1H).

Example 12

4-[(3R)-3-(Methylamino)pyrrolidin-1-yl]-N-(1-methylethyl)pyridin-2-amine

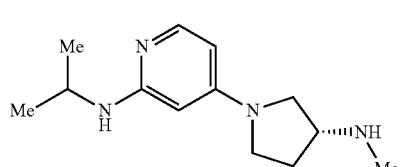

MS (ESI): mass calcd. for C$_{13}$H$_{22}$N$_4$, 234.4; m/z found, 235.3 [M+H]$^+$. $^1$H NMR (CD$_3$OD): 7.56 (d, J=6.2, 1H), 5.92 (dd, J=6.2, 2.2, 1H), 5.53 (d, J=2.1, 1H), 3.82 (hept, J=6.4, 1H), 3.51 (dd, J=10.0, 6.4, 1H), 3.48-3.40 (m, 1H), 3.38-3.26 (m, 2H), 3.10 (dd, J=10.0, 5.2, 1H), 2.27-2.17 (m, 1H), 1.96-1.79 (m, 1H), 1.18 (d, J=6.4, 6H).

Example 13

4-[(3R)-3-Aminopyrrolidin-1-yl]-N-(1-methylethyl)pyridin-2-amine

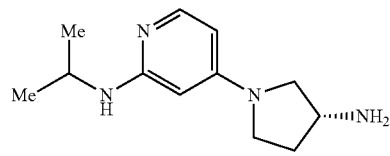

MS (ESI): mass calcd. for C$_{12}$H$_{20}$N$_4$, 220.3; m/z found, 221.2 [M+H]$^+$. $^1$H NMR (CD$_3$OD): 7.55 (d, J=7.4, 1H), 6.35 (dd, J=7.4, 2.4, 1H), 5.74 (d, J=2.3, 1H), 4.12 (s, 1H), 3.83 (dt, J=12.7, 6.4, 2H), 3.78-3.66 (m, 1H), 3.66-3.54 (m, 2H), 3.40-3.24 (m, 4H), 2.53 (dd, J=14.9, 6.5, 1H), 2.26 (d, J=5.3, 1H), 1.28 (d, J=6.4, 6H).

Example 14

4-[(3S)-3-Aminopyrrolidin-1-yl]-N-(2-methylpropyl)pyridin-2-amine

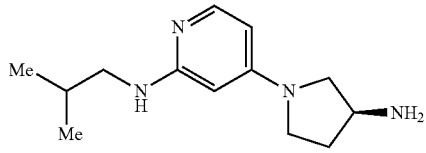 [SMILES: CC(C)CNc1cc(N2CC[C@H](N)C2)ccn1]

MS (ESI): mass calcd. for C$_{13}$H$_{22}$N$_4$, 234.4; m/z found, 235.2 [M+H]$^+$. $^1$H NMR (CD$_3$OD): 7.49 (d, J=7.3, 1H), 6.23 (dd, J=7.3, 2.4, 1H), 5.64 (d, J=2.3, 1H), 3.78-3.69 (m, 1H), 3.66-3.56 (m, 2H), 3.51-3.41 (m, 1H), 3.33-3.27 (m, 1H), 3.20 (dd, J=10.8, 4.5, 1H), 3.06 (d, J=6.9, 2H), 2.32-2.20 (m, 1H), 1.97-1.85 (m, 2H), 1.01 (d, J=6.7, 6H).

Example 15

4-[(3S)-3-(Methylamino)pyrrolidin-1-yl]-N-(2-methylpropyl)pyridin-2-amine

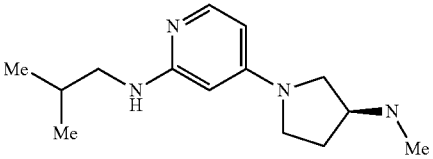 [SMILES: CN[C@H]1CCN(c2ccnc(NCC(C)C)c2)C1]

MS (ESI): mass calcd. for C$_{14}$H$_{24}$N$_4$, 248.4; m/z found, 249.2 [M+H]$^+$. $^1$H NMR CD$_3$OD): 7.55 (d, J=6.4, 1H), 6.02 (dd, J=6.5, 2.2, 1H), 5.57 (d, J=2.1, 1H), 3.56 (dd, J=10.2, 6.3, 1H), 3.53-3.46 (m, 1H), 3.42-3.34 (m, 2H), 3.16 (dd, J=10.2, 5.1, 1H), 3.03 (d, J=6.9, 2H), 2.34-2.18 (m, 1H), 1.91 (m, 2H), 0.99 (d, J=6.7, 6H).

Example 16

N-Cyclopentyl-4-piperazin-1-ylpyridin-2-amine

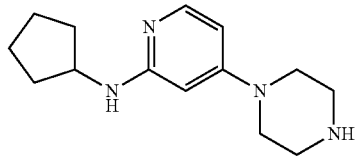

4-(2-Chloro-pyridin-4-yl)-piperazine-1-carboxylic acid tert-butyl ester. To a stirring solution of 2-chloro-4-bromopyridine (4.3 g, 22.5 mmol) in toluene (100 mL) was added piperazine-1-carboxylic acid tert-butyl ester (3.2 g, 17.2 mmol) and sodium tert-butoxide (2.5 g, 26.0 mmol). The flask was evacuated and flushed with $N_{2(g)}$ twice. A mixture of Xantphos (600 mg, 1.0 mmol) and $Pd_2(dba)_3$ (318 mg, 0.35 mmol) was added in one portion and the mixture was heated at 85° C. for 20 h. The mixture was cooled to rt, diluted with $H_2O$ (75 mL), and extracted with EtOAc (3×). The combined organic layers were dried and concentrated to give a clear golden oil. The oil was purified on FCC (0 to 5% 2 M $NH_3$ in MeOH/$CH_2Cl_2$) to give the title product as a beige solid (5.1 g, 100%). MS (ESI): mass calcd. for $C_{14}H_{20}ClN_3O_2$, 297.1; m/z found, 298.2 [M+H]$^+$. $^1$H NMR (DMSO-$d_6$): 7.95 (d, J=5.9, 1H), 6.88-6.78 (m, 2H), 3.46-3.32 (m, 8H), 1.42 (s, 9H).

tert-Butyl 4-[2-(cyclopentylamino)pyridin-4-yl]piperazine-1-carboxylate. To a stirring solution of 4-(2-chloro-pyridin-4-yl)-piperazine-1-carboxylic acid tert-butyl ester (163 mg, 0.55 mmol) in toluene (2 mL) in a vial was added cyclopentylamine (136 μL, 1.38 mmol) and sodium tert-butoxide (161 mg, 1.68 mmol). A mixture of racemic BINAP (20 mg, 0.032 mmol) and Pd(OAc)$_2$ (18 mg, 0.027 mmol) was added in one portion and the mixture was heated at 85° C. for 20 h. The mixture was cooled to rt and purified directly by FCC (0 to 5% 2 M $NH_3$ in MeOH/$CH_2Cl_2$) to provide the title compound as a white solid (34 mg, 17%). MS (ESI): mass calcd. for $C_{16}H_{30}N_4O_2$, 346.2; m/z found, 347.3 [M+H]$^+$. $^1$H NMR (DMSO-$d_6$): 7.65 (d, J=6.0, 1H), 6.10 (d, J=6.0, 1H), 5.92 (d, J=7.1, 1H), 5.78 (s, 1H) 4.08-4.02 (m, 1H), 3.41 (t, J=5.4, 4H), 3.16 (t, J=5.4, 4H), 1.89-1.82 (m, 2H), 1.67-1.61 (m, 2H), 1.59-1.48 (m, 2H), 1.42 (s, 9H), 1.43-1.35 (m, 2H).

N-Cyclopentyl-4-piperazin-1-ylpyridin-2-amine dihydrochloride. To a stirring solution of tert-butyl 4-[2-(cyclopentylamino)pyridin-4-yl]piperazine-1-carboxylate (34 mg, 0.1 mmol) in 96% formic acid (4 mL) was added 6 N aq HCl (2 drops). The mixture was stirred for 2 h and concentrated to give the desired product as a white solid (26 mg, 93%). MS (ESI): mass calcd. for $C_{14}H_{22}N_4$, 246.2; m/z found, 247.2 [M+H]$^+$. $^1$H NMR (DMSO-$d_6$): 9.32 (s, 2H), 7.89 (d, J=7.1, 1H), 7.69 (d, J=7.5, 1H), 6.58 (d, J=7.6, 1H), 6.04 (s, 1H), 4.03-3.96 (m, 1H), 3.73 (t, J=4.9, 4H), 3.20 (t, J=5.0, 4H), 2.03-1.95 (m, 2H), 1.73-1.68 (m, 2H), 1.64-1.52 (m, 2H), 1.50-1.42 (M, 2H).

The compounds in Example 17 through Example 20 were prepared using methods analogous to those described for Example 16.

Example 17

4-piperazin-1-yl-N-propylpyridin-2-amine dihydrochloride

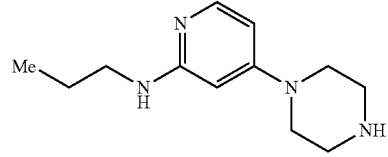 [SMILES: CCCNc1cc(N2CCNCC2)ccn1]

MS (ESI): mass calcd. for $C_{12}H_{20}N_4$, 220.2; m/z found, 221.2 [M+H]$^+$. $^1$H NMR (DMSO-$d_6$): 9.35 (br s, 2H), 7.87-7.82 (m, 1H), 7.69 (d, J=7.5, 1H), 6.57 (dd, J=7.5, 2.4, 1H), 6.05 (s, 1H), 3.79-3.69 (m, 4H), 3.32-3.13 (m, 6H), 1.63-1.51 (m, 2H), 0.94 (t, J=7.3, 3H).

Example 18

N-Benzyl-4-piperazin-1-ylpyridin-2-amine dihydrochloride?

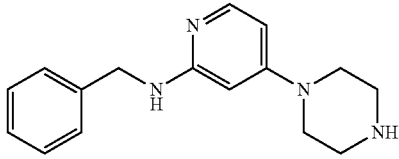 [SMILES: c1ccc(CNc2cc(N3CCNCC3)ccn2)cc1]

MS (ESI): mass calcd. for $C_{16}H_{20}N_4$, 268.4; m/z found, 269.2 [M+H]$^+$. $^1$H NMR (CD$_3$OD): 7.62 (d, J=7.5, 1H), 7.46-7.24 (m, 5H), 6.65 (dd, J=7.5, 2.1, 1H), 6.13 (d, J=2.0, 1H), 4.55 (s, 2H), 3.90-3.74 (m, 4H), 3.41-3.33 (m, 4H).

Example 19

N-(2-Methylpropyl)-4-piperazin-1-ylpyridin-2-amine dihydrochloride

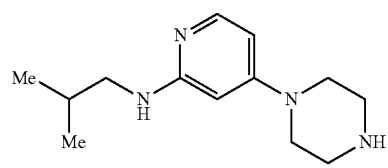 [SMILES: CC(C)CNc1cc(N2CCNCC2)ccn1]

MS (ESI): mass calcd. for $C_{13}H_{22}N_4$, 234.4; m/z found, 235.3 [M+H]$^+$. $^1$H NMR (CDCl$_3$): 7.81 (d, J=6.1, 1H), 6.11 (dd, J=6.1, 2.3, 1H), 5.69 (d, J=2.0, 1H), 4.47 (s, 1H), 3.43-

3.18 (m, 4H), 3.03 (t, J=6.2, 2H), 3.02-2.84 (m, 4H), 1.88 (pent, J=6.7, 1H), 0.99 (d, J=6.7, 6H).

Example 20

4-[(3R)-3-Aminopyrrolidin-1-yl]-N-(2-methylpropyl)pyridin-2-amine dihydrochloride

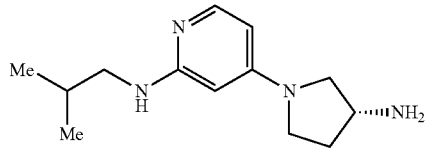 [SMILES: CC(C)CNc1cc(N2CC[C@@H](N)C2)ccn1]

MS (ESI): mass calcd. for $C_{13}H_{22}N_4$, 234.4; m/z found, 235.3 [M+H]$^+$. $^1$H NMR (CD$_3$OD): 7.54 (d, J=6.3, 1H), 5.97 (dd, J=6.4, 2.2, 1H), 5.53 (d, J=2.1, 1H), 3.67-3.60 (pent, J=5.5, 1H), 3.56-3.45 (m, 2H), 3.39-3.32 (m, 1H), 3.06 (dd, J=10.0, 4.9, 1H), 3.01 (d, J=6.9, 2H), 2.28-2.14 (m, 1H), 1.94-1.78 (m, 2H), 0.98 (d, J=6.7 Hz, 6H).

Example 21

4-(4-Methylpiperazin-1-yl)-N-(2-methylpropyl)pyridin-2-amine

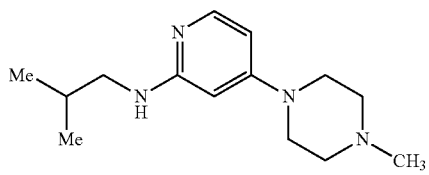 [SMILES: CC(C)CNc1cc(N2CCN(C)CC2)ccn1]

Method A
(4-Iodo-pyridin-2-yl)-isobutyl-amine. A solution of 2-fluoro-4-iodopyridine (2.2 g, 1.0 mmol) in N-methylpyrrolidinone (10 mL) at rt was treated with isobutylamine (2.5 mL, 2.5 mmol) and the mixture was heated at 100° C. for 6 h. The mixture was cooled to rt, diluted with EtOAc (50 mL), and washed with water (2×10 mL). The combined aqueous extracts were back-extracted with EtOAc and the combined organic layers were dried and concentrated to yield a thick oil which solidified on standing (2.6 g, 95%). The solid was used without further purification. $^1$H NMR (CDCl$_3$): 7.72 (d, J=5.3, 1H), 6.89 (dd, J=5.3, 1.4, 1H), 6.77 (d, J=1.1, 1H), 4.58 (s, 1H), 3.04 (dd, J=6.8, 5.9, 2H), 1.87 (dp, J=13.4, 6.7, 1H), 0.98 (d, J=6.7, 6H).
4-(4-Methylpiperazin-1-yl)-N-(2-methylpropyl)pyridin-2-amine. A suspension of (4-iodo-pyridin-2-yl)-isobutyl-amine (78 mg, 0.3 mmol), N-methyl piperazine (0.04 mL, 0.4 mmol) 2-dicyclohexylphosphino-2',4',6'-triisopropylbiphenyl (X-phos) (5.4 mg, 4 mol %), Pd$_2$ dba$_3$ (3.2 mg, 2 mol %) in THF (1 mL) was treated with lithium bis(trimethylsilyl) amide (1.0 M in THF; 0.8 mL, 0.8 mmol) and heated at 65° C. for 16 h. The resulting solution was cooled to rt and concentrated to minimum volume, then purified directly by FCC (0 to 10% 2 M NH$_3$ in MeOH/CH$_2$Cl$_2$) to yield the desired product (29 mg, 41%). MS (ESI): mass calcd. for $C_{14}H_{24}N_4$, 248.4; m/z found, 249.3 [M+H]$^+$. $^1$H NMR (CDCl$_3$): 7.79 (d, J=6.1, 1H), 6.12 (dd, J=6.2, 2.3, 1H), 5.69 (d, J=2.2, 1H), 4.62 (s, 1H), 3.54-3.23 (m, 4H), 3.03 (dd, J=6.7, 5.8, 2H), 2.59-2.22 (m, 7H), 1.89 (dp, J=13.4, 6.7, 1H), 1.19-0.78 (m, 6H).
Method B
4-bromo-N-isobutylpyridin-2-amine. A solution of 4-bromo-2-fluoropyridine (352 mg, 2 mmol) and 2-methylpropan-1-amine (584 mg, 8 mmol) in N-methyl-2-pyrrolidinone (NMP, 10 mL) was stirred at 100° C. for 1 hr. The reaction was allowed to cool to room temperature and diluted with DCM (50 mL), washed with water (10 mL*2). The organic layer was dried over Na$_2$SO$_4$, filtered and concentrated. The residue was purified by column chromatography (0-20% EtOAc-petroleum ether gradient elution) to afford the desired product as oil (382 mg, 83%). $^1$H NMR (300 MHz, CDCl$_3$): 7.86 (d, J=5.1 Hz, 1H), 6.98 (d, J=5.4 Hz, 1H), 6.53 (s, 1H), 4.75 (s, 1H), 3.03 (dd, J=6.6 Hz, 6.0 Hz, 2H), 1.88-1.86 (m, 1H), 0.98 (s, 3H), 0.96 (s, 3H); LC-MS: m/z=229.2, 231.2 [M+H]$^+$.
N-isobutyl-4-(4-methylpiperazin-1-yl)pyridin-2-amine. A mixture of 4-bromo-N-isobutylpyridin-2-amine (153 mg, 0.7 mmol), 1-methylpiperazine (80 mg, 0.8 mmol), Pd$_2$(dba)$_3$ (6.1 mg, 0.007 mmol) and X-phos (12.7 mg, 0.028 mmol) in anhydrous THF (4 mL) was treated with LiHMDS (1.0M, 2.0 mL, 2 mmol) under atmosphere of nitrogen. The resulting reaction was stirred at 65° C. for 3 hrs and diluted with DCM (20 mL), washed with water (4 mL). The organic layer was dried over Na$_2$SO$_4$, filtered and concentrated. The residue was purified by column chromatography (0-10% MeOH-DCM gradient elution) to afford the desired product (60 mg, 34%). $^1$H NMR (300 MHz, CDCl$_3$): 7.74 (d, J=6.6 Hz, 1H), 6.12 (d, J=6.3 Hz, 1H), 5.66 (s, 1H), 3.31 (t, J=5.4 Hz, 4H), 3.01 (d, J=6.0 Hz, 2H), 2.51 (t, J=5.4 Hz, 4H), 2.34 (s, 3H), 1.90-1.88 (m, 1H), 1.00 (s, 3H), 0.98 (s, 3H); LC-MS: m/z=249.1 [M+H]$^+$.
N-isobutyl-4-(4-methylpiperazin-1-yl)pyridin-2-amine dihydrochloride. N-isobutyl-4-(4-methylpiperazin-1-yl)pyridin-2-amine (60 mg, 0.24 mmol) was dissolved in MeOH (1 mL) and aqueous HCl solution (6N, 0.5 mL) was added. The resulting reaction was stirred at 30° C. for 2 hrs. The reaction was concentrated under reduced pressure to afford the desired product (80 mg, 93%). $^1$H NMR (300 MHz, DMSO-d$_6$): 12.59 (s, 1H), 11.49 (br s, 1H), 7.97 (s, 1H), 7.72 (m, 1H), 6.60 (d, J=6.9 Hz, 1H), 6.12 (s, 1H), 4.20 (d, J=14 Hz, 2H), 4.00 (br s, 2H), 3.50-3.42 (m, 2H), 3.10 (m, 4H), 2.77 (s, 3H), 1.88-1.79 (m, 1H), 0.94 (d, J=6.6 Hz, 6H); LC-MS, m/z=249.2 [M+H]$^+$, $t_R$=0.1 min; HPLC: 96% (214 nm), 96% (254 nm), $t_R$=4.5 min.

Example 22

4-[(3R)-3-(Methylamino)pyrrolidin-1-yl]-N-(2-methylpropyl)pyridin-2-amine

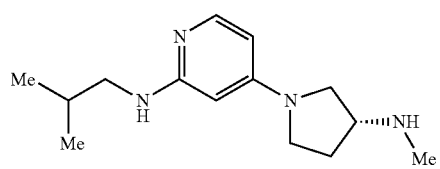 [SMILES: CN[C@@H]1CCN(c2ccnc(NCC(C)C)c2)C1]

A solution of (4-iodo-pyridin-2-yl)-isobutyl-amine (96 mg, 0.4 mmol), (3R)-(methylamino)pyrrolidine (0.08 mL, 0.8 mmol), and Yb(OTf)$_3$ (215 mg, 0.4 mmol) in DMA (2 mL) was heated at 200° C. for 2 h in a microwave. The resulting solution was cooled to rt and concentrated to a minimum volume, then purified directly by FCC (0 to 10% 2 M NH$_3$ in MeOH/CH$_2$Cl$_2$). The material obtained (58 mg) was further purified by reversed-phase HPLC (Dionex conditions) to yield the title compound (10 mg, 11%). MS (ESI): mass calcd. for C$_{14}$H$_{24}$N$_4$, 248.4; m/z found, 249.3 [M+H]$^+$. $^1$H NMR (CDCl$_3$): 7.73 (d, J=6.0, 1H), 5.86 (dd, J=6.1, 2.0, 1H), 5.38 (d, J=2.0, 1H), 4.70-4.45 (m, 1H), 3.51 (dd, J=9.8, 6.2, 1H), 3.44 (dd, J=14.7, 8.7, 1H), 3.39-3.29 (m, 2H), 3.10 (dd, J=9.7, 4.9, 1H), 3.03-2.97 (m, 2H), 2.48 (s, 3H), 2.20 (dd, J=12.6, 7.6, 1H), 1.96-1.77 (m, 2H), 0.99 (d, J=6.7, 7H).

Example 23

4-[(3R)-3-Aminopyrrolidin-1-yl]-N-(2-methylpropyl)pyrimidin-2-amine

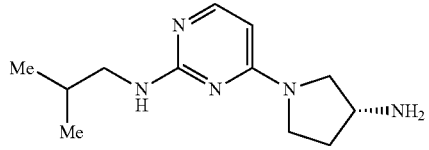 [SMILES: CC(C)CNc1nccc(N2CC[C@@H](N)C2)n1]

[(3R)-1-(2-Chloro-pyrimidin-4-yl)-pyrrolidin-3-yl]-carbamic acid tert-butyl ester. To a slurry of 2,4-dichloropyrimidine (2.05 g, 13.7 mmol) and N,N-diisopropylethylamine (3.60 mL, 20.6 mmol) in i-PrOH (12 mL) was added (R)-3-N-Boc-amino pyrrolidine (2.69 g. 14.4 mmol). The mixture was heated at 160° C. in a microwave for 2 h. The reaction was cooled to rt and concentrated, and the crude residue was purified by FCC (0 to 50% EtOAc/hexanes) to yield a white solid (2.10 g, 51%). MS (ESI): mass calcd. for C$_{13}$H$_{19}$ClN$_4$O$_2$, 298.1; m/z found, 299.1 [M+H]$^+$. $^1$H NMR (CDCl$_3$): 8.02 (d, J=6.0, 1H), 6.19 (d, J=6.0, 1H), 4.85-4.47 (m, 1H), 4.40-4.16 (m, 1H), 3.94-3.08 (m, 4H), 2.46-2.17 (m, 1H), 2.12-1.78 (m, 1H), 1.45 (s, 9H).

[(3R)-1-(2-Isobutylamino-pyrimidin-4-yl)-pyrrolidin-3-yl]-carbamic acid tert-butyl ester. To a slurry of [(3R)-1-(2-chloro-pyrimidin-4-yl)-pyrrolidin-3-yl]-carbamic acid tert-butyl ester (103 mg, 0.35 mmol) and N,N-diisopropylethylamine (0.09 mL, 0.52 mmol) in i-PrOH (1.5 mL) was added isobutylamine (30 mg. 0.41 mmol). The mixture was heated to 140° C. in a microwave for 6 h. The reaction was cooled to room temperature and concentrated. The crude residue was purified by FCC (0 to 10% MeOH/CH$_2$Cl$_2$) to yield the desired product (93 mg, 80%). MS (ESI): mass calcd. for C$_{17}$H$_{29}$N$_5$O$_2$, 335.2; m/z found, 336.3 [M+H]$^+$. $^1$H NMR (CDCl$_3$): 7.83 (d, J=5.9, 1H), 5.64 (d, J=5.9, 1H), 4.98-4.80 (m, 1H), 4.78-4.61 (m, 1H), 4.38-4.20 (m, 1H), 3.79-3.26 (m, 4H), 3.23-3.11 (m, 2H), 2.32-2.09 (m, 1H), 1.99-1.77 (m, 2H), 1.45 (s, 9H), 0.95 (d, J=6.7, 6H).

4-[(3R)-3-Aminopyrrolidin-1-yl]-N-(2-methylpropyl)pyrimidin-2-amine. To a solution of [(3R)-1-(2-isobutylamino-pyrimidin-4-yl)-pyrrolidin-3-yl]-carbamic acid tert-butyl ester (93 mg, 0.28 mmol) in MeOH (0.5 mL) was added HCl (4.0 M in 1,4-dioxane; 1.0 mL). The reaction was stirred at rt for 2 h, concentrated, and the crude residue was purified by FCC (0 to 20% 2 M NH$_3$ in MeOH/CH$_2$Cl$_2$) to yield the desired product (65 mg, 100%). MS (ESI): mass calcd. for C$_{12}$H$_{21}$N$_5$, 235.2; m/z found, 236.2 [M+H]$^+$. $^1$H NMR (CDCl$_3$): 7.82 (d, J=5.9, 1H), 5.65 (d, J=5.9, 1H), 4.87 (s, 1H), 3.75-3.51 (m, 3H), 3.48-3.38 (m, 1H), 3.20 (dd, J=6.7, 6.1, 3H), 2.16 (d, J=6.3, 1H), 1.87 (dt, J=13.4, 6.7, 1H), 1.81-1.71 (m, 1H), 1.47 (s, 2H), 0.95 (d, J=6.7, 6H).

The compounds in Example 24 through Example 30 were prepared using methods analogous to those described for Example 23.

Example 24

4-[(3R)-3-Aminopyrrolidin-1-yl]-N-(cyclopropylmethyl)pyrimidin-2-amine

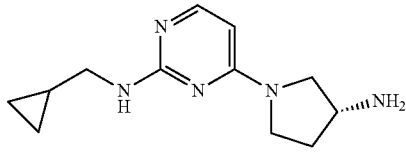 [SMILES: N[C@@H]1CCN(c2ccnc(NCC3CC3)n2)C1]

MS (ESI): mass calcd. for C$_{12}$H$_{19}$N$_5$, 233.2; m/z found, 234.2 [M+H]$^+$. $^1$H NMR (CDCl$_3$): 7.83 (d, J=5.9, 1H), 5.66 (d, J=5.9, 1H), 4.89 (s, 1H), 3.76-3.37 (m, 4H), 3.23 (dd, J=7.0, 5.6, 2H), 3.20-3.11 (m, 1H), 2.21-2.10 (m, 1H), 1.82-1.70 (m, 1H), 1.40 (s, 2H), 1.16-0.97 (m, 1H), 0.59-0.39 (m, 2H), 0.32-0.14 (m, 2H).

Example 25

4-[(3R)-3-Aminopyrrolidin-1-yl]-N-cyclopentylpyrimidin-2-amine

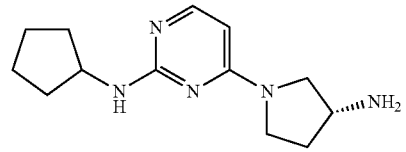 [SMILES: N[C@@H]1CCN(c2ccnc(NC3CCCC3)n2)C1]

MS (ESI): mass calcd. for C$_{13}$H$_{21}$N$_5$, 247.2; m/z found, 248.2 [M+H]$^+$. $^1$H NMR (CDCl$_3$): 7.83 (d, J=5.9, 1H), 5.65 (d, J=5.9, 1H), 4.74 (d, J=6.6, 1H), 4.33-4.11 (m, 1H), 3.80-2.93 (m, 5H), 2.22-2.10 (m, 1H), 2.08-1.96 (m, 2H), 1.82-1.54 (m, 5H), 1.51-1.17 (m, 4H).

Example 26

4-[(3R)-3-Aminopyrrolidin-1-yl]-N-(2,2-dimethylpropyl)pyrimidin-2-amine

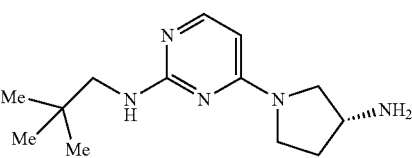 [SMILES: CC(C)(C)CNc1nccc(N2CC[C@@H](N)C2)n1]

MS (ESI): mass calcd. for C$_{13}$H$_{23}$N$_5$, 249.2; m/z found, 250.2 [M+H]$^+$. $^1$H NMR (CDCl$_3$): 7.82 (d, J=5.9, 1H), 5.64 (d, J=5.9, 1H), 4.96-4.66 (m, 1H), 3.80-3.33 (m, 4H), 3.23 (d, J=6.4, 2H), 3.20-3.08 (m, 1H), 2.27-2.04 (m, J=6.2, 1H), 1.85-1.63 (m, 1H), 1.26 (s, 2H), 0.95 (s, 9H).

Example 27

1-({4-[(3R)-3-Aminopyrrolidin-1-yl]pyrimidin-2-yl}amino)-2-methylpropan-2-ol

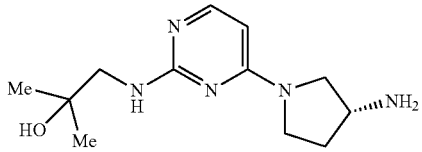

MS (ESI): mass calcd. for $C_{12}H_{21}N_5O$, 251.2; m/z found, 252.2 $[M+H]^+$. $^1$H NMR (CDCl$_3$): 7.79 (d, J=6.0, 1H), 5.93 (br s, 1H), 5.69 (d, J=6.0, 1H), 5.23 (s, 1H), 3.77-3.30 (m, 6H), 3.28-2.93 (m, 1H), 2.24-2.05 (m, 1H), 1.86-1.71 (m, 1H), 1.66-1.33 (m, 2H), 1.23 (s, 6H).

Example 28

4-[(3R)-3-Aminopyrrolidin-1-yl]-N-cyclobutylpyrimidin-2-amine

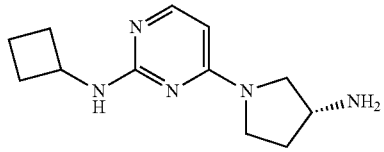 [SMILES: N[C@@H]1CCN(c2ccnc(NC3CCC3)n2)C1]

MS (ESI): mass calcd. for $C_{12}H_{19}N_5$, 233.2; m/z found, 234.2 $[M+H]^+$. $^1$H NMR (CDCl$_3$): 7.82 (d, J=5.9, 1H), 5.65 (d, J=5.9, 1H), 5.00-4.83 (m, 1H), 4.51-4.35 (m, 1H), 3.76-3.32 (m, 4H), 3.25-2.96 (m, 1H), 2.47-2.30 (m, 2H), 2.23-2.06 (m, 1H), 1.94-1.60 (m, 5H), 1.57-1.31 (m, 2H).

Example 29

4-[(3R)-3-Aminopyrrolidin-1-yl]-N-[(3R)-tetrahydrofuran-3-yl]pyrimidin-2-amine

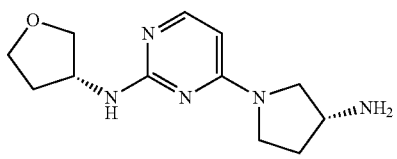 [SMILES: N[C@@H]1CCN(c2ccnc(N[C@@H]3CCOC3)n2)C1]

MS (ESI): mass calcd. for $C_{12}H_{19}N_5O$, 249.2; m/z found, 250.2 $[M+H]^+$. $^1$H NMR (CDCl$_3$): 7.83 (d, J=5.9, 1H), 5.69 (d, J=5.9, 1H), 4.98-4.84 (m, 1H), 4.61-4.47 (m, 1H), 4.05-3.88 (m, 2H), 3.88-3.77 (m, 1H), 3.73-3.32 (m, 5H), 3.26-3.02 (m, 1H), 2.35-2.22 (m, 1H), 2.20-2.10 (m, 1H), 1.92-1.69 (m, 2H), 1.54-1.16 (m, 2H).

Example 30

4-[(3R)-3-Aminopyrrolidin-1-yl]-N-(tetrahydro-2H-pyran-4-yl)pyrimidin-2-amine

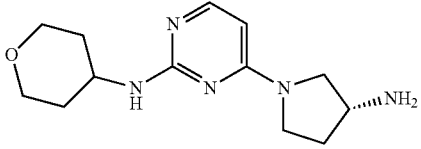 [SMILES: N[C@@H]1CCN(c2ccnc(NC3CCOCC3)n2)C1]

MS (ESI): mass calcd. for $C_{13}H_{21}N_5O$, 263.2; m/z found, 264.2 $[M+H]^+$. $^1$H NMR (CDCl$_3$): 7.83 (d, J=5.9, 1H), 5.68 (d, J=5.9, 1H), 4.71 (d, J=7.5, 1H), 4.09-3.84 (m, 3H), 3.75-3.34 (m, 6H), 3.26-2.99 (m, 1H), 2.24-2.09 (m, 1H), 2.03 (d, J=12.3, 2H), 1.86-1.69 (m, 1H), 1.60-1.19 (m, 4H).

Example 31

Isobutyl-[4-(4-methyl-piperazin-1-yl)-pyrimidin-2-yl]-amine

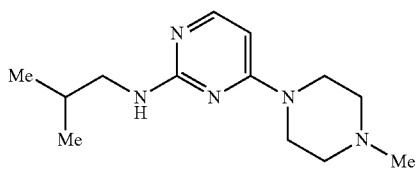 [SMILES: CC(C)CNc1nccc(N2CCN(C)CC2)n1]

(4-Chloro-pyrimidin-2-yl)-isobutyl-amine and (2-Chloro-pyrimidin-4-yl)-isobutyl-amine. To a slurry of 2,4-dichloropyrimidine (1.48 g, 10.0 mmol) and N,N-diisopropylethylamine (2.60 mL, 15.0 mmol) in i-PrOH (8 mL) was added isobutylamine (0.77 g. 10.5 mmol). The mixture was heated at 160° C. in a microwave for 1 h. The mixture was cooled to rt and concentrated to provide a mixture of regioisomers. (4-Chloro-pyrimidin-2-yl)-isobutyl-amine. MS (ESI): mass calcd. for $C_8H_{12}ClN_3$, 185.1; m/z found, 186.1 $[M+H]^+$. $^1$H NMR (CDCl$_3$): 8.13 (s, 1H), 6.53 (d, J=5.2, 1H), 5.43 (s, 1H), 3.25 (dd, J=6.9, 6.0, 2H), 1.98-1.79 (m, 1H), 0.97 (d, J=6.7, 6H). (2-Chloro-pyrimidin-4-yl)-isobutyl-amine. MS (ESI): mass calcd. for $C_8H_{12}ClN_3$, 185.1; m/z found, 186.1 $[M+H]^+$. $^1$H NMR (CDCl$_3$): 8.19-7.75 (m, 1H), 6.69-6.18 (m, 2H), 3.40-2.98 (m, 2H), 1.98-1.83 (m, 1H), 0.96 (d, J=6.6, 6H). Isobutyl-[4-(4-methyl-piperazin-1-yl)-pyrimidin-2-yl]-amine. To a slurry of an unmeasured portion of the mixture from the previous step (60 mg, 0.32 mmol) in i-PrOH (2.0 mL) was added 1-methylpiperazine (80 mg, 0.80 mmol). The mixture was heated at 160° C. in a microwave for 1 h. The mixture was cooled to rt and concentrated, and the crude residue was purified by preparatory TLC (7% 2 M NH$_3$ in MeOH/CH$_2$Cl$_2$) to yield the desired product (12 mg). MS (ESI): mass calcd. for $C_{13}H_{23}N_5$, 249.2; m/z found, 250.3 $[M+H]^+$. $^1$H NMR (CDCl$_3$): 7.87 (d, J=6.0, 1H), 5.85 (d, J=6.1, 1H), 4.87 (s, 1H), 3.70-3.51 (m, 4H), 3.19 (dd, J=6.7, 6.0, 2H), 2.52-2.38 (m, 4H), 2.33 (s, 3H), 1.92-1.79 (m, 1H), 0.96 (d, J=6.7, 6H).

Example 32 was prepared using methods analogous to Example 31.

Example 32

4-[(3R)-3-(Methylamino)pyrrolidin-1-yl]-N-(2-methylpropyl)pyrimidin-2-amine

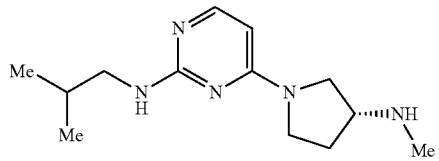 [SMILES: CN[C@@H]1CCN(c2ccnc(NCC(C)C)n2)C1]

MS (ESI): mass calcd. for C$_{13}$H$_{23}$N$_{5}$, 249.2; m/z found, 250.3 [M+H]$^+$. $^1$H NMR (CDCl$_3$): 7.82 (d, J=5.9, 1H), 5.65 (d, J=5.9, 1H), 4.86 (s, 1H), 3.79-3.26 (m, 4H), 3.24-3.15 (m, 3H), 2.48 (s, 3H), 2.23-2.09 (m, 1H), 1.93-1.74 (m, 3H), 0.95 (d, J=6.7, 6H).

The compounds in Example 33 through Example 42 were prepared using methods analogous to those described for Example 1 or Example 16.

Example 33

4-[(3R)-3-(Methylamino)pyrrolidin-1-yl]-N-phenylpyridin-2-amine

MS (ESI): mass calcd. for C$_{13}$H$_{21}$N$_{5}$, 247.2 m/z found, 248.2 [M+H]$^+$. $^1$H NMR (CDCl$_3$): 7.94 (d, J=6.1, 1H), 5.83 (d, J=6.1, 1H), 3.67-3.58 (m, 4H), 3.57-3.50 (m, 4H), 2.50-2.41 (m, 4H), 2.33 (s, 3H), 2.00-1.84 (m, 4H).

Example 34

4-[3-(Methylamino)azetidin-1-yl]-N-(2-methylpropyl)pyridin-2-amine

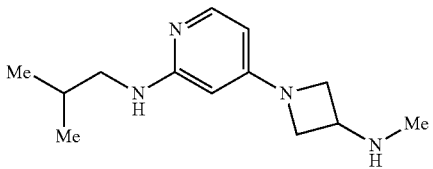 [SMILES: CNC1CN(c2ccnc(NCC(C)C)c2)C1]

MS (ESI): mass calcd. for C$_{13}$H$_{22}$N$_{4}$, 268.4 m/z found, 269.2 [M+H]$^+$. $^1$H NMR (CD$_3$OD): 7.70 (d, J=6.1, 1H), 7.35-7.28 (m, 2H), 7.28-7.18 (m, 2H), 6.92 (tt, J=7.4, 1.3, 1H), 6.08 (dd, J=6.1, 2.2, 1H), 5.95 (d, J=2.1, 1H), 3.49 (dd, J=10.0, 6.4, 1H), 3.46-3.37 (m, 1H), 3.37-3.24 (m, 3H), 3.09 (dd, J=10.0, 5.2, 1H), 2.21 (dq, J=7.7, 5.9, 1H), 1.93-1.80 (m, 1H).

Example 35

N-(Cyclopropylmethyl)-4-piperazin-1-ylpyridin-2-amine

MS (ESI): mass calcd. for C$_{13}$H$_{20}$N$_{4}$, 232.3 m/z found, 233.2 [M+H]$^+$. $^1$H NMR (CDCl$_3$): 7.81 (d, J=6.1, 1H), 6.12 (dd, J=6.1, 2.3, 1H), 5.70 (d, J=2.2, 1H), 4.58 (s, 1H), 3.23 (dd, J=6.1, 4.1, 4H), 3.08 (dd, J=6.5, 4.4, 2H), 3.02-2.93 (m, 4H), 1.99 (s, 2H), 1.17-0.99 (m, 1H), 0.63-0.39 (m, 2H), 0.33-0.10 (m, 2H).

Example 36

N-Butyl-4-piperazin-1-ylpyridin-2-amine

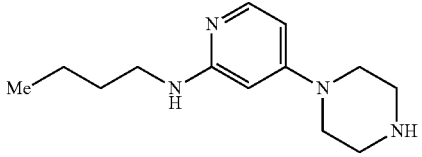 [SMILES: CCCCNc1cc(N2CCNCC2)ccn1]

MS (ESI): mass calcd. for C$_{13}$H$_{22}$N$_{4}$, 234.3 m/z found, 235.2 [M+H]$^+$. $^1$H NMR (CD$_3$OD): 7.61 (d, J=6.3, 1H), 6.20 (dd, J=6.4, 2.4, 1H), 5.84 (d, J=2.3, 1H), 3.26 (dd, J=6.1, 4.2, 4H), 3.20 (t, J=7.0, 2H), 2.91 (dd, J=6.2, 4.1, 4H), 1.64-1.52 (m, 2H), 1.43 (dq, J=14.2, 7.2, 2H), 0.96 (dd, J=9.7, 5.0, 3H).

Example 37

N-(2-Methoxyethyl)-4-piperazin-1-ylpyridin-2-amine

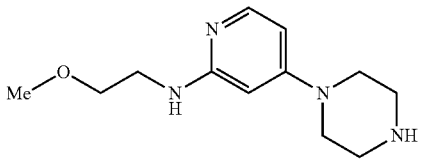 [SMILES: COCCNc1cc(N2CCNCC2)ccn1]

MS (ESI): mass calcd. for C$_{12}$H$_{20}$N$_{4}$O, 236.3 m/z found, 237.2 [M+H]$^+$. $^1$H NMR (CD$_3$OD): 7.63 (d, J=6.3, 1H), 6.23

(dd, J=6.3, 2.3, 1H), 5.91 (d, J=2.3, 1H), 3.55 (t, J=5.5, 2H), 3.40 (t, J=5.4, 2H), 3.37 (s, 3H), 3.28-3.24 (m, 4H), 2.91 (dd, J=6.1, 4.2, 4H).

Example 38

N-Phenyl-4-piperazin-1-ylpyridin-2-amine

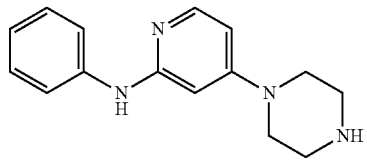 [SMILES: c1ccc(Nc2cc(N3CCNCC3)ccn2)cc1]

MS (ESI): mass calcd. for $C_{16}H_{18}N_4$, 254.3 m/z found, 255.2 [M+H]$^+$. $^1$H NMR (DMSO-d$_6$): 12.89-12.43 (m, 1H), 10.17 (s, 1H), 9.70 (s, 2H), 7.81 (d, J=7.5 Hz, 1H), 7.45 (t, J=7.8, Hz, 2H), 7.31 (d, J=7.7 Hz, 2H), 7.24 (t, J=7.3, Hz, 1H), 6.75 (dd, J=7.4, 2.1 Hz, 1H), 6.35 (d, J=2.0 Hz, 1H), 3.75 (s, 4H), 3.20 (s, 4H).

Example 39

4-piperazin-1-yl-N-(tetrahydrofuran-2-ylmethyl)pyridin-2-amine

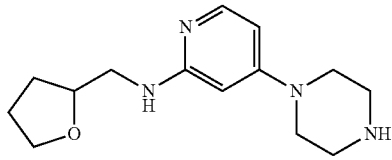 [SMILES: c1cc(N2CCNCC2)cc(NCC2CCCO2)n1]

MS (ESI): mass calcd. for $C_{14}H_{22}N_4O$, 262.4 m/z found, 263.2 [M+H]$^+$. $^1$H NMR (CDCl$_3$): 7.82 (d, J=6.1, 1H), 6.13 (dd, J=6.1, 2.3, 1H), 5.76 (d, J=2.2, 1H), 4.65 (s, 1H), 4.09 (qd, J=7.0, 4.0, 1H), 3.88 (dt, J=8.2, 6.7, 1H), 3.77 (dd, J=14.4, 7.6, 1H), 3.52 (ddd, J=13.0, 6.5, 4.0, 1H), 3.26 (dd, J=7.2, 5.1, 1H), 3.22 (dd, J=6.1, 4.0, 4H), 2.97 (dd, J=6.1, 4.1, 4H), 2.61 (s, 1H), 2.06-1.96 (m, 1H), 1.96-1.85 (m, 2H), 1.79 (s, 2H), 1.72-1.60 (m, 1H).

Example 40

N-(4-Fluorobenzyl)-4-piperazin-1-ylpyridin-2-amine

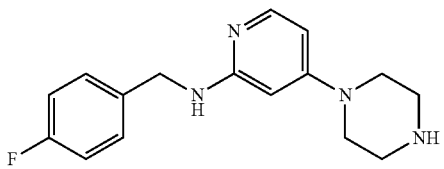 [SMILES: Fc1ccc(CNc2cc(N3CCNCC3)ccn2)cc1]

MS (ESI): mass calcd. for $C_{16}H_{19}FN_4$, 286.4 m/z found, 287.2 [M+H]$^+$. $^1$H NMR (CDCl$_3$): 7.84 (d, J=6.1, 1H), 7.39-7.29 (m, 2H), 7.08-6.93 (m, 2H), 6.16 (dd, J=6.1, 2.3, 1H), 5.68 (d, J=2.2, 1H), 4.68 (s, 1H), 4.44 (d, J=5.6, 2H), 3.18 (dd, J=6.2, 4.1, 4H), 2.95 (dd, J=6.2, 4.1, 4H).

Example 41

N-(2,2-Dimethylpropyl)-4-[(3R)-3-(methylamino)pyrrolidin-1-yl]pyridin-2-amine

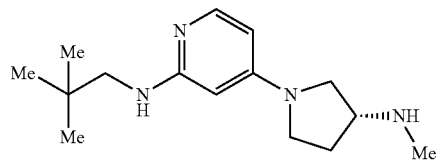 [SMILES: CN[C@@H]1CCN(c2ccnc(NCC(C)(C)C)c2)C1]

MS (ESI): mass calcd. for $C_{15}H_{26}N_4O$, 262.4 m/z found, 263.2 [M+H]$^+$. $^1$H NMR (DMSO-d$_6$): 12.30 (s, 1H), 9.39 (br s, 2H), 7.70-7.60 (m, 2H), 6.26 (dd, J=7.4, 2.2, 1H), 5.79 (s, 1H), 3.89 (s, 1H), 3.81-3.3.62 (m, 3H), 3.53 (br s, 1H), 3.08 (d, J=6.0, 2H), 2.61 (s, 3H), 2.43-2.21 (m, 2H), 0.96 (s, 9H).

Example 42

N-(2-Methoxyethyl)-4-[(3R)-3-(methylamino)pyrrolidin-1-yl]pyridin-2-amine

MS (ESI): mass calcd. for $C_{13}H_{22}N_4O$, 250.4 m/z found, 251.2 [M+H]$^+$. $^1$H NMR (DMSO-d$_6$): 12.13 (s, 1H), 9.53 (s, 1H), 9.41 (s, 1H), 7.70-7.60 (m, 2H), 6.29 (dd, J=7.4, 2.2, 1H), 5.75 (s, 1H), 3.89 (s, 1H), 3.85-3.62 (m, 4H), 3.50 (t, J=4.8, 2H), 3.44 (t, J=5.5, 2H), 3.29 (s, 3H), 2.60 (s, 3H), 2.45-2.33 (m, 2H).

The compounds in Example 43 through Example 83 were prepared using methods analogous to those described for Example 23.

Example 43

4-[(3R)-3-Aminopyrrolidin-1-yl]-N-[bicyclo[2.2.1]hept-2-yl]pyrimidin-2-amine

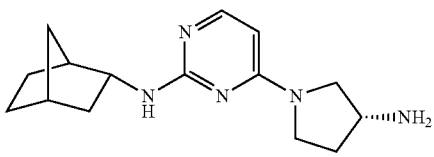 [SMILES: N[C@@H]1CCN(c2ccnc(NC3CC4CCC3C4)n2)C1]

MS (ESI): mass calcd. for $C_{16}H_{23}N_5$, 273.4 m/z found, 274.2 [M+H]. $^1$H NMR (D$_2$O): 8.69-8.29 (m, 1H), 7.64 (s, 1H), 6.14 (s, 1H), 4.25-3.52 (m, 6H), 2.63-2.12 (m, 4H), 1.96-1.74 (m, 1H), 1.65-1.04 (m, 8H).

Example 44

N-[Bicyclo[2.2.1]hept-2-yl]-4-(4-methylpiperazin-1-yl)pyrimidin-2-amine

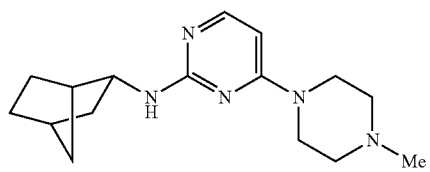 [SMILES: CN1CCN(c2ccnc(NC3CC4CCC3C4)n2)CC1]

MS (ESI): mass calcd. for $C_{16}H_{25}N_5$, 287.41 m/z found, 288.2 [M+H]. $^1$H NMR (CDCl$_3$): 7.87 (d, J=6.0, 1H), 5.84 (d, J=6.1, 1H), 4.69 (d, J=6.5, 1H), 3.75-3.67 (m, 1H), 3.63-3.52 (m, 4H), 2.48-2.39 (m, 4H), 2.32 (s, 3H), 2.29-2.22 (m, 2H), 1.86-1.75 (m, 1H), 1.56-1.38 (m, 3H), 1.30-1.09 (m, 4H).

Example 45

N-(Cyclopropylmethyl)-4-(4-methylpiperazin-1-yl)pyrimidin-2-amine

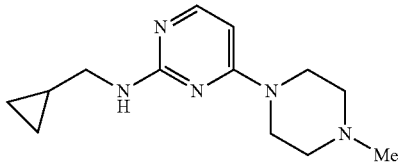 [SMILES: CN1CCN(c2ccnc(NCC3CC3)n2)CC1]

MS (ESI): mass calcd. for $C_{13}H_{21}N_5$, 247.4 m/z found, 248.2 [M+H]. $^1$H NMR (D$_2$O): 7.88 (d, J=6.1, 1H), 5.86 (d, J=6.1, 1H), 4.93 (s, 1H), 3.65-3.55 (m, 4H), 3.22 (dd, J=7.0, 5.5, 2H), 2.47-2.41 (m, 4H), 2.32 (s, 3H), 1.11-0.99 (m, 1H), 0.53-0.46 (m, 2H), 0.25-0.18 (m, 2H).

Example 46

4-[(3R)-3-Aminopyrrolidin-1-yl]-N-butylpyrimidin-2-amine

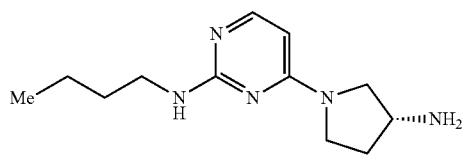 [SMILES: CCCCNc1nccc(N2CC[C@@H](N)C2)n1]

MS (ESI): mass calcd. for $C_{12}H_{21}N_5$, 235.3 m/z found, 236.2 [M+H]. $^1$H NMR (CDCl$_3$): 7.83 (d, J=5.9, 1H), 5.65 (d, J=5.9, 1H), 4.75 (s, 1H), 3.75-3.00 (m, 7H), 2.23-2.07 (m, 1H), 1.85-1.67 (m, 1H), 1.64-1.28 (m, 6H), 0.94 (t, J=7.3, 3H).

Example 47

N-Butyl-4-(4-methylpiperazin-1-yl)pyrimidin-2-amine

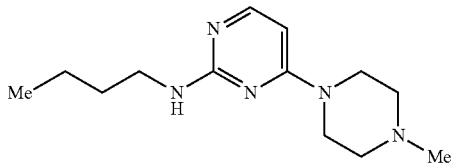 [SMILES: CCCCNc1nccc(N2CCN(C)CC2)n1]

MS (ESI): mass calcd. for $C_{13}H_{23}N_5$, 249.4 m/z found, 250.2 [M+H]. $^1$H NMR (CDCl$_3$): 7.87 (d, J=6.0, 1H), 5.85 (d, J=6.1, 1H), 4.78 (s, 1H), 3.65-3.53 (m, 4H), 3.41-3.28 (m, 2H), 2.47-2.40 (m, 4H), 2.32 (s, 3H), 1.63-1.48 (m, 2H), 1.45-1.31 (m, 2H), 0.94 (t, J=7.3, 3H).

Example 48

N-Cyclopentyl-4-(4-methylpiperazin-1-yl)pyrimidin-2-amine

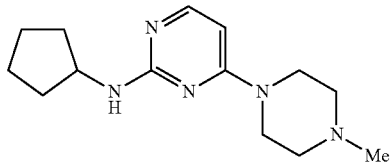 [SMILES: CN1CCN(c2ccnc(NC3CCCC3)n2)CC1]

MS (ESI): mass calcd. for $C_{14}H_{23}N_5$, 261.4 m/z found, 262.2 [M+H]. $^1$H NMR (CDCl$_3$): 7.87 (d, J=6.1, 1H), 5.85 (d, J=6.1, 1H), 4.79 (d, J=6.6, 1H), 4.28-4.13 (m, 1H), 3.70-3.51 (m, 4H), 2.48-2.38 (m, 4H), 2.32 (s, 3H), 2.07-1.94 (m, 2H), 1.77-1.53 (m, 4H), 1.51-1.37 (m, 2H).

Example 49

N-(2,2-Dimethylpropyl)-4-(4-methylpiperazin-1-yl)pyrimidin-2-amine

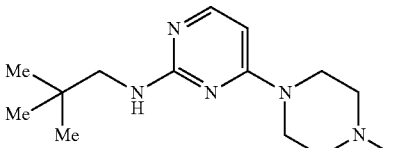

MS (ESI): mass calcd. for $C_{14}H_{25}N_5$, 263.4 m/z found, 264.2 [M+H]. $^1$H NMR (CDCl$_3$): 7.86 (d, J=6.0, 1H), 5.84 (d, J=6.1, 1H), 4.84 (s, 1H), 3.67-3.53 (m, 4H), 3.21 (d, J=6.3, 2H), 2.51-2.38 (m, 4H), 2.30 (s, 3H), 0.95 (s, 9H).

Example 50

4-(4-Methylpiperazin-1-yl)-N-(tetrahydrofuran-2-ylmethyl)pyrimidin-2-amine

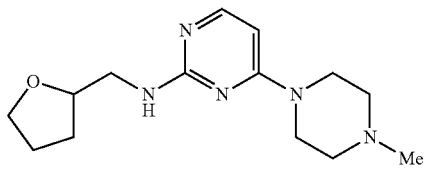 [SMILES: CN1CCN(c2ccnc(NCC3CCCO3)n2)CC1]

MS (ESI): mass calcd. for C$_{14}$H$_{23}$N$_5$O, 277.4 m/z found, 278.2 [M+H]. $^1$H NMR (CDCl$_3$): 7.87 (d, J=6.1, 1H), 5.86 (d, J=6.1, 1H), 5.07 (s, 1H), 4.11-4.01 (m, 1H), 3.92-3.84 (m, 1H), 3.79-3.71 (m, 1H), 3.63-3.51 (m, 5H), 3.47-3.36 (m, 1H), 2.47-2.39 (m, 4H), 2.32 (s, 3H), 2.03-1.83 (m, 3H), 1.69-1.58 (m, 1H).

Example 51

4-[(3R)-3-Aminopyrrolidin-1-yl]-N-(tetrahydrofuran-2-ylmethyl)pyrimidin-2-amine

MS (ESI): mass calcd. for C$_{13}$H$_{21}$N$_5$O, 263.4 m/z found, 264.2 [M+H]. $^1$H NMR (D$_2$O): 8.74-8.23 (m, 1H), 7.65 (d, J=7.2, 1H), 6.16 (s, 1H), 4.28-3.41 (m, 11H), 2.64-2.41 (m, 1H), 2.37-2.15 (m, 1H), 2.12-1.83 (m, 4H), 1.76-1.59 (m, 1H).

Example 52

4-[(3R)-3-Aminopyrrolidin-1-yl]-N-(1-methylethyl)pyrimidin-2-amine

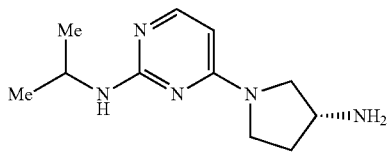 [SMILES: CC(C)Nc1nccc(N2CC[C@@H](N)C2)n1]

MS (ESI): mass calcd. for C$_{11}$H$_{19}$N$_5$, 221.3 m/z found, 222.2 [M+H]. $^1$H NMR (D$_2$O): 8.64-8.31 (m, 1H), 7.62 (d, J=7.3, 1H), 6.14 (d, J=6.3, 1H), 4.24-3.59 (m, 6H), 2.65-2.40 (m, 1H), 2.37-2.11 (m, 1H), 1.23 (d, J=6.5, 6H).

Example 53

N-(1-Methylethyl)-4-(4-methylpiperazin-1-yl)pyrimidin-2-amine

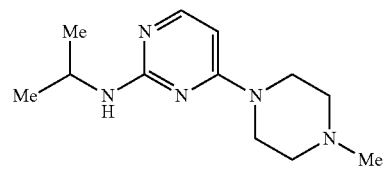 [SMILES: CC(C)Nc1nccc(N2CCN(C)CC2)n1]

MS (ESI): mass calcd. for C$_{12}$H$_{21}$N$_5$, 235.3 m/z found, 236.2 [M+H]. $^1$H NMR (CDCl$_3$): 7.87 (d, J=6.1, 1H), 5.84 (d, J=6.1, 1H), 4.63 (d, J=7.4, 1H), 4.16-4.00 (m, 1H), 3.66-3.50 (m, 4H), 2.49-2.39 (m, 4H), 2.32 (s, 3H), 1.21 (d, J=6.5, 6H).

Example 54

N-Cyclobutyl-4-(4-methylpiperazin-1-yl)pyrimidin-2-amine

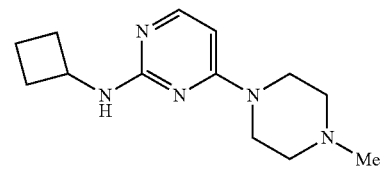 [SMILES: CN1CCN(c2ccnc(NC3CCC3)n2)CC1]

MS (ESI): mass calcd. for C$_{13}$H$_{21}$N$_5$, 247.4 m/z found, 248.2 [M+H]. $^1$H NMR (CDCl$_3$): 7.86 (d, J=6.1, 1H), 5.85 (d, J=6.1, 1H), 4.99 (d, J=7.0, 1H), 4.46-4.35 (m, 1H), 3.65-3.53 (m, 4H), 2.47-2.34 (m, 6H), 2.32 (s, 3H), 1.93-1.80 (m, 2H), 1.77-1.63 (m, 2H).

Example 55

4-[(3R)-3-Aminopyrrolidin-1-yl]-N-cyclopropylpyrimidin-2-amine

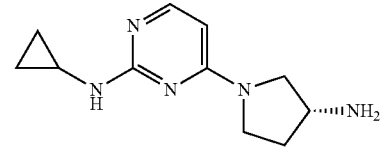 [SMILES: N[C@@H]1CCN(c2ccnc(NC3CC3)n2)C1]

MS (ESI): mass calcd. for C$_{11}$H$_{17}$N$_5$, 219.3 m/z found, 220.2 [M+H]. $^1$H NMR (D$_2$O): 8.64-8.30 (m, 1H), 7.71 (d, J=7.3, 1H), 6.23 (d, J=7.3, 1H), 4.22-4.02 (m, 1H), 4.00-3.88

(m, 1H), 3.85-3.59 (m, 3H), 2.76-2.59 (m, 1H), 2.56-2.38 (m, 1H), 2.32-2.11 (m, 1H), 0.98-0.80 (m, 2H), 0.72-0.58 (m, 2H).

Example 56

N-Cyclopropyl-4-(4-methylpiperazin-1-yl)pyrimidin-2-amine

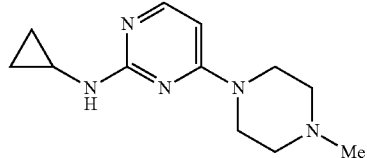 [SMILES: CN1CCN(c2ccnc(NC3CC3)n2)CC1]

MS (ESI): mass calcd. for $C_{12}H_{19}N_5$, 233.3 m/z found, 234.2 [M+H]. $^1$H NMR (CDCl$_3$): 7.93 (d, J=6.1, 1H), 5.91 (d, J=6.1, 1H), 5.02 (s, 1H), 3.65-3.55 (m, 4H), 2.78-2.68 (m, 1H), 2.48-2.39 (m, 4H), 2.32 (s, 3H), 0.79-0.70 (m, 2H), 0.54-0.47 (m, 2H).

Example 57

4-[(3R)-3-Aminopyrrolidin-1-yl]-N-(4-fluorobenzyl)pyrimidin-2-amine

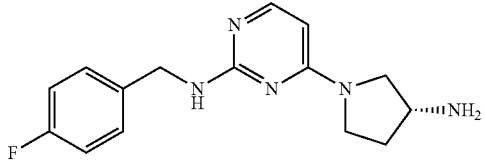 [SMILES: N[C@@H]1CCN(c2ccnc(NCc3ccc(F)cc3)n2)C1]

MS (ESI): mass calcd. for $C_{15}H_{18}FN_5$, 287.3 m/z found, 288.2 [M+H]. $^1$H NMR (D$_2$O): 8.65-8.24 (m, 1H), 7.65 (d, J=7.1, 1H), 7.48-7.30 (m, 2H), 7.19-7.01 (m, 2H), 6.14 (d, J=7.0, 1H), 4.58 (s, 2H), 4.22-4.02 (m, 1H), 3.97-3.58 (m, 4H), 2.62-2.36 (m, 1H), 2.31-2.11 (m, 1H).

Example 58

N-(4-Fluorobenzyl)-4-(4-methylpiperazin-1-yl)pyrimidin-2-amine

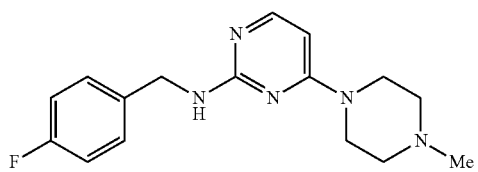 [SMILES: CN1CCN(c2ccnc(NCc3ccc(F)cc3)n2)CC1]

MS (ESI): mass calcd. for $C_{16}H_{20}FN_5$, 301.4 m/z found, 302.2 [M+H]. $^1$H NMR (CDCl$_3$): 7.85 (d, J=6.1, 1H), 7.34-7.26 (m, 2H), 7.03-6.92 (m, 2H), 5.88 (d, J=6.1, 1H), 5.30 (s, 1H), 4.54 (d, J=5.9, 2H), 3.61-3.53 (m, 4H), 2.45-2.37 (m, 4H), 2.31 (s, 3H).

Example 59

4-[(3R)-3-Aminopyrrolidin-1-yl]-N-(2-methoxyethyl)pyrimidin-2-amine

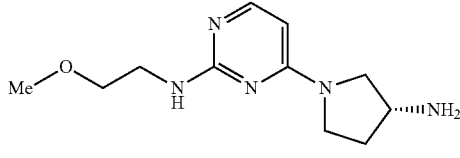 [SMILES: COCCNc1nccc(N2CC[C@@H](N)C2)n1]

MS (ESI): mass calcd. for $C_{11}H_{19}N_5O$, 237.3 m/z found, 238.2 [M+H]. $^1$H NMR (CDCl$_3$): 7.83 (d, J=5.9, 1H), 5.67 (d, J=5.9, 1H), 5.06 (s, 1H), 3.79-3.39 (m, 8H), 3.37 (s, 3H), 3.24-3.00 (m, 1H), 2.26-2.05 (m, 1H), 1.84-1.69 (m, 1H), 1.65-1.21 (m, 2H).

Example 60

N-(2-Methoxyethyl)-4-(4-methylpiperazin-1-yl)pyrimidin-2-amine

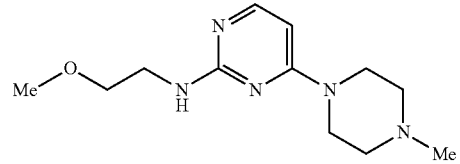 [SMILES: COCCNc1nccc(N2CCN(C)CC2)n1]

MS (ESI): mass calcd. for $C_{12}H_{21}N_5O$, 251.3 m/z found, 252.2 [M+H]. $^1$H NMR (CDCl$_3$): 7.88 (d, J=6.1, 1H), 5.87 (d, J=6.1, 1H), 5.09 (s, 1H), 3.65-3.50 (m, 8H), 3.37 (s, 3H), 2.48-2.39 (m, 4H), 2.32 (s, 3H).

Example 61

4-[(3R)-3-Aminopyrrolidin-1-yl]-N-(pyridin-2-ylmethyl)pyrimidin-2-amine

MS (ESI): mass calcd. for $C_{14}H_{18}N_6$, 270.3 m/z found, 271.2 [M+H]. $^1$H NMR (CDCl$_3$): 8.54 (d, J=4.2, 1H), 7.86 (d, J=5.9, 1H), 7.61 (td, J=7.7, 1.8, 1H), 7.34 (d, J=7.8, 1H), 7.16-7.10 (m, 1H), 5.72-5.61 (m, 2H), 4.73 (d, J=5.8, 2H), 3.71-3.32 (m, 4H), 3.21-3.04 (m, 1H), 2.20-2.05 (m, 1H), 1.80-1.68 (m, 1H), 1.38-1.13 (m, 2H).

Example 62

4-(4-Methylpiperazin-1-yl)-N-(pyridin-2-ylmethyl)pyrimidin-2-amine

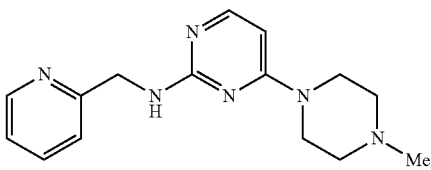 [SMILES: CN1CCN(c2ccnc(NCc3ccccn3)n2)CC1]

MS (ESI): mass calcd. for $C_{15}H_{20}N_6$, 284.4 m/z found, 285.2 [M+H]. $^1$H NMR (CDCl$_3$): 8.55 (ddd, J=4.8, 1.6, 0.8, 1H), 7.91 (d, J=6.1, 1H), 7.61 (td, J=7.7, 1.8, 1H), 7.33 (d, J=7.8, 1H), 7.17-7.11 (m, 1H), 5.89 (d, J=6.1, 1H), 5.72-5.66 (m, 1H), 4.71 (d, J=5.7, 2H), 3.61-3.53 (m, 4H), 2.43-2.37 (m, 4H), 2.31 (s, 3H).

Example 63

Cyclopentyl-(4-piperazin-1-yl-pyrimidin-2-yl)-amine

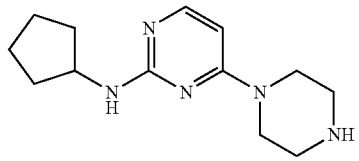 [SMILES: c1cc(N2CCNCC2)nc(NC2CCCC2)n1]

MS (ESI): mass calcd. for $C_{13}H_{21}N_5$, 247.3 m/z found, 248.3 [M+H]$^+$. $^1$H NMR (CD$_3$OD): 7.89-7.84 (m, 1H), 5.87-5.83 (m, 1H), 4.26-4.18 (m, 1H), 3.62-3.52 (m, 4H), 2.95-2.87 (m, 4H), 2.07-1.98 (m, 2H), 1.77-1.67 (m, 2H), 1.66-1.58 (m, 2H), 1.51-1.41 (m, 2H).

Example 64

(2,2-Dimethyl-propyl)-(4-piperazin-1-yl-pyrimidin-2-yl)-amine

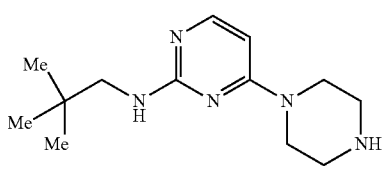 [SMILES: CC(C)(C)CNc1nccc(N2CCNCC2)n1]

Method A:
The titled compound was prepared using methods analogous to those described for Example 23. MS (ESI): mass calcd. for $C_{13}H_{23}N_5$, 249.4 m/z found, 250.2 [M+H]$^+$. $^1$H NMR (CDCl$_3$): 7.92-7.86 (m, 1H), 5.86-5.83 (m, 1H), 4.97-4.84 (m, 1H), 3.63-3.55 (m, 4H), 3.53-3.47 (m, 4H), 3.24-3.19 (m, 2H), 1.51-1.47 (m, 9H). Method B:

t-butyl 4-(2-chloropyrimidin-4-yl)piperazine-1-carboxylate.

To a mixture of 2,4-dichloropyrimidine (20 g, 0.135 mol, 1 eq.) and DIPEA (26 g, 0.203 mol, 1.5 eq) in i-PrOH (400 mL) was added tert-butyl piperazine-1-carboxylate (27 g, 0.148 mol, 1.1 eq) by portions at 0° C., and the resulting reaction was stirred overnight (about 15 hrs) at 10° C. A lot of white solid precipitated and TLC showed that there was still a little 2,4-dichloropyrimidine. The solid was filtered and recrystallized from DCM to afford the title product (18 g, 45% yield) as a white solid. $^1$H NMR (300 MHz, CDCl$_3$): 8.08 (d, J=6.2 Hz, 1H), 6.41 (d, J=6.2 Hz, 1H), 3.67 (s, 4H), 3.56-3.41 (m, 4H), 1.48 (s, 9H). t-butyl 4-(2-(neopentylamino)pyrimidin-4-yl)piperazine-1-carboxylate. A solution of tert-butyl 4-(2-chloropyrimidin-4-yl)piperazine-1-carboxylate (300 mg, 1 mmol) 2,2-dimethylpropan-1-amine (131 mg, 1.5 mmol) and DIPEA (259 mg, 2 mmol) in pentan-1-ol (15 mL) was stirred at reflux for 18 hrs. The solvent was removed under reduced pressure and the residue was purified by column chromatography (100% ethyl acetate) to afford the desired product. $^1$H NMR (300 MHz, CDCl$_3$): 7.88 (d, J=5.7 Hz, 1H), 5.84 (d, J=6.3 Hz, 1H), 4.97 (br s, 1H), 3.58 (m, 4H), 3.50 (m, 4H), 3.21 (d, J=6.3 Hz, 2H), 1.48 (s, 9H), 0.96 (s, 9H).

N-neopentyl-4-(piperazin-1-yl)pyrimidin-2-amine dihydrochloride.

t-butyl 4-(2-(neopentylamino)pyrimidin-4-yl)piperazine-1-carboxylate obtained from the previous stey was dissolved in MeOH (4 mL) and 7N HCl/Et$_2$O solution (20 mL) was added. The resulting solution was stirred at ambient temperature for 18 hrs. The solvent was concentrated to give the desired product as a yellow solid (130 mg, 40% yield in two steps). $^1$H NMR (300 MHz, CD$_3$OD): 7.84 (d, J=7.2 Hz, 1H), 6.56 (d, J=7.2 Hz, 1H), 4.27 (br s, 2H), 4.02 (br s, 2H), 3.40 (br s, 4H), 3.33 (br s, 2H), 1.01 (s, 9H); LC-MS, m/z=250.2 [M+H]$^+$, $t_R$=0.8 min; HPLC: 99% (214 nm), 98% (254 nm), $t_R$=4.7 min.

Example 65

Isobutyl-(4-piperazin-1-yl-pyrimidin-2-yl)-amine

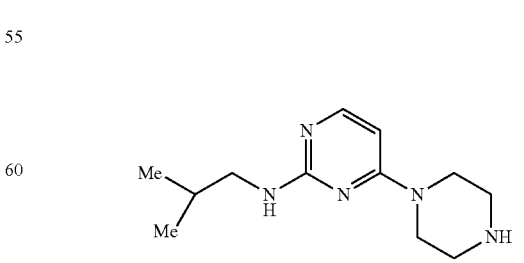

MS (ESI): mass calcd. for $C_{12}H_{21}N_5$, 235.3 m/z found, 236.2 [M+H]$^+$. $^1$H NMR (CD$_3$OD): 7.89-7.78 (m, 1H), 6.62-

6.52 (m, 1H), 4.13-3.97 (m, 2H), 3.44-3.37 (m, 4H), 3.35-3.18 (m, 4H), 2.02-1.89 (m, 1H), 1.04-0.97 (m, 6H).

Example 66

Cyclopropylmethyl-(4-piperazin-1-yl-pyrimidin-2-yl)-amine

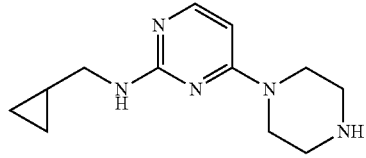 [SMILES: c1cc(N2CCNCC2)nc(NCC2CC2)n1]

MS (ESI): mass calcd. for $C_{12}H_{19}N_5$, 233.3 m/z found, 234.2 [M+H]$^+$. $^1$H NMR (CD$_3$OD): 7.87-7.78 (m, 1H), 6.64-6.53 (m, 1H), 3.46-3.36 (m, 4H), 3.35-3.29 (m, 4H), 1.20-1.07 (m, 1H), 0.65-0.53 (m, 2H), 0.37-0.28 (m, 2H).

Example 67

Isopropyl-(4-piperazin-1-yl-pyrimidin-2-yl)-amine

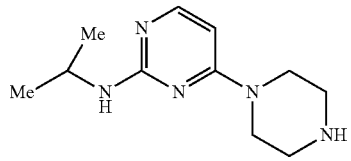 [SMILES: CC(C)Nc1nccc(N2CCNCC2)n1]

MS (ESI): mass calcd. for $C_{12}H_{19}N_5$, 221.3 m/z found, 222.2 [M+H]$^+$. $^1$H NMR (CD$_3$OD): 7.83-7.77 (m, 1H), 6.59-6.50 (m, 1H), 4.36-3.98 (m, 4H), 3.46-3.29 (m, 4H), 1.44-1.36 (m, 1H), 1.31-1.24 (m, 6H).

Example 68

Butyl-(4-piperazin-1-yl-pyrimidin-2-yl)-amine

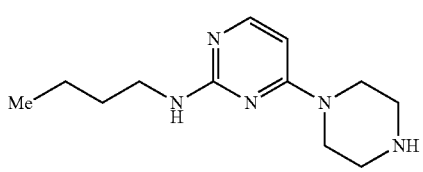 [SMILES: CCCCNc1nccc(N2CCNCC2)n1]

MS (ESI): mass calcd. for $C_{12}H_{21}N_5$, 235.3 m/z found, 236.2 [M+H]$^+$. $^1$H NMR (CD$_3$OD): 7.87-7.79 (m, 1H), 6.65-

6.53 (m, 1H), 4.38-3.99 (m, 4H), 3.55-3.29 (m, 6H), 1.73-1.60 (m, 2H), 1.50-1.40 (m, 2H), 1.03-0.95 (m, 3H).

Example 69

(R)-(4-piperazin-1-yl-pyrimidin-2-yl)-(-tetrahydro-furan-2-ylmethyl)-amine

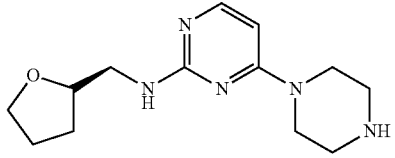

MS (ESI): mass calcd. for $C_{13}H_{21}N_5O$, 263.3 m/z found, 264.3 [M+H]$^+$. $^1$H NMR (CD$_3$OD): 7.86-7.79 (m, 1H), 5.86-5.82 (m, 1H), 5.21-5.09 (m, 1H), 4.11-4.01 (m, 1H), 3.91-3.80 (m, 1H), 3.78-3.70 (m, 1H), 3.59-3.49 (m, 4H), 3.41-3.34 (m, 1H), 2.91-2.84 (m, 4H), 2.45-2.11 (m, 2H), 2.03-1.81 (m, 4H), 1.68-1.56 (m, 1H).

Example 70

Bicyclo[2.2.1]hept-2-yl-(4-piperazin-1-yl-pyrimidin-2-yl)-amine

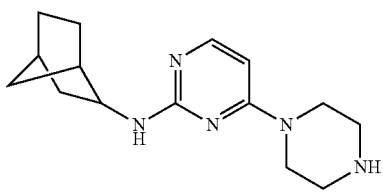 [SMILES: c1cc(N2CCNCC2)nc(NC2CC3CCC2C3)n1]

MS (ESI): mass calcd. for $C_{15}H_{23}N_5$, 273.4 m/z found, 274.2 [M+H]$^+$. $^1$H NMR (CDCl$_3$): 7.93-7.82 (m, 1H), 5.87-5.81 (m, 1H), 4.99-4.74 (m, 1H), 3.75-3.67 (m, 1H), 3.62-3.54 (m, 4H), 3.52-3.44 (m, 4H), 2.30-2.22 (m, 2H), 1.85-1.77 (m, 1H), 1.59-1.51 (m, 1H), 1.46-1.40 (m, 1.6H), 1.29-1.20 (m, 2.4H), 1.19-1.11 (m, 2H).

Example 71

(4-piperazin-1-yl-pyrimidin-2-yl)-(2,6,6-trimethyl-bicyclo[3.1.1]hept-3-yl)-amine

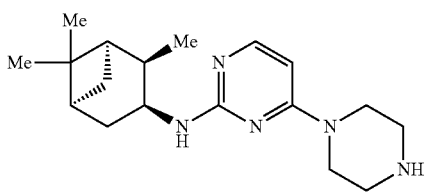 [SMILES: C[C@H]1[C@@H](Nc2nccc(N3CCNCC3)n2)C[C@@H]2C[C@H]1C2(C)C]

MS (ESI): mass calcd. for $C_{18}H_{29}N_5$, 315.5 m/z found, 316.2 [M+H]$^+$. $^1$H NMR (CD$_3$OD): 7.54-7.41 (m, 1H), 6.25-6.14 (m, 1H), 4.33-4.12 (m, 1H), 4.10-3.91 (m, 2H), 3.88-3.62 (m, 2H), 3.29-3.13 (m, 4H), 2.52-2.37 (m, 1H), 2.32-

2.19 (m, 1H), 1.91-1.73 (m, 2H), 1.72-1.63 (m, 1H), 1.53-1.41 (m, 1H), 1.02 (s, 3H), 0.94-0.88 (m, 3H), 0.85 (s, 3H), 0.77-0.71 (m, 2H).

Example 72

N-(2-Methoxyethyl)-4-piperazin-1-ylpyrimidin-2-amine

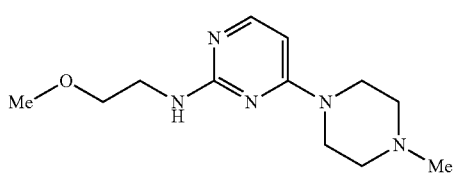 [SMILES: COCCNc1nccc(N2CCN(C)CC2)n1]

MS (ESI): mass calcd. for $C_{11}H_{19}N_5O$, 237.3 m/z found, 238.3 [M+H]$^+$. $^1$H NMR (CD$_3$OD): 7.84 (d, 1H, J=7.4), 6.59 (d, 1H, J=7.3), 4.29 (bs, 2H), 4.04 (bs, 2H), 3.59-3.67 (m, 4H), 3.35-3.45 (m, 7H).

Example 73

Butyl-[4-(3R)-(3-methylamino-pyrrolidin-1-yl)-pyrimidin-2-yl]-amine

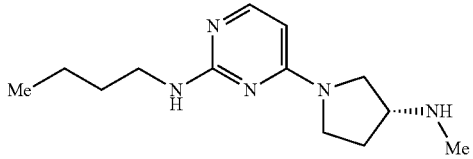 [SMILES: CCCCNc1nccc(N2CC[C@@H](NC)C2)n1]

MS (ESI): mass calcd. for $C_{13}H_{23}N_5$, 249.2 m/z found, 250.2 [M+H]$^+$. $^1$H NMR (CDCl$_3$): 7.82 (d, J=5.9, 1H), 5.64 (d, J=5.9, 1H), 4.90 (s, 1H), 3.77-3.08 (m, 7H), 2.46 (s, 3H), 2.14 (td, J=13.1, 6.1, 1H), 1.81 (d, J=6.1, 1H), 1.67-1.29 (m, 5H), 0.93 (t, J=7.3, 3H).

Example 74

Bicyclo[2.2.1]hept-2-yl-[4-(3R)-(3-methylamino-pyrrolidin-1-yl)-pyrimidin-2-yl]-amine

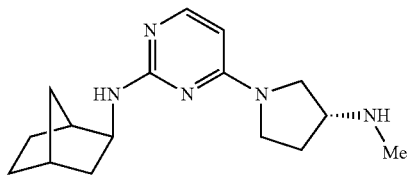 [SMILES: CN[C@@H]1CCN(c2ccnc(NC3CC4CCC3C4)n2)C1]

MS (ESI): mass calcd. for $C_{16}H_{25}N_5$, 287.2 m/z found, 288.2 [M+H]. $^1$H NMR (CDCl$_3$): 7.76 (d, J=5.8, 1H), 5.60 (d, J=5.9, 1H), 5.12-4.88 (m, 1H), 3.69 (s, 2H), 3.29 (s, 2H), 2.61-1.98 (m, 6H), 1.95-0.92 (m, 12H).

Example 75

Cyclopentyl-[4-(3R)-(3-methylamino-pyrrolidin-1-yl)-pyrimidin-2-yl]-amine

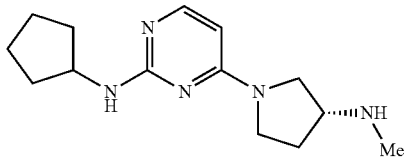 [SMILES: CN[C@@H]1CCN(c2ccnc(NC3CCCC3)n2)C1]

MS (ESI): mass calcd. for $C_{14}H_{23}N_5$, 261.2 m/z found, 262.2 [M+H]. $^1$H NMR (CDCl$_3$): 7.75 (d, J=5.9, 1H), 5.58 (d, J=5.9, 1H), 4.97 (s, 1H), 4.17 (dd, J=13.6, 6.8, 1H), 3.53 (s, 1H), 3.25 (s, 3H), 2.40 (s, 3H), 2.18-1.28 (m, 12H).

Example 76

(2,2-Dimethyl-propyl)-[4-(3R)-(3-methylamino-pyrrolidin-1-yl)-pyrimidin-2-yl]-amine

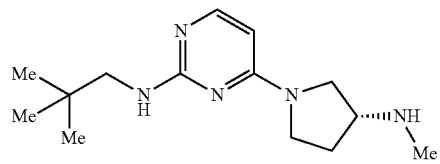 [SMILES: CN[C@@H]1CCN(c2ccnc(NCC(C)(C)C)n2)C1]

MS (ESI): mass calcd. for $C_{14}H_{25}N_5$, 263.2 m/z found, 264.2 [M+H]. $^1$H NMR (CDCl$_3$): 7.77 (d, J=5.8, 1H), 5.59 (d, J=5.9, 1H), 4.92 (s, 1H), 3.56 (s, 1H), 3.22-3.15 (m, 5H), 2.43 (s, 3H), 2.11 (d, J=6.0, 1H), 1.78 (s, 1H), 1.08-0.73 (m, 11H).

Example 77

Cyclopropylmethyl-[4-(3R)-(3-methylamino-pyrrolidin-1-yl)-pyrimidin-2-yl]-amine

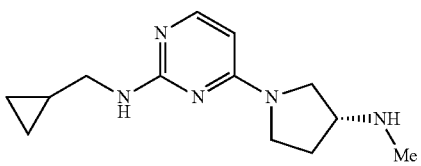 [SMILES: CN[C@@H]1CCN(c2ccnc(NCC3CC3)n2)C1]

MS (ESI): mass calcd. for $C_{13}H_{21}N_5$, 247.2 m/z found, 248.2 [M+H]. $^1$H NMR (CDCl$_3$): 7.61 (d, J=5.9, 1H), 5.44 (d, J=5.9, 1H), 4.87 (s, 1H), 3.57-2.78 (m, 7H), 2.46-2.04 (m, 3H), 1.93 (td, J=13.3, 6.0, 1H), 1.60 (d, J=6.1, 1H), 1.32-0.60 (m, 2H), 0.38-0.16 (m, 2H), 0.14-0.10 (m, 2H).

Example 78

Isopropyl-[4-(3R)-(3-methylamino-pyrrolidin-1-yl)-pyrimidin-2-yl]-amine

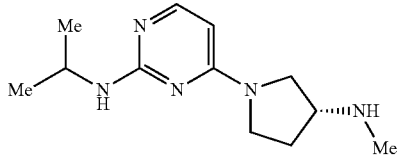 [SMILES: CN[C@@H]1CCN(c2ccnc(NC(C)C)n2)C1]

MS (ESI): mass calcd. for $C_{12}H_{21}N_5$, 235.2 m/z found, 236.2 [M+H]+. 1H NMR (CDCl3): 7.81 (d, J=5.9, 1H), 5.64 (d, J=5.9, 1H), 4.82 (d, J=7.3, 1H), 4.21-4.00 (m, 1H), 3.77-3.08 (m, 5H), 2.67-2.25 (m, 3H), 2.24-1.71 (m, 2H), 1.67-0.90 (m, 7H).

Example 79

(4-Fluoro-benzyl)-[4-(3R)-(3-methylamino-pyrrolidin-1-yl)-pyrimidin-2-yl]-amine

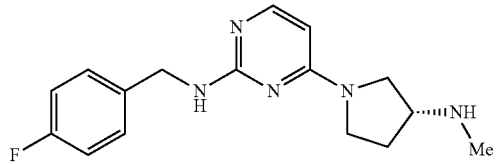 [SMILES: CN[C@@H]1CCN(c2ccnc(NCc3ccc(F)cc3)n2)C1]

MS (ESI): mass calcd. for $C_{16}H_{20}FN_5$, 301.2 m/z found, 302.2 [M+H]. 1H NMR (CDCl3): 7.76 (d, J=5.7, 1H), 7.40-7.20 (m, 2H), 7.06-6.86 (m, 2H), 5.65 (d, J=5.9, 2H), 4.53 (d, J=5.9, 2H), 3.56-3.46 (m, 2H), 3.29 (s, 3H), 2.44 (s, 3H), 2.11 (s, 1H), 1.79 (s, 1H), 1.40-1.32 (m, 1H).

Example 80

Cyclopropyl-[4-(3R)-(3-methylamino-pyrrolidin-1-yl)-pyrimidin-2-yl]-amine

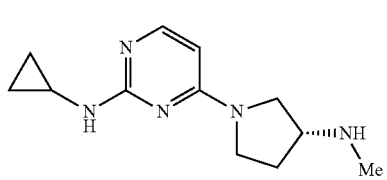 [SMILES: CN[C@@H]1CCN(c2ccnc(NC3CC3)n2)C1]

MS (ESI): mass calcd. for $C_{12}H_{19}N_5$, 233.2 m/z found, 234.2 [M+H]. 1H NMR (CDCl3) 7.89 (d, J=5.9, 1H), 5.71 (d, J=6.0, 1H), 5.13 (s, 1H), 3.76-3.11 (m, 5H), 2.82-2.39 (m, 4H), 2.15 (td, J=13.2, 6.0, 1H), 1.82 (d, J=6.1, 1H), 1.46 (s, 1H), 0.85-0.64 (m, 2H), 0.60-0.40 (m, 2H).

Example 81

[4-(3R)-(3-Methylamino-pyrrolidin-1-yl)-pyrimidin-2-yl]-(tetrahydro-furan-2-ylmethyl)-amine

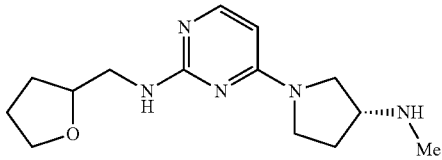 [SMILES: CN[C@@H]1CCN(c2ccnc(NCC3CCCO3)n2)C1]

MS (ESI): mass calcd. for $C_{14}H_{23}N_5O$, 277.2 m/z found, 278.2 [M+H]. 1H NMR (CDCl3): 7.82 (d, J=5.9, 1H), 5.66 (d, J=5.9, 1H), 5.11 (s, 1H), 4.15-3.99 (m, 1H), 3.96-3.12 (m, 9H), 2.55 (s, 3H), 2.34-2.05 (m, 1H), 2.05-1.56 (m, 6H).

Example 82

(2-Methoxy-ethyl)-[4-(3R)-(3-methylamino-pyrrolidin-1-yl)-pyrimidin-2-yl]-amine

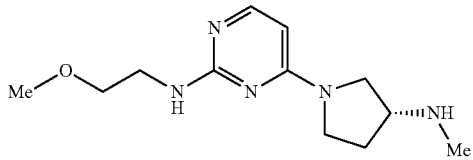

MS (ESI): mass calcd. for $C_{12}H_{21}N_5O$, 251.2 m/z found, 252.2 [M+H]+. 1H NMR (CDCl3): 7.82 (d, J=5.9, 1H), 5.66 (d, J=5.9, 1H), 5.17 (s, 1H), 3.79-3.07 (m, 13H), 2.55 (s, 3H), 2.15 (td, J=13.3, 6.0, 1H), 1.82 (d, J=6.1, 1H).

Example 83

[4-(3R)-(3-Methylamino-pyrrolidin-1-yl)-pyrimidin-2-yl]-pyridin-2-ylmethyl-amine

MS (ESI): mass calcd. for $C_{15}H_{20}N_6$, 284.2 m/z found, 285.2 [M+H]+. 1H NMR (CDCl3) 8.46 (d, J=4.8, 1H), 7.75 (d, J=5.9, 1H), 7.63-7.39 (m, 1H), 7.28 (d, J=7.8, 1H), 7.16-6.95 (m, 1H), 6.04 (s, 1H), 5.60 (d, J=5.9, 1H), 4.66 (d, J=5.8, 2H), 3.49 (s, 1H), 3.40-3.31 (m, 1H), 3.22 (s, 2H), 2.36 (s, 3H), 2.03 (s, 1H), 1.72 (s, 1H), 1.44-1.35 (m, 1H).

Example 84

[4-(3-Amino-azetidin-1-yl)-pyrimidin-2-yl]butyl-amine

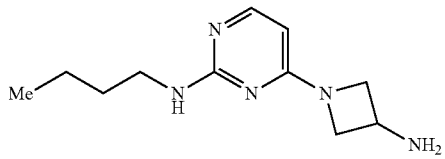 [SMILES: CCCCNc1nccc(N2CC(N)C2)n1]

[1-(2-Chloro-pyrimidin-4-yl)-azetidin-3-yl]-carbamic acid tert-butyl ester To a flask containing 2,4-dichloropyrimidine (1.6 g, 10.7 mmol) and N,N-diisopropylethylamine (3.5 mL, 20.1 mmol) in i-PrOH (40 mL) was added azetidin-3-yl-carbamic acid tert-butyl ester monohydrochloride (2.1 g. 12.2 mmol). The reaction mixture was heated to 70° C. for 72 h. The reaction was cooled to room temperature, concentrated and the crude residue was purified by flash chromatography on $SiO_2$ (100% hexane increasing gradient to 60% EtOAc-Hexane) to yield two isomeric products. The minor upper $R_f$ product was obtained as a white solid (326 mg, 11%), and the desired major lower $R_f$ product was also obtained as a white solid (2.1 g, 69%).

[1-(2-Butylamino-pyrimidin-4-yl)azetidin-3-yl]-carbamic acid tert-butyl ester. To a solution of [1-(2-chloro-pyrimidin-4-yl)-azetidin-3-yl]-carbamic acid tert-butyl ester (250 mg, 0.778 mmol) in i-PrOH (3.0 mL) was added butylamine (600 µL, 6.0 mmol). The reaction mixture was heated to 95° C. in a sealed tube for 36-48 h followed by cooling to room temperature. The reaction mixture was then concentrated and the crude residue purified by flash chromatography on $SiO_2$ using (100% EtOAc increasing the gradient gradually to 5% 2M $NH_3$-MeOH) to yield the desired product (260 mg, 92%).

[4-(3-Amino-azetidin-1-yl)-pyrimidin-2-yl]-butyl-amine. To a solution of [1-(2-butylamino-pyrimidin-4-yl)-azetidin-3-yl]-carbamic acid tert-butyl ester (250 mg, 0.778 mmol) in formic acid (4 mL) was added 6N HCl (300 µL). The reaction mixture was stirred at room temperature for 15-30 minutes. Then, MeOH (10 mL) was added and stirred for 10 minutes. The contents were then concentrated and the crude residue purified by flash chromatography on $SiO_2$ using an increasing gradient of (0 to 10% $NH_3$/MeOH in $CH_2Cl_2$) to yield the desired product (225 mg, 98%) as the free base. MS (ESI): mass calcd. for $C_{11}H_{19}N_5$, 221.3 m/z found, 222.2 [M+H]$^+$. $^1$H NMR ($CD_3OD$): 7.61 (d, J=7.3, 1H), 5.99 (d, J=7.1, 1H), 4.6-4.7 (m, 2H), 4.28-4.48 (m, 3H), 3.40 (bs, 1H), 1.54-1.62 (m, 2H), 1.31-1.41 (m, 2H), 0.90 (t, J=7.4, 3H).

The compounds in Example 85 through Example 94 were prepared using methods analogous to those described for Example 84.

Example 85

4-(3-Aminoazetidin-1-yl)-N-cyclopentylpyrimidin-2-amine

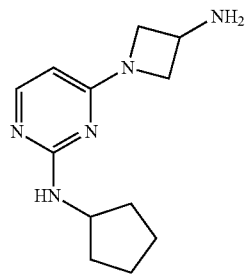 [SMILES: NC1CN(c2ccnc(NC3CCCC3)n2)C1]

MS (ESI): mass calcd. for $C_{12}H_{19}N_5$, 233.3 m/z found, 234.2 [M+H]. $^1$H NMR ($CDCl_3$): 7.84 (d, J=6.0, 1H), 5.54 (d, J=5.8, 1H), 4.47 (bs, 1H), 4.20-4.28 (m, 3H), 3.90-3.98 (m, 1H), 3.60-3.65 (m, 2H), 1.97-2.06 (m, 2H), 1.55-1.75 (m, 6H), 1.39-1.48 (m, 2H).

Example 86

4-(3-Aminoazetidin-1-yl)-N-(cyclopropylmethyl)pyrimidin-2-amine

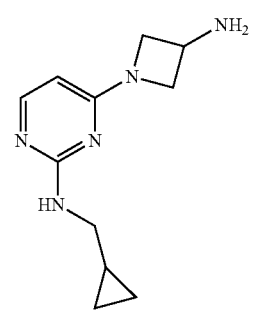 [SMILES: NC1CN(c2ccnc(NCC3CC3)n2)C1]

MS (ESI): mass calcd. for $C_{11}H_{17}N_5$, 219.3 m/z found, 220.2 [M+H]. $^1$H NMR ($CDCl_3$): 7.62 (d, J=7.3, 1H), 6.00 (d, J=7.3, 1H), 4.6-4.7 (m, 2H), 4.28-4.40 (m, 3H), 3.24 (d, J=6.9, 2H), 1.05-1.15 (m, 1H), 0.52-0.59 (m, 2H), 0.23-0.30 (m, 2H).

Example 87

4-(3-Aminoazetidin-1-yl)-N-bicyclo[2.2.1]hept-2-ylpyrimidin-2-amine

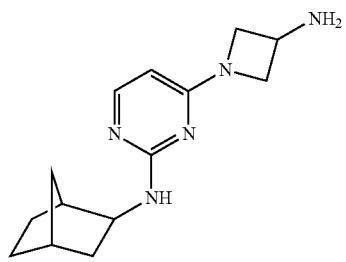 [SMILES: NC1CN(c2ccnc(NC3CC4CCC3C4)n2)C1]

MS (ESI): mass calcd. for $C_{14}H_{21}N_5$, 259.4 m/z found, 260.2 [M+H]. $^1$H NMR ($CDCl_3$): 7.60 (d, J=7.2, 1H), 6.00 (d, J=6.8, 1H), 4.55-4.70 (m, 2H), 4.25-4.43 (m, 3H), 3.65 (bs, 1H), 2.25-2.35 (m, 2H), 1.80-1.84 (m, 1H), 1.32-1.60 (m, 4H), 1.10-1.30 (m, 3H).

Example 88

4-(3-Aminoazetidin-1-yl)-N-(2,2-dimethylpropyl)pyrimidin-2-amine

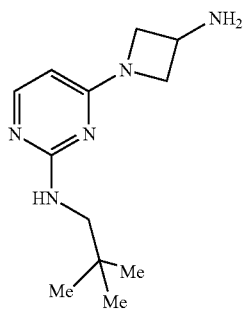 [SMILES: CC(C)(C)CNc1nccc(N2CC(N)C2)n1]

MS (ESI): mass calcd. for $C_{12}H_{21}N_5$, 235.3 m/z found, 236.2 [M+H]. $^1$H NMR (CDCl$_3$): 7.61 (d, J=7.2, 1H), 5.99 (d, J=7.1, 1H), 4.58-4.70 (m, 2H), 4.28-4.42 (m, 2H), 3.22 (bs, 1H), 0.934 (s, 9H).

Example 89

4-(3-Aminoazetidin-1-yl)-N-(2-methylpropyl)pyrimidin-2-amine

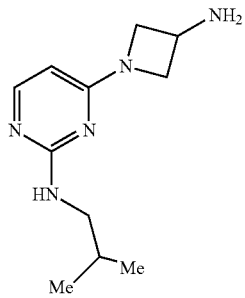 [SMILES: CC(C)CNc1nccc(N2CC(N)C2)n1]

MS (ESI): mass calcd. for $C_{11}H_{19}N_5$, 221.3 m/z found, 222.2 [M+H]. $^1$H NMR (CDCl$_3$): 7.61 (d, J=7.3, 1H), 6.00 (d, J=7.0, 1H), 4.59-4.70 (m, 2H), 4.29-4.45 (m, 3H), 3.20 (bs, 2H), 1.85-1.94 (m, 1H), 0.92 (d, J=6.7, 6H).

Example 90

4-(3-Aminoazetidin-1-yl)-N-(1-methylethyl)pyrimidin-2-amine

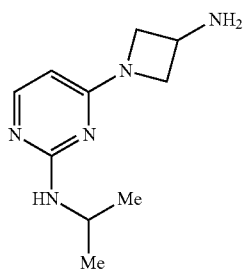 [SMILES: CC(C)Nc1nccc(N2CC(N)C2)n1]

MS (ESI): mass calcd. for $C_{10}H_{17}N_5$, 207.3 m/z found, 208.2 [M+H]. $^1$H NMR (CDCl$_3$): 7.83 (d, J=5.6, 1H), 5.54 (d, J=5.2, 1H), 4.7 (bs, 1H), 4.24 (apparent t, J=7.6 and 8.4, 2H), 4.05-4.15 (m, 1H), 3.90-3.98 (m, 1H), 3.60-3.65 (m, 2H), 1.75 (bs, 2H), 1.19 (d, J=6.4, 6H).

Example 91

4-(3-Aminoazetidin-1-yl)-N-cyclopropylpyrimidin-2-amine

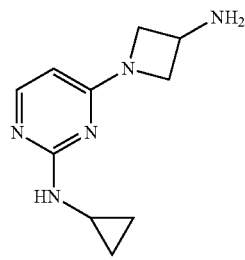 [SMILES: NC1CN(c2ccnc(NC3CC3)n2)C1]

MS (ESI): mass calcd. for $C_{10}H_{15}N_5$, 205.3 m/z found, 206.2 [M+H]. $^1$H NMR (CDCl$_3$): 7.69 (d, J=7.3, 1H), 6.01 (d, J=7.3, 1H), 4.55-4.70 (m, 5H), 4.25-4.42 (m, 3H), 2.65 (bs, 1H), 0.85-0.95 (m, 2H), 0.66-0.71 (m, 2H).

Example 92

4-(3-Aminoazetidin-1-yl)-N-(4-fluorobenzyl)pyrimidin-2-amine

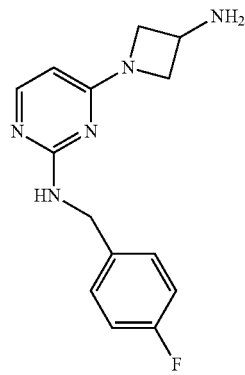 [SMILES: NC1CN(c2ccnc(NCc3ccc(F)cc3)n2)C1]

MS (ESI): mass calcd. for $C_{14}H_{16}FN_5$, 273.3 m/z found, 274.2 [M+H]. $^1$H NMR (CDCl$_3$): 7.62 (d, J=7.3, 1H), 7.39 (dd, J=5.7, 8.2, 2H), 7.12 (t, J=8.9, 2H), 6.00 (d, J=7.3, 1H), 4.52-4.65 (m, 4H), 4.23-4.40 (m, 3H).

Example 93

4-(3-Aminoazetidin-1-yl)-N-[(3R)-tetrahydrofuran-3-yl]pyrimidin-2-amine

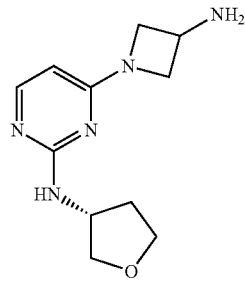 [SMILES: NC1CN(c2ccnc(N[C@@H]3CCOC3)n2)C1]

MS (ESI): mass calcd. for $C_{11}H_{17}N_5O$, 235.3 m/z found, 236.2 [M+H]. $^1$H NMR (CDCl$_3$): 7.64 (d, J=7.3, 1H), 6.04 (d, J=7.3, 1H), 4.55-4.68 (m, 3H), 4.30-4.41 (m, 3H), 3.94-4.10 (m, 2H), 3.85-3.91 (m, 1H), 3.79 (apparent dd, J=3.0, 9.6, 1H), 2.30-2.40 (m, 1H), 1.96-2.40 (m, 1H).

Example 94

4-(3-Aminoazetidin-1-yl)-N-[(2R)-tetrahydrofuran-2-ylmethyl]pyrimidin-2-amine

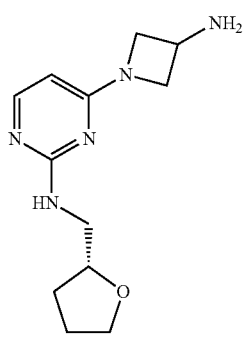 [SMILES: NC1CN(c2ccnc(NC[C@H]3CCCO3)n2)C1]

MS (ESI): mass calcd. for $C_{12}H_{19}N_5O$, 249.3 m/z found, 250.2 [M+H]. $^1$H NMR ($D_2O$): 7.63 (d, J=7.31, 1H), 6.02 (d, J=7.29, 1H), 4.58-4.68 (m, 2H), 4.30-4.41 (m, 3H), 4.12-4.20 (m, 1H), 3.75-3.90 (m, 2H), 3.48-3.55 (bs, 2H), 1.87-2.10 (m, 3H), 1.16-1.171 (m, 1H).

Example 95

5-[(3R)-3-(Methylamino)pyrrolidin-1-yl]-N-(2-methylpropyl)pyridazin-3-amine

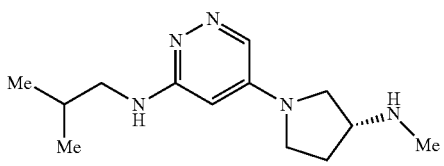 [SMILES: CN[C@@H]1CCN(c2cnnc(NCC(C)C)c2)C1]

[1-(6-Chloro-pyridazin-4-yl)-pyrrolidin-3-yl]-methyl-carbamic acid tert-butyl ester. A solution of 3,5-dichloropyridazine (149 mg, 1.0 mmol) in THF (3 mL) at 23° C. was treated with (R)-methyl-pyrrolidin-3-yl-carbamic acid tert-butyl ester (440 mg, 2.2 mmol) and the reaction stirred at 23° C. for 18 h. The reaction diluted with EtOAc (30 ml) and solution washed with water (2×5 ml) and combined organic solution dried and concentrated and crude material purified on 16 g $SiO_2$ (0 to 30% EtOAc: Hex) to yield 283 mg (91% yield) of the desired regioisomer and 17 mg (5% yield) of the undesired regioisomer. MS (ESI): mass calcd. for $C_{14}H_{21}ClN_4O_2$, 312.5 m/z found, 313.5 [M+H]$^+$. [1-(6-Isobutylamino-pyridazin-4-yl)-pyrrolidin-3-yl]-methyl-carbamic acid tert-butyl ester. A solution of [1-(6-chloro-pyridazin-4-yl)-pyrrolidin-3-yl]-methyl-carbamic acid tert-butyl ester (32 mg, 0.1 mmol) in isobutylamine (1.0 ml) in a sealed tube was heated to 120° C. for 72 h. The resulting solution was purified directly on 12 g $SiO_2$ (0 to 5% $NH_3$/MeOH:$CH_2Cl_2$) to yield 20 mg (55% yield). Isobutyl-[5-(3-methylamino-pyrrolidin-1-yl)-pyridazin-3-yl]-amine dihydrochloride. To a stirring solution of [1-(6-isobutylamino-pyridazin-4-yl)-pyrrolidin-3-yl]-methyl-carbamic acid tert-butyl ester (19 mg, 0.06 mmol) in 96% formic acid (0.5 mL) was added 0.05 ml of aqueous 6N HCl. The mixture was stirred for 2 hr, diluted with MeOH and concentrated under reduced pressure (repeat 3×) to give the desired product as a white solid (101 mg, >99%). MS (ESI): mass calcd. for $C_{13}H_{23}N_5$, 249.4 m/z found, 250.2 [M+H]. $^1$H NMR (400 MHz, $CD_3OD$): 8.12 (d, J=2.5, 1H), 6.08 (s, 1H), 4.11-4.01 (m, 1H), 4.04-3.47 (m, 4H), 3.35 (s, 1H), 3.15 (d, J=7.0, 2H), 2.82 (s, 3H), 2.65-2.53 (m, 1H), 2.43-2.31 (m, J=5.6, 1H), 1.96 (dt, J=13.4, 6.7, 1H), 1.03 (d, J=6.7, 6H).

The compounds in Example 96 through Example 100 were prepared using methods analogous to those described for Example 95.

Example 96

N-Bicyclo[2.2.1]hept-2-yl-5-[(3R)-3-(methylamino)pyrrolidin-1-yl]pyridazin-3-amine

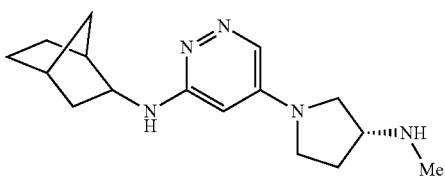 [SMILES: CN[C@@H]1CCN(c2cnnc(NC3CC4CCC3C4)c2)C1]

MS (ESI): mass calcd. for $C_{16}H_{25}N_5$, 287.4 m/z found, 288.2 [M+H]$^+$. $^1$H NMR ($CDCl_3$): 8.07 (d, J=2.5, 1H), 5.44 (d, J=2.2, 1H), 4.60 (s, 1H), 3.51 (dd, J=15.3, 9.3, 2H), 3.40 (dd, J=12.2, 6.6, 3H), 3.14 (dd, J=9.9, 4.5, 1H), 2.49 (s, 3H), 2.29 (d, J=12.1, 2H), 2.21 (dd, J=14.0, 6.4, 1H), 1.95-1.79 (m, 2H), 1.49 (dd, J=20.4, 9.0, 4H), 1.33-1.10 (m, 5H).

Example 97

5-[(3R)-3-(Methylamino)pyrrolidin-1-yl]-N-[(1S,2S,3S,5R)-2,6,6-trimethylbicyclo[3.1.1]hept-3-yl]pyridazin-3-amine

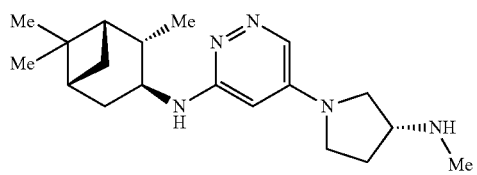

MS (ESI): mass calcd. for $C_{19}H_{31}N_5$, 329.5 m/z found, 330.3 [M+H]$^+$. $^1$H NMR ($CDCl_3$): 8.07 (d, J=2.4, 1H), 5.49 (d, J=2.4, 1H), 4.58 (s, 1H), 3.93 (s, 1H), 3.58-3.44 (m, 3H), 3.44-3.29 (m, 3H), 3.14 (dd, J=9.8, 4.6, 1H), 2.67 (s, 1H), 2.49 (s, 3H), 2.40 (s, 1H), 2.21 (dd, J=13.4, 7.0, 1H), 1.98 (s, 1H), 1.88 (t, J=13.2, 3H), 1.65 (d, J=14.0, 2H), 1.50-1.43 (m, 2H), 1.24 (s, 3H), 1.17 (d, J=7.1, 3H), 1.07 (s, 3H), 0.96 (d, J=9.8, 1H).

Example 98

N-Cyclohexyl-5-[(3R)-3-(methylamino)pyrrolidin-1-yl]pyridazin-3-amine

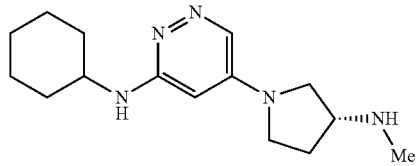 [SMILES: CN[C@@H]1CCN(c2cnnc(NC3CCCCC3)c2)C1]

MS (ESI): mass calcd. for $C_{15}H_{25}N_5$, 275.4 m/z found, 276.2 [M+H]$^+$. $^1$H NMR (D$_2$O): 7.99 (d, J=2.3, 1H), 5.90 (s, 1H), 4.08 (s, 1H), 3.76 (s, 4H), 3.52 (s, 1H), 2.81 (s, 3H), 2.64-2.49 (m, 1H), 2.34 (d, J=5.8, 1H), 1.98 (s, 2H), 1.74 (s, 2H), 1.60 (s, 1H), 1.45-1.13 (m, 5H).

Example 99

N-(Cyclopropylmethyl)-5-[(3R)-3-(methylamino)pyrrolidin-1-yl]pyridazin-3-amine

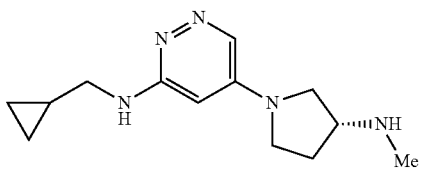 [SMILES: CN[C@@H]1CCN(c2cnnc(NCC3CC3)c2)C1]

MS (ESI): mass calcd. for $C_{13}H_{21}N_5$, 247.4 m/z found, 248.2 [M+H]$^+$. $^1$H NMR (CDCl$_3$): 8.09 (d, J=2.5, 1H), 5.47 (d, J=2.5, 1H), 4.70 (s, 1H), 3.56-3.44 (m, 2H), 3.43-3.29 (m, 2H), 3.13 (dd, J=7.0, 5.4, 3H), 2.48 (s, 3H), 2.25-2.12 (m, 1H), 1.89 (td, J=13.1, 5.8, 1H), 1.15-1.00 (m, 1H), 0.59-0.49 (m, 2H), 0.28-0.22 (m, 2H).

Example 100

N-Butyl-5-[(3R)-3-(methylamino)pyrrolidin-1-yl]pyridazin-3-amine

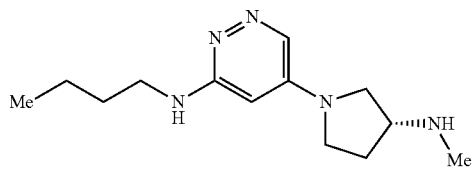 [SMILES: CCCCNc1cc(N2CC[C@@H](NC)C2)cnn1]

MS (ESI): mass calcd. for $C_{13}H_{23}N_5$, 249.4 m/z found, 250.2 [M+H]$^+$. $^1$H NMR (D$_2$O): 8.01 (s, 1H), 5.93 (s, 1H), 4.09 (s, 1H), 3.74 (s, 4H), 3.31 (dd, J=13.2, 6.2, 2H), 2.81 (s, 3H), 2.59 (d, J=6.8, 1H), 2.35 (s, 1H), 1.69-1.55 (m, 2H), 1.39 (dd, J=14.9, 7.4, 2H), 0.91 (t, J=7.4, 3H).

Example 101

5-(4-Methylpiperazin-1-yl)-N-(2-methylpropyl)pyridazin-3-amine

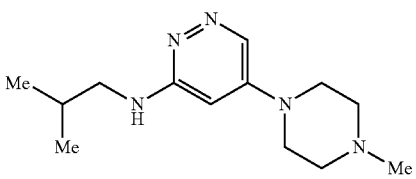 [SMILES: CC(C)CNc1cc(N2CCN(C)CC2)cnn1]

3-Chloro-5-(4-methyl-piperazin-1-yl)-pyridazine. A solution of 3,5-dichloropyridazine (298 mg, 2.0 mmol) in THF (6 mL) at 23° C. was treated with N-methyl piperazine (490 µL, 2.2 mmol) and the reaction stirred at 23° C. for 18 h. The reaction diluted with EtOAc (30 ml) and solution washed with water (2×5 ml), and the aqueous back extracted with chloroform and combined organic solution dried and concentrated and crude material purified on 12 g SiO$_2$ (0 to 5% NH$_3$/MeOH: CH$_2$Cl$_2$) to yield 267 mg (60% yield) of the desired regioisomer. MS (ESI): mass calcd. for $C_9H_{13}ClN_4$, 212.5 m/z found, 213.3 [M+H]$^+$.

5-(4-Methylpiperazin-1-yl)-N-(2-methylpropyl)pyridazin-3-amine. A solution of 3-chloro-5-(4-methyl-piperazin-1-yl)-pyridazine (103 mg, 0.5 mmol) in DME was treated with isobutylamine (145 µL, 1.5 mmol), Pd(OAc)$_2$ (23 mg, 0.03 mmol), and BINAP (22 mg, 0.04 mmol) in a sealed tube and heated to 85° C. for 1 h. The reaction was diluted with chloroform (15 ml), washed with water (5 ml) and the combined organics dried and concentrated and purified directly on 12 g SiO$_2$ (0 to 5% NH$_3$/MeOH:CH$_2$Cl$_2$) to yield 34 mg (28% yield). The HCl salt was prepared by dissolving the product in chloroform and adding 1.0 N HCl (0.3 mL, 0.3 mmol) in diethyl ether, and concentrating. MS (ESI): mass calcd. for $C_9H_{20}N_6$, 249.4 m/z found, 250.2 [M+H]$^+$. $^1$H NMR (DMSO-d$_6$): 14.04-13.83 (m, 1H), 11.61-11.35 (m, 1H), 8.46 (s, 2H), 8.33 (s, 1H), 6.51 (s, 1H), 4.38-4.16 (m, 2H), 3.64-3.48 (m, 4H), 3.22-3.06 (m, 4H), 2.86-2.73 (m, 3H), 1.91-1.78 (m, 1H), 0.95 (d, J=6.6, 6H).

The compounds in Example 102 through Example 206 were prepared using methods analogous to those described in Example 64, Method B.

Example 102

N-(Cyclohexylmethyl)-4-[3-(methylamino)azetidin-1-yl]pyrimidin-2-amine

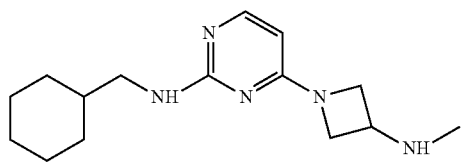 [SMILES: CNC1CN(c2ccnc(NCC3CCCCC3)n2)C1]

MS (ESI): mass calcd. for $C_{15}H_{25}N_5$, 275.4 m/z found, 276.2 [M+H]$^+$. $^1$H NMR (300 MHz, CD$_3$OD): 7.74 (d, J=7.2

Hz, 1H), 6.10 (d, J=6.9 Hz, 1H), 4.67-4.57 (m, 2H), 4.42-4.28 (m, 3H), 2.79 (s, 3H), 1.80-1.63 (m, 6H), 1.39-1.26 (m, 4H), 1.07-1.00 (m, 2H).

Example 103

4-[(3R)-3-Aminopyrrolidin-1-yl]-N-[(1R)-1-cyclohexylethyl]pyrimidin-2-amine

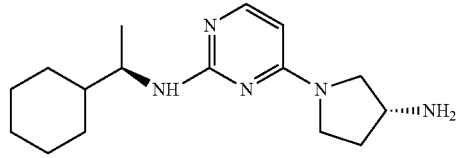 [SMILES: C[C@@H](Nc1nccc(N2CC[C@@H](N)C2)n1)C1CCCCC1]

MS (ESI): mass calcd. for $C_{16}H_{27}N_5$, 289.43 m/z found, 290.2 [M+H]$^+$. $^1$H NMR (300 MHz, CD$_3$OD): 7.76 (d, J=7.2 Hz, 1H), 6.26 (t, J=7.2 Hz, 1H), 4.15-3.68 (m, 6H), 2.60-2.48 (m, 1H), 2.32-2.21 (m, 1H), 1.90-1.70 (m, 5H), 1.60-1.40 (m, 1H), 1.40-1.30 (m, 3H), 1.25 (d, J=6.6 Hz, 3H), 1.20-1.00 (m, 2H).

Example 104

N-{[(1S,2S,5S)-6,6-Dimethylbicyclo[3.1.1]hept-2-yl]methyl}-4-[(3aR,6aR)-hexahydropyrrolo[3,4-b]pyrrol-5(1H)-yl]pyrimidin-2-amine

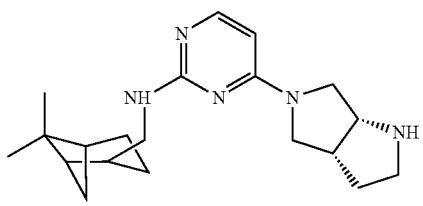 [SMILES: CC1(C)C2CCC(CNc3nccc(N4C[C@H]5CCN[C@H]5C4)n3)C1C2]

MS (ESI): mass calcd. for $C_{20}H_{31}N_5$, 341.5 m/z found, 342.3 [M+H]$^+$. $^1$H NMR (300 MHz, CD$_3$OD): 7.75 (d, J=7.5 Hz, 1H), 6.27 (d, J=7.2 Hz, 1H), 4.60-3.92 (m, 5H), 3.74-3.44 (m, 5H), 2.45-2.32 (m, 3H), 2.20-2.00 (m, 6H), 1.97-1.60 (m, 1H), 1.32 (s, 3H), 1.13 (s, 3H), 1.00-0.93 (m, 1H).

Example 105

N-[(6,6-Dimethylbicyclo[3.1.1]hept-2-yl)methyl]-4-[3-(methylamino)azetidin-1-yl]pyrimidin-2-amine

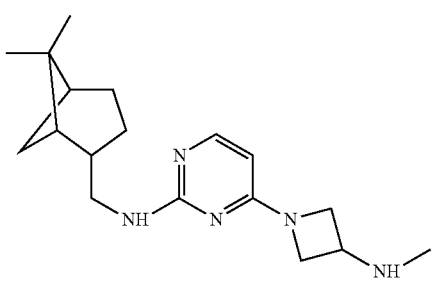

MS (ESI): mass calcd. for $C_{18}H_{29}N_5$, 315.47 m/z found, 316.3 [M+H]$^+$. $^1$H NMR (300 MHz, CD$_3$OD): 7.74 (d, J=7.2 Hz, 1H), 6.10 (d, J=7.2 Hz, 1H), 4.75-4.57 (m, 2H), 4.42-4.28 (m, 3H), 3.55-3.45 (m, 2H), 2.79 (s, 3H), 2.44-2.36 (m, 2H), 2.04-1.96 (m, 5H), 1.60-1.57 (m, 1H), 1.25 (s, 3H), 1.12 (s, 3H), 0.99-0.95 (m, 1H).

Example 106

4-[(3R)-3-Aminopyrrolidin-1-yl]-N-[(6,6-dimethylbicyclo[3.1.1]hept-2-yl)methyl]pyrimidin-2-amine

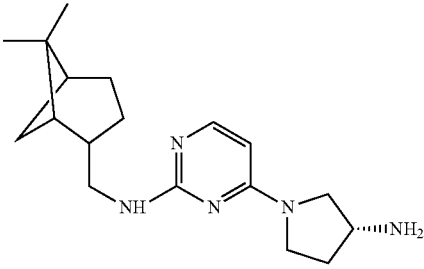 [SMILES: CC1(C)C2CCC(CNc3nccc(N4CC[C@@H](N)C4)n3)C1C2]

MS (ESI): mass calcd. for $C_{18}H_{29}N_5$, 315.47 m/z found, 316.3 [M+H]$^+$. $^1$H NMR (300 MHz, CD$_3$OD): 7.75 (d, J=7.5 Hz, 1H), 6.28-6.23 (m, 1H), 4.14-3.67 (m, 5H), 3.55-3.45 (m, 2H), 2.59-2.41 (m, 3H), 2.30-2.20 (m, 1H), 2.03-1.88 (m, 5H), 1.63-1.58 (m, 1H), 1.25 (s, 3H), 1.12 (s, 3H), 0.98-0.88 (m, 1H).

Example 107

N-(Cyclohexylmethyl)-4-[(3aR,6aR)-hexahydropyrrolo[3,4-b]pyrrol-5(1H)-yl]pyrimidin-2-amine

MS (ESI): mass calcd. for $C_{17}H_{27}N_5$, 301.44 m/z found, 302.2 [M+H]$^+$. $^1$H NMR (300 MHz, CD$_3$OD): 7.77 (d, J=7.2 Hz, 1H), 6.28 (d, J=6.6 Hz, 1H), 4.52-3.93 (m, 4H), 3.77-3.38 (m, 6H), 2.44-2.37 m, 1H), 2.20-2.00 (m, 1H), 1.90-1.60 (m, 6H), 1.35-1.03 (m, 5H).

Example 108

4-[3-(Methylamino)azetidin-1-yl]-N-(tetrahydro-2H-pyran-4-yl)pyrimidin-2-amine

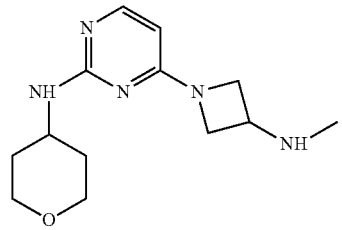 [SMILES: CNC1CN(c2ccnc(NC3CCOCC3)n2)C1]

MS (ESI): mass calcd. for $C_{13}H_{21}N_5O$, 263.35 m/z found, 264.2 [M+H]$^+$. $^1$H NMR (300 MHz, CD$_3$OD): 7.75 (d, J=7.2 Hz, 1H), 6.13 (d, J=7.2 Hz, 1H), 4.70-4.60 (m, 2H), 4.50-4.28

(m, 3H), 4.20-3.96 (m, 3H), 3.56-3.52 (m, 2H), 2.78 (s, 3H), 2.00-1.90 (m, 2H), 1.66-1.61 (m, 2H).

Example 109

4-[(3S)-3-Aminopyrrolidin-1-yl]-N-(cyclopropylmethyl)pyrimidin-2-amine

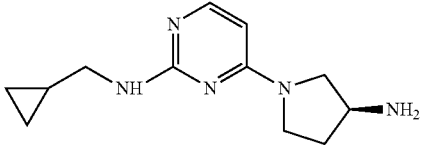 [SMILES: N[C@H]1CCN(c2ccnc(NCC3CC3)n2)C1]

MS (ESI): mass calcd. for $C_{12}H_{19}N_5$, 233.32 m/z found, 234.2 [M+H]$^+$. $^1$H NMR (300 MHz, CD$_3$OD): 7.76 (d, J=7.2 Hz, 1H), 6.29-6.25 (m, 1H), 4.15-3.70 (m, 5H), 2.59-2.46 (m, 1H), 2.32-2.21 (m, 1H), 1.20-1.16 (m, 1H), 0.59 (d, J=7.5 Hz, 2H), 0.33 (d, J=4.8 Hz, 2H).

Example 110

1-({4-[(3S)-3-Aminopyrrolidin-1-yl]pyrimidin-2-yl}amino)-2-methylpropan-2-ol

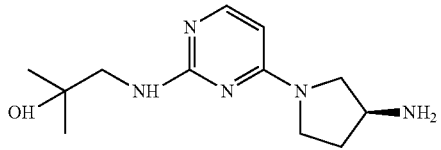 [SMILES: CC(C)(O)CNc1nccc(N2CC[C@H](N)C2)n1]

MS (ESI): mass calcd. for $C_{12}H_{21}N_5O$, 251.33 m/z found, 252.2 [M+H]$^+$. $^1$H NMR (300 MHz, CD$_3$OD): 7.79 (d, J=7.2 Hz, 1H), 6.29-6.25 (m, 1H), 4.07-3.67 (m, 5H), 3.49-3.48 (m, 2H), 2.59-2.46 (m, 1H), 2.30-2.17 (m, 1H), 1.26 (s, 6H).

Example 111

4-[(3S)-3-Aminopyrrolidin-1-yl]-N-(2,2-dimethylpropyl)pyrimidin-2-amine

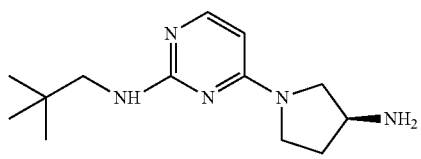 [SMILES: CC(C)(C)CNc1nccc(N2CC[C@H](N)C2)n1]

MS (ESI): mass calcd. for $C_{13}H_{23}N_5$, 249.36 m/z found, 250.2 [M+H]$^+$. $^1$H NMR (300 MHz, CD$_3$OD): 7.78 (d, J=7.5 Hz, 1H), 6.28-6.24 (m, 1H), 4.49-3.67 (m, 5H), 2.61-2.47 (m, 1H), 2.30-2.18 (m, 1H), 1.00 (s, 9H).

Example 112

N-Cyclopropyl-4-piperazin-1-ylpyrimidin-2-amine

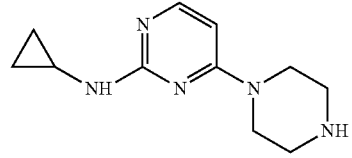 [SMILES: c1cc(N2CCNCC2)nc(NC2CC2)n1]

MS (ESI): mass calcd. for $C_{11}H_{17}N_5$, 219.29 m/z found, 220.1 [M+H]$^+$. $^1$H NMR (300 MHz, CD$_3$OD): 7.75 (d, J=7.5 Hz, 1H), 6.53 (d, J=7.5 Hz, 1H), 4.13 (br s, 2H), 3.90 (br s, 2H), 3.27 (br s, 4H), 2.56 (br s, 1H), 1.00-0.70 (m, 2H), 0.58 (br s, 2H).

Example 113

N-[(1R)-1-Cyclohexylethyl]-4-[3-(methylamino)azetidin-1-yl]pyrimidin-2-amine

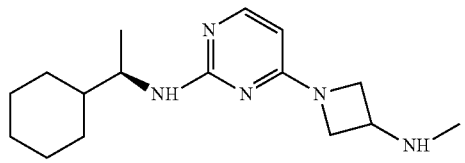 [SMILES: CNC1CN(c2ccnc(N[C@H](C)C3CCCCC3)n2)C1]

MS (ESI): mass calcd. for $C_{16}H_{27}N_5$, 289.43 m/z found, 290.3 [M+H]$^+$. $^1$H NMR (300 MHz, CD$_3$OD): 7.73 (d, J=7.2 Hz, 1H), 6.09 (d, J=7.2 Hz, 1H), 4.67-4.55 (m, 2H), 4.43-4.25 (m, 3H), 4.10-4.00 (m, 1H), 2.78 (s, 3H), 1.80-1.68 (m, 5H), 1.60-1.04 (m, 6H), 1.21 (d, J=6.6 Hz, 3H).

Example 114

2-Methyl-1-({4-[(3R)-3-(methylamino)pyrrolidin-1-yl]pyrimidin-2-yl}amino)propan-2-ol

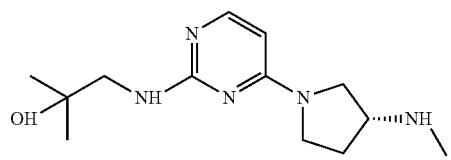 [SMILES: CN[C@@H]1CCN(c2ccnc(NCC(C)(C)O)n2)C1]

MS (ESI): mass calcd. for $C_{13}H_{23}N_5O$, 265.36 m/z found, 266.1 [M+H]$^+$. $^1$H NMR (300 MHz, CD$_3$OD): 7.80 (d, J=7.5

Hz, 1H), 6.28 (d, J=7.2 Hz, 1H), 4.06-3.50 (m, 7H), 2.84 (s, 3H), 2.60-2.55 (m, 1H), 2.50-2.30 (m, 1H), 1.28 (s, 6H).

Example 115

N-[(1R)-1-Cyclohexylethyl]-4-[(3aR,6aR)-hexahydropyrrolo[3,4-b]pyrrol-5(1H)-yl]pyrimidin-2-amine

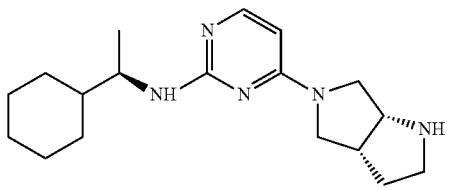 [SMILES: C[C@@H](Nc1nccc(N2C[C@H]3CCN[C@H]3C2)n1)C1CCCCC1]

MS (ESI): mass calcd. for C$_{18}$H$_{29}$N$_5$, 315.47 m/z found, 316.3 [M+H]$^+$. $^1$H NMR (300 MHz, CD$_3$OD): 7.76 (d, J=7.5 Hz, 1H), 6.26 (d, J=7.2 Hz, 1H), 4.60-4.40 (m, 2H), 4.20-3.90 (m, 3H), 3.73-3.58 (m, 1H), 3.70-3.60 (m, 3H), 2.45-2.33 (m, 1H), 2.20-2.00 (m, 1H), 1.90-1.70 (m, 5H), 1.60-1.40 (m, 1H), 1.40-1.30 (m, 3H), 1.25 (d, J=6.6 Hz, 3H), 1.20-1.00 (m, 2H).

Example 116

4-[(3R)-3-Aminopyrrolidin-1-yl]-N-[(1S,2S,3S,5R)-2,6,6-trimethylbicyclo[3.1.1]hept-3-yl]pyrimidin-2-amine

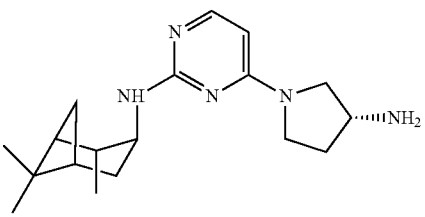 [SMILES: CC1C(Nc2nccc(N3CC[C@@H](N)C3)n2)CC2CC1C2(C)C]

MS (ESI): mass calcd. for C$_{18}$H$_{29}$N$_5$, 315.47 m/z found, 316.2 [M+H]$^+$. $^1$H NMR (300 MHz, CD$_3$OD): 7.77 (d, J=7.2 Hz, 1H), 6.28 (br s, 1H), 4.62-4.41 (m, 1H), 4.18-3.64 (m, 5H), 2.78-2.41 (m, 3H), 2.32-1.75 (m, 5H), 1.21 (s, 3H), 1.21-1.08 (m, 7H).

Example 117

4-[(3R)-3-Aminopyrrolidin-1-yl]-N-(2-phenylethyl)pyrimidin-2-amine

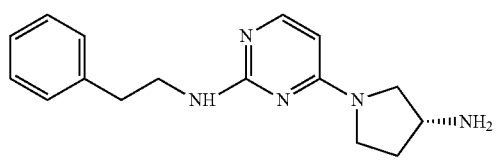 [SMILES: N[C@@H]1CCN(c2ccnc(NCCc3ccccc3)n2)C1]

MS (ESI): mass calcd. for C$_{16}$H$_{21}$N$_5$, 283.38 m/z found, 284.1 [M+H]$^+$. $^1$H NMR (300 MHz, CD$_3$OD): 7.74 (d, J=7.2 Hz, 1H), 7.32-7.23 (m, 5H), 6.28-6.26 (m, 1H), 4.10-3.71 (m, 7H), 2.97 (t, J=7.2 Hz, 2H), 2.41-2.18 (m, 2H).

Example 118

4-[(3S)-3-Aminopyrrolidin-1-yl]-N-(pyridin-2-ylmethyl)pyrimidin-2-amine

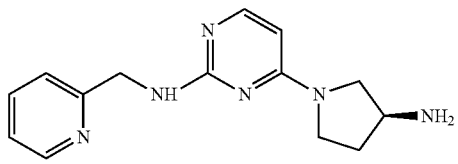 [SMILES: N[C@H]1CCN(c2ccnc(NCc3ccccn3)n2)C1]

MS (ESI): mass calcd. for C$_{14}$H$_{18}$N$_6$, 270.34 m/z found, 271.2 [M+H]$^+$. $^1$H NMR (300 MHz, CD$_3$OD): 8.88-8.86 (m, 1H), 8.65-8.63 (m, 1H), 8.20 (d, J=7.8 Hz, 1H), 8.05 (t, J=6.6 Hz, 1H), 7.91 (d, J=7.2 HZ, 1H), 6.41-6.38 (m, 1H), 5.11 (s, 2H), 4.12-3.98 (m, 1H), 3.84-3.35 (m, 4H), 2.61-2.38 (m, 1H), 2.29-2.08 (m, 1H).

Example 119

N-(Cyclopentylmethyl)-4-(4-methylpiperazin-1-yl)pyrimidin-2-amine

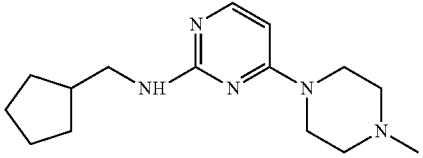 [SMILES: CN1CCN(c2ccnc(NCC3CCCC3)n2)CC1]

MS (ESI): mass calcd. for C$_{15}$H$_{25}$N$_5$, 275.4 m/z found, 276.2 [M+H]$^+$. $^1$H NMR (300 MHz, CD$_3$OD): 7.83 (d, J=6.0 Hz, 1H), 6.59 (br s, 1H), 5.15 (m, 1H), 4.42 (m, 1H), 3.71-3.27 (m, 8H), 2.99 (s, 3H), 2.22 (m, 1H), 1.90-1.60 (m, 6H), 1.31 (m, 2H).

Example 120

2-Methyl-1-{[4-(4-methylpiperazin-1-yl)pyrimidin-2-yl]-amino}propan-2-ol

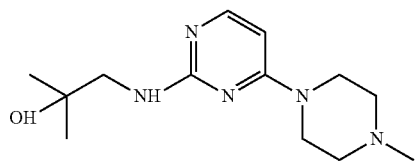 [SMILES: CN1CCN(c2ccnc(NCC(C)(C)O)n2)CC1]

MS (ESI): mass calcd. for C$_{13}$H$_{23}$N$_5$O, 265.36 m/z found, 266.2 [M+H]$^+$. $^1$H NMR (300 MHz, CD$_3$OD): 7.87 (d, J=7.2

Hz, 1H), 6.59 (d, J=7.2 Hz, 1H), 5.19 (m, 1H), 4.45 (m, 1H), 3.75-3.26 (m, 8H), 2.99 (s, 3H), 1.28 (s, 6H).

Example 121

N-(Cyclopentylmethyl)-4-[(3R)-3-(methylamino)pyrrolidin-1-yl]pyrimidin-2-amine

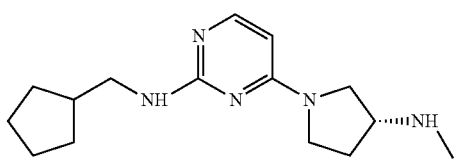 [SMILES: CN[C@@H]1CCN(c2ccnc(NCC3CCCC3)n2)C1]

MS (ESI): mass calcd. for C$_{15}$H$_{25}$N$_5$, 275.4 m/z found, 276.2 [M+H]$^+$. $^1$H NMR (300 MHz, CD$_3$OD): 7.74 (d, J=7.5 Hz, 1H), 6.24 (m, 1H), 4.03-3.37 (m, 7H), 2.59 (s, 3H), 2.70-2.50 (m, 1H), 2.30-2.22 (m, 2H), 1.83-1.64 (m, 6H), 1.34-1.30 (m, 2H).

Example 122

2-Methyl-1-({4-[3-(methylamino)azetidin-1-yl]pyrimidin-2-yl}amino)propan-2-ol

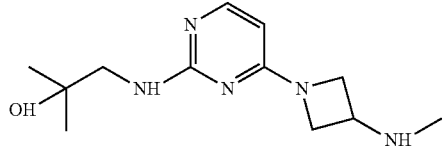 [SMILES: CNC1CN(c2ccnc(NCC(C)(C)O)n2)C1]

MS (ESI): mass calcd. for C$_{12}$H$_{21}$N$_5$O, 251.33 m/z found, 252.1 [M+H]$^+$. $^1$H NMR (300 MHz, CD$_3$OD): 7.78 (d, J=7.2 Hz, 1H), 6.13 (d, J=6.9 Hz, 1H), 4.69-4.58 (m, 2H), 4.45-4.30 (m, 3H), 3.55-3.48 (m, 2H), 2.80 (s, 3H), 1.22 (s, 6H).

Example 123

4-[(3R)-3-Aminopyrrolidin-1-yl]-N-(cyclopentylmethyl)pyrimidin-2-amine

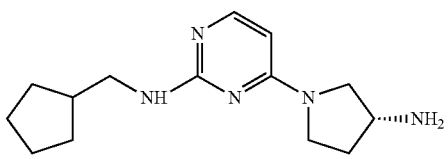 [SMILES: N[C@@H]1CCN(c2ccnc(NCC3CCCC3)n2)C1]

MS (ESI): mass calcd. for C$_{14}$H$_{23}$N$_5$, 261.37 m/z found, 262.1 [M+H]$^+$. $^1$H NMR (300 MHz, CD$_3$OD): 7.76 (d, J=7.2 Hz, 1H), 6.29-6.26 (m, 1H), 4.08-3.50 (m, 7H), 2.60-2.40 (m, 1H), 2.40-2.20 (m, 2H), 1.83-1.65 (m, 6H), 1.34-1.32 (m, 2H).

Example 124

N-[2-(Methylsulfanyl)ethyl]-4-piperazin-1-ylpyrimidin-2-amine

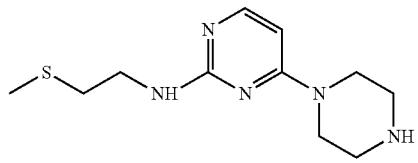 [SMILES: CSCCNc1nccc(N2CCNCC2)n1]

MS (ESI): mass calcd. for C$_{11}$H$_{19}$N$_5$S, 253.37 m/z found, 254.1 [M+H]$^+$. $^1$H NMR (300 MHz, CD$_3$OD): 7.73 (d, J=7.8 Hz, 1H), 6.47 (d, J=7.8 Hz, 1H), 4.16 (br s, 2H), 3.92 (br s, 2H), 3.58 (m, 2H), 3.31-3.28 (m, 4H), 2.66 (t, J=6.6 Hz, 2H), 2.05 (s, 3H).

Example 125

4-[(3aR,6aR)-Hexahydropyrrolo[3,4-b]pyrrol-5(1H)-yl]-N-[(1R,2S,4R)-1,7,7-trimethylbicyclo[2.2.1]hept-2-yl]pyrimidin-2-amine

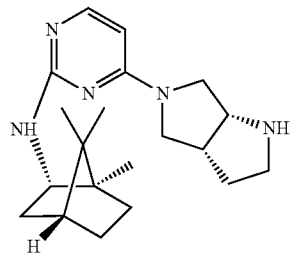 [SMILES: CC1(C)[C@@H]2CC[C@@]1(C)[C@@H](Nc1nccc(N3C[C@H]4CCN[C@H]4C3)n1)C2]

MS (ESI): mass calcd. for C$_{20}$H$_{31}$N$_5$, 341.5 m/z found, 342.2 [M+H]$^+$. $^1$H NMR (300 MHz, CD$_3$OD): 7.71 (d, J=7.2 Hz, 1H), 6.18 (d, J=7.5 Hz, 1H), 4.50-4.30 (m, 2H), 4.10-3.80 (m, 3H), 3.70-3.40 (m, 4H), 2.37-2.27 (m, 2H), 2.10-1.20 (m, 7H), 0.98 (s, 3H), 0.90 (s, 3H), 0.85 (s, 3H).

Example 126

4-[3-(Methylamino)azetidin-1-yl]-N-[(1R,2S,4R)-1,7,7-trimethylbicyclo[2.2.1]hept-2-yl]pyrimidin-2-amine

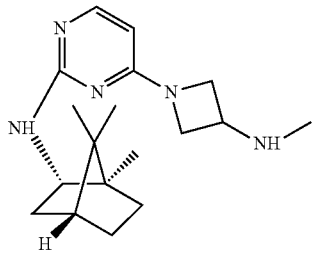 [SMILES: CNC1CN(c2ccnc(N[C@H]3C[C@H]4CC[C@]3(C)C4(C)C)n2)C1]

MS (ESI): mass calcd. for C$_{18}$H$_{29}$N$_5$, 315.47 m/z found, 316.3 [M+H]$^+$. $^1$H NMR (300 MHz, CD$_3$OD): 7.77 (d, J=7.2 Hz, 1H), 6.11 (d, J=7.2 Hz, 1H), 4.73-4.56 (m, 2H), 4.44-4.29

(m, 3H), 2.80 (s, 3H), 2.50-2.40 (m, 1H), 2.00-1.30 (m, 6H), 1.04 (s, 3H), 0.97 (s, 3H), 0.91 (s, 3H).

Example 127

4-[(3R)-3-Aminopyrrolidin-1-yl]-N-[(1R,2S,4R)-1,7,7-trimethylbicyclo[2.2.1]hept-2-yl]pyrimidin-2-amine

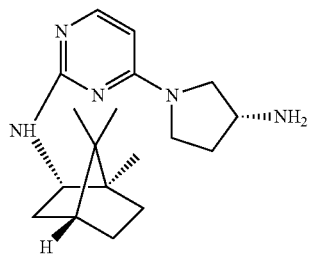 [SMILES: CC1(C)[C@@H]2CC[C@@]1(C)[C@@H](Nc1nccc(N3CC[C@@H](N)C3)n1)C2]

MS (ESI): mass calcd. for $C_{18}H_{29}N_5$, 315.47 m/z found, 316.2 [M+H]$^+$. $^1$H NMR (300 MHz, CD$_3$OD): 7.78 (d, J=7.5 Hz, 1H), 6.28-6.24 (m, 1H), 4.60-4.40 (m, 1H), 4.16-3.73 (m, 5H), 2.60-2.26 (m, 3H), 1.90-1.74 (m, 3H), 1.53-1.30 (m, 3H), 1.13 (s, 3H), 1.00 (s, 3H), 0.92 (s, 3H).

Example 128

4-[(3S)-3-Aminopyrrolidin-1-yl]-N-(2-methoxyethyl)pyrimidin-2-amine

MS (ESI): mass calcd. for $C_{11}H_{19}N_5O$, 237.31 m/z found, 238.2 [M+H]$^+$. $^1$H NMR (300 MHz, CD$_3$OD): 7.77 (d, J=7.2 Hz, 1H), 6.30-6.25 (m, 1H), 4.15-3.73 (m, 5H), 3.70-3.59 (m, 4H), 3.39 (s, 3H), 2.59-2.48 (m, 1H), 2.31-2.20 (m, 1H).

Example 129

4-[(3S)-3-Aminopyrrolidin-1-yl]-N-cyclohexylpyrimidin-2-amine

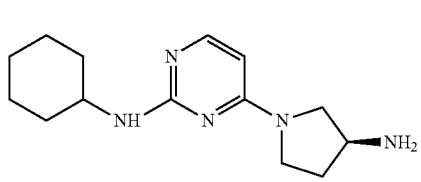 [SMILES: N[C@H]1CCN(c2ccnc(NC3CCCCC3)n2)C1]

MS (ESI): mass calcd. for $C_{14}H_{23}N_5$, 261.37 m/z found, 262.2 [M+H]$^+$. $^1$H NMR (300 MHz, CD$_3$OD): 7.75 (d, J=7.5 Hz, 1H), 6.25 (t, J=6.9 Hz, 1H), 4.07-3.68 (m, 6H), 2.59-2.49 (m, 1H), 2.31-2.20 (m, 1H), 2.03-2.00 (m, 2H), 1.83-1.81 (m, 2H), 1.50-1.31 (m, 6H).

Example 130

3-({4-[(3S)-3-Aminopyrrolidin-1-yl]pyrimidin-2-yl}amino)-2,2-dimethylpropan-1-ol

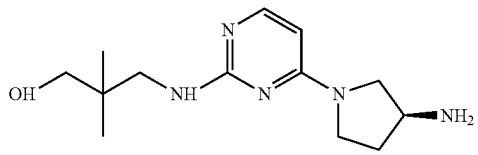 [SMILES: CC(C)(CO)CNc1nccc(N2CC[C@H](N)C2)n1]

MS (ESI): mass calcd. for $C_{13}H_{23}N_5O$, 265.36 m/z found, 266.2 [M+H]$^+$. $^1$H NMR (300 MHz, CD$_3$OD): 7.72 (d, J=7.5 Hz, 1H), 6.21 (d, J=7.2 Hz, 1H), 4.08-3.61 (m, 5H), 3.50-3.26 (m, 4H), 2.53-2.41 (m, 1H), 2.24-2.14 (m, 1H), 0.91 (s, 6H).

Example 131

N-Benzyl-4-piperazin-1-ylpyrimidin-2-amine

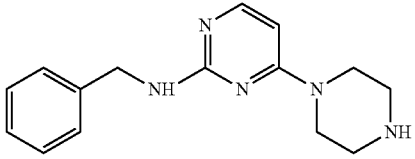 [SMILES: c1ccc(CNc2nccc(N3CCNCC3)n2)cc1]

MS (ESI): mass calcd. for $C_{16}H_{19}N_5$, 269.35 m/z found, 270.2 [M+H]$^+$. $^1$H NMR (300 MHz, DMSO-d$_6$): 12.57 (br s, 1H), 9.44 (br s, 2H), 8.74 (br s, 1H), 7.93 (d, J=7.2 Hz, 1H), 7.34-7.24 (m, 5H), 6.52 (d, J=7.5 Hz, 1H), 4.54 (d, J=5.7 Hz, 2H), 3.95 (br s, 4H), 3.13 (br s, 4H).

Example 132

N-(2-Phenylethyl)-4-piperazin-1-ylpyrimidin-2-amine

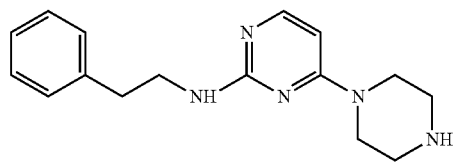 [SMILES: c1ccc(CCNc2nccc(N3CCNCC3)n2)cc1]

MS (ESI): mass calcd. for $C_{16}H_{21}N_5$, 283.38 m/z found, 284.2 [M+H]$^+$. $^1$H NMR (300 MHz, DMSO-d$_6$): 12.48 (br s, 1H), 9.58 (br s, 2H), 8.26 (br s, 1H), 7.91 (d, J=7.2 Hz, 1H), 7.30-7.18 (m, 5H), 6.50 (d, J=7.2 Hz, 1H), 3.97 (br s, 4H), 3.58-3.54 (m, 2H), 3.18 (br s, 4H), 2.82 (t, J=7.2 Hz, 2H).

Example 133

N-Bicyclo[2.2.1]hept-2-yl-4-piperazin-1-ylpyrimidin-2-amine

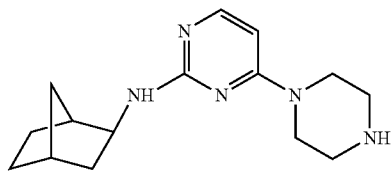 [SMILES: c1cc(N2CCNCC2)nc(NC2CC3CCC2C3)n1]

MS (ESI): mass calcd. for $C_{16}H_{23}N_5$, 273.38 m/z found, 274.2 [M+H]$^+$. $^1$H NMR (300 MHz, DMSO-d$_6$): 9.43 (br, s, 1H), 8.48 (d, J=4.8 Hz, 1H), 7.95 (br, s, 1H), 6.54 (d, J=7.2 Hz, 1H), 4.01 (br, s, 5H), 3.70-3.52 (m, 4H), 2.27-2.21 (m, 2H), 1.79-1.72 (m, 1H), 1.48-1.16 (m, 7H).

Example 134

4-piperazin-1-yl-N-[(1S,2S,3S,5R)-2,6,6-trimethyl-bicyclo[3.1.1]hept-3-yl]pyrimidin-2-amine

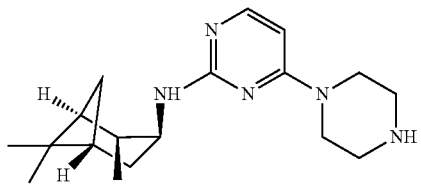 [SMILES: C[C@@H]1[C@@H](Nc2nccc(N3CCNCC3)n2)C[C@H]2C[C@@H]1C2(C)C]

MS (ESI): mass calcd. for $C_{18}H_{29}N_5$, 315.47 m/z found, 316.3 [M+H]$^+$. $^1$H NMR (300 MHz, CD$_3$OD): 7.80 (d, J=7.5 Hz, 1H), 6.54 (d, J=7.2 Hz, 1H), 4.42 (br, s, 1H), 4.11 (br, s, 4H), 3.61-3.58 (m, 1H), 3.38-3.03 (m, 4H), 2.67 (m, 1H), 2.50-2.48 (m, 1H), 2.05-2.00 (m, 2H), 1.91-1.83 (m, 2H), 1.73-1.66 (m, 1H), 1.25 (s, 3H), 1.16 (d, J=7.2 Hz, 3H), 1.07 (s, 3H), 1.04-1.00 (m, 1H).

Example 135

3-({4-[3-(Methylamino)azetidin-1-yl]pyrimidin-2-yl}amino)propan-1-ol

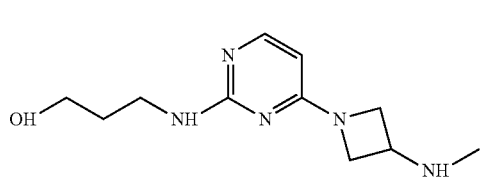 [SMILES: CNC1CN(c2ccnc(NCCCO)n2)C1]

MS (ESI): mass calcd. for $C_{11}H_{19}N_5O$, 237.31 m/z found, 238.2 [M+H]$^+$. $^1$H NMR (300 MHz, CD$_3$OD): 7.72 (d, J=72 Hz, 1H), 6.01 (d, J=7.2 Hz, 1H), 4.62-4.59 (m, 2H), 4.40-4.26 (m, 3H), 3.67-3.43 (m, 4H), 1.85-1.79 (m, 2H).

Example 136

2,2-Dimethyl-3-({4-[3-(methylamino)azetidin-1-yl]pyrimidin-2-yl}amino)propan-1-ol

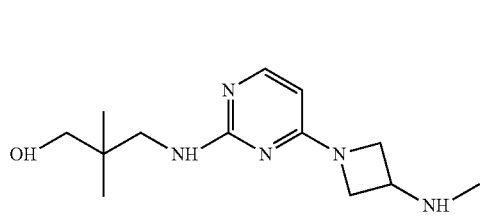 [SMILES: CNC1CN(c2ccnc(NCC(C)(C)CO)n2)C1]

MS (ESI): mass calcd. for $C_{13}H_{23}N_5O$, 265.36 m/z found, 266.2 [M+H]$^+$. $^1$H NMR (300 MHz, CD$_3$OD): 7.71 (d, J=7.2 Hz, 1H), 6.05 (d, J=6.9 Hz, 1H), 4.58-4.52 (m, 2H), 4.32-4.22 (m, 3H), 2.73 (s, 3H), 0.90 (s, 6H).

Example 137

3-[(4-piperazin-1-ylpyrimidin-2-yl)amino]propan-1-ol

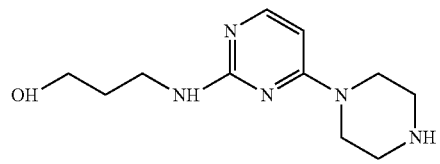 [SMILES: OCCCNc1nccc(N2CCNCC2)n1]

MS (ESI): mass calcd. for $C_{11}H_{19}N_5O$, 237.31 m/z found, 238.2 [M+H]$^+$. $^1$H NMR (300 MHz, CD$_3$OD): 7.71 (d, J=7.5 Hz, 1H), 6.44 (d, J=7.2 Hz, 1H), 4.16 (br s, 2H), 3.89 (br s, 2H), 3.59-3.44 (m, 4H), 3.28-3.25 (m, 4H), 1.79-1.71 (m, 2H).

Example 138

4-[(3aR,6aR)-Hexahydropyrrolo[3,4-b]pyrrol-5(1H)-yl]-N-(2-methylpropyl)pyrimidin-2-amine

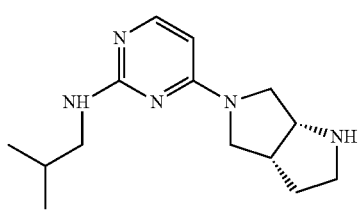 [SMILES: CC(C)CNc1nccc(N2C[C@H]3CCN[C@H]3C2)n1]

MS (ESI): mass calcd. for $C_{14}H_{23}N_5$, 261.37 m/z found, 262.1 [M+H]$^+$. $^1$H NMR (300 MHz, D$_2$O): 7.52 (d, J=7.2 Hz, 1H), 6.05 (br s, 1H), 4.43-4.36 (m, 1H), 4.17-3.13 (m, 9H), 2.29-2.22 (m, 1H), 1.99-1.93 (m, 1H), 1.91-1.77 (m, 1H), 0.82 (d, J=6.6 Hz, 6H).

Example 139

N-Cyclopentyl-4-[(3aR,6aR)-hexahydropyrrolo[3,4-b]pyrrol-5(1H)-yl]pyrimidin-2-amine

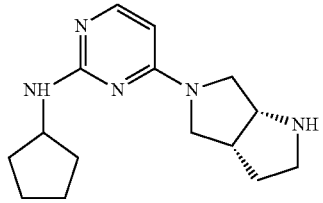 [SMILES: c1cc(N2C[C@H]3CCN[C@H]3C2)nc(NC2CCCC2)n1]

MS (ESI): mass calcd. for $C_{15}H_{23}N_5$, 273.38 m/z found, 274.1 [M+H]$^+$. $^1$H NMR (300 MHz, CD$_3$OD): 7.72 (d, J=6.0 Hz, 1H), 6.22 (br s, 1H), 4.44-3.43 (m, 9H), 2.34 (m, 1H), 2.07 (br s, 3H), 1.77-1.62 (m, 6H).

Example 140

4-[(3aR,6aR)-Hexahydropyrrolo[3,4-b]pyrrol-5(1H)-yl]-N-(2-methoxyethyl)pyrimidin-2-amine

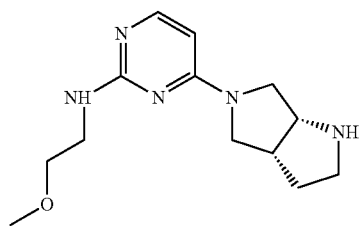 [SMILES: COCCNc1nccc(N2C[C@H]3CCN[C@H]3C2)n1]

MS (ESI): mass calcd. for $C_{13}H_{21}N_5O$, 263.35 m/z found, 264.1 [M+H]$^+$. $^1$H NMR (300 MHz, D$_2$O): 7.54 (d, J=7.2 Hz, 1H), 6.09-6.06 (m, 1H), 4.43-4.15 (m, 2H), 3.91-3.27 (m, 10H), 3.55 (s, 3H), 2.26-2.24 (m, 1H), 1.96-1.93 (m, 1H).

Example 141

4-[(3aR,6aR)-Hexahydropyrrolo[3,4-b]pyrrol-5(1H)-yl]-N-[(1R)-1-phenylethyl]pyrimidin-2-amine

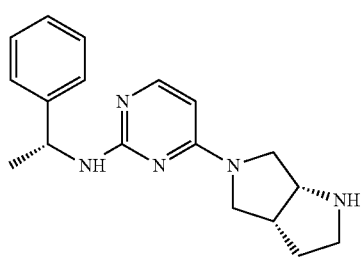 [SMILES: C[C@@H](Nc1nccc(N2C[C@H]3CCN[C@H]3C2)n1)c1ccccc1]

MS (ESI): mass calcd. for $C_{18}H_{23}N_5$, 309.42 m/z found, 310.2 [M+H]$^+$. $^1$H NMR (300 MHz, CD$_3$OD): 7.63 (d, J=6.9 Hz, 1H), 7.38-7.13 (m, 5H), 6.12 (d, J=7.2 Hz, 1H), 5.03 (br s, 1H), 4.37-4.17 (m, 2H), 3.95-3.72 (m, 2H), 3.51-3.33 (m, 4H), 2.28-2.19 (m, 1H), 1.98-1.94 (m, 1H), 1.48 (d, J=7.2 Hz, 3H).

Example 142

N-(4-Fluorobenzyl)-4-[(3aR,6aR)-hexahydropyrrolo[3,4-b]pyrrol-5(1H)-yl]pyrimidin-2-amine

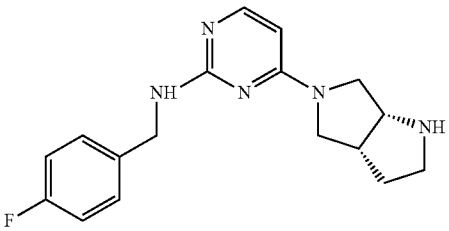 [SMILES: Fc1ccc(CNc2nccc(N3C[C@H]4CCN[C@H]4C3)n2)cc1]

MS (ESI): mass calcd. for $C_{17}H_{20}FN_5$, 313.38 m/z found, 314.1 [M+H]$^+$. $^1$H NMR (300 MHz, D$_2$O): 7.55 (d, J=7.2 Hz, 1H), 7.33-7.29 (m, 2H), 7.05-6.99 (m, 2H), 6.08-6.04 (m, 1H), 4.55 (s, 2H), 4.44-4.35 (m, 1H), 4.11-3.32 (m, 7H), 2.26-2.24 (m, 1H), 1.91 (m, 1H).

Example 143

N-Cyclopropyl-4-[(3aR,6aR)-hexahydropyrrolo[3,4-b]pyrrol-5(1H)-yl]pyrimidin-2-amine

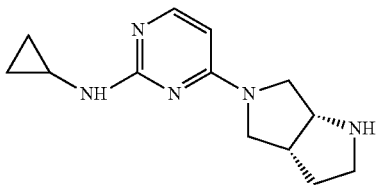 [SMILES: c1cc(N2C[C@H]3CCN[C@H]3C2)nc(NC2CC2)n1]

MS (ESI): mass calcd. for $C_{13}H_{19}N_5$, 245.33 m/z found, 246.1 [M+H]$^+$. $^1$H NMR (300 MHz, CD$_3$OD): 7.69 (d, J=7.2 Hz, 1H), 6.24 (d, J=7.5 Hz, 1H), 4.39-3.79 (m, 4H), 3.60-3.34 (m, 4H), 2.60-2.50 (m, 1H), 2.30-2.22 (m, 1H), 2.00-1.90 (m, 1H), 0.84 (m, 2H), 0.57 (br s, 2H).

Example 144

N-(4-Methoxybenzyl)-4-piperazin-1-ylpyrimidin-2-amine

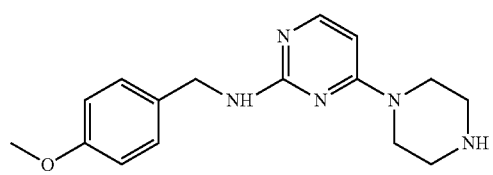 [SMILES: COc1ccc(CNc2nccc(N3CCNCC3)n2)cc1]

MS (ESI): mass calcd. for $C_{16}H_{21}N_5O$, 299.38 m/z found, 300.2 [M+H]$^+$. $^1$H NMR (300 MHz, CD$_3$OD): 7.72 (d, J=7.5

Hz, 1H), 7.20 (d, J=8.7 Hz, 2H), 6.81 (d, J=8.4 Hz, 2H), 6.45 (d, J=7.2 Hz, 1H), 4.46 (s, 2H), 4.13 (br s, 2H), 3.89 (br s, 2H), 3.68 (s, 3H), 3.22 (br s, 4H).

Example 145

N-Cyclopropyl-4-[(3S)-3-(methylamino)pyrrolidin-1-yl]pyrimidin-2-amine

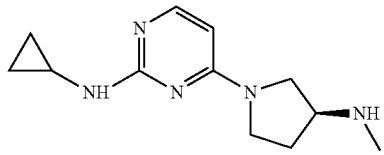 [SMILES: CN[C@H]1CCN(c2ccnc(NC3CC3)n2)C1]

MS (ESI): mass calcd. for $C_{12}H_{19}N_5$, 233.32 m/z found, 234.2 [M+H]$^+$. $^1$H NMR (300 MHz, CD$_3$OD): 7.72 (d, J=7.5 Hz, 1H), 6.28 (d, J=7.5 Hz, 1H), 3.97-3.49 (m, 5H), 2.75 (s, 3H), 2.65-2.33 (m, 3H), 0.92-0.85 (m, 2H), 0.63 (s, 2H).

Example 146

4-[(3S)-3-Aminopyrrolidin-1-yl]-N-bicyclo[2.2.1]hept-2-ylpyrimidin-2-amine

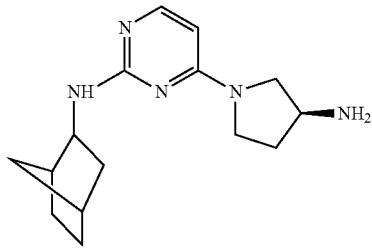 [SMILES: N[C@H]1CCN(c2ccnc(NC3CC4CCC3C4)n2)C1]

MS (ESI): mass calcd. for $C_{15}H_{23}N_5$, 273.38 m/z found, 274.2 [M+H]$^+$. $^1$H NMR (300 MHz, CD$_3$OD): 7.77 (d, J=7.2 Hz, 1H), 6.28 (s, 1H), 4.10-3.81 (m, 6H), 2.56-2.53 (m, 1H), 2.36-2.20 (m, 2H), 1.93-1.86 (m, 1H), 1.61-1.24 (m, 8H).

Example 147

N-Bicyclo[2.2.1]hept-2-yl-4-[3-(methylamino)azetidin-1-yl]pyrimidin-2-amine

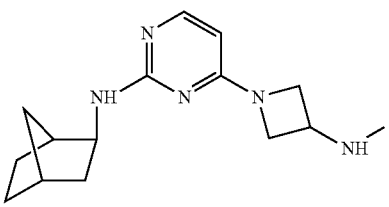 [SMILES: CNC1CN(c2ccnc(NC3CC4CCC3C4)n2)C1]

MS (ESI): mass calcd. for $C_{15}H_{23}N_5$, 273.38 m/z found, 274.1 [M+H]$^+$. $^1$H NMR (300 MHz, CD$_3$OD): 7.77 (d, J=7.2 Hz, 1H), 6.15 (d, J=7.2 Hz, 1H), 4.67-4.31 (m, 5H), 3.60-3.50 (m, 1H), 2.83 (s, 3H), 2.39-2.33 (m, 2H), 1.93-1.86 (m, 1H), 1.62-1.49 (m, 4H), 1.35-1.20 (m, 3H).

Example 148

3-({4-[(3aR,6aR)-Hexahydropyrrolo[3,4-b]pyrrol-5(1H)-yl]pyrimidin-2-yl}amino)-2,2-dimethylpropan-1-ol

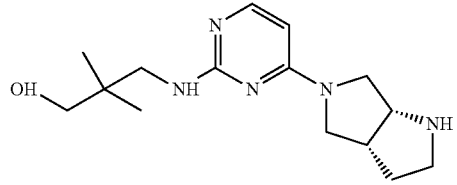 [SMILES: CC(C)(CO)CNc1nccc(N2C[C@H]3CCN[C@H]3C2)n1]

MS (ESI): mass calcd. for $C_{15}H_{25}N_5O$, 291.4 m/z found, 292.2 [M+H]$^+$. $^1$H NMR (300 MHz, CD$_3$OD): 7.72 (d, J=7.5 Hz, 1H), 6.20 (d, J=5.4 Hz, 1H), 4.43-4.38 (m, 1H), 4.38-4.24 (m, 1H), 4.00-3.84 (m, 2H), 3.70-3.50 (m, 1H), 3.42-3.26 (m, 6H), 2.36-2.26 (m, 1H), 2.04 (br, s, 1H), 0.91 (s, 6H).

Example 149

4-[(3S)-3-Aminopyrrolidin-1-yl]-N-(cyclopentylmethyl)pyrimidin-2-amine

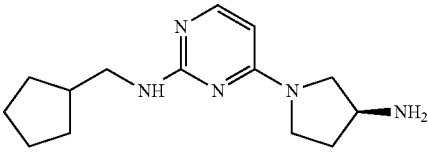 [SMILES: N[C@H]1CCN(c2ccnc(NCC3CCCC3)n2)C1]

MS (ESI): mass calcd. for $C_{14}H_{23}N_5$, 261.37 m/z found, 262.2 [M+H]$^+$. $^1$H NMR (300 MHz, CD$_3$OD): 7.75 (d, J=7.2 Hz, 1H), 6.28-6.26 (m, 1H), 4.15-3.69 (m, 5H), 3.39-3.32 (m, 2H), 2.61-2.46 (m, 1H), 2.29-2.22 (m, 2H), 1.82-1.62 (m, 6H), 1.34-1.31 (m, 2H).

Example 150

4-[(3R)-3-Aminopyrrolidin-1-yl]-N-(4,4,4-trifluorobutyl)pyrimidin-2-amine

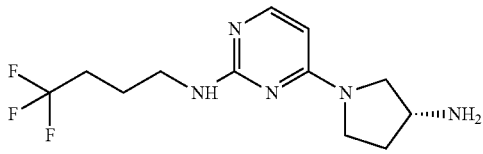 [SMILES: N[C@@H]1CCN(c2ccnc(NCCCC(F)(F)F)n2)C1]

MS (ESI): mass calcd. for $C_{12}H_{18}F_3N_5$, 289.31 m/z found, 290.2 [M+H]$^+$. $^1$H NMR (300 MHz, CD$_3$OD): 7.77 (d, J=7.2

Hz, 1H), 6.31-6.27 (m, 1H), 4.08-3.70 (m, 5H), 3.60-3.55 (m, 2H), 2.59-2.47 (m, 1H), 2.34-2.21 (m, 3H), 1.97-1.88 (m, 2H).

Example 151

3-{[4-(3-Aminoazetidin-1-yl)pyrimidin-2-yl]-amino}-2,2-dimethylpropan-1-ol

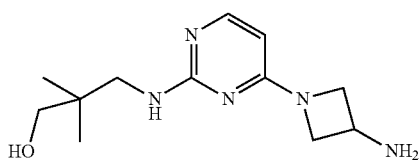 [SMILES: CC(C)(CO)CNc1nccc(N2CC(N)C2)n1]

MS (ESI): mass calcd. for $C_{12}H_{21}N_5O$, 251.33 m/z found, 252.2 [M+H]$^+$. $^1$H NMR (300 MHz, CD$_3$OD): 7.73 (d, J=7.5 Hz, 1H), 6.08 (d, J=6.9 Hz, 1H), 4.64-4.59 (m, 2H), 4.35-4.26 (m, 3H), 3.39-3.29 (m, 4H), 0.94 (s, 6H).

Example 152

3-({4-[(3S)-3-(Methylamino)pyrrolidin-1-yl]pyrimidin-2-yl}amino)propan-1-ol

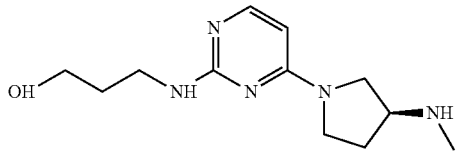 [SMILES: CN[C@H]1CCN(c2ccnc(NCCCO)n2)C1]

MS (ESI): mass calcd. for $C_{12}H_{21}N_5O$, 251.33 m/z found, 252.2 [M+H]$^+$. $^1$H NMR (300 MHz, CD$_3$OD): 7.65 (d, J=7.2 Hz, 1H), 6.16 (d, J=6.9 Hz, 1H), 3.94-3.46 (m, 9H), 2.71 (s, 3H), 2.50-2.40 (m, 1H), 2.27-2.15 (m, 1H), 1.80-1.71 (m, 2H).

Example 153

3-({4-[(3R)-3-Aminopyrrolidin-1-yl]pyrimidin-2-yl}amino)-2,2-dimethylpropan-1-ol

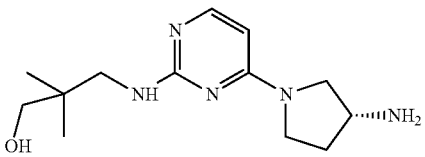 [SMILES: CC(C)(CO)CNc1nccc(N2CC[C@@H](N)C2)n1]

MS (ESI): mass calcd. for $C_{13}H_{23}N_5O$, 265.36 m/z found, 266.2 [M+H]$^+$. $^1$H NMR (300 MHz, CD$_3$OD): 7.73 (d, J=7.5 Hz, 1H), 6.08 (d, J=6.9 Hz, 1H), 4.64-4.59 (m, 2H), 4.35-4.26 (m, 3H), 3.39-3.29 (m, 4H), 0.94 (s, 6H).

Example 154

3-({4-[(3R)-3-Aminopyrrolidin-1-yl]pyrimidin-2-yl}amino)propan-1-ol

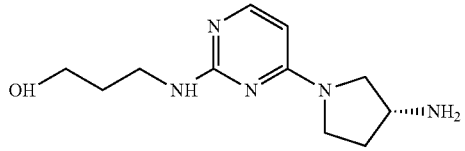 [SMILES: N[C@@H]1CCN(c2ccnc(NCCCO)n2)C1]

MS (ESI): mass calcd. for $C_{11}H_{19}N_5O$, 237.31 m/z found, 238.2 [M+H]$^+$. $^1$H NMR (300 MHz, CD$_3$OD): 7.73 (d, J=7.5 Hz, 1H), 6.26 (d, J=6.9 Hz, 1H), 4.05-3.54 (m, 9H), 2.65-2.40 (m, 1H), 2.38-2.05 (m, 1H), 1.90-1.81 (m, 2H).

Example 155

3-{[4-(3-Aminoazetidin-1-yl)pyrimidin-2-yl]-amino}propan-1-ol

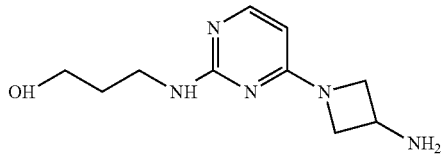 [SMILES: NC1CN(c2ccnc(NCCCO)n2)C1]

MS (ESI): mass calcd. for $C_{10}H_{17}N_5O$, 223.28 m/z found, 224.2 [M+H]$^+$. $^1$H NMR (300 MHz, CD$_3$OD): 7.71 (d, J=7.2 Hz, 1H), 6.09 (d, J=6.6 Hz, 1H), 4.62-4.60 (m, 2H), 4.33-4.26 (m, 3H), 3.65 (t, J=6.3 Hz, 2H), 3.51 (br, s, 2H), 1.85-1.79 (m, 2H).

Example 156

N-(4-Methylbenzyl)-4-piperazin-1-ylpyrimidin-2-amine

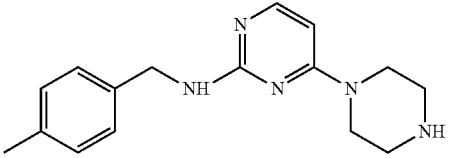 [SMILES: Cc1ccc(CNc2nccc(N3CCNCC3)n2)cc1]

MS (ESI): mass calcd. for $C_{16}H_{21}N_5$, 283.38 m/z found, 284.2 [M+H]$^+$. $^1$H NMR (300 MHz, CD$_3$OD): 7.81 (d, J=7.2

Hz, 1H), 7.25-7.15 (m, 4H), 6.54 (d, J=7.5 Hz, 1H), 4.57 (s, 2H), 4.19 (br, s, 2H), 3.96 (br, s, 2H), 3.31-3.29 (m, 4H), 2.31 (s, 3H).

Example 157

4-piperazin-1-yl-N-(pyridin-2-ylmethyl)pyrimidin-2-amine

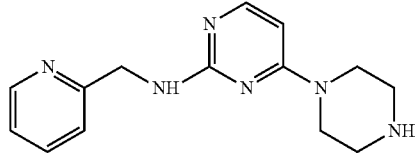 [SMILES: c1ccc(CNc2nccc(N3CCNCC3)n2)nc1]

MS (ESI): mass calcd. for $C_{14}H_{18}N_6$, 270.34 m/z found, 271.2 [M+H]$^+$. $^1$H NMR (300 MHz, CD$_3$OD): 8.82 (d, J=5.7 Hz, 1H), 8.62 (t, J=7.5 Hz, 1H), 8.14 (d, J=7.5 Hz, 1H), 8.02 (t, J=6.6 Hz, 1H), 7.94 (d, J=7.5 Hz, 1H), 6.65 (d, J=7.5 Hz, 1H), 5.12 (s, 2H), 3.99 (br, s, 4H).

Example 158

2,2-Dimethyl-3-({4-[(3S)-3-(methylamino)pyrrolidin-1-yl]pyrimidin-2-yl}amino)propan-1-ol

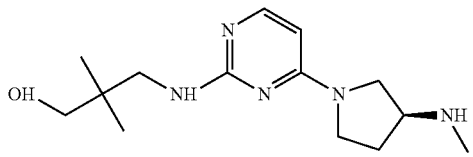 [SMILES: CN[C@H]1CCN(c2ccnc(NCC(C)(C)CO)n2)C1]

MS (ESI): mass calcd. for $C_{14}H_{25}N_5O$, 279.39 m/z found, 280.2 [M+H]$^+$. $^1$H NMR (300 MHz, CD$_3$OD): 7.71 (d, J=7.2 Hz, 1H), 6.22 (s, 1H), 3.99-3.96 (m, 3H), 3.88-3.68 (m, 2H), 3.43-3.26 (m, 4H), 2.76 (s, 3H), 2.57-2.31 (m, 2H), 0.95 (m, 6H).

Example 159

3-({4-[(3aR,6aR)-Hexahydropyrrolo[3,4-b]pyrrol-5(1H)-yl]pyrimidin-2-yl}amino)propan-1-ol

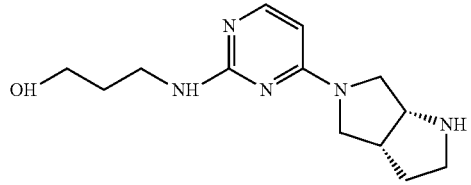 [SMILES: OCCCNc1nccc(N2C[C@H]3CCN[C@H]3C2)n1]

MS (ESI): mass calcd. for $C_{13}H_{21}N_5O$, 263.35 m/z found, 264.2 [M+H]$^+$. $^1$H NMR (300 MHz, CD$_3$OD): 7.64 (d, J=7.5 Hz, 1H), 6.15 (d, J=7.2 Hz, 1H), 4.41-4.17 (m, 2H), 4.01-3.79 (m, 2H), 3.65-3.28 (m, 8H), 2.30-2.23 (m, 1H), 2.00-1.95 (m, 1H), 1.78-1.74 (m, 2H).

Example 160

4-[(3S)-3-Aminopyrrolidin-1-yl]-N-cyclopentylpyrimidin-2-amine

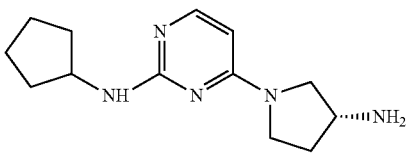 [SMILES: N[C@@H]1CCN(c2ccnc(NC3CCCC3)n2)C1]

MS (ESI): mass calcd. for $C_{13}H_{21}N_5$, 247.35 m/z found, 248.1 [M+H]$^+$. $^1$H NMR (300 MHz, D$_2$O): 7.46 (d, J=7.2 Hz, 1H), 5.99 (d, J=8.7 Hz, 1H), 4.01-3.96 (m, 2H), 3.81-3.57 (m, 4H), 2.40-2.36 (m, 1H), 2.14-2.08 (m, 1H), 1.84-1.78 (m, 2H), 1.54-1.44 (m, 6H).

Example 161

3-{[4-(4-Methylpiperazin-1-yl)pyrimidin-2-yl]amino}propan-1-ol

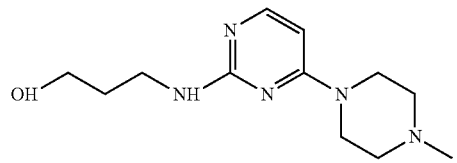 [SMILES: CN1CCN(c2ccnc(NCCCO)n2)CC1]

MS (ESI): mass calcd. for $C_{12}H_{21}N_5O$, 251.33 m/z found, 252.2 [M+H]$^+$. $^1$H NMR (300 MHz, CD$_3$OD): 7.72 (d, J=7.5 Hz, 1H), 6.46 (d, J=7.5 Hz, 1H), 3.59-3.47 (m, 8H), 3.27-3.20 (m, 4H), 2.88 (s, 3H), 1.79-1.71 (m, 2H).

Example 162

N-Bicyclo[2.2.1]hept-2-yl-4-[(3S)-3-(methylamino)pyrrolidin-1-yl]pyrimidin-2-amine

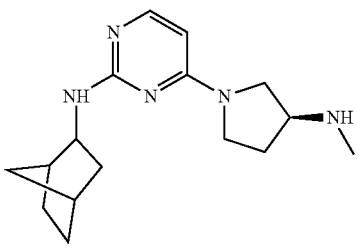 [SMILES: CN[C@H]1CCN(c2ccnc(NC3CC4CCC3C4)n2)C1]

MS (ESI): mass calcd. for $C_{16}H_{25}N_5$, 287.41 m/z found, 288.1 [M+H]$^+$. $^1$H NMR (300 MHz, CD$_3$OD): 7.76 (d, J=6.6

Hz, 1H), 6.31 (br s, 1H), 4.05-3.63 (m, 6H), 2.85 (s, 3H), 2.61-2.37 (m, 4H), 1.89-1.21 (m, 8H).

Example 163

N-(4-Methylbenzyl)-4-(4-methylpiperazin-1-yl)pyrimidin-2-amine

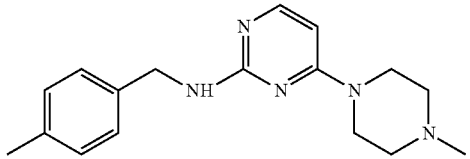

MS (ESI): mass calcd. for $C_{17}H_{23}N_5$, 297.41 m/z found, 298.1 [M+H]$^+$. $^1$H NMR (300 MHz, DMSO-d$_6$): 8.76 (s, 1H), 8.00 (d, J=6.9 Hz, 1H), 7.28 (d, J=7.8 Hz, 2H), 7.18 (d, J=7.8 Hz, 2H), 6.58 (d, J=6.9 Hz, 1H), 4.55 (d, J=5.4 Hz, 2H), 3.60-3.00 (m, 4H), 2.79 (s, 3H), 2.60-2.40 (m, 4H), 2.31 (s, 3H).

Example 164

4-(4-Methylpiperazin-1-yl)-N-[2-(methylsulfanyl)ethyl]pyrimidin-2-amine

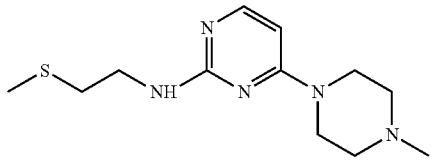

MS (ESI): mass calcd. for $C_{12}H_{21}N_5S$, 267.4 m/z found, 268.1 [M+H]$^+$. Amine $^1$H NMR (300 MHz, CDCl$_3$): 7.87 (d, J=6.0 Hz, 1H), 5.89 (d, J=6.0 Hz, 1H), 5.25 (s, 1H), 3.61-3.55 (m, 6H), 2.73 (t, J=6.6 Hz, 2H), 2.46-2.43 (m, 4H), 2.33 (s, 3H), 2.14 (s, 3H) Salt $^1$H NMR (300 MHz, CD$_3$OD): 7.87 (d, J=7.5 Hz, 1H), 6.60 (d, J=7.5 Hz, 1H), 3.00 (s, 3H), 2.80 (t, J=6.6 Hz, 3H), 2.18 (s, 3H).

Example 165

N-Benzyl-4-(4-methylpiperazin-1-yl)pyrimidin-2-amine

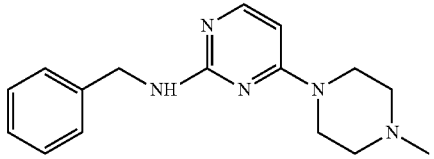 [SMILES: CN1CCN(c2ccnc(NCc3ccccc3)n2)CC1]

MS (ESI): mass calcd. for $C_{16}H_{21}N_5$, 283.38 m/z found, 284.0 [M+H]$^+$. Amine $^1$H NMR (300 MHz, CDCl$_3$): 7.89 (d, J=6.3 Hz, 1H), 7.36-7.24 (m, 5H), 5.90 (d, J=6.0 Hz, 1H), 5.19 (br s, 1H), 4.59 (d, J=5.7 Hz, 2H), 3.59-3.57 (m, 4H), 2.44-2.41 (m, 4H), 2.32 (s, 3H) Salt $^1$H NMR (300 MHz, CD$_3$OD): 7.88 (d, J=6.6 Hz, 1H), 7.40-7.34 (m, 5H), 6.61 (d, J=6.0 Hz, 1H), 5.07-4.43 (m, 4H), 4.67 (s, 2H), 3.66-3.11 (m, 4H), 2.99 (s, 3H).

Example 166

2,2-Dimethyl-3-[(4-piperazin-1-ylpyrimidin-2-yl)amino]propan-1-ol

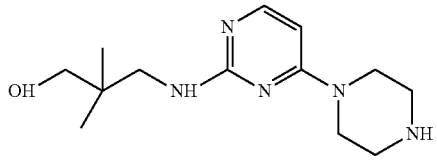 [SMILES: CC(C)(CO)CNc1nccc(N2CCNCC2)n1]

MS (ESI): mass calcd. for $C_{13}H_{23}N_5O$, 265.36 m/z found, 266.2 [M+H]$^+$. $^1$H NMR (300 MHz, CD$_3$OD): 7.81 (d, J=7.5 Hz, 1H), 6.53 (d, J=6.9 Hz, 1H), 4.26 (br, s, 2H), 4.00 (br, s, 2H), 3.42-3.29 (m, 8H), 0.95 (s, 6H).

Example 167

3-({4-[(3R)-3-(Methylamino)pyrrolidin-1-yl]pyrimidin-2-yl}amino)propan-1-ol

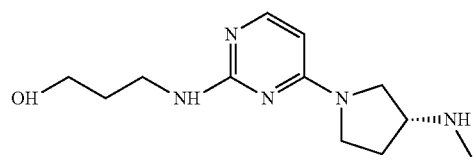 [SMILES: CN[C@@H]1CCN(c2ccnc(NCCCO)n2)C1]

MS (ESI): mass calcd. for $C_{12}H_{21}N_5O$, 251.33 m/z found, [M+H]$^+$. $^1$H NMR (300 MHz, CD$_3$OD): 7.76 (d, J=7.2 Hz, 1H), 6.28 (d, J=7.5 Hz, 1H), 4.09-3.57 (m, 9H), 2.83 (s, 3H), 2.62-2.55 (m, 1H), 2.50-2.30 (m, 1H), 1.92-1.83 (m, 2H).

Example 168

4-(4-Methylpiperazin-1-yl)-N-[(1S,2S,3S,5R)-2,6,6-trimethylbicyclo[3.1.1]hept-3-yl]pyrimidin-2-amine

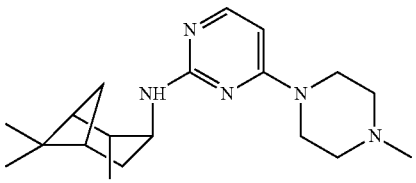

MS (ESI): mass calcd. for $C_{19}H_{31}N_5$, 329.49 m/z found, 330.1 [M+H]$^+$. $^1$H NMR (300 MHz, CD$_3$OD): 7.85 (d, J=7.5 Hz, 1H), 6.59 (d, J=7.5 Hz, 1H), 4.86-4.80 (m, 2H), 4.60-4.40

(m, 2H), 3.80-3.20 (m, 5H), 3.04 (s, 3H), 2.78-2.54 (m, 2H), 2.13-1.74 (m, 4H), 1.35 (s, 3H), 1.23 (d, J=7.2 Hz, 3H), 1.15 (s, 3H), 1.20-1.07 (m, 1H).

Example 169

2,2-Dimethyl-3-({4-[(3R)-3-(methylamino)pyrrolidin-1-yl]pyrimidin-2-yl}amino)propan-1-ol

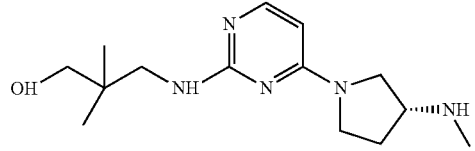 [SMILES: CN[C@@H]1CCN(c2ccnc(NCC(C)(C)CO)n2)C1]

MS (ESI): mass calcd. for $C_{14}H_{25}N_5O$, 279.39 m/z found, 280.1 $[M+H]^+$. $^1H$ NMR (300 MHz, $CD_3OD$): 7.75 (d, J=7.5 Hz, 1H), 6.25 (d, J=6.0 Hz, 1H), 4.04-3.73 (m, 5H), 3.43-3.30 (m, 4H), 2.80 (s, 3H), 2.59-2.36 (m, 2H), 0.95 (s, 6H).

Example 170

4-[(3R)-3-(Methylamino)pyrrolidin-1-yl]-N-(4-methylbenzyl)pyrimidin-2-amine

MS (ESI): mass calcd. for $C_{17}H_{23}N_5$, 297.41 m/z found, 298.1 $[M+H]^+$. $^1H$ NMR (300 MHz, $CD_3OD$): 7.78 (s, br, 1H), 7.28 (s, br, 2H), 7.21 (s, br, 2H), 6.29 (s, br, 1H), 4.62 (s, 2H), 4.03-3.69 (m, 5H), 2.82 (s, 3H), 2.58 (m, 1H), 2.38 (m, 1H), 2.35 (s, 3H).

Example 171

4-[3-(Methylamino)azetidin-1-yl]-N-(2-methylpropyl)pyrimidin-2-amine

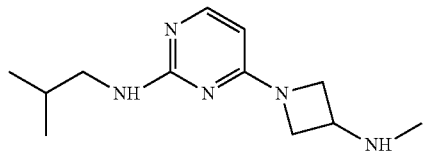 [SMILES: CNC1CN(c2ccnc(NCC(C)C)n2)C1]

MS (ESI): mass calcd. for $C_{12}H_{21}N_5$, 235.33 m/z found, 236.2 $[M+H]^+$. $^1H$ NMR (300 MHz, $CD_3OD$): 7.72 (d, J=7.2 Hz, 1H), 6.09 (br s, 1H), 4.62-4.27 (m, 5H), 2.77 (s, 3H), 1.95-1.90 (m, 1H), 0.97 (d, J=6.3 Hz, 6H) D2O: 7.53 (d, J=7.2 Hz, 1H), 5.91 (br s, 1H), 4.60-4.50 (m, 2H), 4.32-4.21 (m, 3H), 3.12 (br s, 2H), 2.69 (s, 3H), 1.83-1.79 (m, 1H), 0.83 (d, J=6.9 Hz, 6H).

Example 172

N-Cyclopentyl-4-[3-(methylamino)azetidin-1-yl]pyrimidin-2-amine

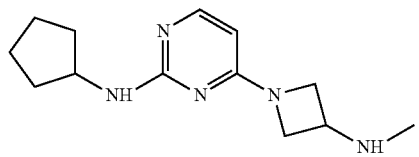 [SMILES: CNC1CN(c2ccnc(NC3CCCC3)n2)C1]

MS (ESI): mass calcd. for $C_{13}H_{21}N_5$, 247.35 m/z found, 248.2 $[M+H]^+$. $^1H$ NMR (300 MHz, $CD_3OD$): 7.71 (d, J=7.2 Hz, 1H), 6.10 (d, J=7.2 Hz, 1H), 4.62-4.28 (m, 5H), 2.77 (s, 3H), 2.06-2.02 (m, 2H), 1.78-1.57 (m, 6H).

Example 173

4-(4-Methylpiperazin-1-yl)-N-(2-phenylethyl)pyrimidin-2-amine

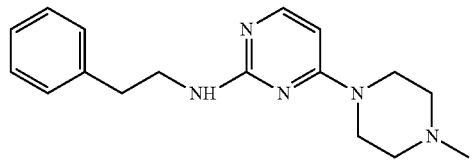 [SMILES: CN1CCN(c2ccnc(NCCc3ccccc3)n2)CC1]

MS (ESI): mass calcd. for $C_{17}H_{23}N_5$, 297.41 m/z found, 298.1 $[M+H]^+$. $^1H$ NMR (300 MHz, $D_2O$): 7.56 (d, J=7.5 Hz, 1H), 7.26-7.20 (m, 5H), 6.22 (d, J=7.2 Hz, 1H), 5.00-4.50 (m, 4H), 3.80-3.60 (m, 2H), 3.40-3.15 (m, 4H), 2.90-2.70 (m, 5H).

Example 174

N-Benzyl-4-[(3R)-3-(methylamino)pyrrolidin-1-yl]pyrimidin-2-amine

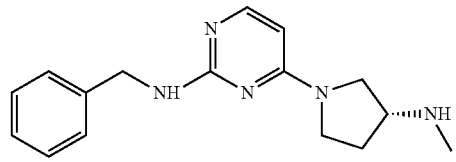 [SMILES: CN[C@@H]1CCN(c2ccnc(NCc3ccccc3)n2)C1]

MS (ESI): mass calcd. for $C_{16}H_{21}N_5$, 283.38 m/z found, 284.1 $[M+H]^+$. $^1H$ NMR (300 MHz, $CD_3OD$): 7.78 (d, J=7.2

Hz, 1H), 7.38-7.32 (m, 5H), 6.28 (d, J=7.2 Hz, 1H), 4.65 (s, 2H), 4.10-3.70 (m, 5H), 2.79 (s, 3H), 2.58-2.46 (m, 2H).

Example 175

4-[(3R)-3-Aminopyrrolidin-1-yl]-N-[(1R)-1-phenyl-ethyl]pyrimidin-2-amine

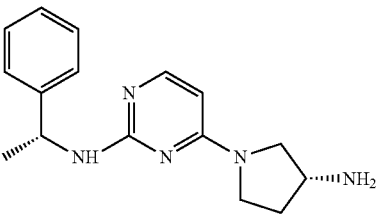 [SMILES: C[C@@H](Nc1nccc(N2CC[C@@H](N)C2)n1)c1ccccc1]

MS (ESI): mass calcd. for $C_{16}H_{21}N_5$, 283.38 m/z found, 284.1 [M+H]$^+$. $^1$H NMR (300 MHz, DMSO-d$_6$): 7.76 (d, J=7.2 Hz, 1H), 7.50-7.30 (m, 5H), 6.24 (t, J=7.8 Hz, 1H), 5.16 (br s, H), 4.20-3.60 (m, 5H), 2.50 (m, 1H), 2.25 (m, 1H), 1.59 (d, J=6.9 Hz, 3H).

Example 176

N-(4-Methoxybenzyl)-4-[(3R)-3-(methylamino)pyr-rolidin-1-yl]pyrimidin-2-amine

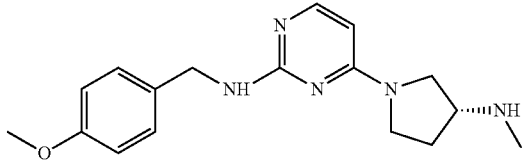

MS (ESI): mass calcd. for $C_{17}H_{23}N_5O$, 313.41 m/z found, 314.2 [M+H]$^+$. $^1$H NMR (300 MHz, CD$_3$OD): 7.77 (d, J=6.6 Hz, 1H), 7.33 (d, J=7.5 Hz, 2H), 6.94 (d, J=7.5 Hz, 2H), 6.29 (d, J=6.9 Hz, 1H), 4.61 (s, 2H), 4.10-3.80 (m, 5H), 3.81 (s, 3H), 2.59 (s, 3H), 2.70-2.50 (m, 1H), 2.40-2.20 (m, 1H).

Example 177

2-Methyl-1-[(4-piperazin-1-ylpyrimidin-2-yl)amino]propan-2-ol

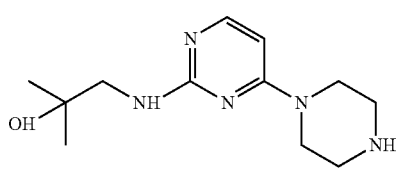 [SMILES: CC(C)(O)CNc1nccc(N2CCNCC2)n1]

MS (ESI): mass calcd. for $C_{12}H_{21}N_5O$, 251.33 m/z found, 252.2 [M+H]$^+$. $^1$H NMR (300 MHz, CD$_3$OD): 7.74 (d, J=7.2

Hz, 1H), 6.46 (d, J=7.2 Hz, 1H), 4.16 (br s, 2H), 3.91 (br s, 2H), 3.37-3.25 (m, 6H), 1.16 (s, 6H).

Example 178

N-(4-Fluorobenzyl)-4-[3-(methylamino)azetidin-1-yl]pyrimidin-2-amine

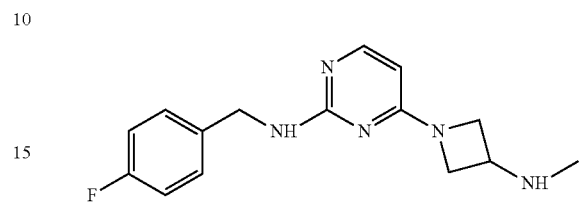

MS (ESI): mass calcd. for $C_{16}H_{18}FN_5$, 287.34 m/z found, 288.2 [M+H]$^+$. $^1$H NMR (300 MHz, CD$_3$OD): 7.77 (d, J=7.2 Hz, 1H), 7.43-7.38 (m, 2H), 7.13-7.07 (m, 2H), 6.13 (d, J=7.2 Hz, 1H), 4.70-4.50 (m, 2H), 4.60 (s, 2H), 4.40-4.28 (m, 3H), 2.79 (s, 3H).

Example 179

4-[(3R)-3-Aminopyrrolidin-1-yl]-N-benzylpyrimi-din-2-amine

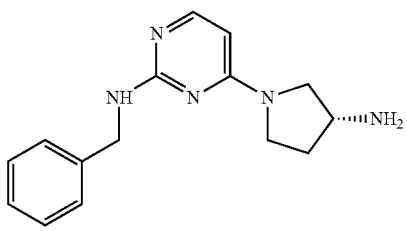 [SMILES: N[C@@H]1CCN(c2ccnc(NCc3ccccc3)n2)C1]

MS (ESI): mass calcd. for $C_{16}H_{19}N_5$, 269.35 m/z found, 270.2 [M+H]$^+$. $^1$H NMR (300 MHz, CD$_3$OD): 7.74 (d, J=7.2 Hz, 1H), 7.43-7.27 (m, 5H), 6.27-6.22 (m, 1H), 4.62 (s, 2H), 4.09-3.52 (m, 5H), 2.56-2.41 (m, 1H), 2.25-2.15 (m, 1H).

Example 180

4-[(3R)-3-(Methylamino)pyrrolidin-1-yl]-N-[(1R)-1-phenylethyl]pyrimidin-2-amine

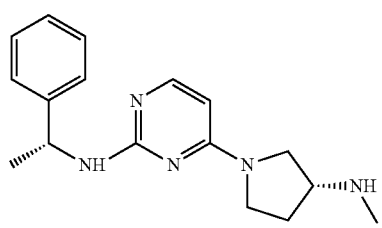 [SMILES: CN[C@@H]1CCN(c2ccnc(N[C@H](C)c3ccccc3)n2)C1]

MS (ESI): mass calcd. for $C_{17}H_{23}N_5$, 297.41 m/z found, 298.2 [M+H]$^+$. $^1$H NMR (300 MHz, DMSO-d$_6$): 8.60 (br s, 1H), 7.86 (d, J=7.2 Hz, 1H), 7.44-7.25 (m, 5H), 6.16 (d, J=7.5

Hz, 1H), 5.15-5.11 (m, 1H), 3.91-3.54 (m, 5H), 2.57 (s, 3H), 2.38-2.27 (m, 2H), 1.53 (d, J=6.9 Hz, 3H).

Example 181

4-[(3R)-3-Aminopyrrolidin-1-yl]-N-cyclohexylpyrimidin-2-amine

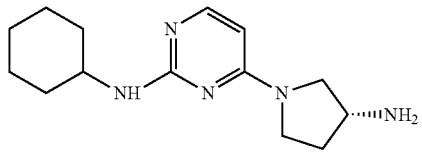 [SMILES: N[C@@H]1CCN(c2ccnc(NC3CCCCC3)n2)C1]

MS (ESI): mass calcd. for $C_{14}H_{23}N_5$, 261.37 m/z found, 262.2 [M+H]$^+$. $^1$H NMR (300 MHz, CD$_3$OD): 7.76 (d, J=7.2 Hz, 1H), 6.27 (dd, J=7.2, 6.9 Hz, 1H), 4.20-3.60 (m, 6H), 2.61-2.48 (m, 1H), 2.31-2.22 (m, 1H), 2.05-1.69 (m, 5H), 1.50-1.20 (m, 5H).

Example 182

N-(2-Methoxyethyl)-4-[3-(methylamino)azetidin-1-yl]pyrimidin-2-amine

MS (ESI): mass calcd. for $C_{11}H_{19}N_5O$, 237.31 m/z found, 238.1 [M+H]$^+$. $^1$H NMR (300 MHz, CD$_3$OD): 7.79 (d, J=7.2 Hz, 1H), 6.16 (d, J=7.2 Hz, 1H), 4.72-4.61 (m, 2H), 4.47-4.33 (m, 3H), 3.63 (br s, 4H), 3.43 (s, 3H), 2.80 (s, 3H).

Example 183

4-[(3R)-3-(Methylamino)pyrrolidin-1-yl]-N-(2-phenylethyl)pyrimidin-2-amine

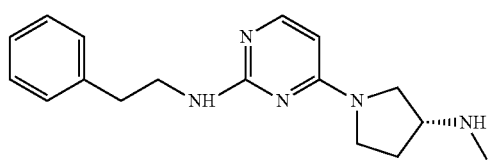 [SMILES: CN[C@@H]1CCN(c2ccnc(NCCc3ccccc3)n2)C1]

MS (ESI): mass calcd. for $C_{17}H_{23}N_5$, 297.41 m/z found, 298.1 [M+H]$^+$. Amine $^1$H NMR (300 MHz, CDCl$_3$): 7.82 (d, J=6.0 Hz, 1H), 7.33-7.23 (m, 5H), 5.68 (d, J=6.0 Hz, 1H), 4.91 (br s, 1H), 3.66-3.30 (m, 7H), 2.90 (t, J=7.2 Hz, 2H), 2.48 (s, 3H), 2.48-2.14 (m, 1H), 1.90-1.80 (m, 1H) Salt $^1$H NMR (300 MHz, CD$_3$OD): 7.75 (d, J=6.6 Hz, 1H), 7.40-7.20 (m, 5H), 6.28 (d, J=6.6 Hz, 1H), 4.20-3.60 (m, 7H), 3.10-2.90 (m, 2H), 2.85 (s, 3H), 2.70-2.20 (m, 2H)

Example 184

4-[(3R)-3-(Methylamino)pyrrolidin-1-yl]-N-[(1S,2S,3S,5R)-2,6,6-trimethylbicyclo[3.1.1]hept-3-yl]pyrimidin-2-amine

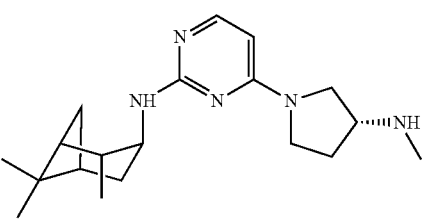

MS (ESI): mass calcd. for $C_{19}H_{31}N_5$, 329.49 m/z found, 330.1 [M+H]$^+$. $^1$H NMR (300 MHz, CD$_3$OD): 7.77 (d, J=6.6 Hz, 1H), 6.28 (d, J=6.6 Hz, 1H), 4.05-3.56 (m, 6H), 2.84 (s, 3H), 2.73-2.20 (m, 3H), 2.05-1.78 (m, 5H), 1.32 (s, 3H), 1.27-1.05 (m, 7H).

Example 185

4-[(3R)-3-Aminopyrrolidin-1-yl]-N-(4-methoxybenzyl)pyrimidin-2-amine

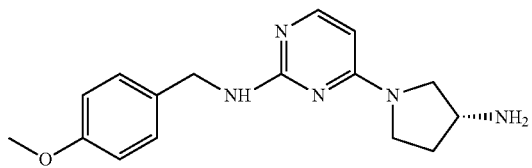 [SMILES: COc1ccc(CNc2nccc(N3CC[C@@H](N)C3)n2)cc1]

MS (ESI): mass calcd. for $C_{16}H_{21}N_5O$, 299.38 m/z found, 300.1 [M+H]$^+$. $^1$H NMR (300 MHz, CD$_3$OD): 7.76 (d, J=7.2 Hz, 1H), 7.30 (d, J=8.1 Hz, 2H), 6.91 (d, J=7.8 Hz, 2H), 6.27 (t, J=7.2 Hz, 1H), 4.57 (s, 2H), 4.20-3.70 (m, 5H), 3.79 (s, 3H), 2.60-2.20 (m, 2H).

Example 186

4-[(3R)-3-Aminopyrrolidin-1-yl]-N-(4-methylbenzyl)pyrimidin-2-amine

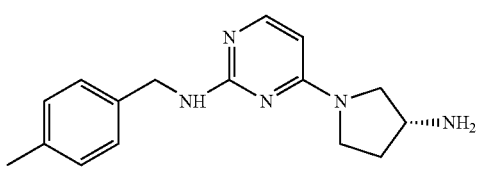 [SMILES: Cc1ccc(CNc2nccc(N3CC[C@@H](N)C3)n2)cc1]

MS (ESI): mass calcd. for $C_{16}H_{21}N_5$, 283.38 m/z found, 284.1 [M+H]$^+$. $^1$H NMR (300 MHz, CD$_3$OD): 7.78 (d, J=7.5 Hz, 1H), 7.28 (d, J=7.5 Hz, 2H), 7.19 (d, J=7.5 Hz, 2H), 6.40-6.20 (m, 1H), 4.62 (s, 2H), 4.20-3.70 (m, 5H), 2.50-2.40 (m, 1H), 2.35 (s, 3H), 3.25-2.20 (m, 1H).

Example 187

N-(Cyclopentylmethyl)-4-piperazin-1-ylpyrimidin-2-amine

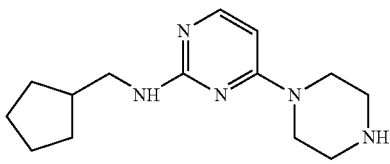 [SMILES: c1cc(N2CCNCC2)nc(NCC2CCCC2)n1]

MS (ESI): mass calcd. for C$_{14}$H$_{23}$N$_5$, 261.37 m/z found, 262.1 [M+H]$^+$. $^1$H NMR (300 MHz, CD$_3$OD): 7.75 (d, J=7.5 Hz, 1H), 6.49 (d, J=7.2 Hz, 1H), 4.20 (br, s, 2H), 3.95 (br, s, 2H), 3.35-3.26 (m, 6H), 2.19-2.14 (m, 1H), 1.77 (br, 2H), 1.64-1.56 (m, 4H), 1.28-1.22 (m, 2H).

Example 188

4-[3-(Methylamino)azetidin-1-yl]-N-(pyridin-2-ylmethyl)pyrimidin-2-amine

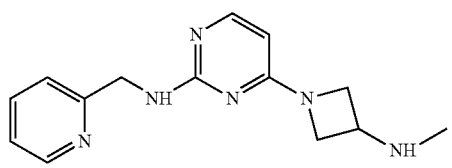 [SMILES: CNC1CN(c2ccnc(NCc3ccccn3)n2)C1]

MS (ESI): mass calcd. for C$_{14}$H$_{18}$N$_6$, 270.34 m/z found, 271.2 [M+H]$^+$. $^1$H NMR (300 MHz, CD$_3$OD): 8.64 (d, J=4.8 Hz, 1H), 8.19-8.14 (m, 1H), 7.81-7.61 (m, 3H), 6.13 (d, J=7.2 Hz, 1H), 4.57-4.55 (m, 1H), 4.38 (br, s, 2H), 4.21 (br, s, 2H), 2.73 (s, 3H).

Example 189

4-[(3R)-3-(Methylamino)pyrrolidin-1-yl]-N-[(3S,5S,7S)-tricyclo[3.3.1.1.3.7]dec-1-ylmethyl]pyrimidin-2-amine

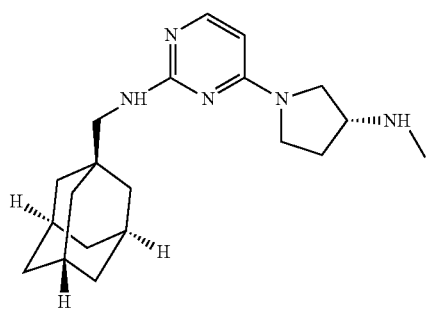 [SMILES: CN[C@@H]1CCN(c2ccnc(NC[C@]34C[C@H]5C[C@H](C[C@H](C5)C3)C4)n2)C1]

MS (ESI): mass calcd. for C$_{20}$H$_{31}$N$_5$, 341.5 m/z found, 342.2 [M+H]$^+$. $^1$H NMR (300 MHz, CD$_3$OD): 7.93 (d, J=7.2 Hz, 1H), 6.43 (d, J=6.9 Hz, 1H), 4.28-3.91 (m, 5H), 3.38 (s, 2H), 2.99 (s, 3H), 2.78-2.70 (m, 1H), 2.56-2.45 (m, 1H), 2.18 (s, 3H), 1.99-1.85 (m, 6H), 1.78 (s, 6H).

Example 190

4-[(3R)-3-(Methylamino)pyrrolidin-1-yl]-N-[(1R,2S,4R)-1,7,7-trimethylbicyclo[2.2.1]hept-2-yl]pyrimidin-2-amine

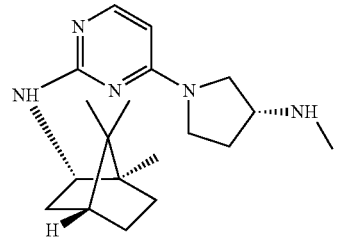 [SMILES: CN[C@@H]1CCN(c2ccnc(N[C@H]3C[C@H]4CC[C@]3(C)C4(C)C)n2)C1]

MS (ESI): mass calcd. for C$_{19}$H$_{31}$N$_5$, 329.49 m/z found, 330.2 [M+H]$^+$. $^1$H NMR (300 MHz, CD$_3$OD): 7.94 (d, J=7.5 Hz, 1H), 6.42 (d, J=7.5 Hz, 1H), 4.70-4.60 (m, 1H), 4.30-3.90 (m, 5H), 2.98 (s, 3H), 2.80-2.40 (m, 3H), 2.20-1.40 (m, 6H), 1.21 (s, 3H), 1.13 (s, 3H), 1.08 (s, 3H).

Example 191

N-(Cyclohexylmethyl)-4-[(3R)-3-(methylamino)pyrrolidin-1-yl]pyrimidin-2-amine

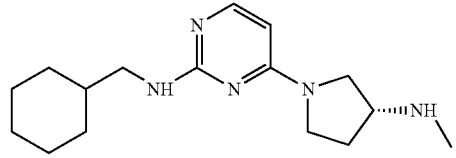 [SMILES: CN[C@@H]1CCN(c2ccnc(NCC3CCCCC3)n2)C1]

MS (ESI): mass calcd. for C$_{16}$H$_{27}$N$_5$, 289.43 m/z found, 290.2 [M+H]$^+$. $^1$H NMR (300 MHz, CD$_3$OD): 7.77 (d, J=7.2 Hz, 1H), 6.30-6.20 (m, 1H), 4.10-3.75 (m, 5H), 3.40-3.30 (m, 2H), 2.83 (s, 3H), 2.62-2.56 (m, 1H), 2.45-2.38 (m, 1H), 1.90-1.60 (m, 6H), 1.40-0.99 (m, 5H).

Example 192

N-Cyclohexyl-4-[(3R)-3-(methylamino)pyrrolidin-1-yl]pyrimidin-2-amine

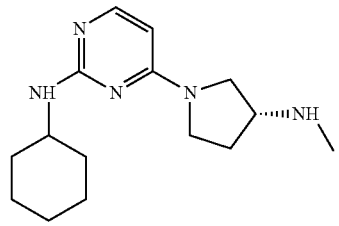 [SMILES: CN[C@@H]1CCN(c2ccnc(NC3CCCCC3)n2)C1]

MS (ESI): mass calcd. for $C_{15}H_{25}N_5$, 275.4 m/z found, 276.1 [M+H]$^+$. $^1$H NMR (300 MHz, CD$_3$OD): 7.76 (d, J=7.2 Hz, 1H), 6.24 (d, J=6.9 Hz, 1H), 4.10-3.70 (m, 6H), 2.81 (s, 3H), 2.60-2.30 (m, 2H), 2.06-1.70 (m, 5H), 1.49-1.33 (m, 5H).

Example 193

N-{[(1S,2S,5S)-6,6-Dimethylbicyclo[3.1.1]hept-2-yl]methyl}-4-[(3R)-3-(methylamino)pyrrolidin-1-yl]pyrimidin-2-amine

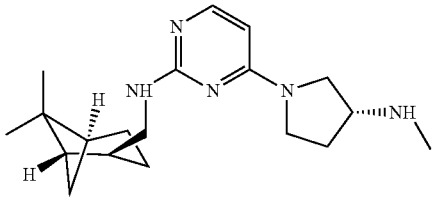

MS (ESI): mass calcd. for $C_{19}H_{31}N_5$, 329.49 m/z found, 330.3 [M+H]$^+$. $^1$H NMR (300 MHz, CD$_3$OD): 7.68 (d, J=7.5 Hz, 1H), 6.20 (d J=7.2 Hz, 1H), 4.10-3.40 (m, 6H), 2.89 (d, J=7.8 Hz, 1H), 2.75 (s, 3H), 2.60-2.20 (m, 3H), 2.03-1.90 (m, 6H), 1.57-1.50 (m, 1H), 1.20 (s, 3H), 1.06 (s, 3H), 0.91 (d, J=9.9 Hz, 1H).

Example 194

4-(1,4-Diazepan-1-yl)-N-(2,2-dimethylpropyl)pyrimidin-2-amine

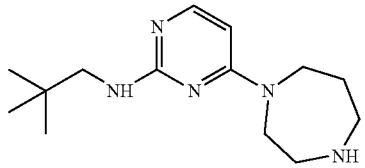 [SMILES: CC(C)(C)CNc1nccc(N2CCCNCC2)n1]

MS (ESI): mass calcd. for $C_{14}H_{25}N_5$, 263.39 m/z found, 264.3 [M+H]$^+$. $^1$H NMR (300 MHz, CD$_3$OD): 7.84 (d, J=7.5 Hz, 1H), 6.53 (d, J=7.5 Hz, 1H), 4.29-4.08 (m, 3H), 3.89-3.85 (m, 1H), 3.60-3.20 (m, 6H), 2.33-2.24 (m, 2H), 1.04 (s, 9H).

Example 195

N-Bicyclo[2.2.1]hept-2-yl-4-(1,4-diazepan-1-yl)pyrimidin-2-amine

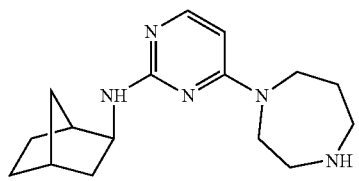 [SMILES: c1cc(N2CCCNCC2)nc(NC2CC3CCC2C3)n1]

MS (ESI): mass calcd. for $C_{16}H_{25}N_5$, 287.41 m/z found, 288.3 [M+H]$^+$. $^1$H NMR (300 MHz, CD$_3$OD): 7.82 (d, J=7.5 Hz, 1H), 6.53 (d, J=7.5 Hz, 1H), 4.30-3.70 (m, 5H), 3.60-3.40 (m, 4H), 2.40-2.20 (m, 4H), 1.93-1.87 (m, 1H), 1.71-1.23 (m, 7H)

Example 196

4-[(3S)-3-Aminopyrrolidin-1-yl]-N-butylpyrimidin-2-amine

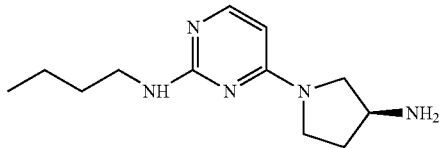 [SMILES: CCCCNc1nccc(N2CC[C@H](N)C2)n1]

MS (ESI): mass calcd. for $C_{16}H_{21}N_5$, 235.33 m/z found, 236.2 [M+H]$^+$. $^1$H NMR (300 MHz, D$_2$O): 7.64 (d, J=7.2 Hz, 1H), 6.19 (s, 1H), 3.72-4.21 (m, 5H), 3.38-3.44 (s, 2H), 2.49-2.60 (m, 1H), 2.25-2.34 (m, 1H), 1.58-1.66 (m, 2H), 1.37-1.44 (m, 2H), 0.92-0.97 (t, J=7.2 Hz, 3H).

Example 197

4-[(3R)-3-Aminopyrrolidin-1-yl]-N-(cyclohexylmethyl)pyrimidin-2-amine

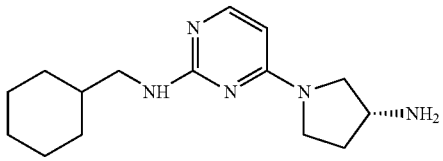 [SMILES: N[C@@H]1CCN(c2ccnc(NCC3CCCCC3)n2)C1]

MS (ESI): mass calcd. for $C_{15}H_{25}N_5$, 275.4 m/z found, 276.2 [M+H]$^+$. $^1$H NMR (300 MHz, CD$_3$OD): 7.75 (d, J=7.5 Hz, 1H), 6.27 (d, J=7.5 Hz, 1H), 4.14-3.68 (m, 5H), 2.61-2.49 (m, 1H), 2.31-2.21 (m, 1H), 1.79-1.69 (m, 6H), 1.28-1.16 (m, 4H), 1.04-0.97 (m, 2H).

Example 198

4-[(3S)-3-Aminopyrrolidin-1-yl]-N-(2-methylpropyl)pyrimidin-2-amine

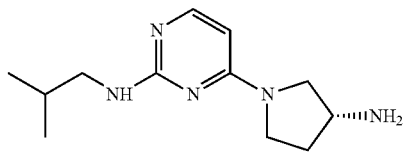 [SMILES: CC(C)CNc1nccc(N2CC[C@@H](N)C2)n1]

MS (ESI): mass calcd. for $C_{12}H_{21}N_5$, 235.33 m/z found, 236.1 [M+H]$^+$. $^1$H NMR (300 MHz, D$_2$O): 7.51 (d, J=7.2 Hz, 1H), 6.07 (s, 1H), 4.07-4.09 (m, 1H), 3.60-3.95 (m, 4H), 3.15 (s, 2H), 2.34-2.49 (m, 1H), 2.10-2.23 (m, 1H), 0.83 (d, J=6.6 Hz, 6H).

Example 199

4-[(3S)-3-Aminopyrrolidin-1-yl]-N-(4-fluorobenzyl)pyrimidin-2-amine

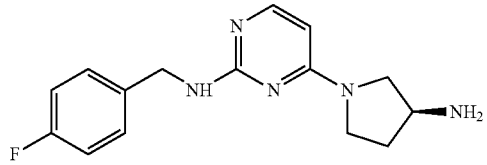 [SMILES: N[C@H]1CCN(c2ccnc(NCc3ccc(F)cc3)n2)C1]

MS (ESI): mass calcd. for $C_{15}H_{18}FN_5$, 287.34 m/z found, 288.1 [M+H]$^+$. $^1$H NMR (300 MHz, D$_2$O): 7.49 (d, J=7.5 Hz, 1H), 7.24-7.29 (m, 2H), 6.95 (m, 2H), 5.98 (m, 1H), 4.45 (s, 2H), 3.95-4.04 (m, 1H), 3.56-3.82 (m, 4H), 2.20-2.41 (m, 1H), 1.98-2.18 (m, 1H).

Example 200

4-[(3S)-3-(Methylamino)pyrrolidin-1-yl]-N-(pyridin-2-ylmethyl)pyrimidin-2-amine

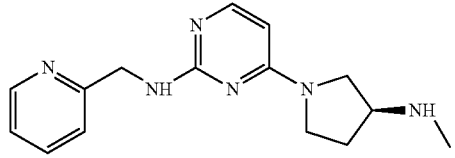 [SMILES: CN[C@H]1CCN(c2ccnc(NCc3ccccn3)n2)C1]

MS (ESI): mass calcd. for $C_{15}H_{20}N_6$, 284.37 m/z found, 285.1 [M+H]$^+$. $^1$H NMR (300 MHz, CD$_3$OD): 8.81 (s, 1H), 8.58 (s, 1H), 8.13 (d, J=6.3 Hz, 1H), 7.97 (s, 1H), 7.87 (d, J=4.8 Hz, 1H), 6.35 (d, J=6.3 Hz, 1H), 5.06 (s, 2H), 4.00-3.54 (m, 5H), 2.76 (s, 3H), 2.54-2.24 (m, 2H).

Example 201

N-Cyclopentyl-4-[(3S)-3-(methylamino)pyrrolidin-1-yl]pyrimidin-2-amine

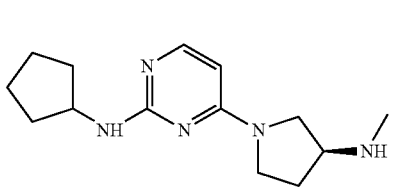 [SMILES: CN[C@H]1CCN(c2ccnc(NC3CCCC3)n2)C1]

MS (ESI): mass calcd. for $C_{14}H_{23}N_5$, 261.37 m/z found, 262.1 [M+H]$^+$. $^1$H NMR (300 MHz, D$_2$O): 7.51 (d, J=7.2 Hz, 1H), 6.07 (s, 1H), 3.83-4.09 (m, 3H), 3.64-3.76 (m, 3H), 2.70 (s, 3H), 2.40-2.50 (m, 1H), 2.17-2.27 (m, 1H), 1.90-1.93 (m, 2H), 1.50-1.60 (m, 6H).

Example 202

4-[(3S)-3-(Methylamino)pyrrolidin-1-yl]-N-(2-methylpropyl)pyrimidin-2-amine

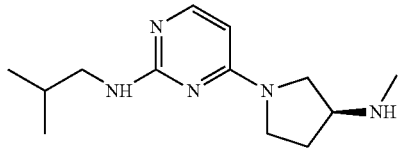 [SMILES: CN[C@H]1CCN(c2ccnc(NCC(C)C)n2)C1]

MS (ESI): mass calcd. for $C_{13}H_{23}N_5$, 249.36 m/z found, 250.1 [M+H]$^+$. $^1$H NMR (300 MHz, CD$_3$OD): 7.53 (d, J=7.2 Hz, 1H), 6.05 (br s, 1H), 3.91-3.63 (m, 5H), 2.70 (s, 3H), 2.50-2.38 (m, 1H), 2.26-2.15 (m, 1H), 1.87-1.78 (m, 1H), 0.84 (d, J=6.6 Hz, 6H).

Example 203

N-(2,2-Dimethylpropyl)-4-[(3S)-3-(methylamino)pyrrolidin-1-yl]pyrimidin-2-amine

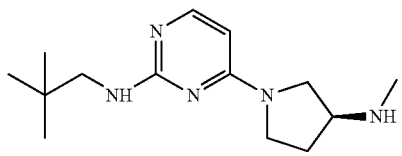 [SMILES: CN[C@H]1CCN(c2ccnc(NCC(C)(C)C)n2)C1]

MS (ESI): mass calcd. for $C_{14}H_{25}N_5$, 263.39 m/z found, 264.1 [M+H]$^+$. $^1$H NMR (300 MHz, D$_2$O): 7.54 (d, J=7.2 Hz, 1H), 6.05 (s, 1H), 3.75-3.91 (m, 3H), 3.62-3.71 (m, 3H), 3.18-3.26 (m, 2H), 2.70 (s, 3H), 2.38-2.50 (m, 1H), 2.15-2.28 (m, 1H), 0.85 (s, 9H).

Example 204

N-Benzyl-4-[(3S)-3-(methylamino)pyrrolidin-1-yl]pyrimidin-2-amine

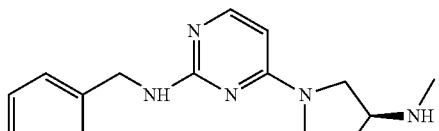

MS (ESI): mass calcd. for $C_{16}H_{21}N_5$, 283.38 m/z found, MISSING $^1$H NMR (300 MHz, CD$_3$OD): 7.79 (d, J=7.2 Hz, 1H), 7.41-7.31 (m, 5H), 6.30 (d, J=6.9 Hz, 1H), 4.68 (s, 2H), 4.06-3.77 (m, 5H), 2.82 (s, 3H), 2.62-2.21 (m, 2H).

Example 205

4-[(3R)-3-Aminopyrrolidin-1-yl]-N-[(1r,5R,7S)-tricyclo[3.3.1.1.3.7]dec-2-yl]pyrimidin-2-amine

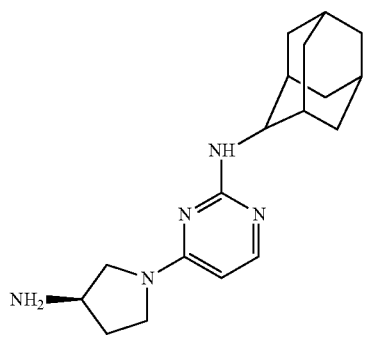 [SMILES: N[C@@H]1CCN(c2ccnc(NC3C4CC5CC(C4)CC3C5)n2)C1]

MS (ESI): mass calcd. for $C_{18}H_{27}N_5$, 313.45 m/z found, 314.3 [M+H]$^+$. $^1$H NMR (300 MHz, CD$_3$OD): 7.81 (d, J=7.5 Hz, 1H), 6.28 (t, J=7.2 Hz, 1H), 4.20-3.61 (m, 6H), 2.60-2.49 (m, 1H), 2.31-2.21 (m, 1H), 2.10-1.72 (m, 14H).

The compounds in Example 206 through Example 253 were prepared using methods analogous to those described in Example 21 Method B.

Example 206

4-[(3S)-3-(Methylamino)pyrrolidin-1-yl]-N-[(1R,2S,4R)-1,7,7-trimethylbicyclo[2.2.1]hept-2-yl]pyridin-2-amine

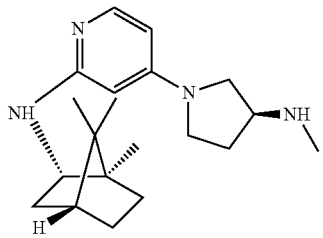 [SMILES: CN[C@H]1CCN(c2ccnc(N[C@H]3C[C@H]4CC[C@]3(C)C4(C)C)c2)C1]

MS (ESI): mass calcd. for $C_{20}H_{32}N_4$, 328.5 m/z found, 329.3 [M+H]$^+$. $^1$H NMR (300 MHz, CD$_3$OD): 7.62 (d, J=7.5 Hz, 1H), 6.42 (dd, J=2.4 Hz, 7.5 Hz, 1H), 5.93 (s, 1H), 4.11-3.69 (m, 6H), 2.88 (s, 3H), 2.67-2.57 (m, 2H), 2.43-2.39 (m, 1H), 2.00-1.35 (m, 6H), 1.11 (s, 3H), 1.02 (s, 3H), 0.98 (s, 3H).

Example 207

Adamantan-2-yl-[4-(4-methyl-piperazin-1-yl)-pyridin-2-yl]-amine

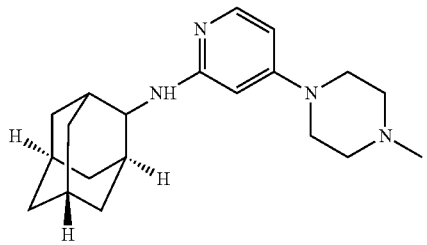 [SMILES: CN1CCN(c2ccnc(NC3C4C[C@H]5C[C@@H](C4)C[C@@H]3C5)c2)CC1]

MS (ESI): mass calcd. for $C_{20}H_{30}N_4$, 326.49 m/z found, 327.3 [M+H]$^+$. $^1$H NMR (300 MHz, CD$_3$OD): 7.65 (d, J=7.8 Hz, 1H), 6.67 (dd, J=2.1 Hz, 7.8 Hz, 1H), 6.32 (s, 1H), 4.30 (d, J=14 Hz, 2H), 3.86 (s, 1H), 3.68 (d, J=12 Hz, 2H), 3.50 (t, J=13 Hz, 2H), 3.40-3.20 (m, 2H), 2.99 (s, 3H), 2.20-1.70 (m, 14H).

Example 208

Adamantan-2-yl-[4-(3R)-(3-methylamino-pyrrolidin-1-yl)-pyridin-2-yl]-amine

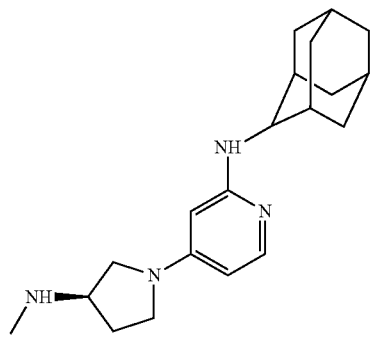 [SMILES: CN[C@@H]1CCN(c2ccnc(NC3C4CC5CC(C4)CC3C5)c2)C1]

MS (ESI): mass calcd. for $C_{20}H_{30}N_4$, 326.49 m/z found, 327.2 [M+H]$^+$. $^1$H NMR (300 MHz, CD$_3$OD): 7.65 (d, J=7.5 Hz, 1H), 6.43 (dd, J=2.1 Hz, 7.5 Hz, 1H), 5.96 (d, J=2.1 Hz, 1H), 4.12-3.69 (m, 6H), 2.88 (s, 3H), 2.66-2.59 (m, 1H), 2.42-2.35 (m, 1H), 2.20-1.75 (m, 14H).

Example 209

N-[(1R)-1-Cyclohexylethyl]-4-[(3R)-3-(methylamino)pyrrolidin-1-yl]pyridin-2-amine

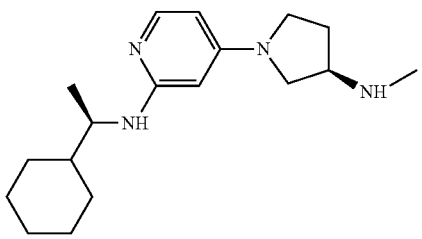 [SMILES: CN[C@@H]1CCN(c2ccnc(N[C@H](C)C3CCCCC3)c2)C1]

MS (ESI): mass calcd. for $C_{18}H_{30}N_4$, 302.47 m/z found, 303.3 [M+H]$^+$. $^1$H NMR (300 MHz, CD$_3$OD): 7.56 (d, J=7.5 Hz, 1H), 6.37 (dd, J=2.1 Hz, 7.5 Hz, 1H), 5.81 (d, J=2.4 Hz, 1H), 4.08-3.53 (m, 6H), 2.84 (s, 3H), 2.62-2.55 (m, 1H), 2.39-2.35 (m, 1H), 1.91-1.71 (m, 5H), 1.60-1.05 (m, 6H), 1.24 (d, J=6.6 Hz, 3H).

Example 210

Adamantan-1-yl-[4-(3S)-(3-methylamino-pyrrolidin-1-yl)-pyridin-2-yl]-amine

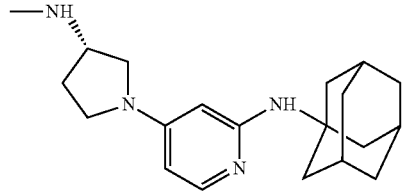 [SMILES: CN[C@H]1CCN(c2ccnc(NC34CC5CC(CC(C5)C3)C4)c2)C1]

105

MS (ESI): mass calcd. for $C_{20}H_{30}N_4$, 326.49 m/z found, 327.3 [M+H]$^+$. $^1$H NMR (300 MHz, CD$_3$OD): 7.53 (d, J=7.5 Hz, 1H), 6.31 (dd, J=2.4 Hz, 7.5 Hz, 1H), 5.80 (s, 1H), 4.00-3.50 (m, 5H), 2.73 (s, 3H), 2.50-2.46 (m, 1H), 2.30-2.20 (m, 1H), 2.13 (s, 3H), 2.01 (s, 6H), 1.75 (s, 6H).

Example 211

N-(Cyclohexylmethyl)-4-[(3R)-3-(methylamino)pyrrolidin-1-yl]pyridin-2-amine

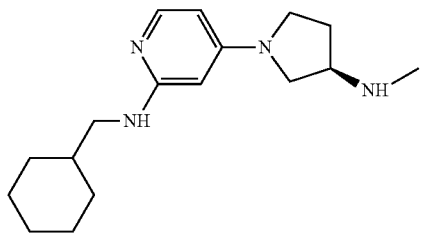 [SMILES: CN[C@@H]1CCN(c2ccnc(NCC3CCCCC3)c2)C1]

MS (ESI): mass calcd. for $C_{17}H_{28}N_4$, 288.44 m/z found, 289.3 [M+H]$^+$. $^1$H NMR (300 MHz, CD$_3$OD): 7.56 (d, J=7.2 Hz, 1H), 6.37 (dd, J=2.4 Hz, 7.2 Hz, 1H), 5.78 (d, J=2.4 Hz, 1H), 4.04-3.60 (m, 5H), 3.12 (d, J=7.2 Hz, 2H), 2.82 (s, 3H), 2.58-2.53 (m, 1H), 2.40-2.20 (m, 1H), 1.87-1.64 (m, 6H), 1.40-1.02 (m, 5H).

Example 212

N-(Cyclohexylmethyl)-4-(4-methylpiperazin-1-yl)pyridin-2-amine

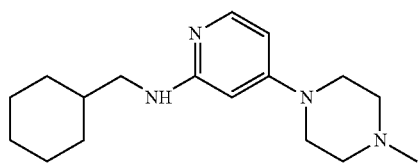 [SMILES: CN1CCN(c2ccnc(NCC3CCCCC3)c2)CC1]

MS (ESI): mass calcd. for $C_{17}H_{28}N_4$, 288.44 m/z found, 289.3 [M+H]$^+$. $^1$H NMR (300 MHz, CD$_3$OD): 7.63 (d, J=7.2 Hz, 1H), 6.68 (d, J=7.8 Hz, 1H), 6.17 (s, 1H), 4.32 (d, J=14.1 Hz, 2H), 3.69 (d, J=12.8 Hz, 2H), 3.50 (t, J=13.6 Hz, 2H), 3.34-3.23 (m, 2H), 3.18 (d, J=7.2 Hz, 2H), 3.01 (s, 3H), 1.90-1.66 (m, 6H), 1.37-1.30 (m, 3H), 1.13-1.05 (m, 2H).

Example 213

N-[(1R)-1-Cyclohexylethyl]-4-[(3S)-3-(methylamino)pyrrolidin-1-yl]pyridin-2-amine

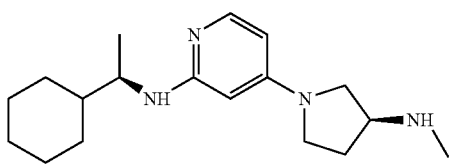 [SMILES: CN[C@H]1CCN(c2ccnc(N[C@H](C)C3CCCCC3)c2)C1]

106

MS (ESI): mass calcd. for $C_{18}H_{30}N_4$, 302.47 m/z found, 303.2 [M+H]$^+$. $^1$H NMR (300 MHz, CD$_3$OD): 7.58 (d, J=7.2 Hz, 1H), 6.39 (d, J=7.5 Hz, 1H), 5.83 (s, 1H), 4.08-3.55 (m, 6H), 2.86 (s, 3H), 2.70-2.50 (m, 1H), 2.40-2.20 (m, 1H), 1.93-1.73 (m, 5H), 1.60-1.08 (m, 6H), 1.26 (d, J=6.3 Hz, 3H).

Example 214

N-[(1R)-1-Cyclohexylethyl]-4-(4-methylpiperazin-1-yl)pyridin-2-amine

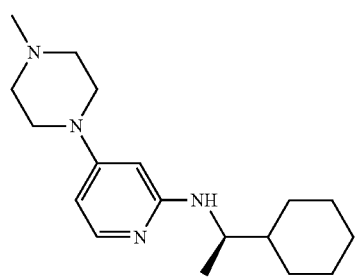 [SMILES: C[C@@H](Nc1cc(N2CCN(C)CC2)ccn1)C1CCCCC1]

MS (ESI): mass calcd. for $C_{18}H_{30}N_4$, 302.47 m/z found, 303.2 [M+H]$^+$. $^1$H NMR (300 MHz, CD$_3$OD): 7.61 (d, J=7.5 Hz, 1H), 6.65 (dd, J=2.4 Hz, 7.5 Hz, 1H), 6.18 (d, J=2.4 Hz, 1H), 4.30 (d, J=14 Hz, 2H), 3.70-3.46 (m, 5H), 3.40-3.20 (m, 2H), 3.00 (s, 3H), 1.91-1.71 (m, 5H), 1.60-1.05 (m, 6H), 1.25 (d, J=6.6 Hz, 3H).

Example 215

Adamantan-2-yl-[4-(3S)-(3-methylamino-pyrrolidin-1-yl)-pyridin-2-yl]-amine

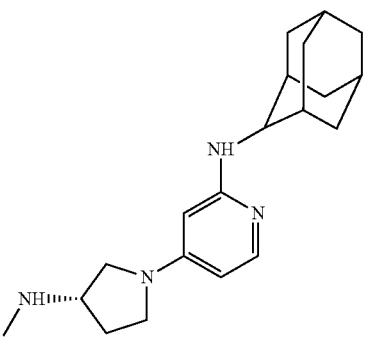 [SMILES: CN[C@H]1CCN(c2ccnc(NC3C4CC5CC(C4)CC3C5)c2)C1]

MS (ESI): mass calcd. for $C_{20}H_{30}N_4$, 326.49 m/z found, 327.2 [M+H]$^+$. $^1$H NMR (300 MHz, CD$_3$OD): 7.65 (d, J=7.5 Hz, 1H), 6.43 (dd, J=2.1 Hz, 7.5 Hz, 1H), 5.96 (d, J=1.8 Hz, 1H), 4.12-3.69 (m, 6H), 2.88 (s, 3H), 2.67-2.59 (m, 1H), 2.43-2.36 (m, 1H), 2.20-1.75 (m, 14H).

Example 216

3-{[4-(4-Methylpiperazin-1-yl)pyridin-2-yl]-amino}propan-1-ol

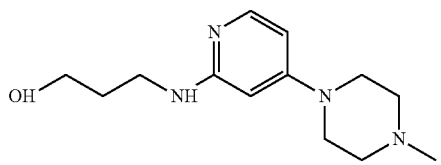 [SMILES: CN1CCN(c2ccnc(NCCCO)c2)CC1]

MS (ESI): mass calcd. for $C_{13}H_{22}N_4O$, 250.35 m/z found, 251.1 [M+H]$^+$. $^1$H NMR (300 MHz, CD$_3$OD): 7.57 (d, J=7.5 Hz, 1H), 6.62-6.59 (m, 1H), 4.25 (d, J=14.4 Hz, 2H), 3.66-3.59 (m, 4H), 3.48-3.15 (m, 6H), 2.93 (s, 3H), 1.86-1.78 (m, 2H).

Example 217

N-{[(1S,2S,5S)-6,6-Dimethylbicyclo[3.1.1]hept-2-yl]methyl}-4-[(3R)-3-(methylamino)pyrrolidin-1-yl] pyridin-2-amine

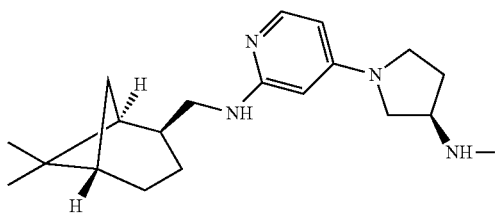

MS (ESI): mass calcd. for $C_{20}H_{32}N_4$, 328.5 m/z found, 329.3 [M+H]$^+$. $^1$H NMR (300 MHz, CD$_3$OD): 7.55 (d, J=7.2 Hz, 1H), 6.36 (dd, J=2.1 Hz, 7.2 Hz, 1H), 5.74 (s, 1H), 4.10-3.50 (m, 5H), 3.40-3.20 (m, 2H), 2.81 (s, 3H), 2.56-2.33 (m, 4H), 2.31-1.94 (m, 5H), 1.60-1.50 (m, 1H), 1.24 (s, 3H), 1.09 (s, 3H), 0.97 (d, J=9.9 Hz, 1H)

Example 218

Adamantan-1-yl-[4-(3R)-(3-methylamino-pyrrolidin-1-yl)-pyridin-2-yl]-amine

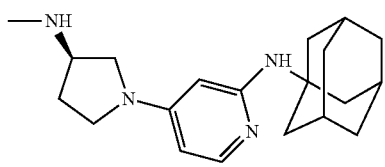 [SMILES: CN[C@@H]1CCN(c2ccnc(NC34CC5CC(CC(C5)C3)C4)c2)C1]

MS (ESI): mass calcd. for $C_{20}H_{30}N_4$, 326.49 m/z found, 327.2 [M+H]$^+$. $^1$H NMR (300 MHz, CD$_3$OD): 7.54 (d, J=7.5 Hz, 1H), 6.32 (dd, J=2.4 Hz, 7.5 Hz, 1H), 5.81 (d, J=2.1 Hz, 1H), 4.00-3.50 (m, 5H), 2.76 (s, 3H), 2.53-2.48 (m, 1H), 2.33-2.28 (m, 1H), 2.12 (br s, 3H), 2.01 (s, 6H), 1.75 (s, 6H).

Example 219

Adamantan-1-yl-[4-(4-methyl-piperazin-1-yl)-pyridin-2-yl]-amine

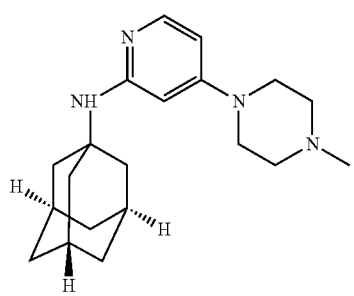 [SMILES: CN1CCN(c2ccnc(NC34C[C@H]5C[C@@H](C3)C[C@@H](C4)C5)c2)CC1]

MS (ESI): mass calcd. for $C_{20}H_{30}N_4$, 326.49 m/z found, 327.2 [M+H]$^+$. $^1$H NMR (300 MHz, CD$_3$OD): 7.59 (d, J=7.8 Hz, 1H), 6.61 (dd, J=2.4 Hz, 7.5 Hz, 1H), 6.15 (d, J=2.1 Hz, 1H), 4.30-4.10 (m, 2H), 3.70-3.40 (m, 6H), 2.93 (s, 3H), 2.13 (s, 3H), 2.01 (s, 6H), 1.75 (t, J=14 Hz, 6H).

Example 220

Adamantan-1-ylmethyl-[4-(3R)-(3-methylamino-pyrrolidin-1-yl)-pyridin-2-yl]-amine

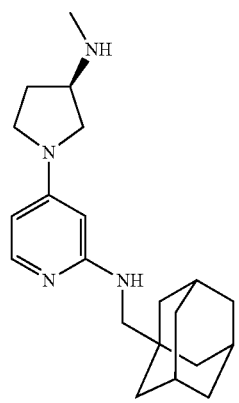 [SMILES: CN[C@@H]1CCN(c2ccnc(NCC34CC5CC(CC(C5)C3)C4)c2)C1]

MS (ESI): mass calcd. for $C_{21}H_{32}N_4$, 340.52 m/z found, 341.3 [M+H]$^+$. $^1$H NMR (300 MHz, CD$_3$OD): 7.61 (d, J=7.5 Hz, 1H), 6.41 (dd, J=2.1 Hz, 7.5 Hz, 1H), 5.91 (d, J=2.1 Hz, 1H), 4.12-3.69 (m, 5H), 3.05 (s, 2H), 2.88 (s, 3H), 2.66-2.59 (m, 1H), 2.43-2.40 (m, 1H), 2.36 (s, 3H), 1.82 (dd, J=12 Hz, 27 Hz, 6H), 1.70 (s, 6H).

Example 221

N-{[(1S,2S,5S)-6,6-Dimethylbicyclo[3.1.1]hept-2-yl]methyl}-4-(4-methylpiperazin-1-yl)pyridin-2-amine

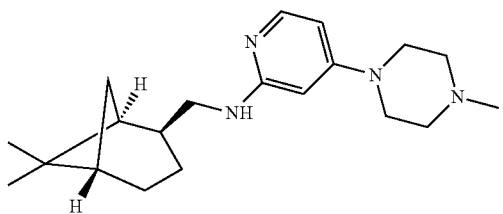

MS (ESI): mass calcd. for $C_{20}H_{32}N_4$, 328.5 m/z found, 329.3 [M+H]$^+$. $^1$H NMR (300 MHz, CD$_3$OD): 7.59 (d, J=7.2 Hz, 1H), 6.64 (dd, J=2.1 Hz, 7.5 Hz, 1H), 5.74 (d, J=2.1 Hz, 1H), 4.27 (d, J=14 Hz, 2H), 3.64 (d, J=12 Hz, 2H), 3.45 (dd, J=14 Hz, 12 Hz, 2H), 3.40-3.20 (m, 4H), 2.97 (s, 3H), 2.43-2.38 (m, 2H), 2.04-1.94 (m, 5H), 1.60-1.50 (m, 1H), 1.24 (s, 3H), 1.09 (s, 3H), 0.98 (d, J=9.6 Hz, 1H).

Example 222

4-[(3R)-3-(Methylamino)pyrrolidin-1-yl]-N-(tetrahydro-2H-pyran-4-yl)pyridin-2-amine

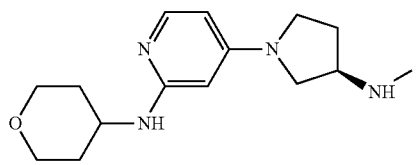 [SMILES: CN[C@@H]1CCN(c2ccnc(NC3CCOCC3)c2)C1]

MS (ESI): mass calcd. for $C_{15}H_{24}N_4O$, 276.38 m/z found, 277.2 [M+H]$^+$. $^1$H NMR (300 MHz, CD$_3$OD): 7.62 (d, J=7.5 Hz, 1H), 6.43 (dd, J=2.1 Hz, 7.5 Hz, 1H), 5.85 (d, J=2.1 Hz, 1H), 4.06-3.61 (m, 10H), 2.86 (s, 3H), 2.70-2.50 (m, 1H), 2.45-2.35 (m, 1H), 2.10-2.00 (m, 2H), 1.70-1.69 (m, 2H).

Example 223

4-(4-Methylpiperazin-1-yl)-N-(tetrahydro-2H-pyran-4-yl)pyridin-2-amine

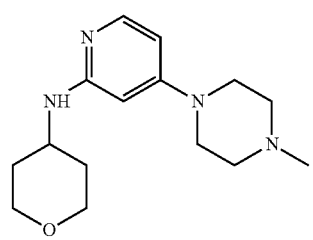 [SMILES: CN1CCN(c2ccnc(NC3CCOCC3)c2)CC1]

MS (ESI): mass calcd. for $C_{15}H_{24}N_4O$, 276.38 m/z found, 277.2 [M+H]$^+$. $^1$H NMR (300 MHz, CD$_3$OD): 7.67 (d, J=7.5 Hz, 1H), 6.64 (dd, J=2.4 Hz, 7.5 Hz, 1H), 6.21 (d, J=2.4 Hz, 1H), 4.35 (d, J=14 Hz, 2H), 4.05-4.01 (m, 2H), 3.88-3.48 (m, 7H), 3.40-3.20 (m, 2H), 3.04 (s, 3H), 2.10-1.90 (m, 2H), 1.72-1.64 (m, 2H).

Example 224

N-{[(1S,2S,5S)-6,6-Dimethylbicyclo[3.1.1]hept-2-yl]methyl}-4-[(3S)-3-(methylamino)pyrrolidin-1-yl]pyridin-2-amine

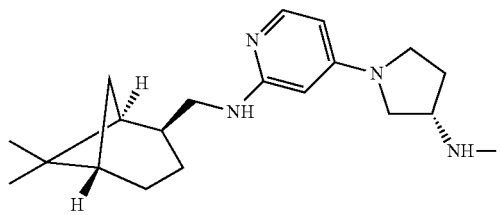

MS (ESI): mass calcd. for $C_{20}H_{32}N_4$, 328.5 m/z found, 329.2 [M+H]$^+$. $^1$H NMR (300 MHz, CD$_3$OD): 7.55 (d, J=7.5 Hz, 1H), 6.36 (dd, J=2.1 Hz, 7.2 Hz, 1H), 5.74 (d, J=1.8 Hz, 1H), 4.10-3.60 (m, 5H), 3.40-3.20 (m, 2H), 2.81 (s, 3H), 2.60-2.20 (m, 4H), 2.10-1.90 (m, 5H), 1.70-1.50 (m, 1H), 1.24 (s, 3H), 1.09 (s, 3H), 0.97 (d, J=9.6 Hz, 1H).

Example 225

N-(Cyclohexylmethyl)-4-[(3S)-3-(methylamino)pyrrolidin-1-yl]pyridin-2-amine

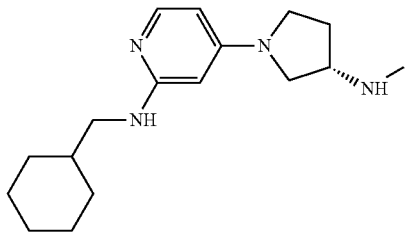 [SMILES: CN[C@H]1CCN(c2ccnc(NCC3CCCCC3)c2)C1]

MS (ESI): mass calcd. for $C_{17}H_{28}N_4$, 288.44 m/z found, 289.3 [M+H]$^+$. $^1$H NMR (300 MHz, CD$_3$OD): 7.56 (d, J=7.2 Hz, 1H), 6.37 (dd, J=2.4 Hz, 7.5 Hz, 1H), 5.77 (d, J=2.4 Hz, 1H), 4.10-3.50 (m, 5H), 3.12 (d, J=6.9 Hz, 2H), 2.82 (s, 3H), 2.60-2.53 (m, 1H), 2.36-2.29 (m, 1H), 1.87-1.60 (m, 6H), 1.38-1.02 (m, 5H).

Example 226

N-(Cyclopentylmethyl)-4-[(3R)-3-(methylamino)pyrrolidin-1-yl]pyridin-2-amine

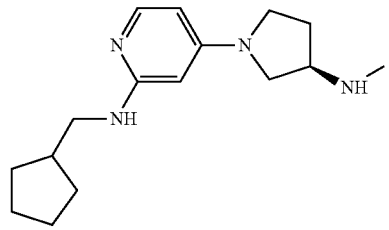 [SMILES: CN[C@@H]1CCN(c2ccnc(NCC3CCCC3)c2)C1]

MS (ESI): mass calcd. for $C_{16}H_{26}N_4$, 274.41 m/z found, 275.2 [M+H]$^+$. $^1$H NMR (300 MHz, CD$_3$OD): 7.56 (d, J=7.2 Hz, 1H), 6.37 (d, J=7.2 Hz, 1H), 5.78 (s, 1H), 4.04-3.62 (m, 5H), 3.20 (d, J=7.2 Hz, 2H), 2.82 (s, 3H), 2.60-2.51 (m, 1H), 2.40-2.17 (m, 2H), 1.89-1.62 (m, 6H), 1.34-1.28 (m, 2H).

Example 227

N-(Cyclopentylmethyl)-4-[(3S)-3-(methylamino)pyrrolidin-1-yl]pyridin-2-amine

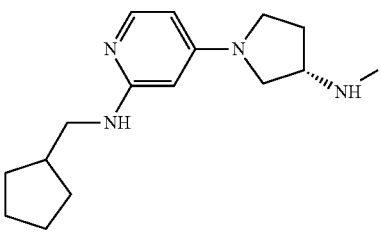 [SMILES: CN[C@H]1CCN(c2ccnc(NCC3CCCC3)c2)C1]

MS (ESI): mass calcd. for $C_{16}H_{26}N_4$, 274.41 m/z found, 275.3 [M+H]$^+$. $^1$H NMR (300 MHz, CD$_3$OD): 7.56 (d, J=7.5 Hz, 1H), 6.37 (d, J=7.2 Hz, 1H), 5.78 (s, 1H), 4.04-3.62 (m, 5H), 3.20 (d, J=7.2 Hz, 2H), 2.82 (s, 3H), 2.58-2.53 (m, 1H), 2.36-2.19 (m, 2H), 1.89-1.62 (m, 6H), 1.34-1.30 (m, 2H).

Example 228

N-Cyclopentyl-4-[(3S)-3-(methylamino)pyrrolidin-1-yl]pyridin-2-amine

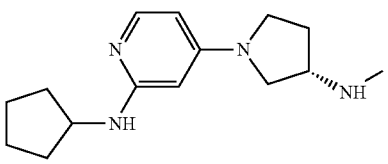 [SMILES: CN[C@H]1CCN(c2ccnc(NC3CCCC3)c2)C1]

MS (ESI): mass calcd. for $C_{16}H_{24}N_4$, 260.39 m/z found, 261.2 [M+H]$^+$. $^1$H NMR (300 MHz, CD$_3$OD): 7.56 (d, J=7.5 Hz, 1H), 6.37 (d, J=7.5 Hz, 1H), 5.76 (s, 1H), 4.05-3.62 (m, 6H), 2.82 (s, 3H), 2.60-2.53 (m, 1H), 2.39-2.33 (m, 1H), 2.11-2.06 (m, 2H), 1.83-1.56 (m, 6H).

Example 229

4-[(3S)-3-(Methylamino)pyrrolidin-1-yl]-N-(pyridin-2-ylmethyl)pyridin-2-amine

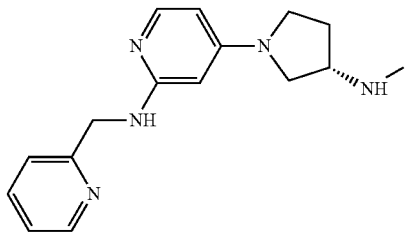 [SMILES: CN[C@H]1CCN(c2ccnc(NCc3ccccn3)c2)C1]

MS (ESI): mass calcd. for $C_{16}H_{21}N_5$, 283.38 m/z found, 284.1 [M+H]$^+$. $^1$H NMR (300 MHz, DMSO-d$_6$): 12.73 (br s, 1H), 9.60 (br s, 2H), 8.72 (d, J=4.5 Hz, 1H), 8.29-8.10 (m, 2H), 7.73-7.36 (m, 3H), 6.34 (d, J=5.7 Hz, 1H), 5.84 (s, 1H), 4.84 (d, J=5.1 Hz, 2H), 3.90-3.42 (m, 5H), 2.60 (s, 3H), 2.40-2.30 (m, 2H).

Example 230

4-[(3S)-3-(Methylamino)pyrrolidin-1-yl]-N-[(1S,5R)-2,6,6-trimethylbicyclo[3.1.1]hept-3-yl]pyridin-2-amine

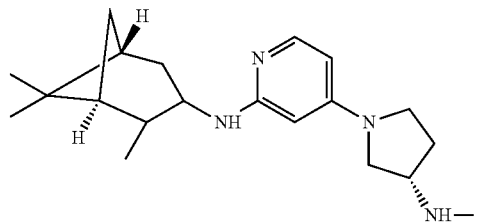

MS (ESI): mass calcd. for $C_{20}H_{32}N_4$, 328.5 m/z found, 329.2 [M+H]$^+$. $^1$H NMR (300 MHz, DMSO-d$_6$): 12.39 (br s, 1H), 9.61 (br s, 2H), 8.05 (d, J=8.4 Hz, 1H), 7.66 (m, 1H), 6.29 (d, J=6.9 Hz, 1H), 5.75 (s, 1H), 3.96-3.40 (m, 6H), 2.60 (s, 3H), 2.50-2.30 (m, 3H), 12.07-1.51 (m, 5H), 1.23 (s, 3H), 1.05 (m, 7H).

Example 231

N-Bicyclo[2.2.1]hept-2-yl-4-[(3S)-3-(methylamino)pyrrolidin-1-yl]pyridin-2-amine

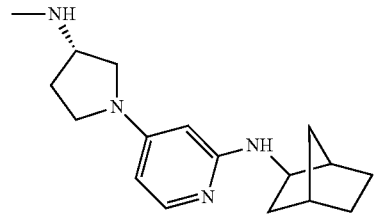 [SMILES: CN[C@H]1CCN(c2ccnc(NC3CC4CCC3C4)c2)C1]

MS (ESI): mass calcd. for $C_{17}H_{26}N_4$, 286.42 m/z found, 287.3 [M+H]$^+$. $^1$H NMR (300 MHz, DMSO-d$_6$): 12.19 (br s, 1H), 9.59 (br s, 2H), 7.90 (d, J=6.0 Hz, 1H), 7.67 (br s, 1H), 6.28 (d, J=6.9 Hz, 1H), 5.65 (s, 1H), 3.89-3.50 (m, 6H), 2.59 (s, 3H), 2.33-2.17 (m, 4H), 1.85-1.79 (m, 1H), 1.48-1.09 (m, 7H).

Example 232

4-(4-Methylpiperazin-1-yl)-N-[(1S,5R)-2,6,6-trimethylbicyclo[3.1.1]hept-3-yl]pyridin-2-amine

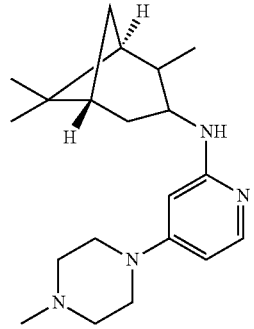 [SMILES: CC1C(Nc2cc(N3CCN(C)CC3)ccn2)C[C@H]2C[C@@H]1C2(C)C]

MS (ESI): mass calcd. for $C_{20}H_{32}N_4$, 328.5 m/z found, 329.2 [M+H]$^+$. $^1$H NMR (300 MHz, CD$_3$OD): 7.53 (d, J=7.5

Hz, 1H), 6.58 (d, J=7.8 Hz, 1H), 6.11 (s, 1H), 4.20 (d, J=14 Hz, 2H), 3.89-3.84 (m, 1H), 3.57 (d, J=12 Hz, 2H), 3.42 (t, J=13 Hz, 2H) 3.17 (t, J=13 Hz, 2H), 2.89 (s, 3H), 2.72-2.64 (m, 1H), 2.40-2.35 (m, 1H), 2.05-1.55 (m, 4H), 1.18 (s, 3H), 1.07 (d, J=7.2 Hz, 3H), 1.05-1.00 (m, 1H), 1.00 (s, 3H).

Example 233

N-tert-Butyl-4-[(3S)-3-(methylamino)pyrrolidin-1-yl]pyridin-2-amine

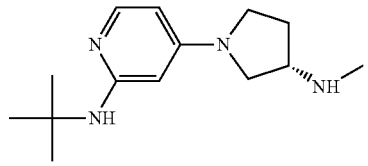 [SMILES: CN[C@H]1CCN(c2ccnc(NC(C)(C)C)c2)C1]

MS (ESI): mass calcd. for $C_{14}H_{24}N_4$, 248.37 m/z found, 249.2 [M+H]$^+$. $^1$H NMR (300 MHz, CD$_3$OD): 7.55 (d, J=7.5 Hz, 1H), 6.34-6.31 (m, 1H), 5.77 (s, 1H), 4.01-3.59 (m, 5H), 2.77 (s, 3H), 2.53-2.49 (m, 1H), 2.33-2.29 (m, 1H), 1.43 (s, 9H).

Example 234

3-({4-[(3S)-3-(Methylamino)pyrrolidin-1-yl]pyridin-2-yl}amino)propan-1-ol

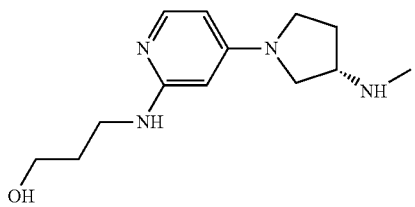 [SMILES: CN[C@H]1CCN(c2ccnc(NCCCO)c2)C1]

MS (ESI): mass calcd. for $C_{13}H_{22}N_4O$, 250.35 m/z found, 251.2 [M+H]$^+$. $^1$H NMR (300 MHz, CD$_3$OD): 7.47 (d, J=7.5 Hz, 1H), 6.27 (d, J=7.2 Hz, 1H), 5.70 (br, 1H), 3.94-3.21 (m, 10H), 2.72 (s, 3H), 2.48-2.43 (m, 1H), 2.27-2.23 (m, 1H), 1.81-1.73 (m, 2H).

Example 235

N-Cyclopropyl-4-[(3S)-3-(methylamino)pyrrolidin-1-yl]pyridin-2-amine

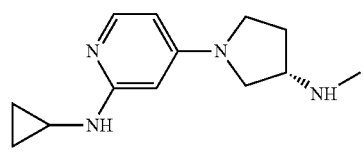 [SMILES: CN[C@H]1CCN(c2ccnc(NC3CC3)c2)C1]

MS (ESI): mass calcd. for $C_{13}H_{20}N_4$, 232.33 m/z found, 233.2 [M+H]$^+$. $^1$H NMR (300 MHz, CD$_3$OD): 7.52 (d, J=7.5 Hz, 1H), 6.33 (dd, J=7.5 Hz, J=2.1 Hz, 1H), 5.76 (d, J=1.5 Hz, 1H), 3.96-3.52 (m, 4H), 2.52-2.41 (m, 2H), 2.30-2.21 (m, 1H), 0.88-0.82 (m, 2H), 0.56-0.51 (m, 2H).

Example 236

N-(Cyclopentylmethyl)-4-(4-methylpiperazin-1-yl)pyridin-2-amine

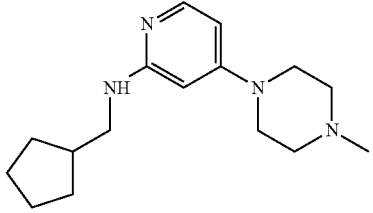 [SMILES: CN1CCN(c2ccnc(NCC3CCCC3)c2)CC1]

MS (ESI): mass calcd. for $C_{16}H_{26}N_4$, 274.41 m/z found, 275.2 [M+H]$^+$. $^1$H NMR (300 MHz, CD$_3$OD): 7.61 (d, J=7.5 Hz, 1H), 6.66 (d, J=7.5 Hz, 1H), 6.16 (s, 1H), 4.29 (d, J=14 Hz, 2H), 3.66 (d, J=12 Hz, 2H), 3.48 (t, J=13 Hz, 2H), 3.40-3.20 (m, 2H), 3.22 (d, J=7.2 Hz, 2H), 2.98 (s, 3H), 2.27-2.17 (m, 1H), 1.90-1.62 (m, 6H), 1.34-1.30 (m, 2H).

Example 237

N-Benzyl-4-[(3S)-3-(methylamino)pyrrolidin-1-yl]pyridin-2-amine

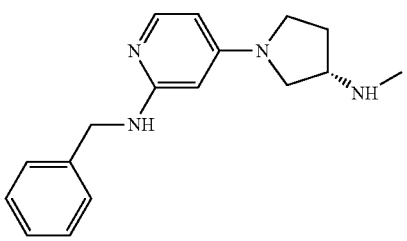 [SMILES: CN[C@H]1CCN(c2ccnc(NCc3ccccc3)c2)C1]

MS (ESI): mass calcd. for $C_{17}H_{22}N_4$, 282.39 m/z found, 283.1 [M+H]$^+$. $^1$H NMR (300 MHz, DMSO-d$_6$): 12.49 (br s, 1H), 9.53 (br s, 2H), 8.22 (s, 1H), 7.69 (s, 1H), 7.41-7.33 (m, 5H), 6.30 (d, J=6.9 Hz, 1H), 5.75 (s, 1H), 4.55 (d, J=5.4 Hz, 2H), 3.89-3.50 (m, 5H), 2.60 (s, 3H), 2.40-2.20 (m, 2H).

Example 238

N-(2-Methoxyethyl)-4-[(3S)-3-(methylamino)pyrrolidin-1-yl]pyridin-2-amine

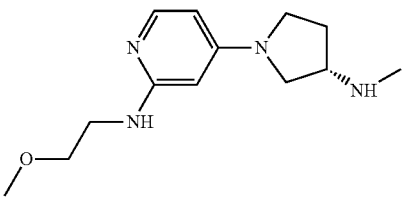

MS (ESI): mass calcd. for $C_{13}H_{22}N_4O$, 250.35 m/z found, 251.2 [M+H]$^+$. $^1$H NMR (300 MHz, CD$_3$OD): 7.59 (d, J=7.5

Hz, 1H), 6.38 (dd, J=7.5 Hz, J=2.4 Hz, 1H), 5.83 (d, J=2.4 Hz, 1H), 4.05-4.02 (m, 1H), 3.93-3.89 (m, 2H), 3.71-3.32 (m, 6H), 3.31 (s, 3H), 2.82 (s, 3H), 2.61-2.54 (m, 1H), 2.37-2.30 (m, 1H).

Example 239

N-(2-Methoxyethyl)-4-(4-methylpiperazin-1-yl)pyridin-2-amine

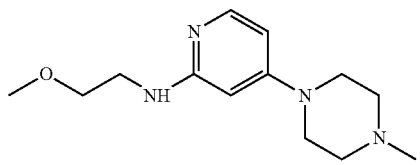

MS (ESI): mass calcd. for $C_{13}H_{22}N_4O$, 250.35 m/z found, 251.2 $[M+H]^+$. $^1$H NMR (300 MHz, $CD_3OD$): 7.64 (d, J=7.5 Hz, 1H), 6.67 (dd, J=7.8 Hz, J=2.4 Hz, 1H), 6.20 (d, J=2.1 Hz, 1H), 4.3 (d, J=14.4 Hz, 2H), 3.67-3.21 (m, 13H), 2.98 (s, 3H).

Example 240

2-Methyl-1-({4-[(3R)-3-(methylamino)pyrrolidin-1-yl]pyridin-2-yl}amino)propan-2-ol

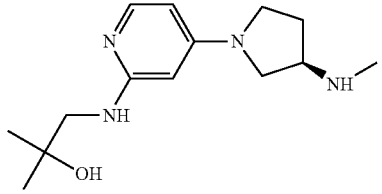 [SMILES: CN[C@@H]1CCN(c2ccnc(NCC(C)(C)O)c2)C1]

MS (ESI): mass calcd. for $C_{14}H_{24}N_4O$, 264.37 m/z found, 265.2 $[M+H]^+$. $^1$H NMR (300 MHz, $CD_3OD$): 7.59 (d, J=7.2 Hz, 1H), 6.37 (br d, J=6.0 Hz, 1H), 5.88 (s, 1H), 4.03-3.63 (m, 5H), 3.26 (s, 2H), 2.82 (s, 3H), 2.58-2.53 (m, 1H), 2.36-2.32 (m, 1H), 1.29 (s, 6H).

Example 241

2-Methyl-1-{[4-(4-methylpiperazin-1-yl)pyridin-2-yl]-amino}propan-2-ol

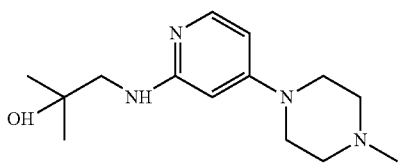 [SMILES: CN1CCN(c2ccnc(NCC(C)(C)O)c2)CC1]

MS (ESI): mass calcd. for $C_{14}H_{24}N_4O$, 264.37 m/z found, 265.2 $[M+H]^+$. $^1$H NMR (300 MHz, $CD_3OD$): 7.69 (d, J=7.8 Hz, 1H), 6.71 (br d, J=5.7 Hz, 1H), 6.30 (s, 1H), 4.36 (d, J=14 Hz, 2H), 3.72-3.48 (m, 6H), 3.30-3.20 (m, 2H), 3.03 (s, 3H), 1.34 (s, 6H).

Example 242

2-Methyl-1-({4-[(3S)-3-(methylamino)pyrrolidin-1-yl]pyridin-2-yl}amino)propan-2-ol

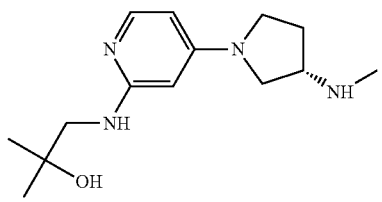 [SMILES: CN[C@H]1CCN(c2ccnc(NCC(C)(C)O)c2)C1]

MS (ESI): mass calcd. for $C_{14}H_{24}N_4O$, 264.37 m/z found, 265.3 $[M+H]^+$. $^1$H NMR (300 MHz, $CD_3OD$): 7.59 (d, J=7.5 Hz, 1H), 6.36 (d, J=7.5 Hz, 1H), 5.87 (s, 1H), 4.06-3.63 (m, 5H), 3.27 (s, 2H), 2.83 (s, 3H), 2.61-2.51 (m, 1H), 2.40-2.31 (m, 1H), 1.30 (s, 6H).

Example 243

N-Butyl-4-[(3S)-3-(methylamino)pyrrolidin-1-yl]pyridin-2-amine

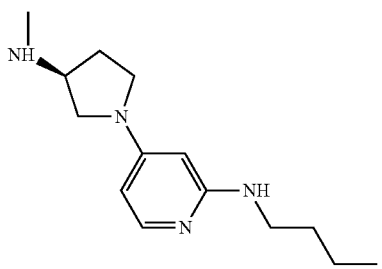 [SMILES: CCCCNc1cc(N2CC[C@H](NC)C2)ccn1]

MS (ESI): mass calcd. for $C_{14}H_{24}N_4$, 248.37 m/z found, 249.3 $[M+H]^+$. $^1$H NMR (300 MHz, $CD_3OD$): 7.59 (d, J=7.2 Hz, 1H), 6.39 (d, J=6.9 Hz, 1H), 5.79 (s, 1H), 4.07-3.64 (m, 5H), 3.31 (t, J=7.2 Hz, 2H), 2.84 (s, 3H), 2.63-2.56 (m, 1H), 2.42-2.36 (m, 1H), 1.73-1.63 (m, 2H), 1.55-1.48 (m, 2H), 1.01 (t, J=7.5 Hz, 3H).

Example 244

4-(4-Methylpiperazin-1-yl)-N-(pyridin-2-ylmethyl)pyridin-2-amine

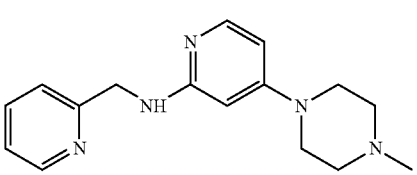 [SMILES: CN1CCN(c2ccnc(NCc3ccccn3)c2)CC1]

MS (ESI): mass calcd. for $C_{16}H_{21}N_5$, 283.38 m/z found, 284.2 $[M+H]^+$. $^1$H NMR (300 MHz, $CD_3OD$): 8.89 (d, J=4.5

Hz, 1H), 8.62 (m, 1H), 8.13-8.05 (m, 2H), 7.80 (d, J=7.2 Hz, 1H), 6.82 (d, J=6.6 Hz, 1H), 6.37 (s, 1H), 5.16 (s, 2H), 4.43 (d, J=13 Hz, 2H), 3.69-3.53 (m, 4H), 3.30-3.20 (m, 2H), 3.01 (s, 3H).

Example 245

4-[(3S)-3-(Methylamino)pyrrolidin-1-yl]-N-(2-phenylethyl)pyridin-2-amine

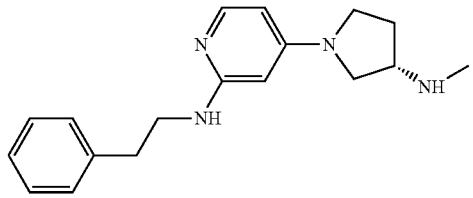 [SMILES: CN[C@H]1CCN(c2ccnc(NCCc3ccccc3)c2)C1]

MS (ESI): mass calcd. for C$_{18}$H$_{24}$N$_4$, 296.42 m/z found, 297.1 [M+H]$^+$. $^1$H NMR (300 MHz, DMSO-d$_6$): 12.40 (br s, 1H), 9.64 (br s, 2H), 7.81 (s, 1H), 7.67 (s, 1H), 7.33-7.25 (m, 5H), 6.29 (s, 1H), 5.69 (s, 1H), 3.89-3.50 (m, 7H), 2.97-2.88 (m, 2H), 2.60 (s, 3H), 2.40-2.20 (m, 2H).

Example 246

N-(4-Fluorobenzyl)-4-[(3S)-3-(methylamino)pyrrolidin-1-yl]pyridin-2-amine

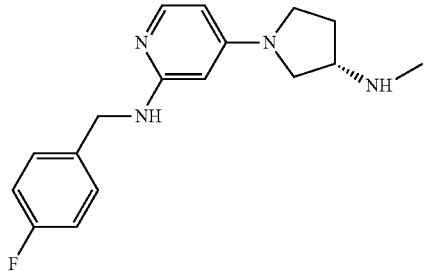 [SMILES: CN[C@H]1CCN(c2ccnc(NCc3ccc(F)cc3)c2)C1]

MS (ESI): mass calcd. for C$_{17}$H$_{21}$FN$_4$, 300.38 m/z found, 301.1 [M+H]$^+$. $^1$H NMR (300 MHz, DMSO-d$_6$): 12.57 (br s, 1H), 9.56 (br s, 2H), 8.25 (s, 1H), 7.69 (d, J=6.9 Hz, 1H), 7.48-7.43 (m, 2H), 7.25-7.19 (m, 2H), 6.30 (d, J=6.6 Hz, 1H), 5.73 (s, 1H), 4.54 (d, J=5.7 Hz, 2H), 3.89-3.61 (m, 5H), 2.59 (s, 3H), 2.40-2.20 (m, 2H).

Example 247

4-[(3R)-3-(Methylamino)pyrrolidin-1-yl]-N-[(1R,2S,4R)-1,7,7-trimethylbicyclo[2.2.1]hept-2-yl]pyridin-2-amine

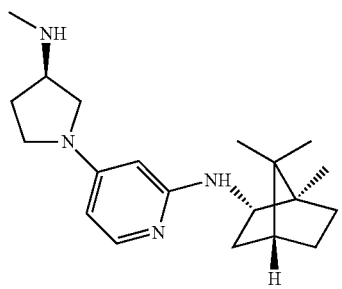 [SMILES: CN[C@@H]1CCN(c2ccnc(N[C@H]3C[C@H]4CC[C@]3(C)C4(C)C)c2)C1]

MS (ESI): mass calcd. for C$_{20}$H$_{32}$N$_4$, 328.5 m/z found, 329.3 [M+H]$^+$. $^1$H NMR (300 MHz, CD$_3$OD): 7.62 (d, J=7.2 Hz, 1H), 6.42 (dd, J=2.1 Hz, 7.2 Hz, 1H), 5.92 (d, J=2.1 Hz, 1H), 4.11-3.69 (m, 6H), 2.87 (s, 3H), 2.64-2.56 (m, 2H), 2.42-2.37 (m, 1H), 2.00-1.35 (m, 6H), 1.11 (s, 3H), 1.02 (s, 3H), 0.98 (s, 3H).

Example 248

N-Cyclopentyl-4-(4-methylpiperazin-1-yl)pyridin-2-amine

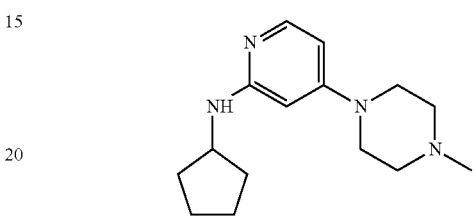

MS (ESI): mass calcd. for C$_{15}$H$_{24}$N$_4$, 260.39 m/z found, MISSING $^1$H NMR (300 MHz, CD$_3$OD): 7.60 (d, J=7.8 Hz, 1H), 6.64 (d, J=7.5 Hz, 1H), 6.11 (s, 1H), 4.27 (d, J=14 Hz, 2H), 3.99-3.97 (m, 1H), 3.64 (d, J=12 Hz, 2H), 3.45 (t, J=14 Hz, 2H), 3.22 (t, J=11 Hz, 2H), 2.97 (s, 3H), 2.09-2.05 (m, 2H), 2.18-1.57 (m, 6H).

Example 249

N-(4-Fluorobenzyl)-4-(4-methylpiperazin-1-yl)pyridin-2-amine

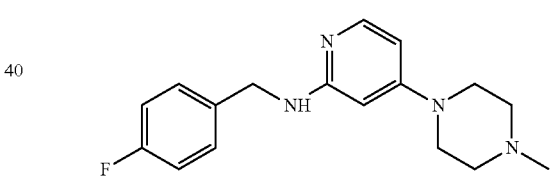

MS (ESI): mass calcd. for C$_{17}$H$_{21}$FN$_4$, 300.38 m/z found, 301.1 [M+H]$^+$. $^1$H NMR (300 MHz, CD$_3$OD): 7.66 (d, J=7.5 Hz, 1H), 7.47-7.42 (m, 2H), 7.17-7.12 (m, 2H), 6.70 (d, J=7.2 Hz, 1H), 6.16 (s, 1H), 4.55 (s, 2H), 4.30 (d, J=14 Hz, 2H), 3.67 (d, J=12 Hz, 2H), 3.47 (t, J=13 Hz, 2H), 3.24 (t, J=12 Hz, 2H), 2.99 (s, 3H).

Example 250

4-(4-Methylpiperazin-1-yl)-N-(2-phenylethyl)pyridin-2-amine

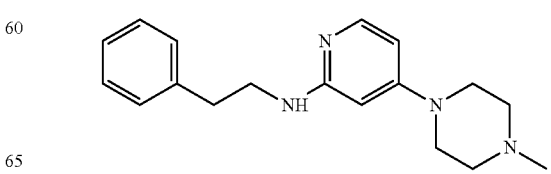

MS (ESI): mass calcd. for $C_{18}H_{24}N_4$, 296.42 m/z found, 297.2 [M+H]$^+$. $^1$H NMR (300 MHz, DMSO-d$_6$): 12.66 (s, 1H), 11.64 (br s, 1H), 7.93 (s, 1H), 7.70 (s, 1H), 7.30-7.22 (m, 5H), 6.59 (d, J=6.9 Hz, 1H), 6.08 (s, 1H), 4.69 (br s, 2H), 4.19 (d, J=13 Hz, 2H), 3.51-3.46 (m, 4H), 3.08-2.84 (m, 4H), 2.76 (s, 3H).

Example 251

Adamantan-1-ylmethyl-[4-(3S)-(3-methylamino-pyrrolidin-1-yl)-pyridin-2-yl]-amine

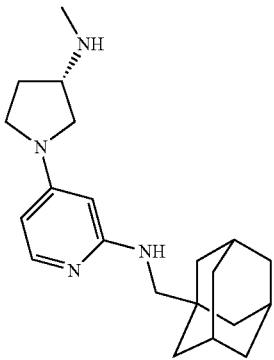 [SMILES: CN[C@H]1CCN(c2ccnc(NCC34CC5CC(CC(C5)C3)C4)c2)C1]

MS (ESI): mass calcd. for $C_{21}H_{32}N_4$, 340.52 m/z found, 341.2 [M+H]$^+$. $^1$H NMR (300 MHz, CD$_3$OD): 7.61 (d, J=7.5 Hz, 1H), 6.41 (dd, J=1.8 Hz, 7.5 Hz, 1H), 5.91 (d, J=1.5 Hz, 1H), 4.11-3.69 (m, 5H), 3.05 (s, 2H), 2.88 (s, 3H), 2.66-2.59 (m, 1H), 2.43-2.40 (m, 1H), 2.38 (s, 3H), 1.82 (dd, J=12 Hz, 27 Hz, 6H), 1.70 (s, 6H).

Example 252

4-(4-Methylpiperazin-1-yl)-N-[(1R,2S,4R)-1,7,7-trimethylbicyclo[2.2.1]hept-2-yl]pyridin-2-amine

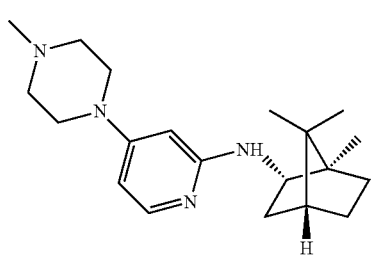 [SMILES: CN1CCN(c2ccnc(N[C@H]3C[C@H]4CC[C@]3(C)C4(C)C)c2)CC1]

MS (ESI): mass calcd. for $C_{20}H_{32}N_4$, 328.5 m/z found, 329.2 [M+H]$^+$. $^1$H NMR (300 MHz, CD$_3$OD): 7.60 (d, J=7.8 Hz, 1H), 6.63 (dd, J=2.4 Hz, 7.8 Hz, 1H), 6.23 (d, J=2.1 Hz, 1H), 4.26 (d, J=14 Hz, 2H), 3.90 (dd, J=2.1 Hz, 11 Hz, 1H), 3.65 (d, J=12 Hz, 2H), 3.47 (t, J=13 Hz, 2H), 3.40-3.20 (m, 2H), 2.97 (s, 3H), 2.54-2.46 (m, 1H), 1.86-1.73 (m, 3H), 1.53-1.27 (m, 2H), 1.10-0.90 (m, 1H), 1.04 (s, 3H), 0.95 (s, 3H), 0.90 (s, 3H).

Example 253

N-(Bicyclo[2.2.1]hept-2-ylmethyl)-4-[(3R)-3-(methylamino)pyrrolidin-1-yl]pyridin-2-amine

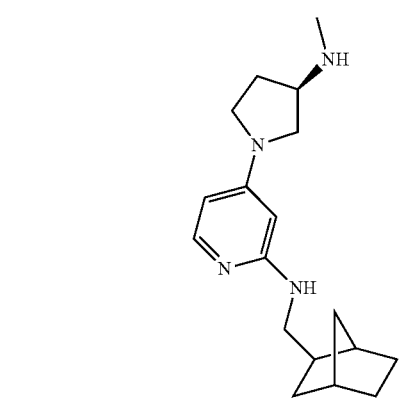 [SMILES: CN[C@@H]1CCN(c2ccnc(NCC3CC4CCC3C4)c2)C1]

MS (ESI): mass calcd. for $C_{18}H_{28}N_4$, 300.45 m/z found, [M+H]$^+$. $^1$H NMR (300 MHz, CD$_3$OD): 7.61 (d, J=7.2 Hz, 1H), 6.41 (dd, J=7.2 Hz, 2.1 Hz, 1H), 5.83 (d, J=2.1 Hz, 1H), 4.09-4.06 (m, 1H), 3.97-3.91 (m, 1H), 3.75-3.66 (m, 3H), 3.36-3.18 (m, 2H), 2.86 (s, 3H), 2.64-2.57 (m, 1H), 2.40-2.21 (m, 3H), 1.92-1.90 (m, 1H), 1.63-1.23 (m, 7H), 0.85-0.79 (m, 1H).

Example 254

4-[(3R)-3-Aminopyrrolidin-1-yl]-N-butylpyridin-2-amine

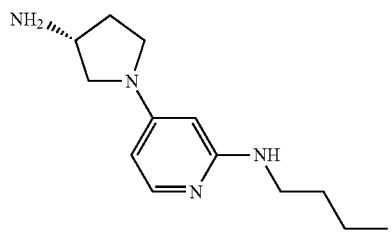 [SMILES: CCCCNc1cc(N2CC[C@@H](N)C2)ccn1]

4-bromo-N-butylpyridin-2-amine. A solution of 4-bromo-2-fluoropyridine (2.0 g, 11.3 mmol) and n-butan-1-amine (752 mg, 10.3 mmol) in N-methyl-2-pyrrolidinone (NMP, 10 mL) was stirred at 100° C. for 1 hr. The reaction was allowed to cool to room temperature and diluted with DCM (50 mL), washed with water (10 mL*2). The organic layer was dried over Na$_2$SO$_4$, filtered and concentrated. The residue was purified by column chromatography (0-20% EtOAc-petroleum ether gradient elution) to afford the desired product (1.4 g, 45%). $^1$H NMR (300 MHz, CDCl$_3$): 7.88 (d, J=5.4 Hz, 1H), 6.70 (d, J=5.4 Hz, 1H), 6.54 (s, 1H), 4.60 (br s, 1H), 3.26-3.19 (m, 2H), 1.63-1.56 (m, 2H), 1.46-1.39 (m, 2H), 0.96 (t, J=7.2 Hz, 3H).

(R)-tert-butyl 1-(2-(butylamino)pyridin-4-yl)pyrrolidin-3-ylcarbamate. To a solution of 4-bromo-N-butylpyridin-2-amine (458 mg, 2 mmol), (R)-tert-butyl pyrrolidin-3-ylcarbamate (410 mg, 2.2 mmol) in anhydrous dioxane (12 mL) was added Pd$_2$(dba)$_3$ (200 mg, 0.22 mmol), 9,9-dimethyl-4,5-bis(diphenylphosphino)xanthene (Xant-phos) (200 mg, 0.24 mmol) and t-BuONa (576 mg, 6 mmol) under atmosphere of argen. The resulting reaction was stirred at 100° C. for 2 hrs and diluted with water (40 mL), extracted with DCM, The combined organic layer was washed with brine, dried over Na$_2$SO$_4$, filtered and concentrated. The residue was purified by column chromatography (0-10% MeOH-DCM gradient elution) to afford the crude product (purity>70%).

(R)-4-(3-aminopyrrolidin-1-yl)-N-butylpyridin-2-amine dihydrochloride. Crude product obtained above was dissolved in MeOH (6 mL) and ether solution of HCl gas (ca. 4N, 10 mL) was added. The resulting reaction was stirred at ambient temperature for 20 hrs. The reaction was concentrated under reduced pressure and purified by prep-HPLC to afford the desired product (50 mg, 6.7% yield in two steps). $^1$H NMR (300 MHz, CD$_3$OD): 7.59 (d, J=7.5 Hz, 1H), 6.39 (d, J=6.9 Hz, 1H), 5.79 (s, 1H), 4.89 (m, 1H), 4.15 (m, 1H), 3.74-3.66 (m, 3H), 3.38-3.29 (m, 2H), 2.60-2.53 (m, 1H), 2.34-2.30 (m, 1H), 1.73-1.64 (m, 2H), 1.56-1.46 (m, 2H), 1.02 (t, J=7.5 Hz, 3H); LC-MS: m/z=235.2 [M+H]$^+$, t$_R$=0.92 min; HPLC: 100% (214 nm), 97% (254 nm), t$_R$=4.84 min.

The compounds in Example 255 through Example 297 were prepared using methods analogous to those described in Example 254.

Example 255

Adamantan-1-ylmethyl-[4-(4-methyl-piperazin-1-yl)-pyridin-2-yl]-amine

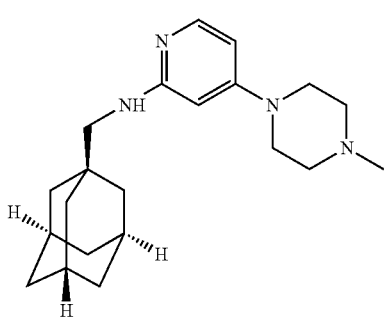 [SMILES: CN1CCN(c2ccnc(NC[C@]34C[C@H]5C[C@H](C[C@H](C5)C3)C4)c2)CC1]

MS (ESI): mass calcd. for C$_{21}$H$_{32}$N$_4$, 340.52 m/z found, 341.2 [M+H]$^+$. $^1$H NMR (300 MHz, CD$_3$OD): 7.66 (d, J=7.2 Hz, 1H), 6.69 (dd, J=2.4 Hz, 7.5 Hz, 1H), 5.29 (d, J=2.1 Hz, 1H), 4.40-4.20 (m, 2H), 3.80-3.20 (m, 6H), 3.07 (s, 2H), 3.04 (s, 3H), 2.07 (s, 3H), 1.82 (dd, J=12 Hz, 27 Hz, 6H), 1.70 (s, 6H).

Example 256

N-(Cyclohexylmethyl)-4-[(3aR,6aR)-hexahydropyrrolo[3,4-b]pyrrol-5(1H)-yl]pyridin-2-amine

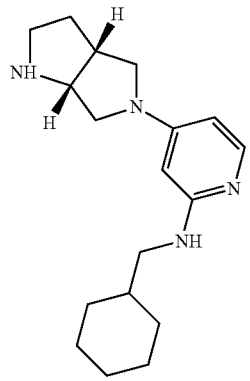 [SMILES: c1cc(N2C[C@H]3CCN[C@H]3C2)cc(NCC2CCCCC2)n1]

MS (ESI): mass calcd. for C$_{18}$H$_{28}$N$_4$, 300.45 m/z found, 301.3 [M+H]$^+$. $^1$H NMR (300 MHz, CD$_3$OD): 7.56 (d, J=7.5 Hz, 1H), 6.37 (dd, J=2.4 Hz, 7.5 Hz, 1H), 5.78 (d, J=2.1 Hz, 1H), 4.55-4.45 (m, 1H), 3.95-3.78 (m, 3H), 3.51-3.37 (m, 4H), 3.12 (d, J=6.9 Hz, 2H), 2.41-2.33 (m, 1H), 2.20-2.00 (m, 1H), 1.87-1.64 (m, 6H), 1.40-1.02 (m, 5H).

Example 257

4-[(3aR,6aR)-Hexahydropyrrolo[3,4-b]pyrrol-5(1H)-yl]-N-(2-methylpropyl)pyridin-2-amine

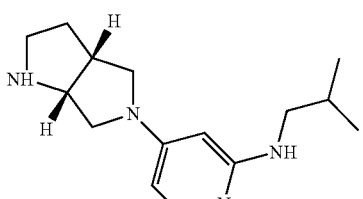

MS (ESI): mass calcd. for C$_{15}$H$_{24}$N$_4$, 260.39 m/z found, 261.2 [M+H]$^+$. $^1$H NMR (300 MHz, CD$_3$OD): 7.57 (d, J=7.5 Hz, 1H), 6.39 (d, J=7.2 Hz, 1H), 5.81 (s, 1H), 4.51-4.48 (m, 1H), 4.02-3.76 (m, 3H), 3.53-3.39 (m, 4H), 3.12 (d, J=6.9 Hz, 2H), 2.39-2.35 (m, 1H), 2.14-1.93 (m, 2H), 1.04 (d, J=6.6 Hz, 6H).

Example 258

4-[(3S)-3-Aminopyrrolidin-1-yl]-N-(pyridin-2-ylmethyl)pyridin-2-amine

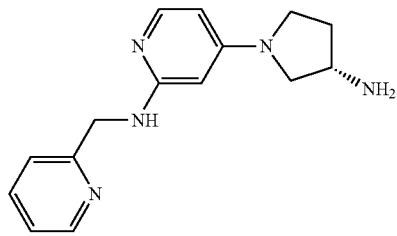 [SMILES: N[C@H]1CCN(c2ccnc(NCc3ccccn3)c2)C1]

MS (ESI): mass calcd. for $C_{15}H_{19}N_5$, 269.35 m/z found, 270.2 [M+H]$^+$. $^1$H NMR (300 MHz, CD$_3$OD): 8.84 (d, J=5.7 Hz, 1H), 8.60 (t, J=7.8 Hz, 1H), 8.11-7.99 (m, 2H), 7.69 (d, J=7.2 Hz, 1H), 6.46 (d, J=6.6 Hz, 1H), 5.90 (s, 1H), 5.09 (s, 2H), 4.09 (br, s, 1H), 3.85-3.34 (m, 4H), 2.58-2.45 (m, 1H), 2.28-2.22 (m, 1H).

Example 259

N-Cyclopentyl-4-[3-(methylamino)azetidin-1-yl]pyridin-2-amine

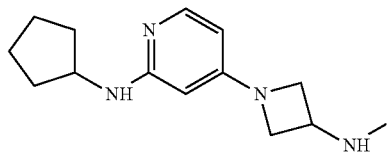 [SMILES: CNC1CN(c2ccnc(NC3CCCC3)c2)C1]

MS (ESI): mass calcd. for $C_{14}H_{22}N_4$, 246.36 m/z found, 247.2 [M+H]$^+$. $^1$H NMR (300 MHz, DMSO-d$_6$): 12.21 (br, s, 1H), 10.06 (br, s, 2H), 8.10 (br, s, 1H), 7.80-7.60 (m, 1H), 6.08 (d, J=6.6 Hz, 1H), 5.59 (s, 1H), 5.20 (br, s, 1H), 4.32-3.95 (m, 7H), 2.53 (s, 3H), 1.71-1.59 (m, 8H).

Example 260

4-piperazin-1-yl-N-(pyridin-2-ylmethyl)pyridin-2-amine

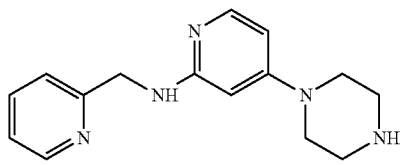 [SMILES: c1ccc(CNc2cc(N3CCNCC3)ccn2)nc1]

MS (ESI): mass calcd. for $C_{15}H_{19}N_5$, 269.35 m/z found, 270.2 [M+H]$^+$. $^1$H NMR (300 MHz, CD$_3$OD): 8.85 (d, J=5.7 Hz, 1H), 6.63 (t, J=4.8 Hz, 1H), 8.12 (d, J=8.1 Hz, 1H), 8.04 (t, J=6.9 Hz, 1H), 7.74 (d, J=7.2 Hz, 1H), 6.77 (d, J=6.9 Hz, 1H), 6.32 (s, 1H), 5.15 (s, 2H), 3.91 (br, s, 4H), 3.36-3.30 (m, 4H).

Example 261

N-(Cyclopentylmethyl)-4-[(3aR,6aR)-hexahydropyrrolo[3,4-b]pyrrol-5(1H)-yl]pyridin-2-amine

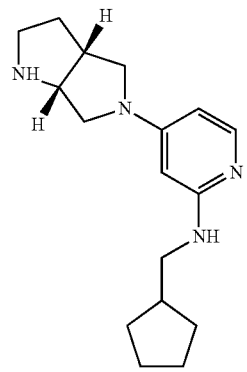 [SMILES: c1cc(N2C[C@H]3CCN[C@H]3C2)cc(NCC2CCCC2)n1]

MS (ESI): mass calcd. for $C_{17}H_{26}N_4$, 286.42 m/z found, 287.1 [M+H]$^+$. $^1$H NMR (300 MHz, CD$_3$OD): 7.57 (d, J=7.2 Hz, 1H), 6.39 (d, J=7.5 Hz, 1H), 5.81 (d, J=1.8 Hz, 1H), 4.52-4.48 (m, 1H), 4.01-3.76 (m, 3H), 3.52-3.37 (m, 4H), 3.21 (d, J=7.2 Hz, 2H), 2.42-2.35 (m, 1H), 2.26-2.08 (m, 2H), 1.92-1.60 (m, 6H), 1.35-1.29 (m, 2H).

Example 262

N-Cyclopentyl-4-[(3aR,6aR)-hexahydropyrrolo[3,4-b]pyrrol-5(1H)-yl]pyridin-2-amine

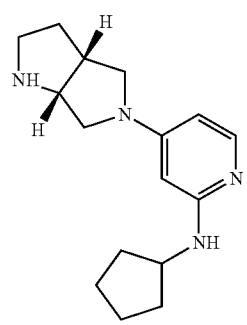 [SMILES: c1cc(N2C[C@H]3CCN[C@H]3C2)cc(NC2CCCC2)n1]

MS (ESI): mass calcd. for $C_{16}H_{24}N_4$, 272.4 m/z found, 273.2 [M+H]$^+$. $^1$H NMR (300 MHz, DMSO-d$_6$): 12.28 (br s, 1H), 9.96 (br s, 1H), 9.68 (br s, 1H), 7.97 (d, J=6.9 Hz, 1H), 7.64-7.60 (m, 1H), 6.22 (d, J=6.9 Hz, 1H), 5.65 (s, 1H), 4.29-3.65 (m, 7H), 3.40-3.20 (m, 2H), 2.14-1.90 (m, 4H), 1.67-1.42 (m, 6H).

Example 263

4-[(3S)-3-Aminopyrrolidin-1-yl]-N-(4-fluorobenzyl)pyridin-2-amine

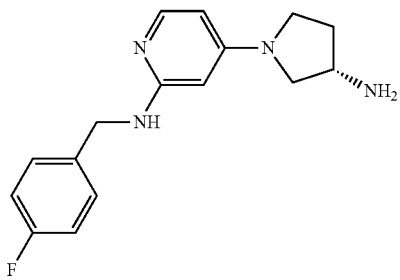 [SMILES: N[C@H]1CCN(c2ccnc(NCc3ccc(F)cc3)c2)C1]

MS (ESI): mass calcd. for $C_{16}H_{19}FN_4$, 286.36 m/z found, 287.2 [M+H]$^+$. $^1$H NMR (300 MHz, CD$_3$OD): 7.54 (s, 1H), 7.40 (br s, 2H), 7.08-7.04 (m, 2H), 6.32 (s, 1H), 5.70 (s, 1H), 4.48 (s, 2H), 3.79 (br s, 1H), 3.90-3.40 (m, 4H), 2.47 (br s, 1H), 2.24 (br s, 1H).

Example 264

4-[(3S)-3-Aminopyrrolidin-1-yl]-N-(2-methoxyethyl)pyridin-2-amine

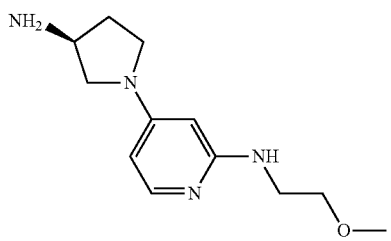 [SMILES: COCCNc1cc(N2CC[C@H](N)C2)ccn1]

MS (ESI): mass calcd. for $C_{12}H_{20}N_4O$, 236.32 m/z found, 237.2 [M+H]$^+$. $^1$H NMR (300 MHz, CD$_3$OD): 7.57 (d, J=7.5 Hz, 1H), 6.36 (d, J=7.2 Hz, 1H), 5.81 (s, 1H), 4.12 (br, s, 1H), 3.89-3.84 (m, 1H), 3.70-3.59 (m, 5H), 3.52-3.50 (m, 2H), 3.47-3.34 (m, 5H), 2.56-2.52 (m, 1H), 2.30-2.26 (m, 1H).

Example 265

N-Bicyclo[2.2.1]hept-2-yl-4-(1,4-diazepan-1-yl)pyridin-2-amine

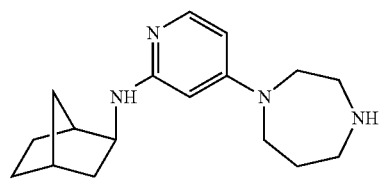 [SMILES: c1cc(N2CCCNCC2)cc(NC2CC3CCC2C3)n1]

MS (ESI): mass calcd. for $C_{17}H_{26}N_4$, 286.42 m/z found, 287.2 [M+H]$^+$. $^1$H NMR (300 MHz, CD$_3$OD): 7.64 (d, J=7.5 Hz, 1H), 6.62 (dd, J=7.5 Hz, 2.1 Hz, 1H), 5.98 (d, J=2.1 Hz, 1H), 4.04-3.98 (m, 2H), 3.78 (t, J=6.0 Hz, 2H), 3.52-3.49 (m, 2H), 3.42-3.36 (m, 3H), 2.41 (br s, 1H), 2.33-2.27 (m, 3H), 2.04-1.97 (m, 1H), 1.68-1.60 (m, 3H), 1.50-1.28 (m, 4H).

Example 266

Adamantan-2-yl-[4-(3aR,6aR)-(hexahydro-pyrrolo[3,4-b]pyrrol-5-yl)-pyridin-2-yl]-amine

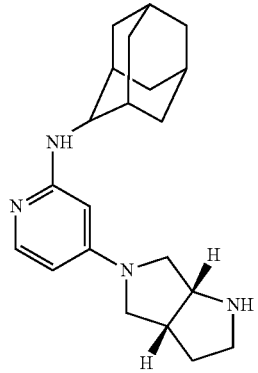 [SMILES: c1cc(N2C[C@H]3CCN[C@H]3C2)cc(NC2C3CC4CC(C3)CC2C4)n1]

MS (ESI): mass calcd. for $C_{21}H_{30}N_4$, 338.5 m/z found, 339.3 [M+H]$^+$. $^1$H NMR (300 MHz, CD$_3$OD): 7.64 (d, J=7.5 Hz, 1H), 6.43 (dd, J=2.1 Hz, 7.2 Hz, 1H), 5.96 (s, 1H), 4.60-4.50 (m, 1H), 4.04-3.81 (m, 4H), 3.60-3.40 (m, 4H), 2.46-2.39 (m, 1H), 2.20-1.75 (m, 15H).

Example 267

4-[(3S)-3-Aminopyrrolidin-1-yl]-N-benzylpyridin-2-amine

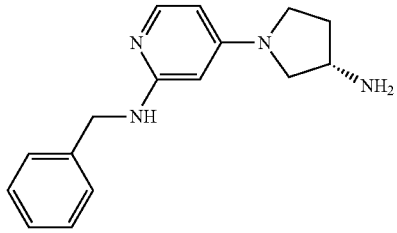 [SMILES: N[C@H]1CCN(c2ccnc(NCc3ccccc3)c2)C1]

MS (ESI): mass calcd. for $C_{16}H_{20}N_4$, 268.36 m/z found, 269.2 [M+H]$^+$. $^1$H NMR (300 MHz, CD$_3$OD): 7.57 (d, J=6.3 Hz, 1H), 7.37-7.28 (m, 5H), 6.34 (d, J=6.0 Hz, 1H), 5.72 (s, 1H), 4.52 (s, 2H), 3.80 (br s, 1H), 3.90-3.40 (m, 4H), 2.48 (br s, 1H), 2.25 (br s, 1H).

Example 268

4-[(3S)-3-Aminopyrrolidin-1-yl]-N-cyclopentylpyridin-2-amine

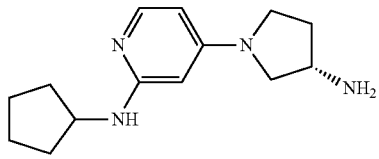 [SMILES: N[C@H]1CCN(c2ccnc(NC3CCCC3)c2)C1]

MS (ESI): mass calcd. for $C_{14}H_{22}N_4$, 246.36 m/z found, 247.2 [M+H]$^+$. $^1$H NMR (300 MHz, CD$_3$OD): 7.54 (d, J=7.2

Hz, 1H), 6.33 (d, J=6.9 Hz, 1H), 5.74 (s, 1H), 4.10-3.61 (m, 6H), 2.55-2.27 (m, 1H), 2.40-2.20 (m, 1H), 2.07-2.03 (m, 2H), 1.77-1.56 (m, 6H).

Example 269

4-Piperazin-1-yl-N-[(1S,5R)-2,6,6-trimethylbicyclo[3.1.1]hept-3-yl]pyridin-2-amine

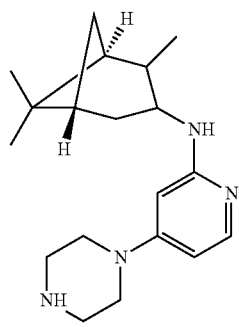 [SMILES: CC1C(Nc2cc(N3CCNCC3)ccn2)C[C@H]2C[C@@H]1C2(C)C]

MS (ESI): mass calcd. for $C_{19}H_{30}N_4$, 314.48 m/z found, 315.3 [M+H]$^+$. $^1$H NMR (300 MHz, CD$_3$OD): 7.61 (d, J=7.5 Hz, 1H), 6.65 (d, J=7.5 Hz, 1H), 6.17 (d, J=1.8 Hz, 1H), 3.98-3.82 (m, 5H), 3.40-3.30 (m, 5H), 2.80-2.72 (m, 1H), 2.50-2.43 (m, 1H), 2.13-2.06 (m, 1H), 2.00-0.87 (m, 2H), 1.69-1.63 (m, 1H), 1.27 (s, 3H), 1.24-1.08 (m, 6H).

Example 270

4-[(3R)-3-Aminopyrrolidin-1-yl]-N-bicyclo[2.2.1]hept-2-ylpyridin-2-amine

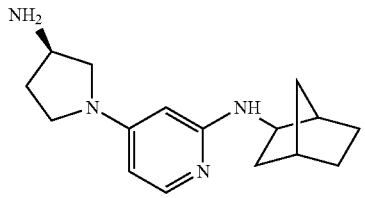 [SMILES: N[C@@H]1CCN(c2ccnc(NC3CC4CCC3C4)c2)C1]

MS (ESI): mass calcd. for $C_{16}H_{24}N_4$, 272.4 m/z found, 273.2 [M+H]$^+$. $^1$H NMR (300 MHz, CD$_3$OD): 7.58 (d, J=7.5 Hz, 1H), 6.37 (dd, J=2.1 Hz, 7.5 Hz, 1H), 5.71 (d, J=2.1 Hz, 1H), 4.12-3.42 (m, 6H), 2.51-2.48 (m, 1H), 2.40-2.21 (m, 3H), 1.95-1.88 (m, 1H), 1.65-1.20 (m, 7H).

Example 271

N-[(1R)-1-Cyclohexylethyl]-4-[(3aR,6aR)-hexahydropyrrolo[3,4-b]pyrrol-5(1H)-yl]pyridin-2-amine

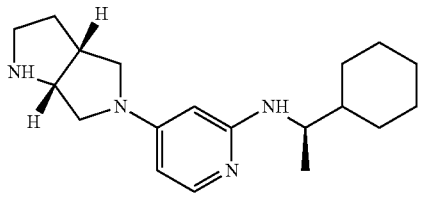 [SMILES: C[C@@H](Nc1cc(N2C[C@H]3CCN[C@H]3C2)ccn1)C1CCCCC1]

MS (ESI): mass calcd. for $C_{19}H_{30}N_4$, 314.48 m/z found, 315.2 [M+H]$^+$. $^1$H NMR (300 MHz, CD$_3$OD): 7.55 (d, J=7.5 Hz, 1H), 6.36 (dd, J=2.4 Hz, 7.5 Hz, 1H), 5.80 (d, J=2.4 Hz, 1H), 4.55-4.46 (m, 1H), 3.97-3.74 (m, 3H), 3.51-3.36 (m, 5H), 2.40-2.33 (m, 1H), 2.20-2.00 (m, 1H), 1.89-1.69 (m, 5H), 1.47-1.02 (m, 6H), 1.22 (d, J=6.3 Hz, 3H).

Example 272

4-[(3S)-3-Aminopyrrolidin-1-yl]-N-[(1S,5R)-2,6,6-trimethylbicyclo[3.1.1]hept-3-yl]pyridin-2-amine

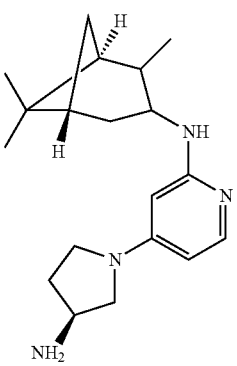 [SMILES: CC1C(Nc2cc(N3CC[C@H](N)C3)ccn2)C[C@H]2C[C@@H]1C2(C)C]

MS (ESI): mass calcd. for $C_{19}H_{30}N_4$, 314.48 m/z found, 315.2 [M+H]$^+$. $^1$H NMR (300 MHz, CD$_3$OD): 7.56 (d, J=6.6 Hz, 1H), 6.35 (d, J=6.0 Hz, 1H), 5.79 (s, 1H), 4.10-3.62 (m, 6H), 2.76-2.70 (m, 1H), 2.47 (br s, 2H), 2.28 (br s, 1H), 2.08-1.62 (m, 4H), 1.26 (s, 3H), 1.20-1.00 (m, 1H), 1.16 (d, J=6.6 Hz, 3H), 1.07 (s, 3H).

Example 273

1-({4-[(3S)-3-Aminopyrrolidin-1-yl]pyridin-2-yl}amino)-2-methylpropan-2-ol

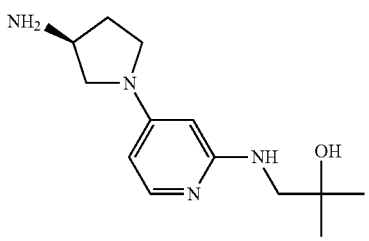 [SMILES: CC(C)(O)CNc1cc(N2CC[C@H](N)C2)ccn1]

MS (ESI): mass calcd. for $C_{13}H_{22}N_4O$, 250.35 m/z found, 251.2 [M+H]$^+$. $^1$H NMR (300 MHz, DMSO-d$_6$): 12.26 (s, 1H), 8.54 (br s, 3H), 7.62 (s, 2H), 6.22 (s, 1H), 5.79 (s, 1H), 3.93-3.40 (m, 5H), 3.18 (m, 2H), 2.29-2.15 (m, 2H), 1.14 (s, 6H).

Example 274

4-[(3R)-3-Aminopyrrolidin-1-yl]-N-cyclohexylpyridin-2-amine

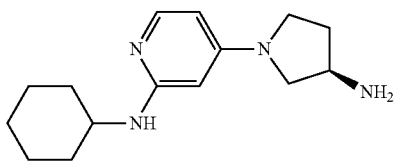 [SMILES: N[C@@H]1CCN(c2ccnc(NC3CCCCC3)c2)C1]

MS (ESI): mass calcd. for C₁₅H₂₄N₄, 260.39 m/z found, 261.3 [M+H]⁺. ¹H NMR (300 MHz, CD₃OD): 7.60 (d, J=7.2 Hz, 1H), 6.40 (d, J=7.2 Hz, 1H), 5.81 (s, 1H), 4.17-3.51 (m, 6H), 2.62-2.53 (m, 1H), 2.40-2.20 (m, 1H), 2.07-1.73 (m, 5H), 1.55-1.32 (m, 5H).

Example 275

N-(Cyclopentylmethyl)-4-[3-(methylamino)azetidin-1-yl]pyridin-2-amine

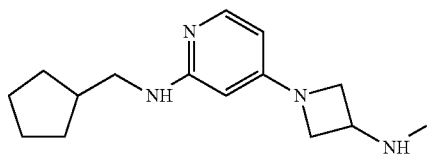 [SMILES: CNC1CN(c2ccnc(NCC3CCCC3)c2)C1]

MS (ESI): mass calcd. for C₁₅H₂₄N₄, 260.39 m/z found, 261.2 [M+H]⁺. ¹H NMR (300 MHz, DMSO-d₆): 12.39 (br, s, 1H), 10.08 (br, s, 2H), 7.92 (br, s, 1H), 7.69-7.66 (m, 1H), 6.10 (d, J=6.6 Hz, 1H), 5.62 (s, 1H), 4.80 (br, s, 1H), 4.34-4.18 (m, 6H), 3.18-3.15 (m, 2H), 2.53 (s, 3H), 2.14-2.09 (m, 1H), 1.79-1.24 (m, 8H).

Example 276

4-[(3S)-3-Aminopyrrolidin-1-yl]-N-(2-phenylethyl)pyridin-2-amine

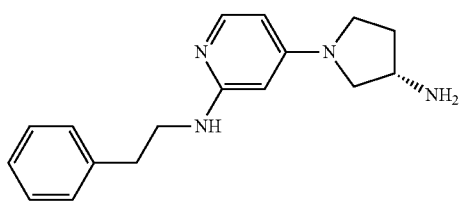 [SMILES: N[C@H]1CCN(c2ccnc(NCCc3ccccc3)c2)C1]

MS (ESI): mass calcd. for C₁₇H₂₂N₄, 282.39 m/z found, 283.2 [M+H]⁺. ¹H NMR (300 MHz, DMSO-d₆): 12.35 (s, 1H), 8.55 (br s, 3H), 7.80 (s, 1H), 7.62 (m, 1H), 7.29-7.22 (m, 5H), 6.25 (d, J=6.0 Hz, 1H), 5.66 (s, 1H), 4.21-3.48 (m, 7H), 2.85 (m, 2H), 2.29-2.16 (m, 2H).

Example 277

4-[(3aR,6aR)-Hexahydropyrrolo[3,4-b]pyrrol-5(1H)-yl]-N-(tetrahydro-2H-pyran-4-yl)pyridin-2-amine

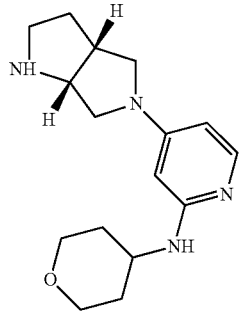 [SMILES: c1cc(N2C[C@H]3CCN[C@H]3C2)cc(NC2CCOCC2)n1]

MS (ESI): mass calcd. for C₁₆H₂₄N₄O, 288.4 m/z found, 289.2 [M+H]⁺. ¹H NMR (300 MHz, CD₃OD): 7.60 (d, J=7.5 Hz, 1H), 6.41 (dd, J=2.1 Hz, 7.5 Hz, 1H), 5.85 (d, J=1.8 Hz, 1H), 4.57-4.50 (m, 1H), 4.04-3.77 (m, 5H), 3.62-2.40 (m, 7H), 2.43-2.33 (m, 1H), 2.20-1.98 (m, 3H), 1.69-1.61 (m, 2H).

Example 278

4-[(3R)-3-Aminopyrrolidin-1-yl]-N-(cyclopentylmethyl)pyridin-2-amine

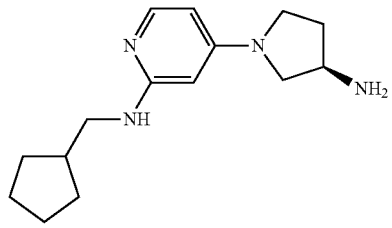 [SMILES: N[C@@H]1CCN(c2ccnc(NCC3CCCC3)c2)C1]

MS (ESI): mass calcd. for C₁₅H₂₄N₄, 260.39 m/z found, 261.2 [M+H]⁺. ¹H NMR (300 MHz, CD₃OD): 7.59 (d, J=7.5 Hz, 1H), 6.39 (dd, J=7.5 Hz, 1.8 Hz, 1H), 5.81 (d, J=1.5 Hz, 1H), 4.89 (m, 1H), 4.15 (m, 1H), 3.89-3.66 (m, 3H), 3.23 (d, J=7.5 Hz, 2H), 2.60-2.53 (m, 1H), 2.31-2.22 (m, 2H), 1.94-1.90 (m, 2H), 1.75-1.65 (m, 4H), 1.37-1.31 (m, 2H).

Example 279

1-({4-[(3R)-3-Aminopyrrolidin-1-yl]pyridin-2-yl}amino)-2-methylpropan-2-ol

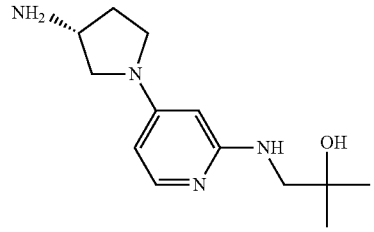 [SMILES: CC(C)(O)CNc1cc(N2CC[C@@H](N)C2)ccn1]

MS (ESI): mass calcd. for C₁₃H₂₂N₄O, 250.35 m/z found, 251.2 [M+H]⁺. ¹H NMR (300 MHz, CD₃OD): 7.62 (d, J=7.2 Hz, 1H), 6.39 (d, J=7.2 Hz, 1H), 5.90 (s, 1H), 4.19 (m, 1H), 3.89 (m, 1H), 3.73-3.65 (m, 3H), 3.29 (s, 2H), 2.58-2.55 (m, 1H), 2.32-2.27 (m, 1H), 1.31 (s, 6H).

Example 280

N-tert-Butyl-4-[3-(methylamino)azetidin-1-yl]pyridin-2-amine

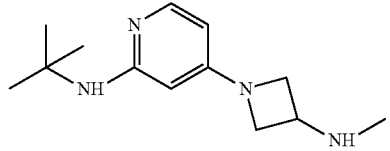 [SMILES: CNC1CN(c2ccnc(NC(C)(C)C)c2)C1]

MS (ESI): mass calcd. for $C_{13}H_{22}N_4$, 234.35 m/z found, 235.2 [M+H]$^+$. $^1$H NMR (300 MHz, DMSO-d$_6$): 12.32 (br, s, 1H), 10.13 (br, s, 2H), 7.75-7.71 (m, 2H), 6.08 (d, J=5.7 Hz, 1H), 5.51-5.39 (m, 3H), 4.40-4.25 (m, 5H), 2.54 (s, 3H), 1.38 (s, 9H).

Example 281

N-Cyclopropyl-4-[3-(methylamino)azetidin-1-yl]pyridin-2-amine

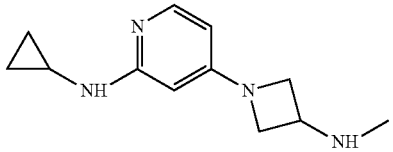 [SMILES: CNC1CN(c2ccnc(NC3CC3)c2)C1]

MS (ESI): mass calcd. for $C_{12}H_{18}N_4$, 218.3 m/z found, 219.2 [M+H]$^+$. $^1$H NMR (300 MHz, DMSO-d$_6$): 12.36 (br, s, 1H), 10.21 (br, s, 2H), 8.33 (br, s, 1H), 7.69 (t, J=6.3 Hz, 1H), 6.15 (d, J=5.4 Hz, 1H), 5.63 (s, 1H), 4.54 (br, s, 4H), 4.34-4.15 (m, 5H), 2.53 (s, 3H), 0.85-0.84 (m, 2H), 0.54 (s, 2H).

Example 282

2-Methyl-1-({4-[3-(methylamino)azetidin-1-yl]pyridin-2-yl}amino)propan-2-ol

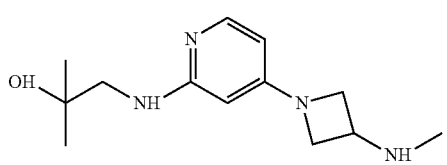 [SMILES: CNC1CN(c2ccnc(NCC(C)(C)O)c2)C1]

MS (ESI): mass calcd. for $C_{13}H_{22}N_4O$, 250.35 m/z found, 251.2 [M+H]$^+$. $^1$H NMR (300 MHz, DMSO-d$_6$): 12.27 (br, s, 1H), 10.02 (br, s, 2H), 7.68-7.61 (m, 2H), 6.08 (d. J=6.6 Hz, 1H), 5.69 s, 1H), 4.33-4.20 (m, 7H), 3.17 (d, J=5.4 Hz, 2H), 2.54 (s, 3H), 1.16 (s, 6H).

Example 283

3-({4-[3-(Methylamino)azetidin-1-yl]pyridin-2-yl}amino)propan-1-ol

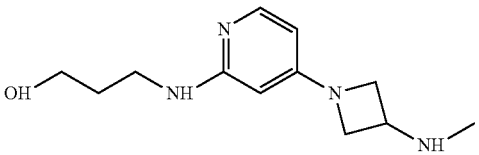 [SMILES: CNC1CN(c2ccnc(NCCCO)c2)C1]

MS (ESI): mass calcd. for $C_{12}H_{20}N_4O$, 236.32 m/z found, 237.2 [M+H]$^+$. $^1$H NMR (300 MHz, DMSO-d$_6$): 12.47 (br, s, 1H), 10.23 (br, s, 2H), 7.88 (br, s, 1H), 7.64 (t, J=6.6 Hz, 1H), 6.08 (d, J=6.6 Hz, 1H), 5.59 (s, 1H), 4.71 (br, s, 4H), 4.33-4.15 (m, 5H), 3.49 (t, J=6.3 Hz, 2H), 2.52 (s, 3H), 1.73-1.65 (m, 2H).

Example 284

4-[3-(Methylamino)azetidin-1-yl]-N-[(1S,5R)-2,6,6-trimethylbicyclo[3.1.1]hept-3-yl]pyridin-2-amine

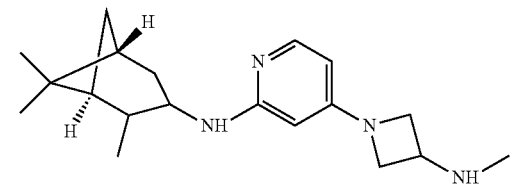

MS (ESI): mass calcd. for $C_{19}H_{30}N_4$, 314.48 m/z found, 315.3 [M+H]$^+$. $^1$H NMR (300 MHz, DMSO-d$_6$): 12.27 (br, s, 1H), 9.97 (br, s, 2H), 8.06 (d, J=8.4 Hz, 1H), 7.65 (d, J=6.6 Hz, 1H), 6.05 (d, J=6.9 Hz, 1H), 5.61 (s, 1H), 4.34-4.15 (m, 7H), 4.15 (br, s, 1H), 2.70-2.63 (m, 1H), 2.55 (s, 3H), 2.37 (br, s, 1H), 2.05-1.94 (m, 2H), 1.84-1.81 (m, 1H), 1.53-1.48 (m, 1H), 1.09 (s, 3H), 1.06-0.94 (m, 6H).

Example 285

N-Benzyl-4-[3-(methylamino)azetidin-1-yl]pyridin-2-amine

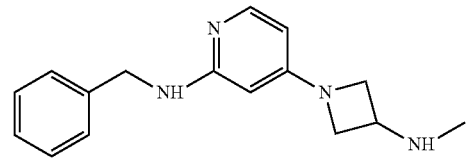 [SMILES: CNC1CN(c2ccnc(NCc3ccccc3)c2)C1]

MS (ESI): mass calcd. for $C_{16}H_{20}N_4$, 268.36 m/z found, 269.2 [M+H]$^+$. $^1$H NMR (300 MHz, DMSO-d$_6$): 12.60 (br, s, 1H), 10.08 (br, s, 2H), 8.32-8.28 (m, 1H), 7.70-7.67 (m, 1H), 7.38-7.28 (m, 5H), 6.10 (d, J=7.2 Hz, 1H), 5.64 (s, 2H), 5.45 (br, s, 2H), 4.52 (d, J=5.7 Hz, 2H), 4.23-4.14 (m, 5H), 2.51 (s, 3H).

Example 286

N-(2-Methoxyethyl)-4-[3-(methylamino)azetidin-1-yl]pyridin-2-amine

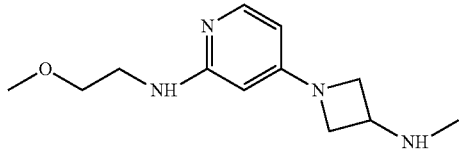

MS (ESI): mass calcd. for C$_{12}$H$_{20}$N$_4$O, 236.32 m/z found, 237.2 [M+H]$^+$. $^1$H NMR (300 MHz, DMSO-d$_6$): 12.43 (br, s, 1H), 10.15 (br, s, 2H), 7.78 (br, s, 1H), 7.65 (t, J=6.3 Hz, 1H), 6.10 (d, J=6.6 Hz, 1H), 5.64 (s, 1H), 4.36-4.14 (m, 9H), 3.48-3.42 (m, 4H), 3.3 (s, 3H), 2.53 (s, 3H).

Example 287

4-[(3aR,6aR)-Hexahydropyrrolo[3,4-b]pyrrol-5(1H)-yl]-N-[(1S,5R)-2,6,6-trimethylbicyclo[3.1.1]hept-3-yl]pyridin-2-amine

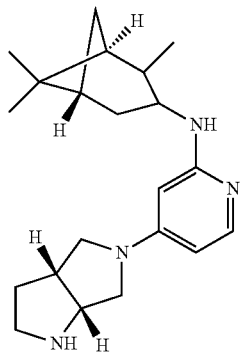 [SMILES: CC1C(Nc2cc(N3C[C@H]4CCN[C@H]4C3)ccn2)C[C@H]2C[C@@H]1C2(C)C]

MS (ESI): mass calcd. for C$_{21}$H$_{32}$N$_4$, 340.52 m/z found, 341.2 [M+H]$^+$. $^1$H NMR (300 MHz, CD$_3$OD): 7.56 (d, J=7.2 Hz, 1H), 6.38 (dd, J=7.5 Hz, J=2.1 Hz, 1H), 5.80 (d, J=1.8 Hz, 1H), 4.50-4.46 (m, 1H), 3.98-3.74 (m, 4H), 3.50-3.41 (m, 4H), 2.77-2.69 (m, 1H), 2.51-2.30 (m, 2H), 2.14-1.67 (m, 4H), 1.64-1.63 (m, 1H), 1.28 (s, 3H), 1.18-1.05 (m, 7H).

Example 288

N-tert-Butyl-4-[(3aR,6aR)-hexahydropyrrolo[3,4-b]pyrrol-5(1H)-yl]pyridin-2-amine

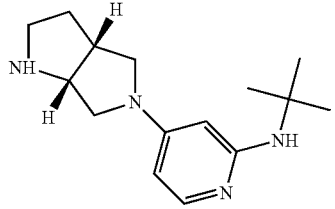 [SMILES: CC(C)(C)Nc1cc(N2C[C@H]3CCN[C@H]3C2)ccn1]

MS (ESI): mass calcd. for C$_{15}$H$_{24}$N$_4$, 260.39 m/z found, 261.3 [M+H]$^+$. $^1$H NMR (300 MHz, CD$_3$OD): 7.60 (d, J=7.5 Hz, 1H), 6.37 (d, J=7.2 Hz, 1H), 5.82 (s, 1H), 4.49 (t, J=6.6 Hz, 1H), 4.01-3.75 (m, 4H), 3.51-3.30 (m, 2H), 2.39-2.32 (m, 1H), 2.12-2.07 (m, 1H), 1.47 (s, 9H).

Example 289

4-[(3R)-3-Aminopyrrolidin-1-yl]-N-(2-methoxyethyl)pyridin-2-amine

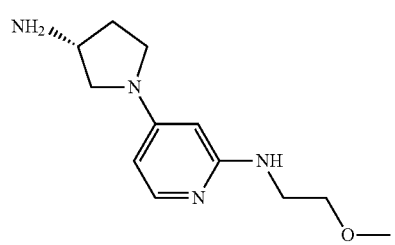 [SMILES: COCCNc1cc(N2CC[C@@H](N)C2)ccn1]

MS (ESI): mass calcd. for C$_{12}$H$_{20}$N$_4$O, 236.32 m/z found, 237.1 [M+H]$^+$. $^1$H NMR (300 MHz, CD$_3$OD): 7.52 (d, J=7.2 Hz, 1H), 6.30 (d, J=6.6 Hz, 1H), 5.74 (s, 1H), 4.06 (m, 1H), 3.79 (m, 1H), 3.57-3.54 (m, 5H), 3.43-3.39 (m, 2H), 3.34 (s, 3H), 2.49-2.44 (m, 1H), 2.21-2.19 (m, 1H).

Example 290

2-Methyl-1-[(4-piperazin-1-ylpyridin-2-yl)amino]propan-2-ol

MS (ESI): mass calcd. for C$_{13}$H$_{22}$N$_4$O, 250.35 m/z found, 251.2 [M+H]$^+$. $^1$H NMR (300 MHz, CD$_3$OD): 7.63 (d, J=7.8 Hz, 1H), 6.64 (dd, J=7.8 Hz, J=2.4 Hz, 1H), 6.23 (d, J=1.8 Hz, 1H), 3.86-3.82 (m, 4H), 3.55 (s, 3H), 3.39-3.36 (m, 4H), 1.28 (s, 6H).

Example 291

N-{[(1S,2S,5S)-6,6-Dimethylbicyclo[3.1.1]hept-2-yl]methyl}-4-[(3aR,6aR)-hexahydropyrrolo[3,4-b]pyrrol-5(1H)-yl]pyridin-2-amine

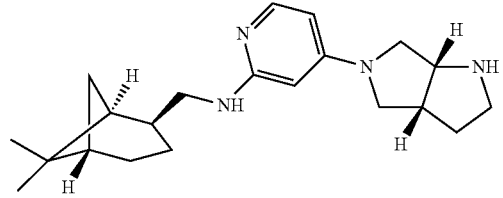 [SMILES: CC1(C)[C@H]2CC[C@H](CNc3cc(N4C[C@H]5CCN[C@H]5C4)ccn3)[C@@H]1C2]

MS (ESI): mass calcd. for C$_{21}$H$_{32}$N$_4$, 340.52 m/z found, 341.3 [M+H]$^+$. $^1$H NMR (300 MHz, CD$_3$OD): 7.50 (d, J=7.5 Hz, 1H), 6.31 (dd, J=2.1 Hz, 7.2 Hz, 1H), 5.71 (s, 1H), 4.43 (t, J=6.0 Hz, 1H), 3.93-3.68 (m, 3H), 3.45-3.20 (m, 6H), 2.44-2.25 (m, 3H), 2.06-1.90 (m, 6H), 1.57-1.52 (m, 1H), 1.52 (s, 3H), 1.19 (s, 3H), 0.93 (d, J=9.6 Hz, 1H).

Example 292

4-[(3R)-3-Aminopyrrolidin-1-yl]-N-cyclopentylpyridin-2-amine

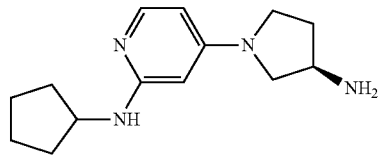 [SMILES: N[C@@H]1CCN(c2ccnc(NC3CCCC3)c2)C1]

MS (ESI): mass calcd. for $C_{14}H_{22}N_4$, 246.36 m/z found, 247.2 [M+H]$^+$. $^1$H NMR (300 MHz, DMSO-d$_6$): 12.25 (br, s, 1H), 8.57 (br, s, 3H), 7.95 (d, J=6.9 Hz, 1H), 7.64 (t, J=6.3 Hz, 1H), 6.27 (d, J=6.6 Hz, 1H), 5.68 (s, 1H), 4.04-3.87 (m, 3H), 3.66-3.40 (m, 4H), 2.38-2.18 (m, 2H), 2.02-1.96 (m, 2H), 1.70-1.24 (m, 6H).

Example 293

N-(2,2-Dimethylpropyl)-4-[(3aR,6aR)-hexahydropyrrolo[3,4-b]pyrrol-5(1H)-yl]pyridin-2-amine

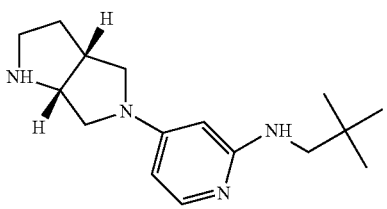 [SMILES: CC(C)(C)CNc1cc(N2C[C@H]3CCN[C@H]3C2)ccn1]

MS (ESI): mass calcd. for $C_{16}H_{26}N_4$, 274.41 m/z found, 275.2 [M+H]$^+$. $^1$H NMR (300 MHz, CD$_3$OD): 7.57 (d, J=7.5 Hz, 1H), 6.38 (dd, J=2.4 Hz, 7.5 Hz, 1H), 5.90 (d, J=2.4 Hz, 1H), 4.51-4.48 (m, 1H), 4.00-3.75 (m, 3H), 3.52-3.37 (m, 4H), 3.11 (s, 2H), 2.40-2.34 (m, 1H), 2.12-2.08 (m, 1H), 1.03 (s, 9H).

Example 294

4-[3-(Methylamino)azetidin-1-yl]-N-(2-phenylethyl)pyridin-2-amine

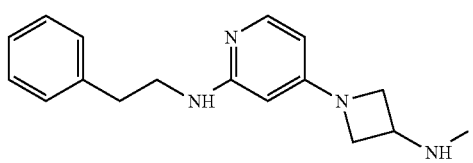 [SMILES: CNC1CN(c2ccnc(NCCc3ccccc3)c2)C1]

MS (ESI): mass calcd. for $C_{17}H_{22}N_4$, 282.39 m/z found, 283.2 [M+H]$^+$. $^1$H NMR (300 MHz, DMSO-d$_6$): 12.38 (br, s, 1H), 10.08 (br, s, 2H), 7.83-7.63 (m, 2H), 7.32-7.22 (m, 5H), 6.09 (d, J=6.9 Hz, 1H), 5.59 (s, 1H), 5.03 (br, s, 2H), 4.33-3.98 (m, 5H), 3.52-3.46 (m, 2H), 2.87 (t, J=7.2 Hz, 2H), 2.54 (s, 3H).

Example 295

N-(4-Fluorobenzyl)-4-[3-(methylamino)azetidin-1-yl]pyridin-2-amine

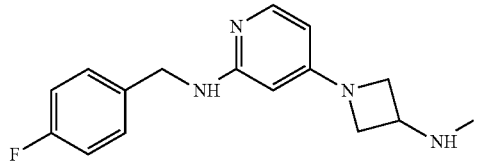 [SMILES: CNC1CN(c2ccnc(NCc3ccc(F)cc3)c2)C1]

MS (ESI): mass calcd. for $C_{16}H_{19}FN_4$, 286.36 m/z found, 287.2 [M+H]$^+$. $^1$H NMR (300 MHz, DMSO-d$_6$): 12.55 (br, s, 1H), 9.99 (br, s, 2H), 8.28 (br, s, 1H), 7.68 (t, J=6.3 Hz, 1H), 7.45-7.41 (m, 2H), 7.24-7.18 (m, 2H), 6.11 (d, J=5.7 Hz, 1H), 5.63 (s, 1H), 4.51 (d, 5.7 Hz, 2H), 4.21-4.14 (m, 7H), 2.53 (s, 3H).

Example 296

Adamantan-1-yl-[4-(3aR,6aR)-(hexahydro-pyrrolo[3,4-b]pyrrol-5-yl)-pyridin-2-yl]-amine

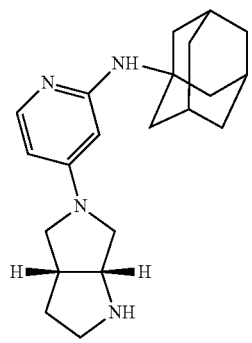 [SMILES: c1cc(N2C[C@H]3CCN[C@H]3C2)cc(NC23CC4CC(CC(C4)C2)C3)n1]

MS (ESI): mass calcd. for $C_{21}H_{30}N_4$, 338.5 m/z found, 339.3 [M+H]$^+$. $^1$H NMR (300 MHz, CD$_3$OD): 7.54 (d, J=7.2 Hz, 1H), 6.32 (d, J=7.5 Hz, 1H), 5.83 (s, 1H), 4.44 (t, J=6.6 Hz, 1H), 3.91-3.68 (m, 4H), 3.46-3.40 (m, 3H), 2.34-2.28 (m, 1H), 2.20-2.00 (m, 1H), 2.13 (s, 3H), 2.06 (s, 6H), 1.75 (s, 6H).

Example 297

4-[3-(Methylamino)azetidin-1-yl]-N-(pyridin-2-ylmethyl)pyridin-2-amine

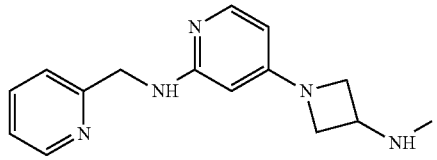 [SMILES: CNC1CN(c2ccnc(NCc3ccccn3)c2)C1]

MS (ESI): mass calcd. for $C_{15}H_{19}N_5$, 269.35 m/z found, 270.1 [M+H]$^+$. $^1$H NMR (300 MHz, CD$_3$OD): 8.76 (d, J=5.4 Hz, 1H), 8.55 (t, J=7.5 Hz, 1H), 8.03 (d, J=7.8 Hz, 1H), 7.96

(t, J=6.6 Hz, 1H), 7.59 (d, J=7.2 Hz, 1H), 6.18 (d, J=6.9 Hz, 1H), 5.74 (s, 1H), 5.01 (s, 2H), 4.41 (br, s, 2H), 4.25-4.21 (m, 3H), 2.65 (s, 3H).

Example 298

5-[(3R)-3-Aminopyrrolidin-1-yl]-N-(2-methoxyethyl)pyridazin-3-amine

3,4,5-trichloropyridazine. A solution of 4,5-dichloropyridazin-3(2H)-one (2 g, 12 mmol) in 20 mL of phosphoryl trichloride was heated to reflux for 2 hrs. The solvent was removed under reduce pressure. The residue was poured into water with stirring and extracted with dichloromathene (50 mL*3). The organic layer was washed with brine, dried over Na₂SO₄, evaporated to give the crude product (U.S. Pat. Appl. Publ. U.S. Pat. No. 6,800,758 (Egis Gyogyszergyar Rt., Hung., Oct. 5, 2004). The crude product was recrystallized with acetone/water to give the product (2 g, 83%). ¹H NMR (300 MHz, CDCl₃): 9.09 (s, 1H); LC-MS: m/z=182.9 [M+H]⁺.

(R)-tert-butyl 1-(5,6-dichloropyridazin-4-yl)pyrrolidin-3-ylcarbamate. To a stirred solution of 3,4,5-trichloropyridazine (500 mg, 5.5 mmol) and DIPEA (1 mL) in propan-2-ol (5 mL) was added (R)-tert-butyl pyrrolidin-3-ylcarbamate (508 mg, 5.5 mmol) at ambient temperature. The solvent was removed and the residue was purified by column chromatography (petroleum ether/ethyl acetate=2/1, v/v) to afford the title desired product (500 mg, 55%). ¹H NMR (300 MHz, CDCl₃): 8.42 (s, 1H), 5.06 (br s, 1H), 4.36 (br s, 1H), 4.05-3.99 (m, 1H), 3.90-3.66 (m, 3H), 2.28-2.23 (m, 1H), 2.09-2.07 (m, 1H), 1.48 (s, 9H); LC-MS: m/z=333.1 [M+H]⁺

(R)-tert-butyl 1-(5-chloro-6-(2-methoxyethylamino)pyridazin-4-yl)pyrrolidin-3-ylcarbamate. A mixture of 100 mg of (R)-tert-butyl 1-(5,6-dichloropyridazin-4-yl)pyrrolidin-3-ylcarbamate and 2-methoxyethanamine (1 mL) was heated at 145° C. for 40 min in microwave. The mixture was concentrated and the crude was purified by silica gel chromatography (EA/PE=1/4, v/v) to give the title product (50 mg, 45%). LC-MS: m/z=372.2 [M+H]⁺.

(R)-tert-butyl 1-(6-(2-methoxyethylamino)pyridazin-4-yl)pyrrolidin-3-ylcarbamate. To the mixture of (R)-tert-butyl 1-(5-chloro-6-(2-methoxyethylamino)pyridazin-4-yl)pyrrolidin-3-ylcarbamate (50 mg, 0.13 mmol) and ammonium formate (HCOONH₄) (85 mg, 1.3 mmol) in MeOH (2 mL) was added 10% Pd/C (20 mg). The resulting mixture was refluxed for 2 hours. The reaction was allowed to cool to room temperature and filtered. The filtrate was concentrated, diluted with EA (20 mL) and washed with brine (10 mL*2). The combined organic layer was dried over Na₂SO₄ and concentrated. The residue was purified by pre-TLC (PE/EA=1/5, v/v) to give the product as oil (20 mg, 44%). ¹H NMR (300 MHz, CDCl₃): 8.02 (s, 1H), 5.46 (s, 1H), 5.10-5.08 (m, 1H), 4.91 (br s, 1H), 4.33-4.26 (m, 1H), 3.59-3.51 (m, 4H), 3.40-3.35 (m, 4H), 3.19-3.15 (m, 1H), 2.28-2.19 (m, 1H), 1.99-1.97 (m, 1H), 1.44 (s, 9H); LC-MS: m/z=338.2 [M+H]⁺.

(R)-5-(3-aminopyrrolidin-1-yl)-N-(2-methoxyethyl)pyridazin-3-amine dihydrochloride. To solution of (R)-tert-butyl 1-(6-(2-methoxyethylamino)pyridazin-4-yl)pyrrolidin-3-ylcarbamate (198 mg, 0.59 mmol) in MeOH (3 mL) was added 7N HCl in ether (10 mL). The reaction was stirred at room temperature for 16 hours. The reaction was concentrated under reduced pressure to give the desired product as a light yellow solid (94.5 mg, 52%). ¹H NMR (300 MHz, CD₃OD): 8.14 (s, 1H), 6.12 (s, 1H), 4.15-3.54 (m, 9H), 3.40 (s, 3H), 2.57-2.52 (m, 1H), 2.32-2.30 (m, 1H); mass calcd. for C₁₁H₁₉N₅O, 237.31, LC-MS: m/z=238.2 [M+H]⁺, t_R=0.3 min; HPLC: 99% (214 nm), 95% (254 nm), t_R=4.4 min.

The compounds in Example 299 through Example 310 were prepared using methods analogous to those described in Example 298.

Example 299

5-[3-(Methylamino)azetidin-1-yl]-N-(4,4,4-trifluorobutyl)pyridazin-3-amine

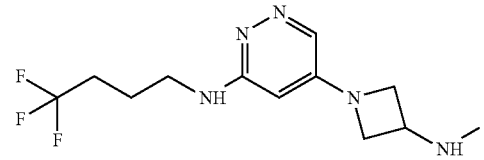 [SMILES: CNC1CN(c2cnnc(NCCCC(F)(F)F)c2)C1]

MS (ESI): mass calcd. for C₁₂H₁₈F₃N₅, 289.31 m/z found, 290.1 [M+H]⁺. ¹H NMR (300 MHz, CD₃OD): 7.84 (d, J=2.1 Hz, 1H), 5.88 (d, J=2.4 Hz, 1H), 4.60-4.40 (m, 2H), 4.31-4.22 (m, 3H), 3.31 (t, J=6.9 Hz, 2H), 2.69 (s, 3H), 2.26-2.18 (m, 2H), 1.86-1.79 (m, 2H).

Example 300

N⁵-(2-Aminoethyl)-N³-(2,2-dimethylpropyl)-N⁵-methylpyridazine-3,5-diamine

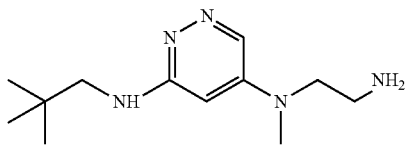 [SMILES: CN(CCN)c1cnnc(NCC(C)(C)C)c1]

MS (ESI): mass calcd. for C₁₂H₂₃N₅, 237.35 m/z found, 238.3 [M+H]⁺. ¹H NMR (300 MHz, CD₃OD): 8.19 (d, J=2.4 Hz, 1H), 6.29 (s, 1H), 3.79 (t, J=6.6 Hz, 2H), 3.21-3.08 (m, 7H), 0.94 (s, 9H).

Example 301

5-[3-(Methylamino)azetidin-1-yl]-N-[(1S,5R)-2,6,6-trimethylbicyclo[3.1.1]hept-3-yl]pyridazin-3-amine

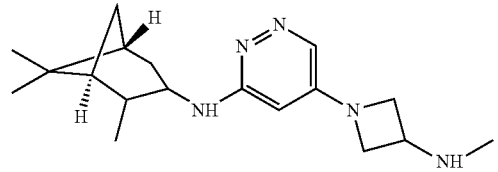

MS (ESI): mass calcd. for C₁₈H₂₉N₅, 315.47 m/z found, 316.3 [M+H]⁺. ¹H NMR (300 MHz, CD₃OD): 7.94 (s, 1H), 5.98 (s, 1H), 4.70-4.30 (m, 5H), 4.02-3.99 (m, 1H), 2.81 (s, 3H), 2.80-2.70 (m, 1H), 2.60-2.50 (m, 1H), 2.16-1.72 (m, 4H), 1.40-1.30 (m, 1H), 1.32 (s, 3H), 1.20 (d, J=7.2 Hz, 3H), 1.09 (s, 3H).

Example 302

N$^5$-(2-Amino-ethyl)-N$^3$-bicyclo[2.2.1]hept-2-yl-N$^5$-methyl-pyridazine-3,5-diamine

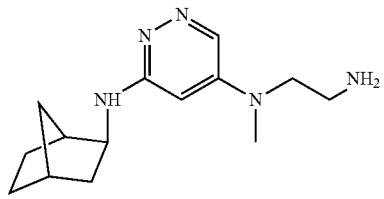 [SMILES: CN(CCN)c1cnnc(NC2CC3CCC2C3)c1]

MS (ESI): mass calcd. for C$_{14}$H$_{23}$N$_5$, 261.37 m/z found, 262.3 [M+H]$^+$. $^1$H NMR (300 MHz, CD$_3$OD): 8.19 (d, J=2.4 Hz, 1H), 6.08 (d, J=2.1 Hz, 1H), 3.77 (t, J=6.9 Hz, 2H), 3.44-3.42 (m, 1H), 3.14 (t, J=6.9 Hz, 2H), 3.09 (s, 3H), 2.24 (d, J=21 Hz, 2H), 1.88-1.81 (m, 1H), 1.58-1.14 (m, 7H).

Example 303

N$^5$-(2-Aminoethyl)-N$^3$-(cyclopentylmethyl)-N$^5$-methylpyridazine-3,5-diamine

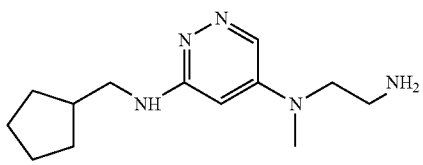 [SMILES: CN(CCN)c1cnnc(NCC2CCCC2)c1]

MS (ESI): mass calcd. for C$_{13}$H$_{23}$N$_5$, 249.36 m/z found, 250.3 [M+H]$^+$. $^1$H NMR (300 MHz, CD$_3$OD): 8.19 (d, J=2.4 Hz, 1H), 6.15 (s, 1H), 3.78 (t, J=6.9 Hz, 2H), 3.21-3.10 (m, 7H), 1.81-1.53 (m, 7H), 1.25-1.20 (m, 2H).

Example 304

5-[(3S)-3-Aminopyrrolidin-1-yl]-N-(bicyclo[2.2.1]hept-2-ylmethyl)pyridazin-3-amine

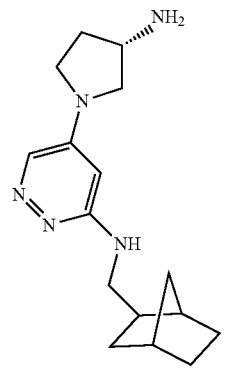 [SMILES: N[C@H]1CCN(c2cnnc(NCC3CC4CCC3C4)c2)C1]

MS (ESI): mass calcd. for C$_{16}$H$_{25}$N$_5$, 287.41 m/z found, 288.2 [M+H]$^+$. $^1$H NMR (300 MHz, CD$_3$OD): 8.18 (d, J=2.1 Hz, 1H), 6.12 (d, J=2.1 Hz, 1H), 4.20-3.50 (m, 5H), 3.40-3.00 (m, 2H), 2.64-2.57 (m, 1H), 2.40-2.20 (m, 3H), 1.96-0.82 (m, 9H).

Example 305

3-({5-[(3aR,6aR)-Hexahydropyrrolo[3,4-b]pyrrol-5 (1H)-yl]pyridazin-3-yl}amino)propan-1-ol

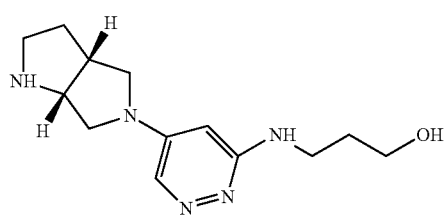 [SMILES: OCCCNc1cc(N2C[C@H]3CCN[C@H]3C2)cnn1]

MS (ESI): mass calcd. for C$_{13}$H$_{21}$N$_5$O, 263.35 m/z found, 264.2 [M+H]$^+$. $^1$H NMR (300 MHz, CD$_3$OD): 8.11 (s, 1H), 6.08 (s, 1H), 4.52-4.48 (m, 1H), 4.05-3.84 (m, 2H), 3.76-3.66 (m, 2H), 3.56-3.41 (m, 5H), 2.39-2.33 (m, 1H), 2.11-2.09 (m, 1H), 1.92-1.83 (m, 2H).

Example 306

5-(3-Aminoazetidin-1-yl)-N-{[(1S,2S,5S)-6,6-dimethylbicyclo[3.1.1]hept-2-yl]methyl}pyridazin-3-amine

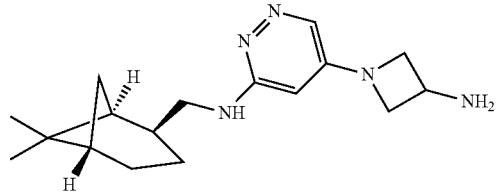 [SMILES: CC1(C)[C@H]2CC[C@H](CNc3cc(N4CC(N)C4)cnn3)[C@@H]1C2]

MS (ESI): mass calcd. for C$_{17}$H$_{27}$N$_5$, 301.44 m/z found, 302.1 [M+H]$^+$. $^1$H NMR (300 MHz, CD$_3$OD): 7.79 (d, J=2.7 Hz, 1H), 5.78 (s, 1H), 4.60-4.40 (m, 2H), 4.30-4.10 (m, 3H), 3.30-3.10 (m, 2H), 2.40-2.20 (m, 2H), 1.94-1.85 (m, 5H), 1.50-1.40 (m, 1H), 1.14 (s, 3H), 0.99 (s, 3H), 0.88 (d, J=9.9 Hz, 1H).

Example 307

5-(1,4-Diazepan-1-yl)-N-(2,2-dimethylpropyl)pyridazin-3-amine

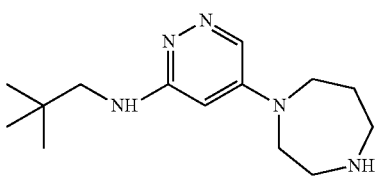 [SMILES: CC(C)(C)CNc1cc(N2CCCNCC2)cnn1]

MS (ESI): mass calcd. for C$_{14}$H$_{25}$N$_5$, 263.39 m/z found, 264.2 [M+H]$^+$. $^1$H NMR (300 MHz, CD$_3$OD): 8.36 (d, J=2.1

Hz, 1H), 6.41 (d, J=2.1 Hz, 1H), 4.04-4.03 (m, 2H), 3.81-3.79 (m, 2H), 3.53-3.49 (m, 2H), 3.43-3.41 (m, 2H), 3.20 (s, 2H), 2.30-2.28 (m, 2H), 1.06 (s, 9H).

Example 308

N-Bicyclo[2.2.1]hept-2-yl-5-(1,4-diazepan-1-yl)pyridazin-3-amine

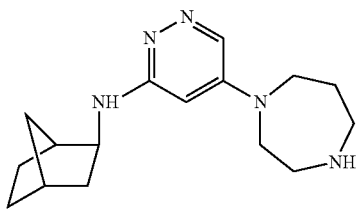 [SMILES: c1nnc(NC2CC3CCC2C3)cc1N1CCCNCC1]

MS (ESI): mass calcd. for $C_{16}H_{25}N_5$, 287.41 m/z found, 288.2 [M+H]$^+$. $^1$H NMR (300 MHz, CD$_3$OD): 8.35 (s, 1H), 6.22 (s, 1H), 4.03-4.02 (m, 2H), 3.79-3.77 (m, 2H), 3.55-3.49 (m, 3H), 3.42-3.37 (m, 3H), 2.32-2.28 (m, 3H), 1.99-1.92 (m, 1H), 1.70-1.62 (m, 3H), 1.59-1.22 (m, 4H).

Example 309

N-Cyclopropyl-5-[(3aR,6aR)-hexahydropyrrolo[3,4-b]pyrrol-5(1H)-yl]pyridazin-3-amine

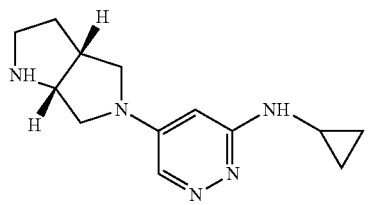 [SMILES: c1nnc(NC2CC2)cc1N1C[C@H]2CCN[C@H]2C1]

MS (ESI): mass calcd. for $C_{13}H_{19}N_5$, 245.33 m/z found, 246.2 [M+H]$^+$. $^1$H NMR (300 MHz, CD$_3$OD): 8.17 (d, J=2.4 Hz, 1H), 6.07 (d, J=2.1 Hz, 1H), 4.53-4.49 (m, 1H), 3.99-3.40 (m, 7H), 2.67-2.62 (m, 1H), 2.41-2.37 (m, 1H), 2.14-2.08 (m, 1H), 1.01-0.95 (m, 2H), 0.71-0.66 (m, 2H).

Example 310

N-Butyl-5-[(3aR,6aR)-hexahydropyrrolo[3,4-b]pyrrol-5(1H)-yl]pyridazin-3-amine

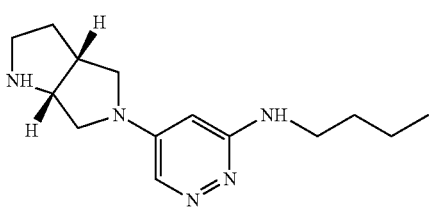 [SMILES: CCCCNc1cc(N2C[C@H]3CCN[C@H]3C2)cnn1]

MS (ESI): mass calcd. for $C_{14}H_{23}N_5$, 261.37 m/z found, 262.3 [M+H]$^+$. $^1$H NMR (300 MHz, CD$_3$OD): 8.13 (d, J=2.4 Hz, 1H), 6.06 (d, J=2.1 Hz, 1H), 4.54-4.50 (m, 1H), 4.08-3.40 (m, 7H), 3.33-3.31 (m, 2H), 2.41-2.34 (m, 1H), 2.14-2.09 (m, 1H), 1.73-1.63 (m, 2H), 1.51-1.44 (m, 2H), 1.00 (t, J=7.5 Hz, 3H).

Example 311

N-(Cyclopentylmethyl)-4-piperazin-1-ylpyridin-2-amine

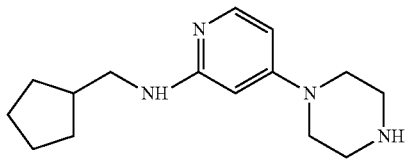 [SMILES: c1cc(N2CCNCC2)cc(NCC2CCCC2)n1]

The titled compound was prepared in a manner analogous to Example 254. MS (ESI): mass calcd. for $C_{15}H_{24}N_4$, 260.39 m/z found, 261.2 [M+H]$^+$. $^1$H NMR (300 MHz, CD$_3$OD): 7.55 (d, J=7.5 Hz, 1H), 6.59 (dd, J=7.5 Hz, J=1.8 Hz, 1H), 6.09 (d. J=1.8 Hz, 1H), 3.79 (t, J=5.7 Hz, 4H), 3.33 (t, J=5.1 Hz, 4H), 3.17 (d, J=7.5 Hz, 2H), 2.20-2.15 (m, 1H), 1.87-1.81 (m, 2H), 1.66-1.58 (m, 4H), 1.29-1.23 (m, 2H).

The compounds in Example 312 through Example 371 were prepared using methods analogous to those described in Example 298.

Example 312

5-[(3R)-3-Aminopyrrolidin-1-yl]-N-(bicyclo[2.2.1]hept-2-ylmethyl)pyridazin-3-amine

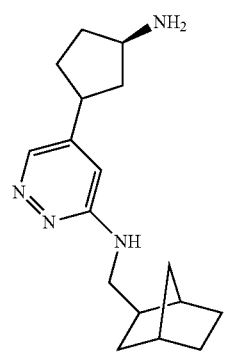 [SMILES: N[C@@H]1CCC(c2cnnc(NCC3CC4CCC3C4)c2)C1]

MS (ESI): mass calcd. for $C_{16}H_{25}N_5$, 287.41 m/z found, 288.3 [M+H]$^+$. $^1$H NMR (300 MHz, CD$_3$OD): 8.18 (d, J=2.1

Hz, 1H), 6.10 (d, J=2.1 Hz, 1H), 4.20-3.50 (m, 5H), 3.40-3.00 (m, 2H), 2.64-2.57 (m, 1H), 2.40-2.20 (m, 3H), 2.00-0.82 (m, 9H).

Example 313

3-({5-[(3R)-3-Aminopyrrolidin-1-yl]pyridazin-3-yl}amino)propan-1-ol

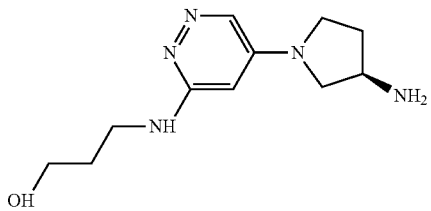 [SMILES: N[C@@H]1CCN(c2cnnc(NCCCO)c2)C1]

MS (ESI): mass calcd. for $C_{11}H_{19}N_5O$, 237.31 m/z found, 238.2 [M+H]$^+$. $^1$H NMR (300 MHz, CD$_3$OD): 8.12 (br, s, 1H), 6.06 (s, 1H), 4.14 (s, 1H), 3.84-3.54 (m, 6H), 3.45-3.41 (m, 2H), 2.55-2.51 (m, 1H), 2.28 (br, s, 1H), 1.88 (t, J=6.6 Hz, 2H).

Example 314

3-[(5-piperazin-1-ylpyridazin-3-yl)amino]propan-1-ol

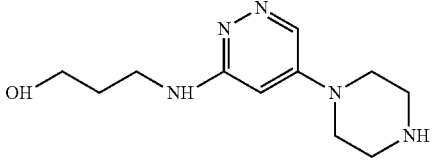 [SMILES: OCCCNc1cc(N2CCNCC2)cnn1]

MS (ESI): mass calcd. for $C_{11}H_{19}N_5O$, 237.31 m/z found, 238.2 [M+H]$^+$. $^1$H NMR (300 MHz, CD$_3$OD): 8.37 (s, 1H), 6.42 (br, s, 1H), 3.89 (br, s, 4H), 3.69 (t, J=5.4 Hz, 2H), 3.47-3.47 (m, 6H), 1.89 (t, J=6.3 Hz, 2H).

Example 315

N-Cyclopropyl-5-piperazin-1-ylpyridazin-3-amine

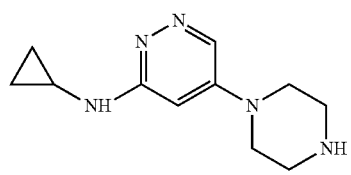 [SMILES: c1nnc(NC2CC2)cc1N1CCNCC1]

MS (ESI): mass calcd. for $C_{11}H_{17}N_5$, 219.29 m/z found, 220.1 [M+H]$^+$. $^1$H NMR (300 MHz, CD$_3$OD): 8.38 (s, 1H), 6.37 (s, 1H), 3.87-3.85 (m, 4H), 3.37-3.36 (m, 4H), 2.62-2.60 (br, s, 1H), 0.97-0.91 (m, 2H), 0.65 (br, s, 2H).

Example 316

N-(Cyclopentylmethyl)-5-(1,4-diazepan-1-yl)pyridazin-3-amine

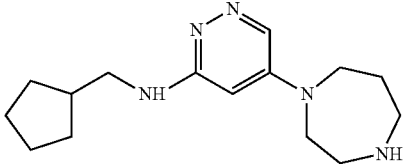 [SMILES: c1nnc(NCC2CCCC2)cc1N1CCCNCC1]

MS (ESI): mass calcd. for $C_{15}H_{25}N_5$, 275.4 m/z found, 276.3 [M+H]$^+$. $^1$H NMR (300 MHz, CD$_3$OD): 8.36 (d, J=2.4 Hz, 1H), 6.39 (d, J=2.4 Hz, 1H), 4.04-4.02 (m, 2H), 3.80-3.78 (m, 2H), 3.52-3.49 (m, 2H), 3.42-3.37 (m, 2H), 3.28 (d, J=7.5 Hz, 2H), 2.30-2.22 (m, 3H), 1.93-1.91 (m, 2H), 1.73-1.65 (m, 4H), 1.34-1.32 (m, 2H).

Example 317

5-[(3S)-3-Aminopyrrolidin-1-yl]-N-(cyclopentylmethyl)pyridazin-3-amine

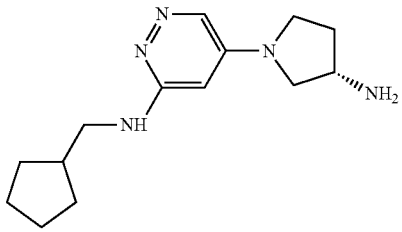 [SMILES: N[C@H]1CCN(c2cnnc(NCC3CCCC3)c2)C1]

MS (ESI): mass calcd. for $C_{14}H_{23}N_5$, 261.37 m/z found, 262.2 [M+H]$^+$. $^1$H NMR (300 MHz, CD$_3$OD): 8.15 (s, 1H), 6.08 (s, 1H), 4.17-4.15 (m, 1H), 4.10-3.54 (m, 4H), 3.27 (d, J=7.2 Hz, 2H), 2.60-2.51 (m, 1H), 2.29-2.20 (m, 2H), 1.92-1.90 (m, 2H), 1.73-1.65 (m, 4H), 1.36-1.32 (m, 2H).

Example 318

5-[(3aR,6aR)-Hexahydropyrrolo[3,4-b]pyrrol-5(1H)-yl]-N-(2-methylpropyl)pyridazin-3-amine

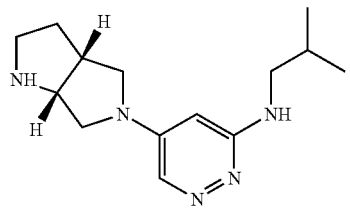 [SMILES: CC(C)CNc1cc(N2C[C@H]3CCN[C@H]3C2)cnn1]

MS (ESI): mass calcd. for $C_{14}H_{23}N_5$, 261.37 m/z found, 262.1 [M+H]$^+$. $^1$H NMR (300 MHz, CD$_3$OD): 8.07 (d, J=2.4 Hz, 1H), 6.04 (d, J=2.1 Hz, 1H), 4.48-4.44 (m, 1H), 4.06-3.77

(m, 3H), 3.53-3.26 (m, 4H), 3.10 (d, J=7.2 Hz, 2H), 2.36-2.29 (m, 1H), 2.09-0.97 (m, 2H), 0.98 (d, J=6.9 Hz, 6H).

Example 319

5-[3-(Methylamino)azetidin-1-yl]-N-(2-methylpropyl)pyridazin-3-amine

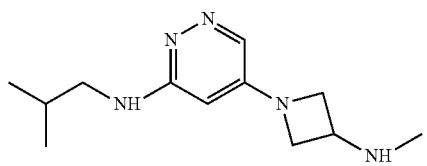 [SMILES: CNC1CN(c2cnnc(NCC(C)C)c2)C1]

MS (ESI): mass calcd. for C₁₂H₂₁N₅, 235.33 m/z found, 236.1 [M+H]⁺. ¹H NMR (300 MHz, CD₃OD): 7.94 (d, J=2.1 Hz, 1H), 5.98 (s, 1H), 4.70-4.34 (m, 5H), 3.17 (d, J=7.2 Hz, 2H), 2.81 (s, 3H), 1.99-1.93 (m, 1H), 1.05 (d, J=6.6 Hz, 6H).

Example 320

N-(2-Methoxyethyl)-5-[3-(methylamino)azetidin-1-yl]pyridazin-3-amine

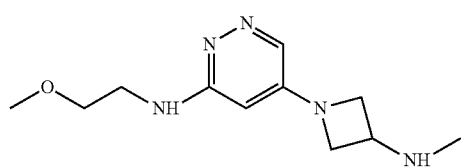

MS (ESI): mass calcd. for C₁₁H₁₉N₅O, 237.31 m/z found, 238.1 [M+H]⁺. ¹H NMR (300 MHz, CD₃OD): 7.94 (d, J=2.4 Hz, 1H), 6.04 (s, 1H), 4.70-4.35 (m, 5H), 3.65-3.62 (m, 2H), 3.56-3.53 (m, 2H), 3.42 (s, 3H), 2.81 (s, 3H).

Example 321

5-[(3R)-3-Aminopyrrolidin-1-yl]-N-[(1R)-1-phenylethyl]pyridazin-3-amine

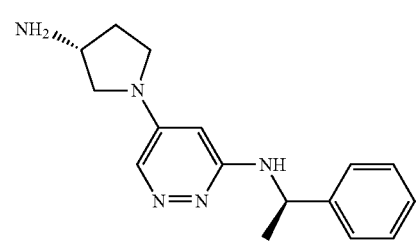 [SMILES: C[C@@H](Nc1cc(N2CC[C@@H](N)C2)cnn1)c1ccccc1]

MS (ESI): mass calcd. for C₁₆H₂₁N₅, 283.38 m/z found, 284.2 [M+H]⁺. ¹H NMR (300 MHz, CD₃OD): 8.09 (s, 1H), 7.39-7.29 (m, 5H), 5.95 (s, 1H), 4.10 (br, s, 1H), 3.98-3.53 (m, 5H), 2.54-2.48 (m, 1H), 2.26-2.22 (m, 1H), 1.61 (d, J=6.9 Hz, 3H).

Example 322

5-(3-Aminoazetidin-1-yl)-N-bicyclo[2.2.1]hept-2-ylpyridazin-3-amine

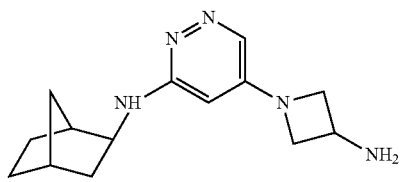 [SMILES: NC1CN(c2cnnc(NC3CC4CCC3C4)c2)C1]

MS (ESI): mass calcd. for C₁₄H₂₁N₅, 259.36 m/z found, 260.2 [M+H]⁺. ¹H NMR (300 MHz, CD₃OD): 7.89 (d, J=1.5 Hz, 1H), 5.87 (s, 1H), 4.59 (br, s, 2H), 4.33 (br, s, 3H), 3.50-3.48 (m, 1H), 2.35-2.27 (m, 2H), 1.94-1.87 (m, 1H), 1.67-1.18 (m, 4H).

Example 323

5-(3-Aminoazetidin-1-yl)-N-(2,2-dimethylpropyl)pyridazin-3-amine

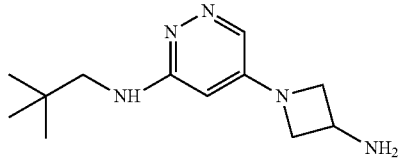 [SMILES: CC(C)(C)CNc1cc(N2CC(N)C2)cnn1]

MS (ESI): mass calcd. for C₁₂H₂₁N₅, 235.33 m/z found, 236.1 [M+H]⁺. ¹H NMR (300 MHz, CD₃OD): 7.90 (s, 1H), 6.06 (s, 1H), 4.62 (br s, 2H), 4.35 (br s, 3H), 3.15 (s, 2H), 1.03 (s, 9H).

Example 324

N-(2,2-Dimethylpropyl)-5-[3-(methylamino)azetidin-1-yl]pyridazin-3-amine

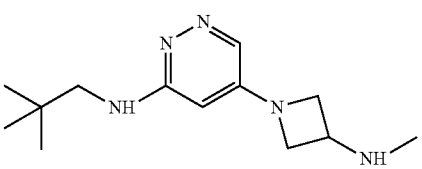 [SMILES: CNC1CN(c2cnnc(NCC(C)(C)C)c2)C1]

MS (ESI): mass calcd. for C₁₃H₂₃N₅, 249.36 m/z found, 250.2 [M+H]⁺. ¹H NMR (300 MHz, CD₃OD): 7.95 (d, J=2.4

Hz, 1H), 6.10 (d, J=2.1 Hz, 1H), 4.70-4.36 (m, 5H), 3.19 (s, 2H), 2.83 (s, 3H), 1.07 (s, 9H).

Example 325

N-Cyclohexyl-5-[3-(methylamino)azetidin-1-yl]pyridazin-3-amine

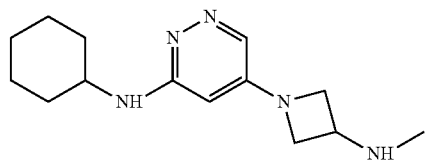 [SMILES: CNC1CN(c2cnnc(NC3CCCCC3)c2)C1]

MS (ESI): mass calcd. for $C_{14}H_{23}N_5$, 261.37 m/z found, 262.2 [M+H]$^+$. $^1$H NMR (300 MHz, CD$_3$OD): 7.84 (s, 1H), 5.86 (s, 1H), 4.53 (br, s, 2H), 4.30-4.26 (m, 3H), 3.57-3.49 (m, 1H), 2.73 (d, J=3.3 Hz, 3H), 1.96-1.92 (m, 2H), 1.79-1.63 (m, 3H), 1.44-1.11 (m, 5H).

Example 326

5-(3-Aminoazetidin-1-yl)-N-cyclopentylpyridazin-3-amine

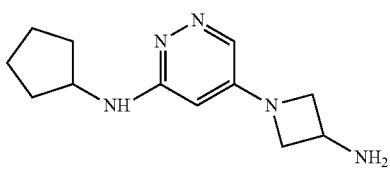 [SMILES: NC1CN(c2cnnc(NC3CCCC3)c2)C1]

MS (ESI): mass calcd. for $C_{12}H_{19}N_5$, 233.32 m/z found, 234.1 [M+H]$^+$. $^1$H NMR (300 MHz, CD$_3$OD): 7.88 (s, 1H), 5.86 (s, 1H), 4.58 (br s, 2H), 4.40-4.20 (m, 3H), 4.00-3.96 (m, 1H), 2.09-2.04 (m, 2H), 1.80-1.58 (m, 6H).

Example 327

N-(Cyclopropylmethyl)-5-[3-(methylamino)azetidin-1-yl]pyridazin-3-amine

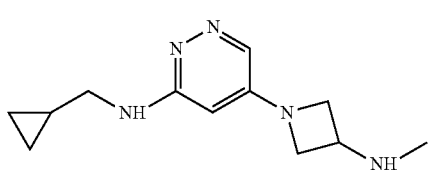 [SMILES: CNC1CN(c2cnnc(NCC3CC3)c2)C1]

MS (ESI): mass calcd. for $C_{12}H_{19}N_5$, 233.32 m/z found, 234.2 [M+H]$^+$. $^1$H NMR (300 MHz, CD$_3$OD): 7.87 (d, J=2.4 Hz, 1H), 5.91 (d, J=2.4 Hz, 1H), 4.56 (br, s, 2H), 4.36-4.26 (m, 3H), 3.16 (d, J=7.2 Hz, 2H), 1.15-1.01 (m, 1H), 0.66-0.60 (m, 2H), 0.34-0.29 (m, 2H).

Example 328

5-(3-Aminoazetidin-1-yl)-N-(2-methylpropyl)pyridazin-3-amine

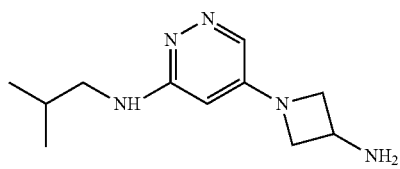 [SMILES: CC(C)CNc1cc(N2CC(N)C2)cnn1]

MS (ESI): mass calcd. for $C_{11}H_{19}N_5$, 221.31 m/z found, 222.1 [M+H]$^+$. $^1$H NMR (300 MHz, CD$_3$OD): 7.90 (s, 1H), 5.94 (s, 1H), 4.70-4.30 (m, 5H), 3.13 (d, J=6.9 Hz, 2H), 1.93-1.92 (m, 1H), 1.02 (d, J=6.3 Hz, 6H).

Example 329

5-(3-Aminoazetidin-1-yl)-N-benzylpyridazin-3-amine

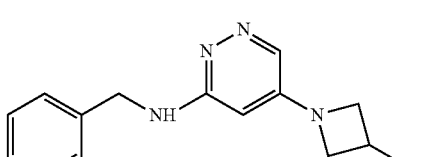

MS (ESI): mass calcd. for $C_{14}H_{17}N_5$, 255.33 m/z found, 256.2 [M+H]$^+$. $^1$H NMR (300 MHz, CD$_3$OD): 7.88 (d, J=2.4 Hz, 2H), 7.38-7.29 (m, 5H), 5.90 (d, J=2.4 Hz, 1H), 4.53 (s, 4H), 4.36-4.30 (m, 3H).

Example 330

N-Benzyl-5-[3-(methylamino)azetidin-1-yl]pyridazin-3-amine

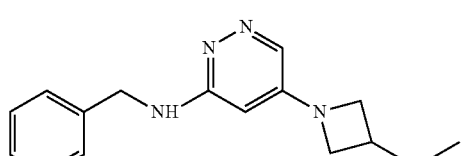

MS (ESI): mass calcd. for $C_{15}H_{19}N_5$, 269.35 m/z found, 270.2 [M+H]$^+$. $^1$H NMR (300 MHz, CD$_3$OD): 7.80 (br, s, 1H), 7.27 (br, s, 5H), 5.82 (s, 1H), 4.44 (s, 4H), 4.19 (br, 3H), 2.66 (s, 3H).

Example 331

N-Bicyclo[2.2.1]hept-2-yl-5-[3-(methylamino)azetidin-1-yl]pyridazin-3-amine

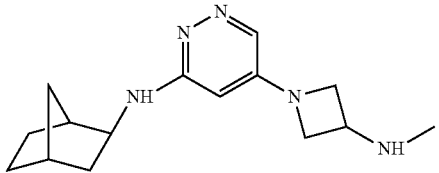 [SMILES: CNC1CN(c2cnnc(NC3CC4CCC3C4)c2)C1]

MS (ESI): mass calcd. for $C_{15}H_{23}N_5$, 273.38 m/z found, 274.2 [M+H]$^+$. $^1$H NMR (300 MHz, CD$_3$OD): 7.88 (s, 1H), 5.82 (d, J=2.7 Hz, 1H), 4.56 (br, s, 2H), 4.35-4.23 (m, 3H), 3.48-3.46 (m, 1H), 2.36 (s, 3H), 2.28-2.27 (m, 2H), 1.94-1.87 (m, 1H), 1.63-1.17 (m, 7H).

Example 332

N-Cyclopentyl-5-[3-(methylamino)azetidin-1-yl]pyridazin-3-amine

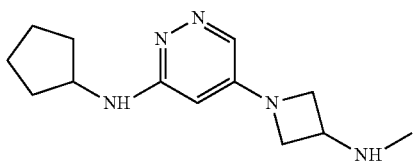 [SMILES: CNC1CN(c2cnnc(NC3CCCC3)c2)C1]

MS (ESI): mass calcd. for $C_{13}H_{21}N_5$, 247.35 m/z found, 248.2 [M+H]$^+$. $^1$H NMR (300 MHz, CD$_3$OD): 7.78 (br, s, 1H), 5.77 (br, s, 1H), 4.46 (br, s, 2H), 4.25-4.21 (m, 3H), 3.88-3.86 (m, 1H), 2.67 (s, 3H), 1.99-1.95 (m, 2H), 1.70-1.48 (m, 6H).

Example 333

5-(3-Aminoazetidin-1-yl)-N-cyclopropylpyridazin-3-amine

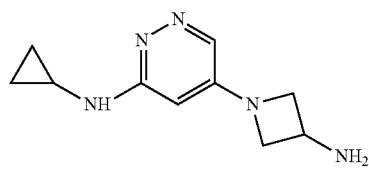 [SMILES: NC1CN(c2cnnc(NC3CC3)c2)C1]

MS (ESI): mass calcd. for $C_{10}H_{15}N_5$, 205.26 m/z found, 206.2 [M+H]$^+$. $^1$H NMR (300 MHz, CD$_3$OD): 7.95 (d, J=2.4 Hz, 1H), 5.92 (d, J=1.8 Hz, 1H), 4.60 (br, s, 2H), 4.37-4.31 (m, 3H), 2.64-2.59 (m, 1H), 0.99-0.93 (m, 2H), 0.69-0.64 (m, 2H).

Example 334

3-({5-[3-(Methylamino)azetidin-1-yl]pyridazin-3-yl}amino)propan-1-ol

MS (ESI): mass calcd. for $C_{11}H_{19}N_5O$, 237.31 m/z found, 238.2 [M+H]$^+$. $^1$H NMR (300 MHz, CD$_3$OD): 7.90 (d. J=2.7 Hz, 1H), 5.97 (d, J=2.4 Hz, 1H), 4.58 (br, s, 2H), 4.39-4.31 (m, 3H), 3.68 (t, J=6.0 Hz, 2H), 3.42 (t, J=6.9 Hz, 2H), 2.77 (s, 3H), 1.91-1.82 (m, 2H).

Example 335

5-(3-Aminoazetidin-1-yl)-N-(2-methoxyethyl)pyridazin-3-amine

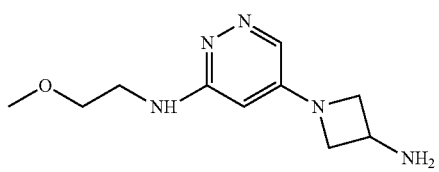 [SMILES: COCCNc1cc(N2CC(N)C2)cnn1]

MS (ESI): mass calcd. for $C_{10}H_{17}N_5O$, 223.28 m/z found, 224.2 [M+H]$^+$. $^1$H NMR (300 MHz, CD$_3$OD): 7.94 (d, J=2.4 Hz, 1H), 6.01 (d, J=2.7 Hz, 1H), 4.64 (br s, 2H), 4.41-4.36 (m, 3H), 3.66-3.63 (m, 2H), 3.56-3.53 (m, 2H), 3.42 (s, 3H).

Example 336

5-[(3S)-3-Aminopyrrolidin-1-yl]-N-cyclopropylpyridazin-3-amine

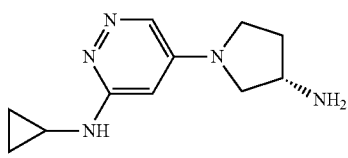 [SMILES: N[C@H]1CCN(c2cnnc(NC3CC3)c2)C1]

MS (ESI): mass calcd. for $C_{11}H_{17}N_5$, 219.29 m/z found, 220.2 [M+H]$^+$. $^1$H NMR (300 MHz, CD$_3$OD): 8.16 (d, J=2.4

Hz, 1H), 6.04 (d, J=2.1 Hz, 1H), 4.13-3.53 (m, 5H), 2.67-2.51 (m, 2H), 2.31-2.24 (m, 1H), 1.00-0.94 (m, 2H), 0.70-0.65 (m, 2H).

Example 337

5-[(3R)-3-Aminopyrrolidin-1-yl]-N-(pyridin-2-ylmethyl)pyridazin-3-amine

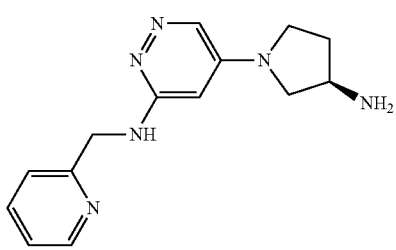 [SMILES: N[C@@H]1CCN(c2cnnc(NCc3ccccn3)c2)C1]

MS (ESI): mass calcd. for $C_{14}H_{18}N_6$, 270.34 m/z found, 271.2 [M+H]$^+$. $^1$H NMR (300 MHz, CD$_3$OD): 8.80 (d, J=5.7 Hz, 1H), 8.53 (t, J=7.8 Hz, 1H), 8.20 (s, 1H), 8.05-7.93 (m, 2H), 6.24 (s, 1H), 5.01 (s, 2H), 4.09 (br, s, 1H), 3.82-3.60 (m, 4H), 2.53-2.46 (m, 1H), 2.24-2.22 (m, 1H).

Example 338

3-({5-[(3S)-3-Aminopyrrolidin-1-yl]pyridazin-3-yl}amino)propan-1-ol

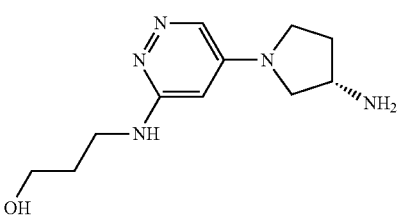 [SMILES: N[C@H]1CCN(c2cnnc(NCCCO)c2)C1]

MS (ESI): mass calcd. for $C_{11}H_{19}N_5O$, 237.31 m/z found, 238.2 [M+H]$^+$. $^1$H NMR (300 MHz, CD$_3$OD): 8.12 (d, J=2.1 Hz, 1H), 6.05 (d, J=2.4 Hz, 1H), 4.13-3.53 (m, 7H), 3.43 (t, J=6.9 Hz, 2H), 2.58-2.48 (m, 1H), 2.30-2.26 (m, 1H), 1.92-1.84 (m, 2H).

Example 339

5-[(3S)-3-Aminopyrrolidin-1-yl]-N-(2-methylpropyl)pyridazin-3-amine

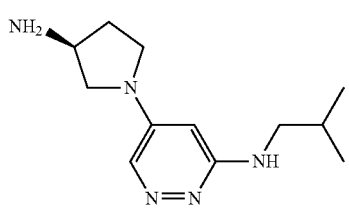 [SMILES: CC(C)CNc1cc(N2CC[C@H](N)C2)cnn1]

MS (ESI): mass calcd. for $C_{12}H_{21}N_5$, 235.33 m/z found, 236.1 [M+H]$^+$. $^1$H NMR (300 MHz, CD$_3$OD): 8.13 (s, 1H), 6.05 (s, 1H), 4.14-3.16 (m, 5H), 3.15 (d, J=6.9 Hz, 2H), 2.58-2.52 (m, 1H), 2.28-2.20 (m, 1H), 2.00-1.91 (m, 1H), 0.93 (d, J=6.9 Hz, 6H).

Example 340

5-[(3R)-3-Aminopyrrolidin-1-yl]-N-benzylpyridazin-3-amine

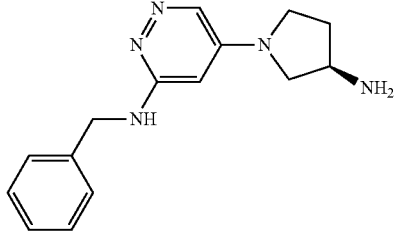 [SMILES: N[C@@H]1CCN(c2cnnc(NCc3ccccc3)c2)C1]

MS (ESI): mass calcd. for $C_{15}H_{19}N_5$, 269.35 m/z found, 270.1 [M+H]$^+$. $^1$H NMR (300 MHz, CD$_3$OD): 8.09 (s, 1H), 7.35-7.29 (m, 5H), 5.98 (s, 1H), 4.52 (s, 2H), 4.07 (br, s, 1H), 3.78-3.41 (m, 4H), 2.52-2.45 (m, 1H), 2.24-2.20 (m, 1H).

Example 341

5-[(3R)-3-Aminopyrrolidin-1-yl]-N-(4-methoxybenzyl)pyridazin-3-amine

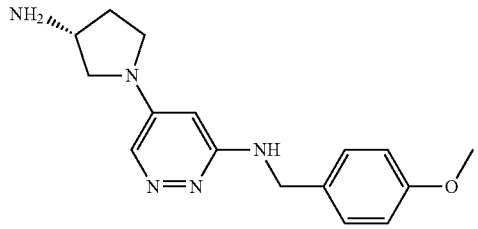 [SMILES: COc1ccc(CNc2cc(N3CC[C@@H](N)C3)cnn2)cc1]

MS (ESI): mass calcd. for $C_{16}H_{21}N_5O$, 299.38 m/z found, 300.2 [M+H]$^+$. $^1$H NMR (300 MHz, CD$_3$OD): 8.16 (s, 1H), 7.34 (d, J=8.7 Hz, 2H), 6.96 (d, J=8.7 Hz, 2H), 6.03 (d, J=2.1 Hz, 1H), 4.50 (s, 2H), 4.14-3.56 (m, 5H), 3.81 (s, 3H), 2.59-2.52 (m, 1H), 2.31-2.27 (m, 1H).

Example 342

5-[(3R)-3-Aminopyrrolidin-1-yl]-N-(4-fluorobenzyl)pyridazin-3-amine

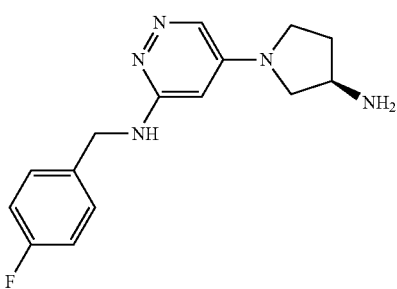 [SMILES: N[C@@H]1CCN(c2cnnc(NCc3ccc(F)cc3)c2)C1]

MS (ESI): mass calcd. for $C_{15}H_{18}FN_5$, 287.34 m/z found, 288.2 [M+H]$^+$. $^1$H NMR (300 MHz, CD$_3$OD): 8.19 (d, J=2.1

Hz, 1H), 7.50-7.45 (m, 2H), 7.20-7.14 (m, 2H), 6.08 (d, J=2.1 Hz, 1H), 4.59 (s, 2H), 4.17-3.58 (m, 5H), 2.61-2.52 (m, 1H), 2.36-2.30 (m, 1H).

Example 343

5-[(3R)-3-Aminopyrrolidin-1-yl]-N-(4-methylbenzyl)pyridazin-3-amine

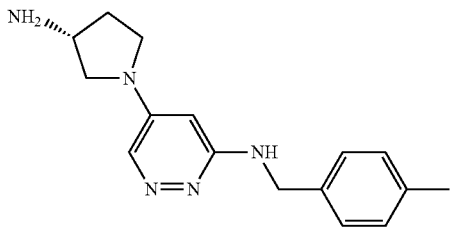 [SMILES: Cc1ccc(CNc2cc(N3CC[C@@H](N)C3)cnn2)cc1]

MS (ESI): mass calcd. for $C_{16}H_{21}N_5$, 283.38 m/z found, 284.2 [M+H]$^+$. $^1$H NMR (300 MHz, CD$_3$OD): 8.17 (d, J=2.7 Hz, 1H), 7.33 (d, J=8.1 Hz, 2H), 7.25 (d, J=7.8 Hz, 2H), 6.08 (d, J=2.4 Hz, 1H), 4.56 (s, 2H), 4.17-3.58 (m, 5H), 2.63-2.51 (m, 1H), 2.40 (s, 3H), 2.37-2.26 (m, 1H).

Example 344

N-(4-Methylbenzyl)-5-piperazin-1-ylpyridazin-3-amine

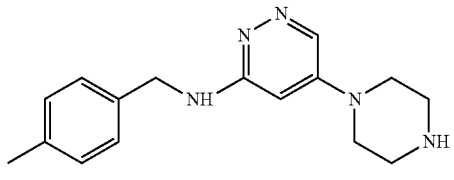 [SMILES: Cc1ccc(CNc2cc(N3CCNCC3)cnn2)cc1]

MS (ESI): mass calcd. for $C_{16}H_{21}N_5$, 283.38 m/z found, 284.1 [M+H]$^+$. $^1$H NMR (300 MHz, CD$_3$OD): 8.29 (d, J=2.4 Hz, 1H), 7.18 (d, J=8.1 Hz, 2H), 7.11 (d, J=8.1 Hz, 2H), 6.29 (d, J=2.4 Hz, 1H), 4.42 (s, 2H), 3.80-3.76 (m, 4H), 3.32-3.29 (m, 4H), 2.24 (s, 3H).

Example 345

N-Cyclopentyl-5-[(3aR,6aR)-hexahydropyrrolo[3,4-b]pyrrol-5(1H)-yl]pyridazin-3-amine

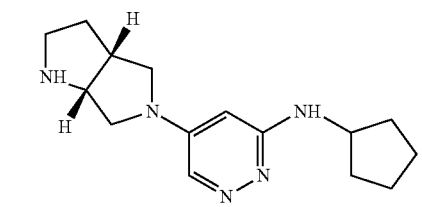 [SMILES: c1nnc(NC2CCCC2)cc1N1C[C@H]2CCN[C@H]2C1]

MS (ESI): mass calcd. for $C_{15}H_{23}N_5$, 273.38 m/z found, 274.1 [M+H]$^+$. $^1$H NMR (300 MHz, CD$_3$OD): 8.13 (s, 1H), 6.06 (br s, 1H), 4.52 (m, 1H), 4.06-3.40 (m, 8H), 2.39-2.35 (m, 1H), 2.10-1.80 (m, 3H), 1.82-1.62 (m, 6H).

Example 346

N-(4-Fluorobenzyl)-5-piperazin-1-ylpyridazin-3-amine

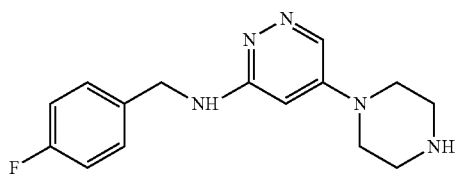 [SMILES: Fc1ccc(CNc2cc(N3CCNCC3)cnn2)cc1]

MS (ESI): mass calcd. for $C_{15}H_{18}FN_5$, 287.34 m/z found, 288.2 [M+H]$^+$. $^1$H NMR (300 MHz, CD$_3$OD): 8.41 (d, J=2.4 Hz, 1H), 7.46-7.42 (m, 2H), 7.17-7.12 (m, 2H), 6.42 (d, J=2.4 Hz, 1H), 4.57 (s, 2H), 3.92-3.88 (m, 4H), 3.43-3.40 (m, 4H)

Example 347

N-(4-Methoxybenzyl)-5-piperazin-1-ylpyridazin-3-amine

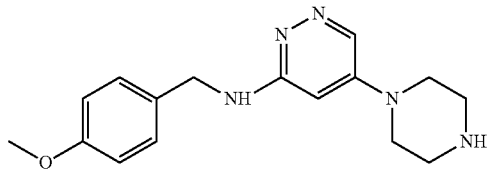 [SMILES: COc1ccc(CNc2cc(N3CCNCC3)cnn2)cc1]

MS (ESI): mass calcd. for $C_{16}H_{21}N_5O$, 299.38 m/z found, 300.2 [M+H]$^+$. $^1$H NMR (300 MHz, CD$_3$OD): 8.39 (s, 1H), 7.33 (d, J=7.2 Hz, 2H), 6.95 (d, J=7.2 Hz, 2H), 6.38 (s, 1H), 4.49 (s, 2H), 3.87 (m, 4H), 3.79 (s, 3H), 3.42-3.39 (m, 4H).

Example 348

N-Benzyl-5-piperazin-1-ylpyridazin-3-amine

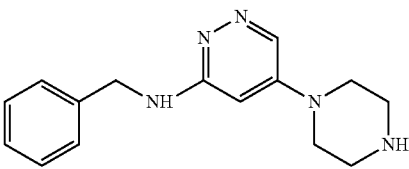 [SMILES: c1ccc(CNc2cc(N3CCNCC3)cnn2)cc1]

MS (ESI): mass calcd. for $C_{15}H_{19}N_5$, 269.35 m/z found, 270.2 [M+H]$^+$. $^1$H NMR (300 MHz, CD$_3$OD): 8.41 (d, J=2.7

Hz, 1H), 7.42-7.35 (m, 5H), 6.41 (d, J=2.7 Hz, 1H), 4.58 (s, 2H), 3.95-3.87 (m, 4H), 3.43-3.36 (m, 4H).

Example 349

N-[(1R)-1-Phenylethyl]-5-piperazin-1-ylpyridazin-3-amine

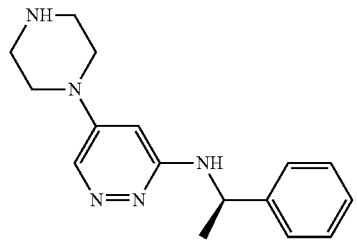 [SMILES: C[C@@H](Nc1cc(N2CCNCC2)cnn1)c1ccccc1]

MS (ESI): mass calcd. for $C_{16}H_{21}N_5$, 283.38 m/z found, 284.2 [M+H]$^+$. $^1$H NMR (300 MHz, CD$_3$OD): 8.36 (s, 1H), 7.41-7.31 (m, 5H), 6.37 (s, 1H), 4.95-4.84 (m, 1H), 3.85 (m, 4H), 3.41-3.38 (m, 4H), 1.63 (d, J=6.9 Hz, 3H).

Example 350

3-({5-[(3R)-3-Aminopyrrolidin-1-yl]pyridazin-3-yl}amino)-2,2-dimethylpropan-1-ol

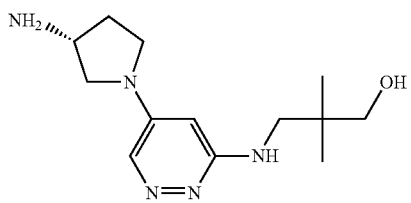 [SMILES: CC(C)(CO)CNc1cc(N2CC[C@@H](N)C2)cnn1]

MS (ESI): mass calcd. for $C_{13}H_{23}N_5O$, 265.36 m/z found, 280.2 [M+H]$^+$. $^1$H NMR (300 MHz, CD$_3$OD): 8.15 (s, 1H), 6.21 (s, 1H), 4.32-3.58 (m, 5H), 3.39 (s, 2H), 3.28 (s, 2H), 2.62-2.52 (m, 1H), 2.32-2.30 (m, 1H), 1.03 (s, 6H).

Example 351

N-Cyclopropyl-5-[3-(methylamino)azetidin-1-yl]pyridazin-3-amine

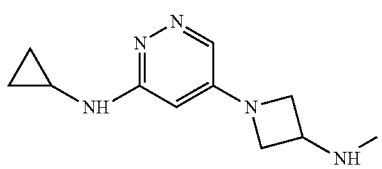 [SMILES: CNC1CN(c2cnnc(NC3CC3)c2)C1]

MS (ESI): mass calcd. for $C_{11}H_{17}N_5$, 219.29 m/z found, 220.2 [M+H]$^+$. $^1$H NMR (300 MHz, CD$_3$OD): 7.95 (d, J=2.1 Hz, 1H), 5.94 (s, 1H), 4.58 (br, s, 2H), 4.39-4.31 (m, 3H), 2.77 (s, 3H), 2.64-2.60 (m, 1H), 0.99-0.93 (m, 2H), 0.69-0.67 (m, 2H).

Example 352

5-[3-(Methylamino)azetidin-1-yl]-N-(pyridin-2-ylmethyl)pyridazin-3-amine

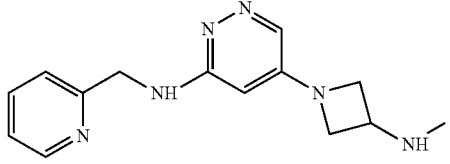 [SMILES: CNC1CN(c2cnnc(NCc3ccccn3)c2)C1]

MS (ESI): mass calcd. for $C_{14}H_{18}N_6$, 270.34 m/z found, 271.2 [M+H]$^+$. $^1$H NMR (300 MHz, CD$_3$OD): 8.82 (d, J=4.8 Hz, 1H), 8.60 (s, 1H), 8.08-7.99 (m, 3H), 6.20 (s, 1H), 5.07 (br, s, 2H), 4.59-4.43 (m, 4H), 4.25 (br, s, 1H), 2.73 (d, J=10.2 Hz, 3H).

Example 353

5-[(3R)-3-Aminopyrrolidin-1-yl]-N-(2-methylpropyl)pyridazin-3-amine

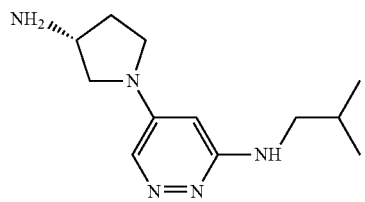 [SMILES: CC(C)CNc1cc(N2CC[C@@H](N)C2)cnn1]

MS (ESI): mass calcd. for $C_{12}H_{21}N_5$, 235.33 m/z found, 236.2 [M+H]$^+$. $^1$H NMR (300 MHz, CD$_3$OD): 8.12 (s, 1H), 6.05 (s, 1H), 4.13-3.59 (m, 5H), 3.15 (d, J=6.9 Hz, 2H), 2.58-2.51 (m, 1H), 2.40-2.20 (m, 1H), 1.99-1.91 (m, 1H), 1.03 (d, J=6.6 Hz, 6H).

Example 354

N-Cyclopentyl-5-piperazin-1-ylpyridazin-3-amine

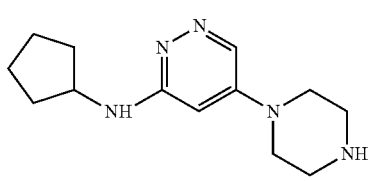 [SMILES: c1nnc(NC2CCCC2)cc1N1CCNCC1]

MS (ESI): mass calcd. for $C_{13}H_{21}N_5$, 247.35 m/z found, 248.2 [M+H]$^+$. $^1$H NMR (300 MHz, CD$_3$OD): 8.32 (d, J=2.4

Hz, 1H), 6.34 (d, J=2.1 Hz, 1H), 4.02-3.94 (m, 1H), 3.86-3.83 (m, 4H), 3.39-3.35 (m, 4H), 2.08-1.99 (m, 2H), 1.79-1.55 (m, 6H).

Example 355

N-Cyclohexyl-5-piperazin-1-ylpyridazin-3-amine

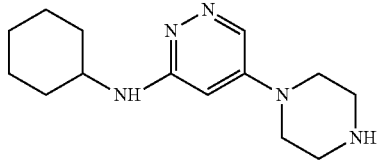 [SMILES: c1nnc(NC2CCCCC2)cc1N1CCNCC1]

MS (ESI): mass calcd. for $C_{14}H_{23}N_5$, 261.37 m/z found, 262.2 [M+H]$^+$. $^1$H NMR (300 MHz, CD$_3$OD): 8.33 (d, J=2.7 Hz, 1H), 6.31 (d, J=2.7 Hz, 1H), 3.84 (t, J=5.1 Hz, 4H), 3.55 (br, 1H), 3.40 (t, J=5.1 Hz, 4H), 2.01-1.80 (m, 4H), 1.62-1.75 (m, 1H), 1.48-1.28 (m, 5H).

Example 356

N-Butyl-5-piperazin-1-ylpyridazin-3-amine

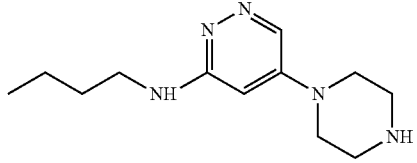 [SMILES: CCCCNc1cc(N2CCNCC2)cnn1]

MS (ESI): mass calcd. for $C_{12}H_{21}N_5$, 235.33 m/z found, 236.2 [M+H]$^+$. $^1$H NMR (300 MHz, CD$_3$OD): 8.36 (s, 1H), 6.37 (s, 1H), 3.88 (t, J=5.4 Hz, 4H), 3.41 (t, J=5.4 Hz, 4H), 3.35-3.29 (m, 2H), 1.69-1.64 (m, 2H), 1.50-1.43 (m, 2H), 0.99 (t, J=7.5 Hz, 3H).

Example 357

N-(2,2-Dimethylpropyl)-5-piperazin-1-ylpyridazin-3-amine

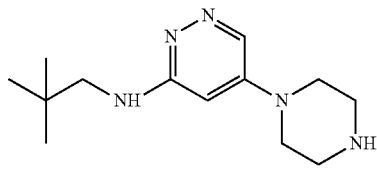 [SMILES: CC(C)(C)CNc1cc(N2CCNCC2)cnn1]

MS (ESI): mass calcd. for $C_{13}H_{23}N_5$, 249.36 m/z found, 250.2 [M+H]$^+$. $^1$H NMR (300 MHz, CD$_3$OD): 8.36 (d, J=2.7 Hz, 1H), 6.52 (d, J=2.4 Hz, 1H), 3.88 (t, J=5.1 Hz, 4H), 3.41 (t, J=5.1 Hz, 4H), 3.17 (s, 2H), 1.03 (s, 9H).

Example 358

5-(3-Aminoazetidin-1-yl)-N-(cyclopentylmethyl)pyridazin-3-amine

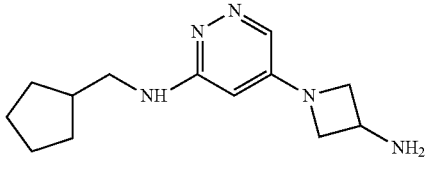 [SMILES: NC1CN(c2cnnc(NCC3CCCC3)c2)C1]

MS (ESI): mass calcd. for $C_{13}H_{21}N_5$, 247.35 m/z found, 248.1 [M+H]$^+$. $^1$H NMR (300 MHz, CD$_3$OD): 7.77 (s, 1H), 5.80 (d, J=2.1 Hz, 1H), 4.48 (br s, 2H), 4.26-4.20 (m, 3H), 3.12 (d, J=7.2 Hz, 2H), 2.15-2.05 (m, 1H), 1.78-1.52 (m, 6H), 1.22-1.16 (m, 2H).

Example 359

5-[(3R)-3-Aminopyrrolidin-1-yl]-N-(cyclopentylmethyl)pyridazin-3-amine

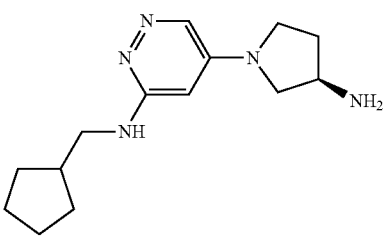 [SMILES: N[C@@H]1CCN(c2cnnc(NCC3CCCC3)c2)C1]

MS (ESI): mass calcd. for $C_{14}H_{23}N_5$, 261.37 m/z found, 262.1 [M+H]$^+$. $^1$H NMR (300 MHz, CD$_3$OD): 8.00 (s, 1H), 5.91 (d, J=2.4 Hz, 1H), 4.03-4.00 (m, 1H), 3.90-3.40 (m, 4H), 3.13 (d, J=7.5 Hz, 2H), 2.47-2.40 (m, 1H), 2.23-2.07 (m, 2H), 1.81-1.52 (m, 6H), 1.23-1.17 (m, 2H).

Example 360

N-(Cyclopentylmethyl)-5-[(3aR,6aR)-hexahydropyrrolo[3,4-b]pyrrol-5(1H)-yl]pyridazin-3-amine

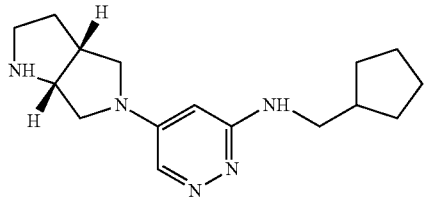 [SMILES: c1nnc(NCC2CCCC2)cc1N1C[C@H]2CCN[C@H]2C1]

MS (ESI): mass calcd. for $C_{16}H_{25}N_5$, 287.41 m/z found, 288.1 [M+H]$^+$. $^1$H NMR (300 MHz, CD$_3$OD): 8.00 (s, 1H), 5.92 (s, 1H), 4.41-4.36 (m, 1H), 3.91-3.70 (m, 3H), 3.44-3.27

(m, 4H), 3.13 (d, J=7.5 Hz, 2H), 2.31-2.23 (m, 1H), 2.14-2.01 (m, 2H), 1.79-1.52 (m, 6H), 1.23-1.17 (m, 2H).

Example 361

N-(Cyclopropylmethyl)-5-piperazin-1-ylpyridazin-3-amine

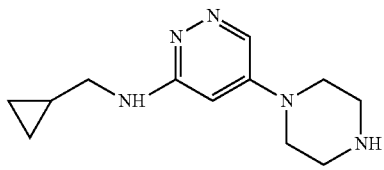 [SMILES: c1nnc(NCC2CC2)cc1N1CCNCC1]

MS (ESI): mass calcd. for $C_{12}H_{19}N_5$, 233.32 m/z found, 234.2 [M+H]$^+$. $^1$H NMR (300 MHz, CD$_3$OD): 8.36 (s, 1H), 6.40 (s, 1H), 3.89 (t, J=7.8 Hz, 4H), 3.41 (t, J=4.8 Hz, 4H), 3.20 (d, J=6.9 Hz, 2H), 1.17-1.15 (m, 1H), 0.64 (d, J=8.1 Hz, 2H), 0.34 (d, J=4.8 Hz, 2H).

Example 362

N-(2-Phenylethyl)-5-piperazin-1-ylpyridazin-3-amine

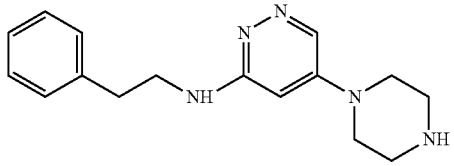 [SMILES: c1ccc(CCNc2cc(N3CCNCC3)cnn2)cc1]

MS (ESI): mass calcd. for $C_{16}H_{21}N_5$, 283.38 m/z found, 284.2 [M+H]$^+$. $^1$H NMR (300 MHz, CD$_3$OD): 8.33 (d, J=2.1 Hz, 1H), 7.30-7.22 (m, 5H), 6.29 (d, J=2.1 Hz, 1H), 3.86 (t, J=5.4 Hz, 4H), 3.63 (t, J=6.9 Hz, 2H), 3.41-3.34 (m, 4H), 2.98 (t, J=6.9 Hz, 2H).

Example 363

N-(Cyclopentylmethyl)-5-piperazin-1-ylpyridazin-3-amine

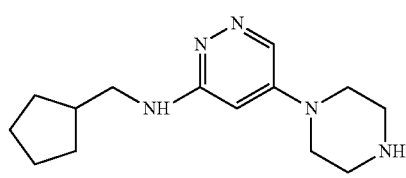 [SMILES: c1nnc(NCC2CCCC2)cc1N1CCNCC1]

MS (ESI): mass calcd. for $C_{14}H_{23}N_5$, 261.37 m/z found, 262.3 [M+H]$^+$. $^1$H NMR (300 MHz, CD$_3$OD): 8.33 (s, 1H), 6.38 (s, 1H), 3.86 (s, 4H), 3.50-3.23 (s, 6H), 2.24-2.17 (m, 1H), 1.86 (br, s, 2H), 1.65 (br, s, 4H), 1.29 (br, s, 2H).

Example 364

5-[(3R)-3-Aminopyrrolidin-1-yl]-N-(2-phenylethyl)pyridazin-3-amine

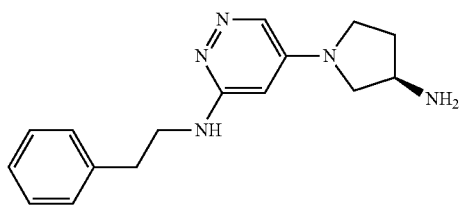 [SMILES: N[C@@H]1CCN(c2cnnc(NCCc3ccccc3)c2)C1]

MS (ESI): mass calcd. for $C_{16}H_{21}N_5$, 283.38 m/z found, 284.2 [M+H]$^+$. $^1$H NMR (300 MHz, CD$_3$OD):: 8.09 (s, 1H), 7.29-7.23 (m, 5H), 5.96 (s, 1H), 4.13-3.64 (m, 5H), 3.62 (t, J=6.6 Hz, 2H), 2.98 (t, J=6.6 Hz, 2H), 2.53 (m, 1H), 2.28 (m, 1H).

Example 365

5-[(3R)-3-Aminopyrrolidin-1-yl]-N-cyclohexylpyridazin-3-amine

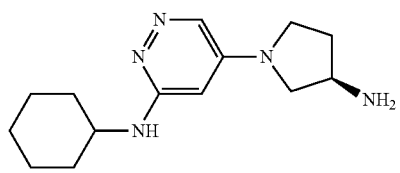 [SMILES: N[C@@H]1CCN(c2cnnc(NC3CCCCC3)c2)C1]

MS (ESI): mass calcd. for $C_{14}H_{23}N_5$, 261.37 m/z found, 262.3 [M+H]$^+$. $^1$H NMR (300 MHz, CD$_3$OD): 8.11 (s, 1H), 6.03 (s, 1H), 4.14-3.56 (m, 6H), 2.58-2.51 (m, 1H), 2.40-2.20 (m, 1H), 1.85-1.68 (m, 5H), 1.54-1.26 (m, 5H).

Example 366

2,2-Dimethyl-3-[(5-piperazin-1-ylpyridazin-3-yl)amino]propan-1-ol

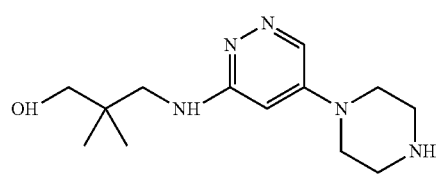 [SMILES: CC(C)(CO)CNc1cc(N2CCNCC2)cnn1]

MS (ESI): mass calcd. for $C_{13}H_{23}N_5O$, 265.36 m/z found, 266.1 [M+H]$^+$. $^1$H NMR (300 MHz, CD$_3$OD): 8.27 (d, J=1.2

Hz, 1H), 6.46 (d, J=2.4 Hz, 1H), 3.81-3.79 (m, 4H), 3.33-3.32 (m, 4H), 3.26 (s, 2H), 3.16 (s, 2H), 1.02 (s, 6H).

Example 367

5-[(3R)-3-Aminopyrrolidin-1-yl]-N-butylpyridazin-3-amine

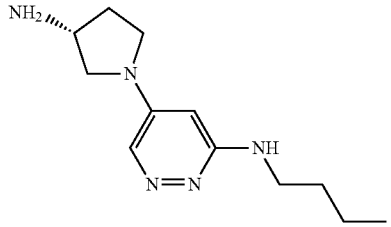 [SMILES: CCCCNc1cc(N2CC[C@@H](N)C2)cnn1]

MS (ESI): mass calcd. for $C_{12}H_{21}N_5$, 235.33 m/z found, 236.1 [M+H]$^+$. $^1$H NMR (300 MHz, CD$_3$OD): 8.02 (s, 1H), 5.92 (d, J=2.1 Hz, 1H), 4.04-3.44 (m, 5H), 3.24-3.20 (m, 2H), 2.48-2.41 (m, 1H), 2.21-2.14 (m, 1H), 1.62-1.52 (m, 2H), 1.41-1.31 (m, 2H), 0.90 (t, J=7.2 Hz, 3H).

Example 368

5-[(3R)-3-Aminopyrrolidin-1-yl]-N-cyclopentylpyridazin-3-amine

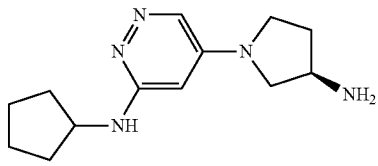 [SMILES: N[C@@H]1CCN(c2cnnc(NC3CCCC3)c2)C1]

MS (ESI): mass calcd. for $C_{13}H_{21}N_5$, 247.35 m/z found, 248.2 [M+H]$^+$. $^1$H NMR (300 MHz, CD$_3$OD): 8.13 (s, 1H), 6.04 (s, 1H), 4.15-3.36 (m, 6H), 2.56-2.52 (m, 1H), 2.31 (m, 1H), 2.09 (br s, 2H), 1.80-1.62 (m, 6H).

Example 369

5-[(3R)-3-Aminopyrrolidin-1-yl]-N-(cyclopropylmethyl)pyridazin-3-amine

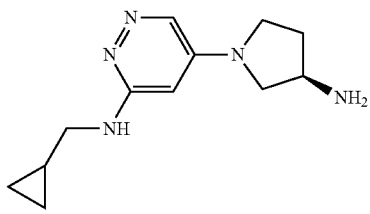 [SMILES: N[C@@H]1CCN(c2cnnc(NCC3CC3)c2)C1]

MS (ESI): mass calcd. for $C_{12}H_{19}N_5$, 233.32 m/z found, 234.1 [M+H]$^+$. $^1$H NMR (300 MHz, CD$_3$OD): 8.12 (br, s, 1H), 6.04 (br, s, 1H), 4.14 (br, s, 1H), 3.92-3.73 (m, 4H), 3.19 (d, J=6.6 Hz, 2H), 2.58-2.51 (m, 1H), 2.29-2.27 (m, 1H), 1.15 (br, s, 1H), 0.66-0.64 (m, 2H), 0.35-0.34 (m, 2H).

Example 370

N-(Cyclopentylmethyl)-5-[3-(methylamino)azetidin-1-yl]pyridazin-3-amine

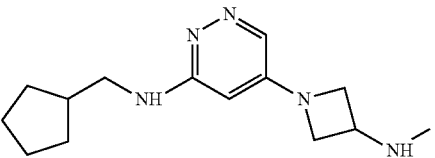 [SMILES: CNC1CN(c2cnnc(NCC3CCCC3)c2)C1]

MS (ESI): mass calcd. for $C_{14}H_{23}N_5$, 261.37 m/z found, 262.2 [M+H]$^+$. $^1$H NMR (300 MHz, CD$_3$OD): 7.89 (d, J=2.1 Hz, 1H), 5.95 (d, J=2.1 Hz, 1H), 4.62-4.57 (m, 2H), 4.40-4.30 (m, 3H), 3.34-3.32 (m, 2H), 2.77 (s, 3H), 2.23-2.18 (m, 1H), 1.88-1.86 (m, 2H), 1.66-1.64 (m, 4H), 1.30-1.28 (m, 2H).

Example 371

5-[(3R)-3-Aminopyrrolidin-1-yl]-N-(2,2-dimethylpropyl)pyridazin-3-amine

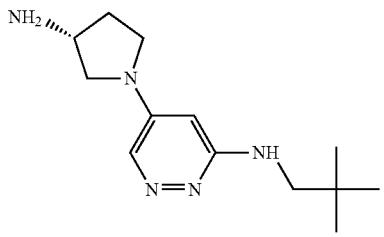 [SMILES: CC(C)(C)CNc1cc(N2CC[C@@H](N)C2)cnn1]

MS (ESI): mass calcd. for $C_{13}H_{23}N_5$, 249.36 m/z found, 250.2 [M+H]$^+$. $^1$H NMR (300 MHz, CD$_3$OD): 8.12 (s, 1H), 6.15 (s, 1H), 4.13-3.50 (m, 5H), 3.15 (s, 2H), 2.57-2.50 (m, 1H), 2.40-2.20 (m, 1H), 1.02 (s, 9H).

Example 372

5-[(3R)-3-(Methylamino)pyrrolidin-1-yl]-N-(2-phenylethyl)pyridazin-3-amine

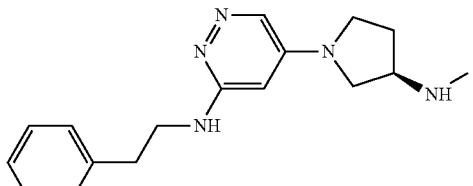

3,4,5-trichloropyridazine. A solution of 4,5-dichloropyridazin-3(2H)-one (2 g, 12 mmol) in 20 mL of phosphoryl trichloride was heated to reflux for 2 hrs. The solvent was removed under reduce pressure. The residue was poured into water with stirring and extracted with dichloromathene (50 mL*3). The organic layer was washed with brine, dried over Na₂SO₄, evaporated to give the crude product. The crude product was recrystallized with acetone/water to give the product (2 g, 89%). ¹H NMR (300 MHz, CDCl₃): 9.09 (s, 1H); LC-MS: m/z=182.9 [M+H]⁺.

(R)-tert-butyl 1-(5,6-dichloropyridazin-4-yl)pyrrolidin-3-ylcarbamate. To a stirred solution of 3,4,5-trichloropyridazine (500 mg, 2.7 mmol) and DIPEA (1 mL) in propan-2-ol (5 mL) was added (R)-tert-butyl pyrrolidin-3-ylcarbamate (508 mg, 2.7 mmol) at ambient temperature (18 h). The solvent was removed and the residue was purified by column chromatography (Petroleum Ether/Ethyl Acetate=2/1, v/v) to afford the title desired product (500 mg, 55%). ¹H NMR (300 MHz, CDCl₃): 8.42 (s, 1H), 5.06 (br s, 1H), 4.36 (br s, 1H), 4.05-3.99 (m, 1H), 3.90-3.66 (m, 3H), 2.28-2.23 (m, 1H), 2.09-2.07 (m, 1H), 1.48 (s, 9H); LC-MS: m/z=333.1 [M+H]⁺

(R)-tert-butyl 1-(5,6-dichloropyridazin-4-yl)pyrrolidin-3-yl(methyl)-carbamate. NaH (60% in oil, 0.72 g, 18.0 mmol) was suspended in 40 mL of anhydrous DMF. A solution of (R)-tert-butyl 1-(5,6-dichloropyridazin-4-yl)pyrrolidin-3-ylcarbamate (5 g, 15 mmol) in anhydrous DMF (40 mL) was added at −5° C. After 40 min, CH₃I (2.55 g, 18 mmol) was added. Then the resulting mixture was stirred at ambient temperature for 2 hours. The reaction was monitored by LC-MS. Water (100 mL) was added and the mixture was extracted with EtOAc (3×200 mL). The organic layer was washed with brine (3×200 mL), dried over anhydrous Na₂SO₄, filtered and concentrated. The residue was purified by silica gel (Petroleum Ether/EtOAc=5/1, v/v) to afford the desired product (4.2 g, 80%). ¹H NMR (300 MHz, CDCl₃) δ 8.39 (s, 1H), 4.77-4.76 (m, 1H), 3.86-3.62 (m, 4H), 2.85 (s, 3H), 2.18-2.11 (m, 2H), 1.46 (s, 9H); LC-MS: m/z=347.1 [M+H]⁺.

(R)-tert-butyl1-(5-chloro-6-(phenethylamino)pyridazin-4-yl)pyrrolidin-3-yl(methyl)-carbamate. A mixture of (R)-tert-butyl 1-(5,6-dichloropyridazin-4-yl)pyrrolidin-3-yl(methyl) carbamate (400 mg, 1.15 mmol) and 2-phenylethanamine (1 mL) was stirred at 150° C. for 40 min in microwave. The mixture was concentrated and the residue was purified by silica gel chromatography (MeOH/DCM=1/50, v/v) to afford the desired product (295 mg, 59%). LC-MS: m/z=432.1 [M+H]⁺.

(R)-tert-butylmethyl(1-(6-(phenethylamino)pyridazin-4-yl)pyrrolidin-3-yl) carbamate. To a mixture of (R)-tert-butyl1-(5-chloro-6-(phenethylamino)pyridazin-4-yl)pyrrolidin-3-yl(methyl)-carbamate (295 mg, 0.68 mmol) and HCOONH₄ (0.5 g, 7.9 mmol) in MeOH (15 mL) was added 10% Pd/C (0.3 g) and the resulting mixture was refluxed 30 min. The reaction was allowed to cool and filtered. The filtrate was concentrated, then diluted with EA (20 mL) and washed with brine (10 mL*2). The combined organic layer was dried over Na₂SO₄, filtered, concentrated and purified by prep-HPLC to give the product as oil (177 mg, 65%). ¹H NMR (300 MHz, CDCl₃): δ 8.80 (s, 1H), 7.70 (d, J=5.4 Hz 1H), 7.30-7.18 (m, 5H), 5.30 (5.30, J=9.6 Hz, 1H), 4.86 (d, J=6.3 Hz, 1H), 3.78-3.73 (m, 1H), 3.49-3.35 (m, 4H), 2.96 (t, J=7.2 Hz, 2H), 2.82 (s, 3H), 2.23 (s, 2H), 1.48 (s, 9H); LC-MS: m/z=398.1 [M+H]⁺.

(R)-5-(3-(methylamino)pyrrolidin-1-yl)-N-phenethylpyridazin-3-amine dihydrochloride. To a solution of (R)-tert-butylmethyl(1-(6-(phenethylamino)pyridazin-4-yl)pyrrolidin-3-yl)carbamate (177 mg, 44 mmol) in MeOH (3 mL) was added ether solution of HCl gas (7N, 10 mL). The reaction was stirred at room temperature for 16 hours. The solution was concentrated under reduced pressure to give the desired product as a white solid (32.2 mg, 20%). ¹H NMR (300 MHz, CD₃OD): 8.13 (d, J=2.4 Hz, 1H), 7.33-7.25 (m, 5H), 5.98 (d, J=2.4 Hz, 1H), 4.01-3.62 (m, 7H), 3.00 (t, J=6.9 Hz, 2H), 2.84 (s, 3H), 2.60-2.30 (m, 2H); LC-MS: m/z=298.3 [M+H]⁺, t_R=1.0 min; HPLC: 98% (214 nm), 99% (254 nm), t_R=7.1 min.

The compounds in Example 373 through Example 403 were prepared using methods analogous to those described in Example 372.

Example 373

N-[(1R)-1-Cyclohexylethyl]-5-[(3S)-3-(methylamino)pyrrolidin-1-yl]pyridazin-3-amine

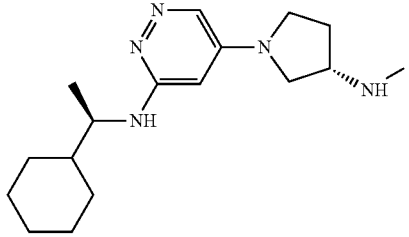 [SMILES: CN[C@H]1CCN(c2cnnc(N[C@H](C)C3CCCCC3)c2)C1]

MS (ESI): mass calcd. for C₁₇H₂₉N₅, 303.45 m/z found, 304.3 [M+H]⁺. ¹H NMR (300 MHz, CD₃OD): 8.11 (s, 1H), 6.04 (s, 1H), 4.05-3.56 (m, 6H), 2.82 (s, 3H), 2.59-2.54 (m, 1H), 2.40-2.30 (m, 1H), 1.90-1.70 (m, 5H), 1.60-1.00 (m, 9H).

Example 374

N-(Bicyclo[2.2.1]hept-2-ylmethyl)-5-[(3S)-3-(methylamino)pyrrolidin-1-yl]pyridazin-3-amine

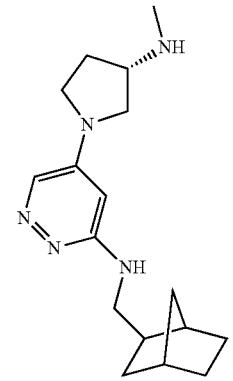 [SMILES: CN[C@H]1CCN(c2cnnc(NCC3CC4CCC3C4)c2)C1]

MS (ESI): mass calcd. for C₁₇H₂₇N₅, 301.44 m/z found, 302.2 [M+H]⁺. ¹H NMR (300 MHz, CD₃OD): 8.18 (d, J=2.1

Hz, 1H), 6.13 (d, J=2.1 Hz, 1H), 4.20-3.50 (m, 5H), 3.40-3.10 (m, 2H), 2.88 (s, 3H), 2.67-2.62 (m, 1H), 2.50-2.20 (m, 3H), 2.00-0.82 (m, 9H).

Example 375

N-(Bicyclo[2.2.1]hept-2-ylmethyl)-5-[(3R)-3-(methylamino)pyrrolidin-1-yl]pyridazin-3-amine

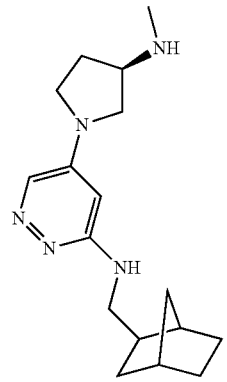 [SMILES: CN[C@@H]1CCN(c2cnnc(NCC3CC4CCC3C4)c2)C1]

MS (ESI): mass calcd. for $C_{17}H_{27}N_5$, 301.44 m/z found, 302.3 [M+H]$^+$. $^1$H NMR (300 MHz, $CD_3OD$): 8.19 (d, J=2.4 Hz, 1H), 6.13 (d, J=2.4 Hz, 1H), 4.20-3.50 (m, 5H), 3.40-3.10 (m, 2H), 2.88 (s, 3H), 2.65-2.60 (m, 1H), 2.50-2.20 (m, 3H), 2.00-0.82 (m, 9H).

Example 376

N-(2-Methoxyethyl)-5-[(3S)-3-(methylamino)pyrrolidin-1-yl]pyridazin-3-amine

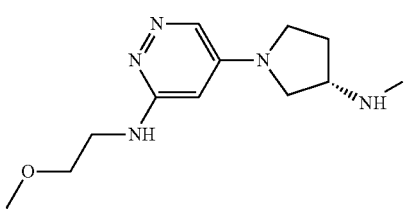

MS (ESI): mass calcd. for $C_{12}H_{21}N_5O$, 251.33 m/z found, 252.1 [M+H]$^+$. $^1$H NMR (300 MHz, $CD_3OD$): 8.18 (s, 1H), 6.14 (s, 1H), 4.10-3.57 (m, 9H), 3.44 (s, 3H), 2.87 (s, 3H), 2.70-2.30 (m, 2H).

Example 377

N-Cyclopropyl-5-[(3R)-3-(methylamino)pyrrolidin-1-yl]pyridazin-3-amine

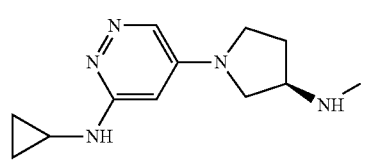 [SMILES: CN[C@@H]1CCN(c2cnnc(NC3CC3)c2)C1]

MS (ESI): mass calcd. for $C_{12}H_{19}N_5$, 233.32 m/z found, 234.2 [M+H]$^+$. $^1$H NMR (300 MHz, $CD_3OD$): 8.13 (s, 1H), 6.01 (s, 1H), 4.01-3.73 (m, 5H), 2.78 (s, 3H), 2.57-2.50 (m, 2H), 2.31-2.29 (m, 1H), 0.94-0.92 (m, 2H), 0.64 (s, 2H).

Example 378

N-[(1R)-1-Cyclohexylethyl]-5-[(3R)-3-(methylamino)pyrrolidin-1-yl]pyridazin-3-amine

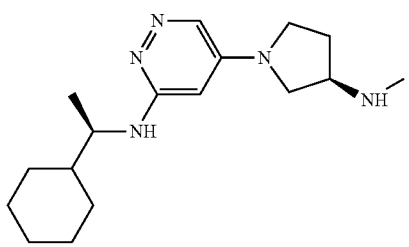 [SMILES: CN[C@@H]1CCN(c2cnnc(N[C@H](C)C3CCCCC3)c2)C1]

MS (ESI): mass calcd. for $C_{17}H_{29}N_5$, 303.45 m/z found, 304.3 [M+H]$^+$. $^1$H NMR (300 MHz, $CD_3OD$): 8.12 (s, 1H), 6.05 (s, 1H), 4.10-3.50 (m, 6H), 2.82 (s, 3H), 2.70-2.50 (m, 1H), 2.40-2.30 (m, 1H), 1.88-1.69 (m, 5H), 1.60-1.03 (m, 9H).

Example 379

5-[(3S)-3-(Methylamino)pyrrolidin-1-yl]-N-(2-methylpropyl)pyridazin-3-amine

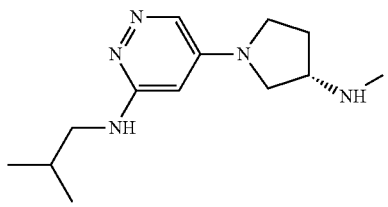 [SMILES: CN[C@H]1CCN(c2cnnc(NCC(C)C)c2)C1]

MS (ESI): mass calcd. for $C_{13}H_{23}N_5$, 249.36 m/z found, 250.1 [M+H]$^+$. $^1$H NMR (300 MHz, $CD_3OD$): 8.14 (s, 1H), 6.05 (s, 1H), 4.05-3.60 (m, 5H), 3.15 (d, J=6.9 Hz, 2H), 2.83 (s, 3H), 2.59-2.55 (m, 1H), 2.35-2.30 (m, 1H), 1.98-1.93 (m, 1H), 1.03 (d, J=6.6 Hz, 6H).

Example 380

N-Cyclopentyl-5-[(3S)-3-(methylamino)pyrrolidin-1-yl]pyridazin-3-amine

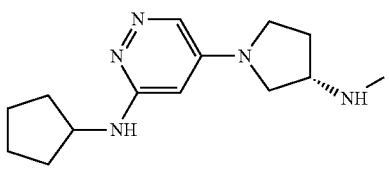 [SMILES: CN[C@H]1CCN(c2cnnc(NC3CCCC3)c2)C1]

MS (ESI): mass calcd. for $C_{14}H_{23}N_5$, 261.37 m/z found, 262.2 [M+H]$^+$. $^1$H NMR (300 MHz, $CD_3OD$): 8.16 (s, 1H), 6.06 (s, 1H), 4.06-3.60 (m, 6H), 2.86 (s, 3H), 2.60 (m, 1H), 2.41 (m, 1H), 2.14-1.33 (m, 8H).

Example 381

N-Bicyclo[2.2.1]hept-2-yl-5-[(3S)-3-(methylamino)pyrrolidin-1-yl]pyridazin-3-amine

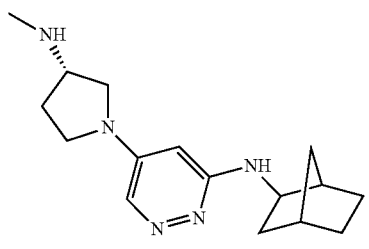 [SMILES: CN[C@H]1CCN(c2cnnc(NC3CC4CCC3C4)c2)C1]

MS (ESI): mass calcd. for $C_{16}H_{25}N_5$, 287.41 m/z found, 288.2 [M+H]$^+$. $^1$H NMR (300 MHz, CD$_3$OD): 8.18 (d, J=2.4 Hz, 1H), 6.04 (d, J=2.1 Hz, 1H), 4.11-3.39 (m, 6H), 2.87 (s, 3H), 2.66-2.59 (m, 1H), 2.42-2.35 (m, 3H), 2.02-1.95 (m, 1H), 1.70-1.24 (m, 7H).

Example 382

N-(Cyclopentylmethyl)-5-[(3S)-3-(methylamino)pyrrolidin-1-yl]pyridazin-3-amine

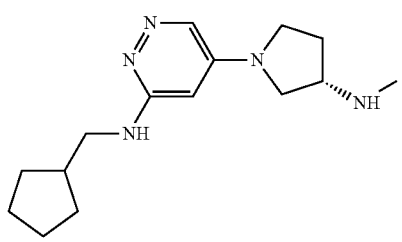 [SMILES: CN[C@H]1CCN(c2cnnc(NCC3CCCC3)c2)C1]

MS (ESI): mass calcd. for $C_{15}H_{25}N_5$, 275.4 m/z found, 276.3 [M+H]$^+$. $^1$H NMR (300 MHz, CD$_3$OD): 8.02 (d, J=1.8 Hz, 1H), 5.97 (s, 1H), 3.96-3.44 (m, 5H), 3.25 (s, 2H), 3.15 (d, J=7.2 Hz, 2H), 2.67 (s, 3H), 2.51-2.44 (m, 1H), 2.30-2.26 (m, 1H), 2.15-2.08 (m, 1H), 1.84-1.78 (m, 2H), 1.60-1.52 (m, 4H), 1.24-1.18 (m, 2H).

Example 383

2,2-Dimethyl-3-({5-[(3S)-3-(methylamino)pyrrolidin-1-yl]pyridazin-3-yl}amino)propan-1-ol

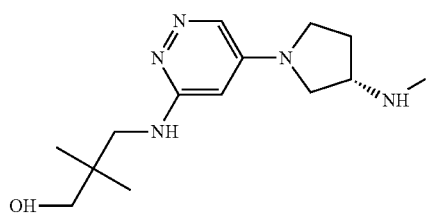 [SMILES: CN[C@H]1CCN(c2cnnc(NCC(C)(C)CO)c2)C1]

MS (ESI): mass calcd. for $C_{14}H_{25}N_5O$, 279.39 m/z found, 266.1 [M+H]$^+$. $^1$H NMR (300 MHz, CD$_3$OD): 8.16 (s, 1H), 6.21 (s, 1H), 4.09-3.58 (m, 5H), 3.39 (s, 2H), 3.28 (s, 2H), 2.81 (s, 3H), 2.62-2.58 (m, 1H), 2.39-2.37 (m, 1H), 1.03 (s, 6H).

Example 384

5-[(3R)-3-(Methylamino)pyrrolidin-1-yl]-N-(4-methylbenzyl)pyridazin-3-amine

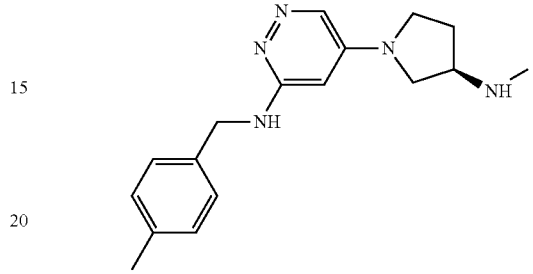

MS (ESI): mass calcd. for $C_{17}H_{23}N_5$, 297.41 m/z found, 298.1 [M+H]$^+$. $^1$H NMR (300 MHz, CD$_3$OD): 8.16 (s, 1H), 7.30 (d, J=7.2 Hz, 2H), 7.22 (d, J=7.2 Hz, 2H), 6.06 (s, 1H), 4.53 (s, 2H), 4.15-3.50 (m, 5H), 2.83 (s, 3H), 2.61-2.55 (m, 1H), 2.40-2.30 (m, 1H), 2.35 (s, 3H).

Example 385

N-(2,2-Dimethylpropyl)-5-[(3S)-3-(methylamino)pyrrolidin-1-yl]pyridazin-3-amine

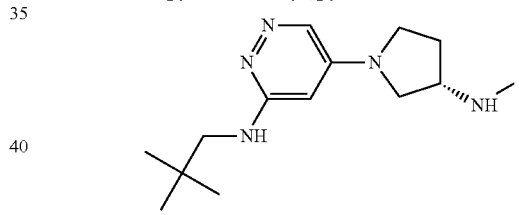

MS (ESI): mass calcd. for $C_{14}H_{25}N_5$, 263.39 m/z found, 264.2 [M+H]$^+$. $^1$H NMR (300 MHz, CD$_3$OD): 8.12 (d, J=1.8 Hz, 1H), 6.15 (s, 1H), 4.08-3.81 (m, 5H), 3.15 (s, 2H), 2.81 (s, 3H), 2.59-2.57 (m, 1H), 2.39-2.36 (m, 1H), 1.03 (s, 9H).

Example 386

5-[(3R)-3-(Methylamino)pyrrolidin-1-yl]-N-(4,4,4-trifluorobutyl)pyridazin-3-amine

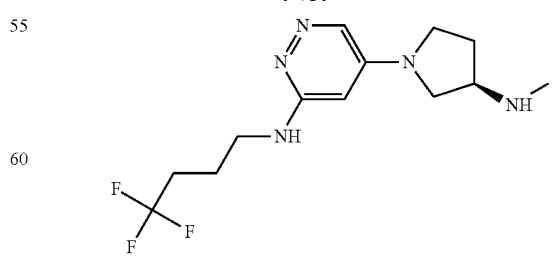

MS (ESI): mass calcd. for $C_{13}H_{20}F_3N_5$, 303.33 m/z found, 304.1 [M+H]$^+$.

CD₃OD: 8.06 (s, 1H), 6.00 (s, 1H), 4.10-3.50 (m, 5H), 3.34 (t, J=6.6 Hz, 2H), 2.73 (s, 3H), 2.60-2.40 (m, 1H), 2.40-2.20 (m, 3H), 1.90-1.80 (m, 2H).

Example 387

N-(Furan-3-ylmethyl)-5-[(3R)-3-(methylamino)pyrrolidin-1-yl]pyridazin-3-amine

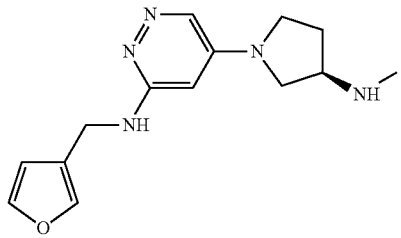 [SMILES: CN[C@@H]1CCN(c2cnnc(NCc3ccoc3)c2)C1]

MS (ESI): mass calcd. for C₁₄H₁₉N₅O, 273.34 m/z found, 274.2 [M+H]⁺. ¹H NMR (300 MHz, CD₃OD): 8.16 (s, 1H), 7.62 (s, 1H), 7.53 (s, 1H), 6.49 (s, 1H), 6.08 (s, 1H), 4.42 (s, 2H), 4.10-3.40 (m, 5H), 2.81 (s, 3H), 2.70-2.50 (m, 1H), 2.40-2.20 (m, 1H).

Example 388

N-[(6,6-Dimethylbicyclo[3.1.1]hept-2-yl)methyl]-5-[(3R)-3-(methylamino)pyrrolidin-1-yl]pyridazin-3-amine

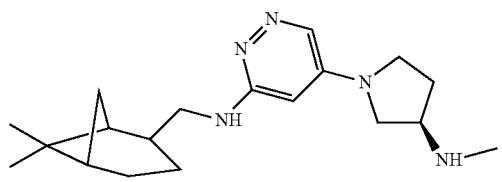

MS (ESI): mass calcd. for C₁₉H₃₁N₅, 329.49 m/z found, 330.2 [M+H]⁺. ¹H NMR (300 MHz, CD₃OD): 8.15 (d, J=2.1 Hz, 1H), 6.06 (s, 1H), 4.08-3.80 (m, 5H), 2.79 (s, 3H), 2.63-2.56 (m, 1H), 2.47-2.35 (m, 4H), 2.08-1.98 (m, 7H, contain paraffin), 1.61-1.56 (m, 1H), 1.27 (s, 3H), 1.12 (s, 3H), 1.06-1.00 (m, 1H).

Example 389

5-[(3S)-3-(Methylamino)pyrrolidin-1-yl]-N-(4,4,4-trifluorobutyl)pyridazin-3-amine

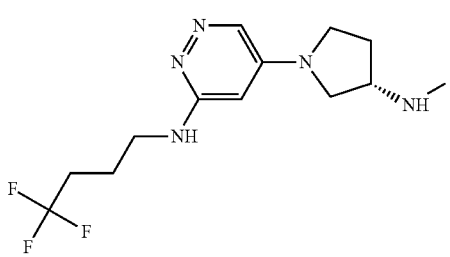 [SMILES: CN[C@H]1CCN(c2cnnc(NCCCC(F)(F)F)c2)C1]

MS (ESI): mass calcd. for C₁₃H₂₀F₃N₅, 303.33 m/z found, 304.1 [M+H]⁺. ¹H NMR (300 MHz, CD₃OD): 8.18 (d, J=1.8 Hz, 1H), 6.08 (s, 1H), 4.08-3.56 (m, 5H), 3.45 (t, J=7.2 Hz, 2H), 2.80 (s, 3H), 2.64-2.57 (m, 1H), 2.40-2.31 (m, 3H), 2.00-1.90 (m, 2H).

Example 390

3-({5-[(3R)-3-(Methylamino)pyrrolidin-1-yl]pyridazin-3-yl}amino)propan-1-ol

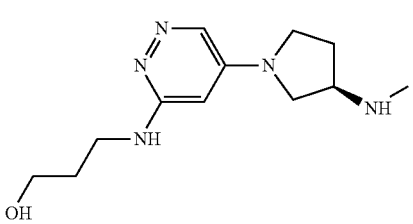 [SMILES: CN[C@@H]1CCN(c2cnnc(NCCCO)c2)C1]

MS (ESI): mass calcd. for C₁₂H₂₁N₅O, 251.33 m/z found, 252.2 [M+H]⁺. ¹H NMR (300 MHz, CD₃OD): 8.08 (s, 1H), 6.02 (s, 1H), 4.01-3.63 (m, 7H), 3.42 (t, J=6.6 Hz, 2H), 2.78 (s, 3H), 2.57-2.50 (m, 1H), 2.30 (br, s, 1H), 1.88-1.80 (m, 2H).

Example 391

N-(Cyclohexylmethyl)-5-[(3R)-3-(methylamino)pyrrolidin-1-yl]pyridazin-3-amine

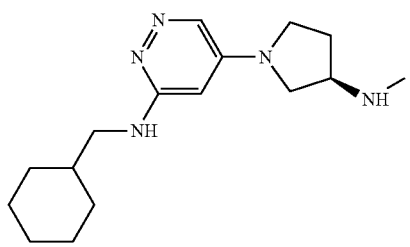 [SMILES: CN[C@@H]1CCN(c2cnnc(NCC3CCCCC3)c2)C1]

MS (ESI): mass calcd. for C₁₆H₂₇N₅, 289.43 m/z found, 290.2 [M+H]⁺. ¹H NMR (300 MHz, CD₃OD): 8.12 (s, 1H), 6.05 (s, 1H), 4.10-3.40 (m, 5H), 3.16 (d, J=6.9 Hz, 2H), 2.82 (s, 3H), 2.70-2.50 (m, 1H), 2.40-2.30 (m, 1H), 1.90-1.60 (m, 6H), 1.40-1.00 (m, 5H).

Example 392

N-(2,2-Dimethylpropyl)-5-[(3R)-3-(methylamino)pyrrolidin-1-yl]pyridazin-3-amine

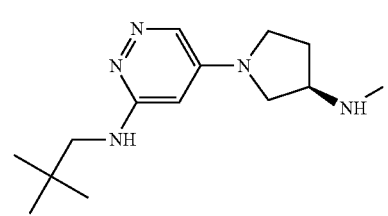 [SMILES: CN[C@@H]1CCN(c2cnnc(NCC(C)(C)C)c2)C1]

MS (ESI): mass calcd. for C₁₄H₂₅N₅, 263.39 m/z found, 264.2 [M+H]⁺. ¹H NMR (300 MHz, CD₃OD): 8.14 (s, 1H), 6.18 (s, 1H), 4.07-3.50 (m, 5H), 3.17 (s, 2H), 2.83 (s, 3H), 2.58 (m, 1H), 2.38 (m, 1H), 1.04 (s, 9H).

Example 393

N-(2-Methoxyethyl)-5-[(3R)-3-(methylamino)pyrrolidin-1-yl]pyridazin-3-amine

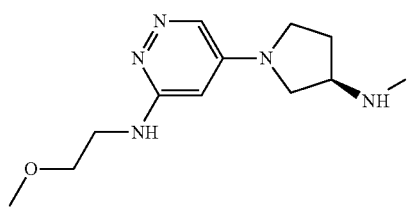

MS (ESI): mass calcd. for $C_{12}H_{21}N_5O$, 251.33 m/z found, 252.2 [M+H]$^+$. $^1$H NMR (300 MHz, CD$_3$OD): 8.13 (s, 1H), 6.11 (s, 1H), 4.06-3.54 (m, 9H), 3.39 (s, 3H), 2.82 (s, 3H), 2.58 (m, 1H), 2.40 (m, 1H).

Example 394

N-[(6,6-Dimethylbicyclo[3.1.1]hept-2-yl)methyl]-5-[(3S)-3-(methylamino)pyrrolidin-1-yl]pyridazin-3-amine

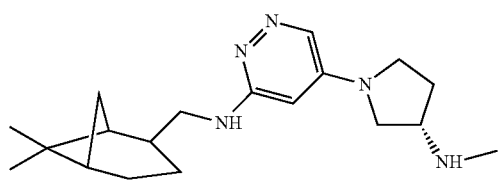

MS (ESI): mass calcd. for $C_{19}H_{31}N_5$, 329.49 m/z found, 330.3 [M+H]$^+$. $^1$H NMR (300 MHz, CD$_3$OD): 8.15 (s, 1H), 6.06 (s, 1H), 4.08-3.58 (m, 5H), 2.84 (s, 3H), 2.63-2.37 (m, 4H), 2.16-1.98 (m, 6H), 1.66-1.59 (m, 1H), 1.37-1.32 (m, 1H), 1.27 (s, 3H), 1.12 (s, 3H), 1.06-1.00 (m, 1H).

Example 395

N-Cyclopropyl-5-[(3S)-3-(methylamino)pyrrolidin-1-yl]pyridazin-3-amine

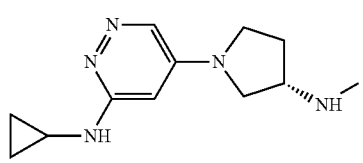 [SMILES: CN[C@H]1CCN(c2cnnc(NC3CC3)c2)C1]

MS (ESI): mass calcd. for $C_{12}H_{19}N_5$, 233.32 m/z found, 234.3 [M+H]$^+$. $^1$H NMR (300 MHz, CD$_3$OD): 8.17 (d, J=2.7 Hz, 1H), 6.05 (d, J=1.8 Hz, 1H), 4.07-3.60 (m, 5H), 2.82 (s, 3H), 2.66-2.54 (m, 2H), 2.39-2.34 (m, 1H), 1.00-0.94 (m, 2H), 0.70-0.65 (m, 2H).

Example 396

N-(Cyclohexylmethyl)-5-[(3S)-3-(methylamino)pyrrolidin-1-yl]pyridazin-3-amine

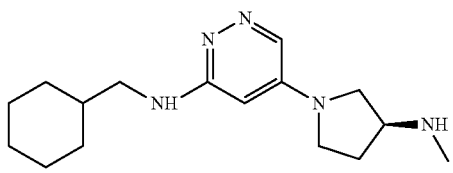 [SMILES: CN[C@H]1CCN(c2cnnc(NCC3CCCCC3)c2)C1]

MS (ESI): mass calcd. for $C_{16}H_{27}N_5$, 289.43 m/z found, 290.2 [M+H]$^+$. $^1$H NMR (300 MHz, CD$_3$OD): 8.12 (s, 1H), 6.05 (s, 1H), 4.10-3.40 (m, 5H), 3.16 (d, J=6.9 Hz, 2H), 2.82 (s, 3H), 2.70-2.50 (m, 1H), 2.40-2.30 (m, 1H), 1.90-1.60 (m, 6H), 1.40-1.00 (m, 5H).

Example 397

N-Benzyl-5-[(3R)-3-(methylamino)pyrrolidin-1-yl]pyridazin-3-amine

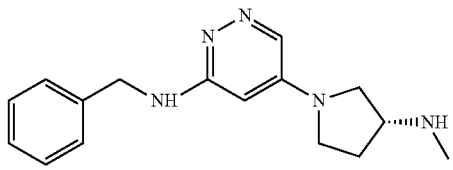 [SMILES: CN[C@@H]1CCN(c2cnnc(NCc3ccccc3)c2)C1]

MS (ESI): mass calcd. for $C_{16}H_{21}N_5$, 283.38 m/z found, 284.1 [M+H]$^+$. $^1$H NMR (300 MHz, CD$_3$OD): 8.19 (d, J=2.1 Hz, 1H), 7.45-7.37 (m, 5H), 6.12 (s, 1H), 4.62 (s, 2H), 4.09-3.52 (m, 5H), 2.86 (s, 3H), 2.62-2.58 (m, 1H), 2.44-2.40 (m, 1H).

Example 398

N-(4-Fluorobenzyl)-5-[(3R)-3-(methylamino)pyrrolidin-1-yl]pyridazin-3-amine

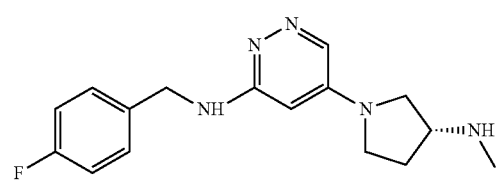 [SMILES: CN[C@@H]1CCN(c2cnnc(NCc3ccc(F)cc3)c2)C1]

MS (ESI): mass calcd. for $C_{16}H_{20}FN_5$, 301.37 m/z found, 302.2 [M+H]$^+$. $^1$H NMR (300 MHz, CD$_3$OD): 8.05 (s, 1H), 7.36-7.32 (m, 2H), 7.05-7.00 (m, 2H), 5.96 (s, 1H), 4.46 (s, 2H), 3.95-3.40 (m, 5H), 2.71 (s, 3H), 2.48-2.43 (m, 1H), 2.40-2.20 (m, 1H).

Example 399

N-(4-Fluorobenzyl)-5-[(3S)-3-(methylamino)pyrrolidin-1-yl]pyridazin-3-amine

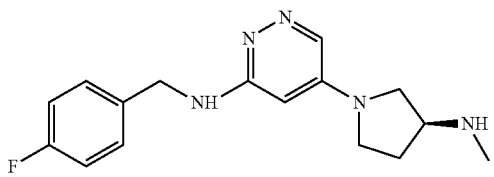 [SMILES: CN[C@H]1CCN(c2cnnc(NCc3ccc(F)cc3)c2)C1]

MS (ESI): mass calcd. for $C_{16}H_{20}FN_5$, 301.37 m/z found, 302.1 [M+H]$^+$. $^1$H NMR (300 MHz, CD$_3$OD): 8.17 (s, 1H), 7.46-7.42 (m, 2H), 7.18-7.12 (m, 2H), 6.06 (s, 1H), 4.56 (s, 2H), 4.15-3.47 (m, 5H), 2.82 (s, 3H), 2.62-2.55 (m, 1H), 2.42-2.34 (m, 1H).

Example 400

N-(4-Methoxybenzyl)-5-[(3R)-3-(methylamino)pyrrolidin-1-yl]pyridazin-3-amine

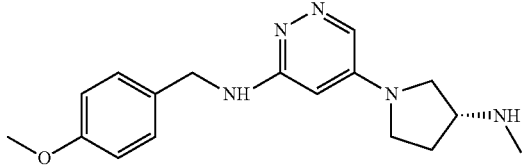

MS (ESI): mass calcd. for $C_{17}H_{23}N_5O$, 313.41 m/z found, 314.1 [M+H]$^+$. $^1$H NMR (300 MHz, CD$_3$OD): 8.16 (d, J=2.1 Hz, 1H), 7.34 (d, J=8.7 Hz, 2H), 6.96 (d, J=8.7 Hz, 2H), 6.06 (s, 1H), 4.50 (s, 2H), 4.13-3.56 (m, 5H), 3.83 (s, 3H), 2.83 (s, 3H), 2.62-2.55 (m, 1H), 2.39-2.35 (m, 1H).

Example 401

5-[(3R)-3-(Methylamino)pyrrolidin-1-yl]-N-[(1R)-1-phenylethyl]pyridazin-3-amine

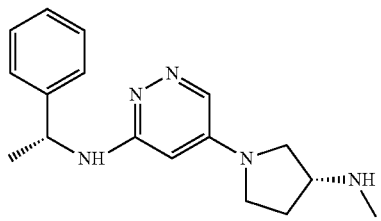 [SMILES: CN[C@@H]1CCN(c2cnnc(N[C@H](C)c3ccccc3)c2)C1]

MS (ESI): mass calcd. for $C_{17}H_{23}N_5$, 297.41 m/z found, 298.1 [M+H]$^+$. CD$_3$OD: 8.12 (d, J=2.4 Hz, 1H), 7.49-7.31 (m, 5H), 6.01 (s, 1H), 4.04-3.36 (m, 6H), 2.82 (s, 3H), 2.58-2.53 (m, 1H), 2.37-2.33 (m, 1H), 1.63 (d, J=6.6 Hz, 3H).

Example 402

5-[(3S)-3-(Methylamino)pyrrolidin-1-yl]-N-(pyridin-2-ylmethyl)pyridazin-3-amine

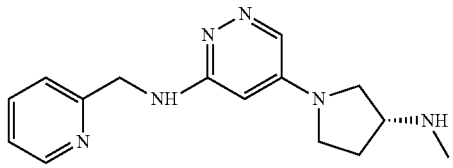 [SMILES: CN[C@@H]1CCN(c2cnnc(NCc3ccccn3)c2)C1]

MS (ESI): mass calcd. for $C_{15}H_{20}N_6$, 284.37 m/z found, 285.2 [M+H]$^+$. $^1$H NMR (300 MHz, CD$_3$OD): 8.79 (d, J=5.1 Hz, 1H), 8.39 (t, J=7.8 Hz, 1H), 8.25 (d, J=2.1 Hz, 1H), 7.94-7.82 (m, 2H), 6.27 (br, s, 1H), 5.01 (s, 2H), 4.07-3.60 (m, 7H), 2.84 (s, 3H), 2.61-2.56 (m, 1H), 2.38-2.36 (m, 1H).

Example 403

3-({5-[(3S)-3-(Methylamino)pyrrolidin-1-yl]pyridazin-3-yl}amino)propan-1-ol

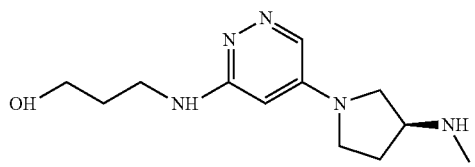 [SMILES: CN[C@H]1CCN(c2cnnc(NCCCO)c2)C1]

MS (ESI): mass calcd. for $C_{12}H_{21}N_5O$, 251.33 m/z found, 252.2 [M+H]$^+$. $^1$H NMR (300 MHz, CD$_3$OD): 8.12 (d, J=2.1 Hz, 1H), 6.05 (d, J=2.1 Hz, 1H), 4.07-3.67 (m, 7H), 3.44 (t, J=6.9 Hz, 2H), 2.77 (s, 3H), 2.61-2.54 (m, 1H), 2.38-2.31 (m, 1H), 1.92-1.84 (m, 2H).

Example 404

N-(2,2-Dimethylpropyl)-5-(4-methylpiperazin-1-yl)pyridazin-3-amine

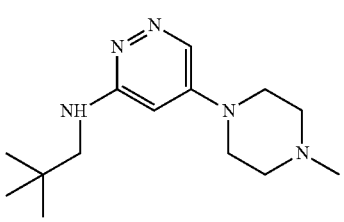 [SMILES: CN1CCN(c2cnnc(NCC(C)(C)C)c2)CC1]

5-iodopyridazin-3(2H)-one. A mixture of 4,5-dichloropyridazin-3(2H)-one (25 g, 0.152 mol) in 250 mL of hydrogen iodide acid (57 w %) was heated to reflux for 18 hrs. The solution was cooled to ambient temperature and filtered. The precipitate was washed with saturated sodium thiosulfate solution. The precipitate was dried to give the desired product as a yellow solid (Int. Pat. Appl. Publ. WO 2008/013838

(Cephalon Inc., Jan. 31, 2008)) (15 g, 45%). ¹H NMR (300 MHz, CDCl₃): 13.26 (br s, 1H), 8.08 (s, 1H), 7.54 (s, 1H); LC-MS: m/z=222.9 [M+H]⁺.

5-(4-methylpiperazin-1-yl)pyridazin-3(2H)-one. A solution of 5-iodopyridazin-3(2H)-one (0.1 g, 0.45 mmol) and 1-methylpiperazine (0.09 g, 0.9 mmol) in ethanol (10 mL) was heated to reflux for 18 hrs. The solvent was removed under reduce pressure to give a crude oil. The crude oil was purified by silica gel chromatography (DCM/MeOH=30/1, v/v) to give yellow solid (60 mg, 68%). ¹H NMR (300 MHz, DMSO-d₆): 12.20 (br s, 1H), 7.92 (s, 1H), 5.72 (s, 1H), 3.33-3.29 (m, 4H), 2.38-2.35 (s, 4H), 2.19 (s, 3H); LC-MS: m/z=195.0 [M+H]⁺.

3-chloro-5-(4-methylpiperazin-1-yl)pyridazine. A solution of 5-(4-methylpiperazin-1-yl)pyridazin-3(2H)-one (5.82 g, 0.03 mol) in 25 mL of phosphoryl trichloride was heated to 80° C. for 3 hrs. The solution was concentrated and diluted with NaOH solution (0.5N) and pH was adjusted to 10. The solution was extracted with DCM (3×150 mL), washed with brine (3×100 mL), dried over Na₂SO₄, concentrated to give the crude oil. The residue was purified by silica gel chromatography (DCM/MeOH=40/1, v/v) to give colorless solid (1.4 g, 22%). ¹H NMR (300 MHz, CDCl₃): 8.75 (s, 1H), 6.68 (s, 1H), 3.47-3.44 (m, 4H), 2.57 (s, 4H), 2.38 (s, 3H); LC-MS: m/z=213.1 [M+H]⁺

5-(4-methylpiperazin-1-yl)-N-neopentylpyridazin-3-amine diformic acid. A solution of 3-chloro-5-(4-methylpiperazin-1-yl)pyridazine (212 mg, 1 mmol) in 1 mL of 2,2-dimethylpropan-1-amine was stirred at 200° C. in microwave for 20 min. The solution was concentrated and purified by silica gel chromatography to give the crude solid which was further purified by prep-HPLC to give the title product (160 mg, 43%). ¹H NMR (300 MHz, CDCl₃): 14.44 (s, 1H), 9.34 (s, 1H), 8.40 (s, 2H), 7.91 (s, 1H), 5.90 (s, 1H), 3.50 (s, 4H), 2.90 (s, 2H), 2.57 (s, 4H), 2.29 (s, 3H), 0.88 (s, 9H); LC-MS: m/z=264.1 [M+H]⁺.

5-(4-methylpiperazin-1-yl)-N-neopentylpyridazin-3-amine dihydro chloride. A solution of hydrogen chloride in ether (7N, 20 mL) was added into a solution of 5-(4-methylpiperazin-1-yl)-N-neopentylpyridazin-3-amine diformic acid in MeOH (3 mL). The mixture was stirred at ambient temperature for 18 hrs. The solvent was removed by reduce pressure to give the title product (160 mg, 100%). ¹H NMR (300 MHz, CD₃OD): 8.41 (s, 1H), 6.58 (s, 1H), 4.40-4.35 (m, 2H), 4.00-3.40 (m, 6H), 3.22 (s, 2H), 3.02 (s, 3H), 1.08 (s, 9H); LC-MS: m/z=264.1 [M+H]⁺. MS (ESI): mass calcd. for C₁₄H₂₅N₅, 263.39 m/z found, 264.1 [M+H]⁺.

The compounds Example 405 through Example 411 were prepared using methods analogous to those described in Example 404.

Example 405

N-(2-Methoxyethyl)-5-(4-methylpiperazin-1-yl)pyridazin-3-amine

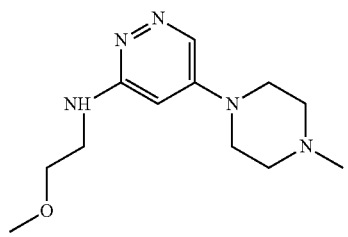

MS (ESI): mass calcd. for C₁₂H₂₁N₅O, 251.33 m/z found, 252.1 [M+H]⁺. ¹H NMR (300 MHz, CD₃OD): 8.38 (s, 1H), 6.46 (s, 1H), 4.35 (br s, 2H), 3.90-3.20 (m, 10H), 3.40 (s, 3H), 2.99 (s, 3H)

Example 406

N-Bicyclo[2.2.1]hept-2-yl-5-(4-methylpiperazin-1-yl)pyridazin-3-amine

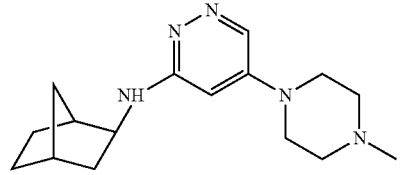 [SMILES: CN1CCN(c2cnnc(NC3CC4CCC3C4)c2)CC1]

MS (ESI): mass calcd. for C₁₆H₂₅N₅, 287.41 m/z found, 288.2 [M+H]⁺. ¹H NMR (300 MHz, CD₃OD): 8.37 (d, J=2.4 Hz, 1H), 6.34 (d, J=2.7 Hz, 1H), 4.28 (br, s, 2H), 3.63-3.51 (m, 6H), 2.98 (m, 3H), 2.37-1.97 (m, 2H), 1.97-1.90 (m, 1H), 1.62-1.19 (m, 8H).

Example 407

N-Cyclopentyl-5-(4-methylpiperazin-1-yl)pyridazin-3-amine

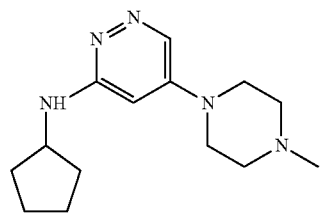 [SMILES: CN1CCN(c2cnnc(NC3CCCC3)c2)CC1]

MS (ESI): mass calcd. for C₁₄H₂₃N₅, 261.37 m/z found, 262.1 [M+H]⁺. ¹H NMR (300 MHz, CD₃OD): 8.41 (s, 1H), 6.41 (s, 1H), 4.33-3.57 (m, 9H), 3.02 (s, 3H), 2.13 (br s, 2H), 1.83-1.69 (m, 6H).

Example 408

N-(Cyclopentylmethyl)-5-(4-methylpiperazin-1-yl)pyridazin-3-amine

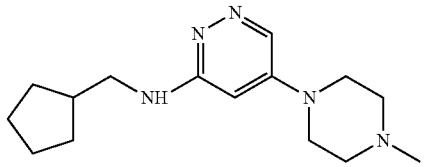 [SMILES: CN1CCN(c2cnnc(NCC3CCCC3)c2)CC1]

MS (ESI): mass calcd. for C₁₅H₂₅N₅, 275.4 m/z found, 276.1 [M+H]⁺. ¹H NMR (300 MHz, CD₃OD): 8.35 (d, J=3.0

Hz, 1H), 6.40 (d, J=2.4 Hz, 1H), 4.91-3.23 (m, 10H), 2.97 (s, 3H), 2.27-2.17 (m, 1H), 1.90-1.82 (m, 2H), 1.72-1.59 (m, 4H), 1.58-1.26 (m, 2H).

Example 409

5-(4-Methylpiperazin-1-yl)-N-(2-phenylethyl)pyridazin-3-amine

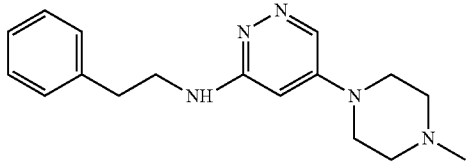 [SMILES: CN1CCN(c2cnnc(NCCc3ccccc3)c2)CC1]

MS (ESI): mass calcd. for $C_{17}H_{23}N_5$, 297.41 m/z found, 298.2 [M+H]$^+$. $^1$H NMR (300 MHz, D$_2$O): 8.04 (s, 1H), 7.27-7.18 (m, 5H), 5.89 (s, 1H), 4.02 (br s, 2H), 3.58-3.54 (m, 4H), 3.32 (br s, 2H), 3.11 (br s, 2H), 2.87 (s, 3H), 2.85 (m, 2H).

Example 410

N-Benzyl-5-(4-methylpiperazin-1-yl)pyridazin-3-amine

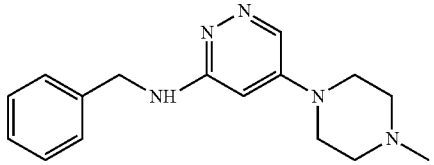 [SMILES: CN1CCN(c2cnnc(NCc3ccccc3)c2)CC1]

MS (ESI): mass calcd. for $C_{16}H_{21}N_5$, 283.38 m/z found, 284.2 [M+H]$^+$. $^1$H NMR (300 MHz, CD$_3$OD): 8.41 (d, J=1.2 Hz, 1H), 7.41-7.31 (m, 5H), 6.48 (s, 1H), 4.60 (s, 2H), 4.35 (br s, 4H), 3.60 (br s, 4H), 2.98 (s, 3H).

Example 411

5-(4-Methylpiperazin-1-yl)-N-(pyridin-2-ylmethyl)pyridazin-3-amine

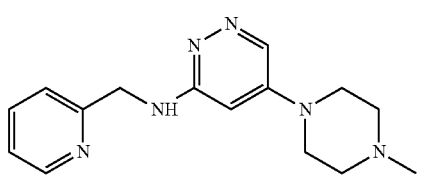 [SMILES: CN1CCN(c2cnnc(NCc3ccccn3)c2)CC1]

MS (ESI): mass calcd. for $C_{15}H_{20}N_6$, 284.37 m/z found, 285.3 $^1$H NMR (300 MHz, CD$_3$OD): 8.77 (d, J=5.4 Hz, 1H), 8.47-8.42 (m, 2H), 7.97-7.85 (m, 2H), 6.63 (s, 1H), 5.03 (s, 2H), 4.38 (br, 2H), 3.59-3.26 (m, 6H), 2.94 (s, 3H), (trace of ether).

Example 412

N-cyclopentyl-5-[(3R)-3-(methylamino)pyrrolidin-1-yl]pyridazin-3-amine

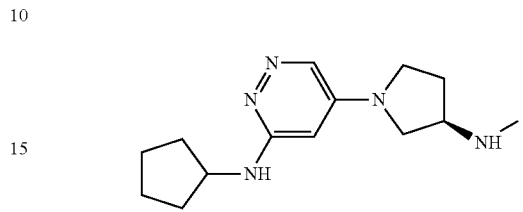

The titled compound was prepared in a manner analogous to Example 101. MS (ESI): mass calcd. for $C_{14}H_{23}N_5$, 261.37 m/z found, 262.2 [M+H]$^+$. $^1$H NMR (400 MHz, D$_2$O) δ 8.01 (d, J=2.5, 1H), 5.90 (d, J=2.4, 1H), 4.12-4.05 (m, 1H), 4.03-3.92 (m, 2H), 3.91-3.57 (m, 3H), 2.80 (s, 3H), 2.64-2.50 (m, 1H), 2.38-2.29 (m, J=5.7, 1H), 2.09-1.95 (m, J=6.6, 2H), 1.79-1.54 (m, 7H).

Example 413

(R)-5-(3-(methylamino)pyrrolidin-1-yl)-N-(1-adamantyl)pyridazin-3-amine dihydrochloride

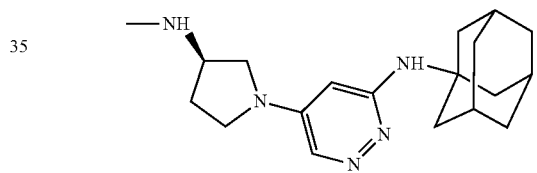

(R)-tert-butyl 1-(6-chloropyridazin-4-yl)pyrrolidin-3-ylcarbamate. A solution of 3,5-dichloropyridazine (4.47 g, 30 mmol), (R)-tert-butyl pyrrolidin-3-ylcarbamate (5.59 g, 30 mmol) and triethylamine (8.1 g, 80 mmol) in THF (50 mL) was stirred at ambient temperature for 20 hrs. The solvent was removed under reduced pressure and the residue was purified by column chromatography to afford the desired product (5.4 g, 60%) as a colorless solid. LC-MS: m/z=299.2 [M+H$^+$]$^+$.

(R)-tert-butyl-1-(6-chloropyridazin-4-yl)pyrrolidin-3-yl (methyl)carbamate. A solution of (R)-tert-butyl 1-(6-chloropyridazin-4-yl)pyrrolidin-3-ylcarbamate (3.6 g, 12.05 mmol) in N,N-dimethylformamide (DMF, 40 mL) was added into a suspension of 60% sodium hydride (0.58 g, 14.5 mmol) in DMF (40 mL) at 0° C. The mixture was stirred at 0° C. for further 30 min then Iodomethane (2.06 g, 14.5 mmol) was added into the mixture and the resulting reaction was stirred for further 3 h at ambient temperature. Water (100 mL) was added and the mixture was extracted with dichloromethane. The combined organic layer was dried over Na$_2$SO$_4$, filtered and concentrated. The solvent was removed under reduced pressure and the residue was purified by column chromatography to afford the desired product (2.5 g, 66%) as a brown solid. $^1$H NMR (300 MHz, CDCl$_3$): 8.47 (d, J=2.4 Hz, 1H), 6.41 (d, J=2.4 Hz, 1H), 4.89 (br s, 1H), 3.58-3.52 (m, 2H), 3.42-3.36 (m, 1H), 3.29-3.23 (m, 1H), 2.82 (s, 3H), 2.27-2.14 (m, 2H), 1.47 (s, 9H).

(R)-tert-butyl methyl(1-(6-(1-adamantylamino)pyridazin-4-yl)pyrrolidin-3-yl)carbamate. A mixture of (R)-tert-butyl 1-(6-chloropyridazin-4-yl)pyrrolidin-3-yl(methyl)carbamate (78 mg, 0.25 mmol), 1-adamantylamine (76 mg, 0.5 mmol), BINAP (10.9 mg, 0.0175 mmol), palladium acetate (3.9 mg, 0.0175 mmol) and t-BuONa (72.1 mg, 0.75 mmol) in 1,2-dimethoxyethane (2 mL) was charged with $N_2$. The reaction mixture was stirred at 80° C. for 1.5 hours. The solution was diluted with ethyl acetate (5 mL) and washed with 5% $NaHCO_3$ solution. The solvent was removed under reduced pressure and the residue was purified by column chromatography 0~3.5% $NH_3$ MeOH/DCM to afford the desired product (64 mg, 60%) as a colorless solid. LC-MS: m/z=428.3 $[M+H]^+$.

(R)-5-(3-(methylamino)pyrrolidin-1-yl)-N-(1-adamantyl)pyridazin-3-amine dihydrochloride. (R)-tert-butyl methyl(1-(6-(1-adamantylamino)pyridazin-4-yl)pyrrolidin-3-yl)carbamate (120 mg, 0.28 mmol) was dissolved in MeOH (4 mL) and 7N $HCl/Et_2O$ solution (20 mL) was added. The resulting solution was stirred at ambient temperature for 18 hrs. The solvent was concentrated to give the desired product as a light yellow solid (73 mg, 60%). MS (ESI): mass calcd. for $C_{19}H_{29}N_5$, 327.48 m/z found, 328.3 $[M+H]^+$. $^1$H NMR (300 MHz, $CD_3OD$): 8.15 (s, 1H), 6.12 (s, 1H), 4.08-3.60 (m, 5H), 2.84 (s, 3H), 2.61-2.56 (m, 1H), 2.42-2.38 (m, 1H), 2.20 (s, 3H), 2.10 (s, 6H), 1.87-1.77 (m, 6H).

The compounds in Examples 414 through 416 were made analogously to Example 413.

Example 414

(R)-5-(3-(methylamino)pyrrolidin-1-yl)-N-(2-adamantyl)pyridazin-3-amine dihydrochloride

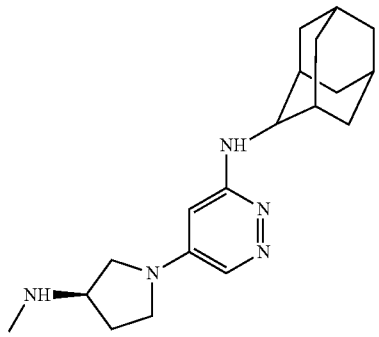 [SMILES: CN[C@@H]1CCN(c2cnnc(NC3C4CC5CC(C4)CC3C5)c2)C1]

MS (ESI): mass calcd. for $C_{19}H_{29}N_5$, 327.48 m/z found, 328.3 $[M+H]^+$. $^1$H NMR (300 MHz, $CD_3OD$): 8.15 (d, J=2.4 Hz, 1H), 6.26 (s, 1H), 4.08-3.60 (m, 6H), 2.84 (s, 3H), 2.60-2.56 (m, 1H), 2.42-2.37 (m, 1H), 2.11-1.85 (m, 12H), 1.76-1.71 (m, 2H).

Example 415

(S)-5-(3-(methylamino)pyrrolidin-1-yl)-N-(2-adamantyl)pyridazin-3-amine dihydrochloride

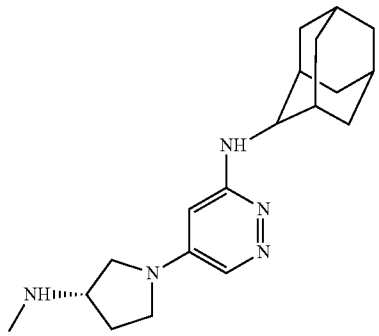 [SMILES: CN[C@H]1CCN(c2cnnc(NC3C4CC5CC(C4)CC3C5)c2)C1]

MS (ESI): mass calcd. for $C_{19}H_{29}N_5$, 327.48 m/z found, 328.2 $[M+H]^+$. $^1$H NMR (300 MHz, $CD_3OD$): 8.15 (d, J=2.1 Hz, 1H), 6.26 (s, 1H), 4.91-3.61 (m, 6H), 2.84 (s, 3H), 2.63-2.56 (m, 1H), 2.42-2.37 (m, 1H), 2.11-1.85 (m, 12H), 1.75-1.71 (m, 2H).

Example 416

(S)-5-(3-(methylamino)pyrrolidin-1-yl)-N-(1-adamantyl)pyridazin-3-amine dihydrochloride

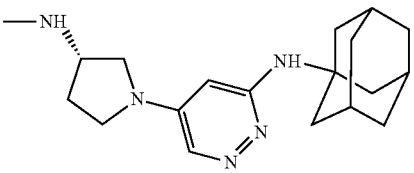 [SMILES: CN[C@H]1CCN(c2cnnc(NC34CC5CC(CC(C5)C3)C4)c2)C1]

MS (ESI): mass calcd. for $C_{19}H_{29}N_5$, 327.48 m/z found, 328.2 $[M+H]^+$. $^1$H NMR (300 MHz, $CD_3OD$): 8.15 (s, 1H), 6.12 (s, 1H), 4.08-3.60 (m, 5H), 2.84 (s, 3H), 2.61-2.56 (m, 1H), 2.42-2.38 (m, 1H), 2.38 (s, 3H), 2.10 (s, 6H), 1.87-1.77 (m, 6H).

Binding Assay on Recombinant Human Histamine $H_4$ Receptor.

Cell pellets from SK-N-MC cells stably or transiently transfected with human $H_4$ receptor (NCBI accession No. AF312230) were used for the binding assays. Cell pellets were homogenized in 50 mM Tris/5 mM EDTA buffer and supernatants from an 800 g spin were collected and recentrifuged at 30,000 g for 30 min. Pellets were rehomogenized in 50 mM Tris/5 mM EDTA buffer. For competition binding studies, cell membranes were incubated with $2 \times K_D$ (10 nM), [$^3$H] histamine (Specific activity: 14.2 to 23 $C_i$/mmol), with or without test compounds for 45 to 60 min at 4 to 25° C. $K_i$ values were calculated based on an experimentally determined appropriate $K_D$ values according to Cheng and Prusoff (*Biochem. Pharmacol.* 1973, 22(23):3099-3108). Membranes were harvested by rapid filtration using the 96 well Brandel system (Table 1, Brandel) or a cell harvester (Table 1, Cell Harvester) using a Whatman GF/C filter or filter plates treated with 0.5% polyethylenimine (PEI), and washed 4 times with ice-cold 50 mM Tris/5 mM EDTA buffer. Filters were then dried, mixed with scintillant and radioactive counts were determined. Results for the compounds tested in these assays are presented in Table 1 as an average of results obtained (NT=not tested, ND=not determined). Compounds were tested in free base, hydrochloride salt, or trifluoroacetic acid form, with no significant differences in activities. Where activity is shown as greater than (>) a particular value, the value is the highest concentration tested

TABLE 1

| Example # | Cell Harvester $K_i$ (nM) | Brandel $K_i$ (nM) |
|---|---|---|
| 1 | 0.5 | 1 |
| 2 | 3.83 | |
| 3 | 7.26 | |
| 4 | 4.9 | |
| 5 | 8.9 | |
| 6 | 35.1 | |
| 7 | 13.7 | |

TABLE 1-continued

| Example # | Cell Harvester $K_i$ (nM) | Brandel $K_i$ (nM) |
|---|---|---|
| 8 | 10.6 | |
| 9 | 0.4 | 1 |
| 10 | 0.5 | 0.5 |
| 11 | 12.9 | |
| 12 | 19.2 | |
| 13 | 26.2 | |
| 14 | 114.39 | |
| 15 | 148.9 | 54.3 |
| 16 | 48.19 | |
| 17 | 375.49 | |
| 18 | 527.35 | |
| 19 | NT | 45.3 |
| 20 | NT | 3.5 |
| 21 | NT | 51.4 |
| 22 | 1.5 | 1.7 |
| 23 | 2.7 | |
| 24 | 3.32 | |
| 25 | 3.8 | |
| 26 | 5.5 | |
| 27 | 67.7 | |
| 28 | 8.4 | |
| 29 | 58.51 | |
| 30 | 91.79 | 42.4 |
| 31 | 76.9 | 69.02 |
| 32 | 1.69 | 3.08 |
| 33 | 0.9 | |
| 34 | 18.1 | |
| 35 | 74.7 | 25.6 |
| 36 | 103.8 | 91.31 |
| 37 | 247.12 | |
| 38 | 275.42 | |
| 39 | 554.24 | |
| 40 | 790.32 | |
| 41 | 2.2 | |
| 42 | 31.8 | |
| 43 | 3.3 | |
| 44 | 85.7 | 31.5 |
| 45 | 7.1 | |
| 46 | 8.4 | |
| 47 | 33.2 | |
| 48 | 26.7 | |
| 49 | 27.6 | |
| 50 | 33.2 | |
| 51 | 123.11 | |
| 52 | 33.4 | |
| 53 | 85.7 | 24.3 |
| 54 | 87.9 | |
| 55 | 101.79 | 137.5 |
| 56 | 567.81 | |
| 57 | 139.7 | |
| 58 | 341.9 | |
| 59 | 190.11 | |
| 60 | 341.9 | |
| 61 | >10,000 | |
| 62 | >10,000 | |
| 63 | 292.69 | |
| 64 | 65.19 | 39 |
| 65 | 68.6 | 46.3 |
| 66 | 56.79 | 12.2 |
| 67 | 275.42 | |
| 68 | 36.7 | |
| 69 | >10,000 | |
| 70 | 73 | 240.27 |
| 71 | 377.14 | |
| 72 | 376.27 | |
| 73 | 0.7 | 2 |
| 74 | 1.2 | |
| 75 | 1.5 | |
| 76 | 1.8 | |
| 77 | 3.3 | |
| 78 | 6 | |
| 79 | 11.6 | |
| 80 | 23.5 | |
| 81 | 24.7 | |
| 82 | 45.5 | |
| 83 | 195.79 | |
| 84 | 33.3 | |
| 85 | 18.2 | |
| 86 | 33.7 | |
| 87 | 33.7 | |
| 88 | 42.7 | |
| 89 | 69.29 | 26.2 |
| 90 | 105.61 | 68.9 |
| 91 | 182.18 | |
| 92 | 615.32 | |
| 93 | 701.62 | |
| 94 | 868.36 | |
| 95 | 15 | 15 |
| 96 | 1 | 1 |
| 97 | 5.9 | 5.9 |
| 98 | 4.8 | 4.8 |
| 99 | 23.9 | 23.9 |
| 100 | 31 | 31 |
| 101 | >10,000 | >10,000 |
| 102 | 45.93 | |
| 103 | 167.9 | |
| 104 | 1053 | |
| 105 | 165 | |
| 106 | 193.9 | |
| 107 | 69.91 | |
| 108 | 140.6 | |
| 109 | 63.96 | |
| 110 | 837.2 | |
| 111 | 93.55 | |
| 112 | 236.1 | |
| 113 | 139.5 | |
| 114 | 45.39 | |
| 115 | 931.7 | |
| 116 | 7.532 | |
| 117 | 246.5 | |
| 118 | >10,000 | |
| 119 | 22.87 | |
| 120 | 302.7 | |
| 121 | 1.569 | |
| 122 | 64.71 | |
| 123 | 2.038 | |
| 124 | 155.4 | |
| 125 | 2.096 | |
| 126 | 19.84 | |
| 127 | 1.659 | |
| 128 | 843.9 | |
| 129 | 141.4 | |
| 130 | 849.2 | |
| 131 | 820.4 | |
| 132 | 1544 | |
| 133 | 128.9 | |
| 134 | 696.8 | |
| 135 | 15.91 | |
| 136 | 193.2 | |
| 137 | 1378 | |
| 138 | 23.82 | |
| 139 | 7.958 | |
| 140 | 135.3 | |
| 141 | 2322 | |
| 142 | 7094 | |
| 143 | 266.8 | |
| 144 | 2533 | |
| 145 | 923 | |
| 146 | 34.09 | |
| 147 | 6.662 | |
| 148 | 249.8 | |
| 149 | 23.84 | |
| 150 | 29.71 | |
| 151 | 1459 | |
| 152 | 2297 | |
| 153 | 43.57 | |
| 154 | 203.6 | |
| 155 | 744.5 | |
| 156 | 413.3 | |
| 157 | 2144 | |
| 158 | 3485 | |
| 159 | 265.9 | |

TABLE 1-continued

| Example # | Cell Harvester $K_i$ (nM) | Brandel $K_i$ (nM) |
|---|---|---|
| 160 | 86.7 | |
| 161 | 1301 | |
| 162 | 7.137 | |
| 163 | 277.7 | |
| 164 | 36.2 | |
| 165 | 731.9 | |
| 166 | >10,000 | |
| 167 | 34.91 | |
| 168 | 483.1 | |
| 169 | 9.672 | |
| 170 | 143.8 | |
| 171 | 3.893 | |
| 172 | 13.74 | |
| 173 | 745.2 | |
| 174 | 19.09 | |
| 175 | 816.3 | |
| 176 | 457.7 | |
| 177 | 522.9 | |
| 178 | 242.8 | |
| 179 | 788.2 | |
| 180 | 116.4 | |
| 181 | 9.066 | |
| 182 | 45.41 | |
| 183 | 15.64 | |
| 184 | 1.576 | |
| 185 | 1732 | |
| 186 | 690.6 | |
| 187 | 71.55 | |
| 188 | 449.7 | |
| 189 | 5.729 | |
| 190 | 1.678 | |
| 191 | 3.575 | |
| 192 | 2.419 | |
| 193 | 15.97 | |
| 194 | 5.07 | |
| 195 | 7.75 | |
| 196 | 224.5 | |
| 197 | 17.34 | |
| 198 | 54.99 | |
| 199 | 2300 | |
| 200 | 859.9 | |
| 201 | 62.29 | |
| 202 | 194.5 | |
| 203 | 61.38 | |
| 204 | NT | |
| 205 | no data | |
| 206 | 44.85 | |
| 207 | 191.1 | |
| 208 | 0.86 | |
| 209 | 1458 | |
| 210 | 295.8 | |
| 211 | 1.684 | |
| 212 | 274.6 | |
| 213 | 156.7 | |
| 214 | 415.9 | |
| 215 | 69.65 | |
| 216 | 1434 | |
| 217 | 24.27 | |
| 218 | 2.615 | |
| 219 | 187.7 | |
| 220 | 6.48 | |
| 221 | 853.2 | |
| 222 | 67.29 | |
| 223 | 722.6 | |
| 224 | 238.7 | |
| 225 | 75.06 | |
| 226 | 3.813 | |
| 227 | 259.5 | |
| 228 | 31.76 | |
| 229 | >10,000 | |
| 230 | 275.9 | |
| 231 | 8.412 | |
| 232 | 716 | |
| 233 | 215 | |
| 234 | 7259 | |
| 235 | 409.3 | |
| 236 | 47.35 | |
| 237 | 584.5 | |
| 238 | 555.4 | |
| 239 | 700.8 | |
| 240 | 54.34 | |
| 241 | 837.5 | |
| 242 | >10,000 | |
| 243 | 167 | |
| 244 | 3883 | |
| 245 | 227.7 | |
| 246 | 395.4 | |
| 247 | 1.41 | |
| 248 | NT | |
| 249 | 257.4 | |
| 250 | 658.9 | |
| 251 | 79.38 | |
| 252 | 190.4 | |
| 253 | 4.33 | |
| 254 | 27.54 | |
| 255 | 1944 | |
| 256 | 616.8 | |
| 257 | 64.49 | |
| 258 | >10,000 | |
| 259 | 5.148 | |
| 260 | >10,000 | |
| 261 | 3563 | |
| 262 | 22.07 | |
| 263 | 3091 | |
| 264 | >10,000 | |
| 265 | 1.71 | |
| 266 | 14.47 | |
| 267 | 1529 | |
| 268 | 246.5 | |
| 269 | 2099 | |
| 270 | 3.526 | |
| 271 | 189.3 | |
| 272 | 2102 | |
| 273 | 3166 | |
| 274 | 10.57 | |
| 275 | 8.548 | |
| 276 | 1638 | |
| 277 | 97.04 | |
| 278 | 7.29 | |
| 279 | 275.6 | |
| 280 | 9.955 | |
| 281 | 21.26 | |
| 282 | 173.2 | |
| 283 | 162.4 | |
| 284 | 42.33 | |
| 285 | 140.9 | |
| 286 | 88.28 | |
| 287 | 98.92 | |
| 288 | 39.47 | |
| 289 | 409.7 | |
| 290 | 1479 | |
| 291 | 238.9 | |
| 292 | 7.01 | |
| 293 | 60.94 | |
| 294 | 103.3 | |
| 295 | 162.9 | |
| 296 | 64.23 | |
| 297 | 1556 | |
| 298 | >10,000 | |
| 299 | 146.2 | |
| 300 | 1857 | |
| 301 | 202.1 | |
| 302 | 98.12 | |
| 303 | 416.8 | |
| 304 | 310.4 | |
| 305 | 1059 | |
| 306 | 7216 | |
| 307 | 535.7 | |
| 308 | 18.43 | |
| 309 | 1597 | |
| 310 | 620.8 | |
| 311 | 226.3 | |

TABLE 1-continued

| Example # | Cell Harvester $K_i$ (nM) | Brandel $K_i$ (nM) |
|---|---|---|
| 312 | 546.8 | |
| 313 | >10,000 | |
| 314 | >10,000 | |
| 315 | 1919 | |
| 316 | 275.4 | |
| 317 | 929.8 | |
| 318 | 1237 | |
| 319 | 478.3 | |
| 320 | 4314 | |
| 321 | 626.2 | |
| 322 | 88.05 | |
| 323 | >10,000 | |
| 324 | 898.7 | |
| 325 | 797.8 | |
| 326 | 2743 | |
| 327 | 95.32 | |
| 328 | 1677 | |
| 329 | >10,000 | |
| 330 | 2586 | |
| 331 | 96.73 | |
| 332 | 1658 | |
| 333 | >10,000 | |
| 334 | 2574 | |
| 335 | >10,000 | |
| 336 | >10,000 | |
| 337 | >10,000 | |
| 338 | >10,000 | |
| 339 | 219.7 | |
| 340 | 2033 | |
| 341 | >10,000 | |
| 342 | 936.4 | |
| 343 | >10,000 | |
| 344 | >10,000 | |
| 345 | 1316 | |
| 346 | >10,000 | |
| 347 | >10,000 | |
| 348 | >10,000 | |
| 349 | >10,000 | |
| 350 | 1723 | |
| 351 | 205.8 | |
| 352 | >10,000 | |
| 353 | 105.6 | |
| 354 | 2131 | |
| 355 | 2900 | |
| 356 | 1597 | |
| 357 | 4370 | |
| 358 | >10,000 | |
| 359 | 161.3 | |
| 360 | 1171 | |
| 361 | 1227 | |
| 362 | 2212 | |
| 363 | 4727 | |
| 364 | 1743 | |
| 365 | 508.1 | |
| 366 | >10,000 | |
| 367 | 866.9 | |
| 368 | 290.4 | |
| 369 | 619.4 | |
| 370 | 223.6 | |
| 371 | 130.3 | |
| 372 | 138.6 | |
| 373 | 143.1 | |
| 374 | 297.8 | |
| 375 | 66.75 | |
| 376 | >10,000 | |
| 377 | 698.9 | |
| 378 | 6.164 | |
| 379 | 296 | |
| 380 | 54.29 | |
| 381 | 5.51 | |
| 382 | 138.5 | |
| 383 | 596 | |
| 384 | 2004 | |
| 385 | 258.8 | |
| 386 | 283.9 | |
| 387 | 835.1 | |
| 388 | 293.4 | |
| 389 | 1745 | |
| 390 | >10,000 | |
| 391 | 36.47 | |
| 392 | 18.35 | |
| 393 | 1807 | |
| 394 | 633.6 | |
| 395 | 1902 | |
| 396 | 380.5 | |
| 397 | 353.4 | |
| 398 | 347.4 | |
| 399 | 3941 | |
| 400 | 2152 | |
| 401 | 79.31 | |
| 402 | >10,000 | |
| 403 | >10,000 | |
| 404 | 4303 | |
| 405 | >10,000 | |
| 406 | 178.1 | |
| 407 | 823.6 | |
| 408 | >10,000 | |
| 409 | >10,000 | |
| 410 | >10,000 | |
| 411 | NT | |
| 412 | 5.6 | |
| 413 | NT | |
| 414 | NT | |
| 415 | NT | |
| 416 | NT | |

Cell-Based cAMP Assay

SK-N-MC cell lines were created that express a reporter gene construct and the human H4 receptor full-coding region (NCBI accession No. AF312230). The reporter gene was β-galactosidase under the control of cyclic AMP-responsive elements. Cells were plated in 96-well plates the night before the assay. Histamine was used as the agonist for all assay. For the H4 receptor, the inhibition of forskolin-stimulated cAMP production was measured. For determination of antagonist activity, compounds were added 10 min prior to the addition of agonist, which was added directly to the cell medium. Forskolin (5 μM final concentration) was added 10 min after the addition of histamine. Cells were returned to the incubator for 6 h at 37° C. The medium was then aspirated, and the cells were washed with 200 mL of phosphate-buffered saline (PBS). Cells were lysed with 25 μL of 0.1× assay buffer (10 mM sodium phosphate, pH 8, 0.2 mM $MgSO_4$, and 0.01 mM $MnCl_2$) and incubated at rt for 10 min. Cells were then incubated for 10 min with 100 μL of 1× assay buffer containing 0.5% (v/v) Triton X-100 and 40 mM β-mercaptoethanol. Color was developed using 25 μL of 1 mg/mL substrate solution (chlorophenol red β-D-galactopyranoside; Roche Applied Science, Indianapolis, Ind.). Color was quantitated on a microplate reader by measuring the absorbance at 570 nm. The data from each concentration-response curve were fitted to a sigmoidal curve to obtain the maximum response, Hill coefficient, and $EC_{50}$ using Prism (GraphPad Software, San Diego, Calif.). Dose ratios were calculated from individual concentration-response curves of agonists at three to five antagonist concentrations. Apparent $pA_2$ values were calculated using a Schild plot (ND=not determined). Results for compounds tested in this assay are presented in Table 2

| Example # | pA₂ |
|---|---|
| 2 | ND |
| 3 | 8.7 |
| 4 | 8.86 |
| 12 | 8.5 |
| 20 | 7.7 |
| 22 | 9.24 |
| 32 | 11 |
| 33 | ND |
| 95 | 7.8 |
| 162 | 8.1 |
| 189 | 8 |
| 193 | 7.9 |
| 201 | 7.7 |
| 203 | 7.8 |
| 217 | 7.5 |
| 220 | 7.6 |
| 228 | 7.4 |
| 231 | 9 |
| 257 | 7.3 |
| 308 | 7.1 |
| 331 | 7.4 |
| 380 | 7.2 |
| 381 | 8.1 |
| 392 | 8.1 |

While the invention has been illustrated by reference to examples, it is understood that the invention is intended not to be limited to the foregoing Insulin Resistance in Diabetes Induced Obese Mouse Model.

The effect of administration of an H4R antagonist, 5-fluoro-4-methyl-2-{5-methyl-2-[4-(1-methyl-piperidin-4-yl)-butoxy]-pyridin-4-yl}-1H-benzoimidazole (U.S. Pat. No. 7,432,378, Example 165), was tested in the treatment of insulin resistance in the diabetes induced obese (DIO) mouse model. 5-Fluoro-4-methyl-2-{5-methyl-2-[4-(1-methyl-piperidin-4-yl)-butoxy]-pyridin-4-yl}-1H-benzoimidazole (20 mg/kg PO) significantly reduced fed and fasted glucose levels and improved insulin sensitivity as determined by an insulin tolerance test. 5-Fluoro-4-methyl-2-{5-methyl-2-[4-(1-methyl-piperidin-4-yl)-butoxy]-pyridin-4-yl}-1H-benzoimidazole significantly reduced fat content in liver and reduced MCP-1 and TNF-α expression. Our data support the claim that H4R antagonists have beneficial properties towards the treatment of type 2 diabetes and related metabolic diseases.

What is claimed is:

1. A chemical entity selected from the compounds of Formula (I)

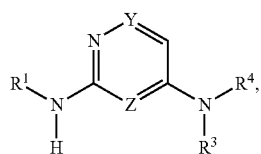

Formula (I)

wherein
Z is CH;
Y is N;
$R^1$ is:
  a) —(CH$_2$)$_2$OCH$_3$, —(CH$_2$)$_2$SCH$_3$, or C$_{1-8}$alkyl, each independently unsubstituted or substituted with —OH or —CF$_3$;
  b) —(CH$_2$)$_{0-2}$—Ar$^1$, —CHR$^2$—Ar$^1$, —(CH$_2$)$_{0-2}$—Ar$^2$, each of said Ar$^1$ and Ar$^2$ independently unsubstituted or substituted with halo, —CH$_3$, —OCH$_3$, Ar$^1$ is a 6-membered aromatic carbocyclic ring,
Ar$^2$ is a 5 to 6-membered heteroaromatic ring containing N, S or O; or
  c) cycloalkyl, —(CH$_2$)-(monocyclic cycloalkyl), —(CH$_2$)-(bridged polycyclic cycloalkyl)$_{0-1}$, —(CHR$^2$)-(monocyclic cycloalkyl), —(CH$_2$)-(fused cycloalkyl), —(CH$_2$)-(bridged monocyclic cycloalkyl), —(CH$_2$)$_{0-1}$-tetrahydrofuranyl, and —(CH$_2$)$_{0-1}$-tetrahydropyranyl, each independently unsubstituted or substituted with one, two, or three C$_{1-4}$alkyl substituents;
$R^2$ is —C$_{1-4}$alkyl;

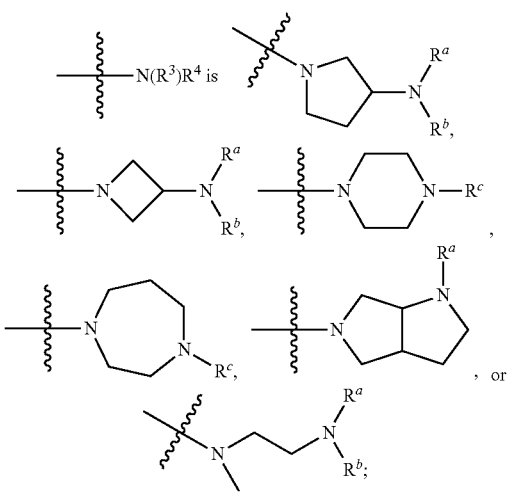

where $R^a$, $R^b$, and $R^c$ are each independently H or C$_{1-3}$alkyl; and pharmaceutically acceptable salts of compounds of Formula (I).

2. A chemical entity of claim 1, wherein $R^1$ is selected from the group consisting of:
  a) C$_{1-8}$alkyl unsubstituted or substituted with —OH or —CF$_3$;
  b) phenyl, pyridyl, benzyl, pyridin-2-ylmethyl, phenylethyl, 1-phenyl-ethyl, each independently unsubstituted or substituted with halo, —CH$_3$, —OCH$_3$; and
  c) cycloalkyl, —(CH$_2$)-(monocyclic cycloalkyl), —(CHR$^2$)-(monocyclic cycloalkyl), —(CH$_2$)-(fused cycloalkyl), —(CH$_2$)-(bridged polycyclic cycloalkyl), —(CH$_2$)$_{0-1}$-tetrahydrofuranyl, and —(CH$_2$)$_{0-1}$-tetrahydropyranyl, each independently unsubstituted or substituted with one, two, or three C$_{1-4}$alkyl substituents.

3. A chemical entity of claim 1, wherein $R^1$ is selected from the group consisting of:
  a) 2,2-dimethylpropanol, 2,2-dimethylpropan-1-ol, 2,2-dimethylpropyl, 2-methyl-1-propan-2-ol, 2-methylpropan-2-ol, 3-propanol, (1-methylethyl), 2,2-dimethylpropyl, 2-methoxyethyl, 2-methylpropyl, 4,4,4-trifluorobutyl, propyl, butyl, tert-butyl, propan-1-ol, 2-(methylsulfanyl)ethyl;
  b) 2-phenylethyl, furan-3-ylmethyl, pyridin-2-ylmethyl, (1R)-1-phenylethyl, benzyl, phenyl, 4-fluorobenzyl, 4-methoxybenzyl, 4-methylbenzyl; and
  c) bicyclo[2.2.1]hept-2-ylmethyl, tetrahydro-2H-pyran-4-yl, tetrahydrofuran-2-ylmethyl, (1R,2R,3R,5S)-2,6,6-trimethylbicyclo[3.1.1]hept-3-yl, (1R,2S,4R)-1,7,7-trimethylbicyclo[2.2.1]hept-2-yl, (1S,2S,3,5R)-2,6,6-trimethylbicyclo[3.1.1]hept-3-yl, (1S,2S,4R)-bicyclo

[2.2.1]hept-2-yl, (1S,5R)-2,6,6-trimethylbicyclo[3.1.1]hept-3-yl, (2R)-tetrahydrofuran-2-ylmethyl, (2S)-bicyclo[2.2.1]hept-2-yl], [(2S)-tetrahydrofuran-2-ylmethyl, (3R)-tetrahydrofuran-3-yl, (6,6-dimethylbicyclo[3.1.1]hept-2-yl)methyl, bicyclo[2.2.1]hept-2-yl, cyclobutyl, cyclohexyl, cyclopentyl, cyclopropyl, cyclohexylmethyl, cyclopentylmethyl, cyclopropylmethyl, adamantan-1-yl, 2-adamantyl, bicyclo[2.2.1]hept-2-yl, and (6,6-dimethyl-bicyclo[3.1.1]hept-2-yl)-methyl.

4. A chemical entity of claim 1, wherein R¹ is selected from the group consisting of:

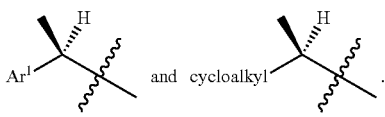

5. A chemical entity of claim 1, wherein

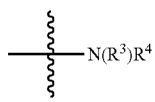

is selected from the group consisting of:

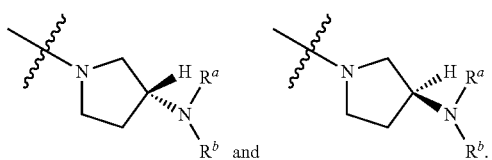

6. A chemical entity of claim 1, wherein

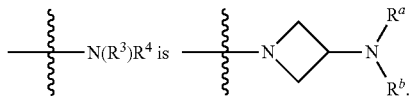

7. A chemical entity of claim 1, wherein

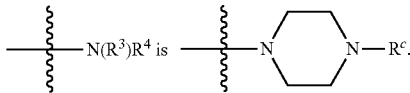

8. A chemical entity of claim 1, wherein

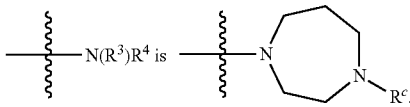

9. A chemical entity of claim 1, wherein

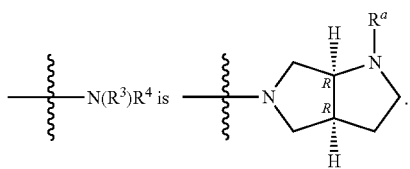

10. A chemical entity of claim 1, wherein

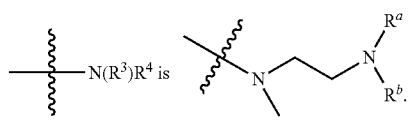

11. A chemical entity of claim 1, wherein $R^a$ is H.
12. A chemical entity of claim 1, wherein $R^b$ is H or methyl.
13. A chemical entity of claim 1, wherein $R^c$ is H or methyl.
14. A chemical entity of claim 1, wherein $R^2$ is methyl.
15. A chemical entity selected from the group consisting of:

5-[(3R)-3-(Methylamino)pyrrolidin-1-yl]-N-(2-methylpropyl)pyridazin-3-amine;
N-Bicyclo[2.2.1]hept-2-yl-5-[(3R)-3-(methylamino)pyrrolidin-1-yl]pyridazin-3-amine;
5-[(3R)-3-(Methylamino)pyrrolidin-1-yl]-N-[(1S,2S,3S,5R)-2,6,6-trimethylbicyclo[3.1.1]hept-3-yl]pyridazin-3-amine;
N-Cyclohexyl-5-[(3R)-3-(methylamino)pyrrolidin-1-yl]pyridazin-3-amine;
N-(Cyclopropylmethyl)-5-[(3R)-3-(methylamino)pyrrolidin-1-yl]pyridazin-3-amine;
N-Butyl-5-[(3R)-3-(methylamino)pyrrolidin-1-yl]pyridazin-3-amine;
5-(4-Methylpiperazin-1-yl)-N-(2-methylpropyl)pyridazin-3-amine;
5-[(3R)-3-Aminopyrrolidin-1-yl]-N-(2-methoxyethyl)pyridazin-3-amine;
5-[3-(Methylamino)azetidin-1-yl]-N-(4,4,4-trifluorobutyl)pyridazin-3-amine;
N5-(2-Aminoethyl)-N3-(2,2-dimethylpropyl)-N5-methylpyridazine-3,5-diamine;
5-[3-(Methylamino)azetidin-1-yl]-N-[(1S,5R)-2,6,6-trimethylbicyclo[3.1.1]hept-3-yl]pyridazin-3-amine;
N5-(2-Amino-ethyl)-N3-bicyclo[2.2.1]hept-2-yl-N5-methyl-pyridazine-3,5-diamine;
N5-(2-Aminoethyl)-N3-(cyclopentylmethyl)-N5-methylpyridazine-3,5-diamine;
5-[(3S)-3-Aminopyrrolidin-1-yl]-N-(bicyclo[2.2.1]hept-2-ylmethyl)pyridazin-3-amine;
3-({5-[(3aR,6aR)-Hexahydropyrrolo[3,4-b]pyrrol-5(1H)-yl]pyridazin-3-yl}amino)propan-1-ol;
5-(3-Aminoazetidin-1-yl)-N-{[(1S,2S,5S)-6,6-dimethylbicyclo[3.1.1]hept-2-yl]methyl}pyridazin-3-amine;
5-(1,4-Diazepan-1-yl)-N-(2,2-dimethylpropyl)pyridazin-3-amine;
N-Bicyclo[2.2.1]hept-2-yl-5-(1,4-diazepan-1-yl)pyridazin-3-amine;
N-Cyclopropyl-5-[(3aR,6aR)-hexahydropyrrolo[3,4-b]pyrrol-5(1H)-yl]pyridazin-3-amine;
N-Butyl-5-[(3aR,6aR)-hexahydropyrrolo[3,4-b]pyrrol-5(1H)-yl]pyridazin-3-amine;

5-[(3R)-3-Aminopyrrolidin-1-yl]-N-(bicyclo[2.2.1]hept-2-ylmethyl)pyridazin-3-amine;
3-({5-[(3R)-3-Aminopyrrolidin-1-yl]pyridazin-3-yl}amino)propan-1-ol;
3-[(5-piperazin-1-ylpyridazin-3-yl)amino]propan-1-ol;
N-Cyclopropyl-5-piperazin-1-ylpyridazin-3-amine;
N-(Cyclopentylmethyl)-5-(1,4-diazepan-1-yl)pyridazin-3-amine;
5-[(3S)-3-Aminopyrrolidin-1-yl]-N-(cyclopentylmethyl)pyridazin-3-amine;
5-[(3aR,6aR)-Hexahydropyrrolo[3,4-b]pyrrol-5 (1H)-yl]-N-(2-methylpropyl)pyridazin-3-amine;
5-[3-(Methylamino)azetidin-1-yl]-N-(2-methylpropyl)pyridazin-3-amine;
N-(2-Methoxyethyl)-5-[3-(methylamino)azetidin-1-yl]pyridazin-3-amine;
5-[(3R)-3-Aminopyrrolidin-1-yl]-N-[(1R)-1-phenylethyl]pyridazin-3-amine;
5-(3-Aminoazetidin-1-yl)-N-bicyclo[2.2.1]hept-2-ylpyridazin-3-amine;
5-(3-Aminoazetidin-1-yl)-N-(2,2-dimethylpropyl)pyridazin-3-amine;
N-(2,2-Dimethylpropyl)-5-[3-(methylamino)azetidin-1-yl]pyridazin-3-amine;
N-Cyclohexyl-5-[3-(methylamino)azetidin-1-yl]pyridazin-3-amine;
5-(3-Aminoazetidin-1-yl)-N-cyclopentylpyridazin-3-amine;
N-(Cyclopropylmethyl)-5-[3-(methylamino)azetidin-1-yl]pyridazin-3-amine;
5-(3-Aminoazetidin-1-yl)-N-(2-methylpropyl)pyridazin-3-amine;
5-(3-Aminoazetidin-1-yl)-N-benzylpyridazin-3-amine;
N-Benzyl-5-[3-(methylamino)azetidin-1-yl]pyridazin-3-amine;
N-Bicyclo[2.2.1]hept-2-yl-5-[3-(methylamino)azetidin-1-yl]pyridazin-3-amine;
N-Cyclopentyl-5-[3-(methylamino)azetidin-1-yl]pyridazin-3-amine;
5-(3-Aminoazetidin-1-yl)-N-cyclopropylpyridazin-3-amine;
3-({5-[3-(Methylamino)azetidin-1-yl]pyridazin-3-yl}amino)propan-1-ol;
5-(3-Aminoazetidin-1-yl)-N-(2-methoxyethyl)pyridazin-3-amine;
5-[(3S)-3-Aminopyrrolidin-1-yl]-N-cyclopropylpyridazin-3-amine;
5-[(3R)-3-Aminopyrrolidin-1-yl]-N-(pyridin-2-ylmethyl)pyridazin-3-amine;
3-({5-[(3S)-3-Aminopyrrolidin-1-yl]pyridazin-3-yl}amino)propan-1-ol;
5-[(3S)-3-Aminopyrrolidin-1-yl]-N-(2-methylpropyl)pyridazin-3-amine;
5-[(3R)-3-Aminopyrrolidin-1-yl]-N-benzylpyridazin-3-amine;
5-[(3R)-3-Aminopyrrolidin-1-yl]-N-(4-methoxybenzyl)pyridazin-3-amine;
5-[(3R)-3-Aminopyrrolidin-1-yl]-N-(4-fluorobenzyl)pyridazin-3-amine;
5-[(3R)-3-Aminopyrrolidin-1-yl]-N-(4-methylbenzyl)pyridazin-3-amine;
N-(4-Methylbenzyl)-5-piperazin-1-ylpyridazin-3-amine;
N-Cyclopentyl-5-[(3aR,6aR)-hexahydropyrrolo[3,4-b]pyrrol-5 (1H)-yl]pyridazin-3-amine;
N-(4-Fluorobenzyl)-5-piperazin-1-ylpyridazin-3-amine;
N-(4-Methoxybenzyl)-5-piperazin-1-ylpyridazin-3-amine;
N-Benzyl-5-piperazin-1-ylpyridazin-3-amine;
N-[(1R)-1-Phenylethyl]-5-piperazin-1-ylpyridazin-3-amine;
3-({5-[(3R)-3-Aminopyrrolidin-1-yl]pyridazin-3-yl}amino)-2,2-dimethylpropan-1-ol;
N-Cyclopropyl-5-[3-(methylamino)azetidin-1-yl]pyridazin-3-amine;
5-[3-(Methylamino)azetidin-1-yl]-N-(pyridin-2-ylmethyl)pyridazin-3-amine;
5-[(3R)-3-Aminopyrrolidin-1-yl]-N-(2-methylpropyl)pyridazin-3-amine;
N-Cyclopentyl-5-piperazin-1-ylpyridazin-3-amine;
N-Cyclohexyl-5-piperazin-1-ylpyridazin-3-amine;
N-Butyl-5-piperazin-1-ylpyridazin-3-amine;
N-(2,2-Dimethylpropyl)-5-piperazin-1-ylpyridazin-3-amine;
5-(3-Aminoazetidin-1-yl)-N-(cyclopentylmethyl)pyridazin-3-amine;
5-[(3R)-3-Aminopyrrolidin-1-yl]-N-(cyclopentylmethyl)pyridazin-3-amine;
N-(Cyclopentylmethyl)-5-[(3aR,6aR)-hexahydropyrrolo[3,4-b]pyrrol-5(1H)-yl]pyridazin-3-amine;
N-(Cyclopropylmethyl)-5-piperazin-1-ylpyridazin-3-amine;
N-(2-Phenylethyl)-5-piperazin-1-ylpyridazin-3-amine;
N-(Cyclopentylmethyl)-5-piperazin-1-ylpyridazin-3-amine;
5-[(3R)-3-Aminopyrrolidin-1-yl]-N-(2-phenylethyl)pyridazin-3-amine;
5-[(3R)-3-Aminopyrrolidin-1-yl]-N-cyclohexylpyridazin-3-amine;
2,2-Dimethyl-3-[(5-piperazin-1-ylpyridazin-3-yl)amino]propan-1-ol;
5-[(3R)-3-Aminopyrrolidin-1-yl]-N-butylpyridazin-3-amine;
5-[(3R)-3-Aminopyrrolidin-1-yl]-N-cyclopentylpyridazin-3-amine;
5-[(3R)-3-Aminopyrrolidin-1-yl]-N-(cyclopropylmethyl)pyridazin-3-amine;
N-(Cyclopentylmethyl)-5-[3-(methylamino)azetidin-1-yl]pyridazin-3-amine;
5-[(3R)-3-Aminopyrrolidin-1-yl]-N-(2,2-dimethylpropyl)pyridazin-3-amine;
5-[(3R)-3-(Methylamino)pyrrolidin-1-yl]-N-(2-phenylethyl)pyridazin-3-amine;
N-[(1R)-1-Cyclohexylethyl]-5-[(3S)-3-(methylamino)pyrrolidin-1-yl]pyridazin-3-amine;
N-(Bicyclo[2.2.1]hept-2-ylmethyl)-5-[(3S)-3-(methylamino)pyrrolidin-1-yl]pyridazin-3-amine;
N-(Bicyclo[2.2.1]hept-2-ylmethyl)-5-[(3R)-3-(methylamino)pyrrolidin-1-yl]pyridazin-3-amine;
N-(2-Methoxyethyl)-5-[(3S)-3-(methylamino)pyrrolidin-1-yl]pyridazin-3-amine;
N-Cyclopropyl-5-[(3R)-3-(methylamino)pyrrolidin-1-yl]pyridazin-3-amine;
N-[(1R)-1-Cyclohexylethyl]-5-[(3R)-3-(methylamino)pyrrolidin-1-yl]pyridazin-3-amine;
5-[(3S)-3-(Methylamino)pyrrolidin-1-yl]-N-(2-methylpropyl)pyridazin-3-amine;
N-Cyclopentyl-5-[(3S)-3-(methylamino)pyrrolidin-1-yl]pyridazin-3-amine;
N-Bicyclo[2.2.1]hept-2-yl-5-[(3S)-3-(methylamino)pyrrolidin-1-yl]pyridazin-3-amine;
N-(Cyclopentylmethyl)-5-[(3S)-3-(methylamino)pyrrolidin-1-yl]pyridazin-3-amine;
2,2-Dimethyl-3-({5-[(3S)-3-(methylamino)pyrrolidin-1-yl]pyridazin-3-yl}amino)propan-1-ol;

5-[(3R)-3-(Methylamino)pyrrolidin-1-yl]-N-(4-methylbenzyl)pyridazin-3-amine;
N-(2,2-Dimethylpropyl)-5-[(3S)-3-(methylamino)pyrrolidin-1-yl]pyridazin-3-amine;
5-[(3R)-3-(Methylamino)pyrrolidin-1-yl]-N-(4,4,4-trifluorobutyl)pyridazin-3-amine;
N-(Furan-3-ylmethyl)-5-[(3R)-3-(methylamino)pyrrolidin-1-yl]pyridazin-3-amine;
N-[(6,6-Dimethylbicyclo[3.1.1]hept-2-yl)methyl]-5-[(3R)-3-(methylamino)pyrrolidin-1-yl]pyridazin-3-amine;
5-[(3S)-3-(Methylamino)pyrrolidin-1-yl]-N-(4,4,4-trifluorobutyl)pyridazin-3-amine;
3-({5-[(3R)-3-(Methylamino)pyrrolidin-1-yl]pyridazin-3-yl}amino)propan-1-ol;
N-(Cyclohexylmethyl)-5-[(3R)-3-(methylamino)pyrrolidin-1-yl]pyridazin-3-amine;
N-(2,2-Dimethylpropyl)-5-[(3R)-3-(methylamino)pyrrolidin-1-yl]pyridazin-3-amine;
N-(2-Methoxyethyl)-5-[(3R)-3-(methylamino)pyrrolidin-1-yl]pyridazin-3-amine;
N-[(6,6-Dimethylbicyclo[3.1.1]hept-2-yl)methyl]-5-[(3S)-3-(methylamino)pyrrolidin-1-yl]pyridazin-3-amine;
N-Cyclopropyl-5-[(3S)-3-(methylamino)pyrrolidin-1-yl]pyridazin-3-amine;
N-(Cyclohexylmethyl)-5-[(3S)-3-(methylamino)pyrrolidin-1-yl]pyridazin-3-amine;
N-Benzyl-5-[(3R)-3-(methylamino)pyrrolidin-1-yl]pyridazin-3-amine;
N-(4-Fluorobenzyl)-5-[(3R)-3-(methylamino)pyrrolidin-1-yl]pyridazin-3-amine;
N-(4-Fluorobenzyl)-5-[(3S)-3-(methylamino)pyrrolidin-1-yl]pyridazin-3-amine;
N-(4-Methoxybenzyl)-5-[(3R)-3-(methylamino)pyrrolidin-1-yl]pyridazin-3-amine;
5-[(3R)-3-(Methylamino)pyrrolidin-1-yl]-N-[(1R)-1-phenylethyl]pyridazin-3-amine;
5-[(3S)-3-(Methylamino)pyrrolidin-1-yl]-N-(pyridin-2-ylmethyl)pyridazin-3-amine;
3-({5-[(3S)-3-(Methylamino)pyrrolidin-1-yl]pyridazin-3-yl}amino)propan-1-ol;
N-(2,2-Dimethylpropyl)-5-(4-methylpiperazin-1-yl)pyridazin-3-amine;
N-(2-Methoxyethyl)-5-(4-methylpiperazin-1-yl)pyridazin-3-amine;
N-Bicyclo[2.2.1]hept-2-yl-5-(4-methylpiperazin-1-yl)pyridazin-3-amine;
N-Cyclopentyl-5-(4-methylpiperazin-1-yl)pyridazin-3-amine;
N-(Cyclopentylmethyl)-5-(4-methylpiperazin-1-yl)pyridazin-3-amine;
5-(4-Methylpiperazin-1-yl)-N-(2-phenylethyl)pyridazin-3-amine;
N-Benzyl-5-(4-methylpiperazin-1-yl)pyridazin-3-amine;
5-(4-Methylpiperazin-1-yl)-N-(pyridin-2-ylmethyl)pyridazin-3-amine;
N-cyclopentyl-5-[(3R)-3-(methylamino)pyrrolidin-1-yl]pyridazin-3-amine;
(R)-5-(3-(methylamino)pyrrolidin-1-yl)-N-(1-adamantyl)pyridazin-3-amine dihydrochloride;
(R)-5-(3-(methylamino)pyrrolidin-1-yl)-N-(2-adamantyl)pyridazin-3-amine dihydrochloride;
(S)-5-(3-(methylamino)pyrrolidin-1-yl)-N-(2-adamantyl)pyridazin-3-amine dihydrochloride;
(S)-5-(3-(methylamino)pyrrolidin-1-yl)-N-(1-adamantyl)pyridazin-3-amine dihydrochloride, and pharmaceutically acceptable salts thereof.

16. A pharmaceutical composition comprising an effective amount of at least one chemical entity selected from the compounds of Formula (I)

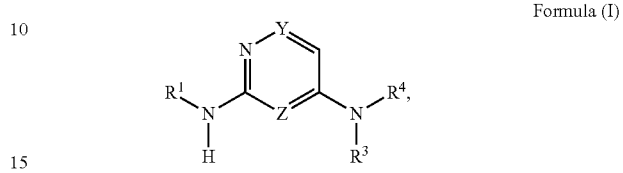

Formula (I)

wherein
Z is CH;
Y is N;
$R^1$ is:
a) —$(CH_2)_2OCH_3$, —$(CH_2)_2SCH_3$, or $C_{1-8}$alkyl, each independently unsubstituted or substituted with —OH or —$CF_3$;
b) —$(CH_2)_{0-2}$—$Ar^1$, —$CHR^2$—$Ar^1$, —$(CH_2)_{0-2}$—$Ar^2$, each of said $Ar^1$ and $Ar^2$ independently unsubstituted or substituted with halo, —$CH_3$, —$OCH_3$,
$Ar^1$ is a 6-membered aromatic carbocyclic ring,
$Ar^2$ is a 5 to 6-membered heteroaromatic ring containing N, S or O; or
c) cycloalkyl, —$(CH_2)$-(monocyclic cycloalkyl), —$(CH_2)$-(bridged polycyclic cycloalkyl)$_{0-1}$, —$(CHR^2)$-(monocyclic cycloalkyl), —$(CH_2)$-(fused cycloalkyl), —$(CH_2)$-(bridged monocyclic cycloalkyl), —$(CH_2)_{0-1}$-tetrahydrofuranyl, or —$(CH_2)_{0-1}$-tetrahydropyranyl, each independently unsubstituted or substituted with one, two, or three $C_{1-4}$alkyl substituents;
$R^2$ is —$C_{1-4}$alkyl;

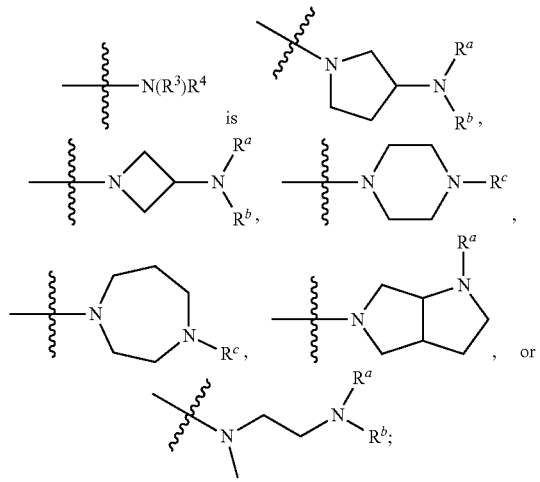

where $R^a$, $R^b$, and $R^c$ are each independently H or $C_{1-3}$alkyl; and
pharmaceutically acceptable salts of compounds of Formula (I).

17. A pharmaceutical composition comprising an effective amount of at least one chemical entity of claim 15.

18. A method of treating a subject suffering from or diagnosed with a disease, disorder, or medical condition mediated by histamine $H_4$ receptor activity, comprising administering to a subject in need of such treatment an effective amount of at least one chemical entity selected from compounds of Formula (I)

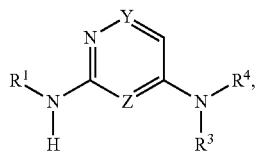

Formula (I)

wherein
Z is CH;
Y is N;
$R^1$ is:
a) —$(CH_2)_2OCH_3$, —$(CH_2)_2SCH_3$, or $C_{1-8}$alkyl, each independently unsubstituted or substituted with —OH or —$CF_3$;
b) —$(CH_2)_{0-2}$—$Ar^1$, —$CHR^2$—$Ar^1$, —$(CH_2)_{0-2}$—$Ar^2$, each of said $Ar^1$ and $Ar^2$ independently unsubstituted or substituted with halo, —$CH_3$, —$OCH_3$,
$Ar^1$ is a 6-membered aromatic carbocyclic ring,
$Ar^2$ is a 5 to 6-membered heteroaromatic ring containing N, S or O; or
c) cycloalkyl, —$(CH_2)$-(monocyclic cycloalkyl), —$(CH_2)$-(bridged polycyclic cycloalkyl)$_{0-1}$, —$(CHR^2)$-(monocyclic cycloalkyl), —$(CH_2)$-(fused cycloalkyl), —$(CH_2)$-(bridged monocyclic cycloalkyl), —$(CH_2)_{0-1}$-tetrahydrofuranyl, or —$(CH_2)_{0-1}$-tetrahydropyranyl, each independently unsubstituted or substituted with one, two, or three $C_{1-4}$-alkyl substituents;
$R^2$ is —$C_{1-4}$alkyl;

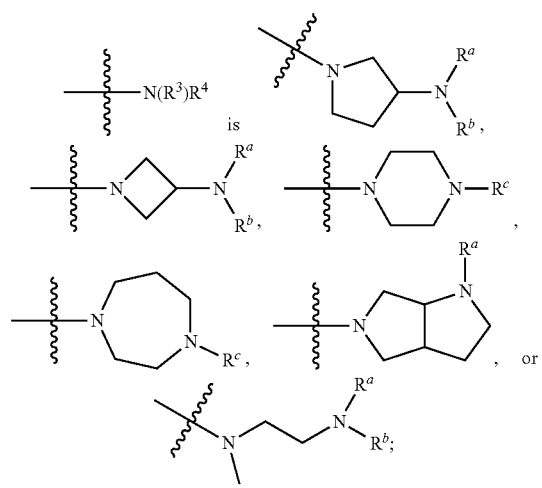

where $R^a$, $R^b$, and $R^c$ are each independently H or $C_{1-3}$alkyl; and
pharmaceutically acceptable salts of compounds of Formula (I).

19. A method of treating a subject suffering from or diagnosed with a disease, disorder, or medical condition mediated by histamine $H_4$ receptor activity, comprising administering to a subject in need of such treatment an effective amount of at least one chemical entity of claim 15.

20. A method as in claim 18, wherein the disease, disorder or medical condition is inflammation.

21. A method as in claim 18, wherein the disease, disorder, or medical condition is selected from the group consisting of: inflammatory disorders, allergic disorders, dermatological disorders, autoimmune disease, lymphatic disorders, and immunodeficiency disorders.

22. A method as in claim 18, wherein the disease, disorder, or medical condition is selected from: allergy, asthma, dry eye, chronic obstructed pulmonary disease (COPD), atherosclerosis, rheumatoid arthritis, multiple sclerosis, inflammatory bowel diseases, colitis, Crohn's disease, ulcerative colitis, psoriasis, pruritus, itchy skin, atopic dermatitis, urticaria, hives, ocular inflammation, conjunctivitis, dry eye, nasal polyps, allergic rhinitis, nasal itch, scleroderma, autoimmune thyroid diseases, post-operative adhesion, immune-mediated diabetes mellitus (type 1), type 2 diabetes, chronic renal failure, hepatic cholestasis, lupus, Myasthenia gravis, autoimmune neuropathies, Guillain-Barré, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, dermatitis herpetiformis, pemphigus vulgaris, vitiligio, primary biliary cirrhosis, autoimmune hepatitis, autoimmune oophoritis, autoimmune orchitis, autoimmune disease of the adrenal gland, polymyositis, dermatomyositis, spondyloarthropathies, ankylosing spondylitis, Sjogren's syndrome, major depression disorder, bipolar disorder, treatment-resistant major depression disorder, treatment-resistant bipolar disorder, generalized anxiety disorder, social phobia, post traumatic stress disorder, and pain.

23. A method as in claim 18, wherein the disease, disorder, or medical condition is selected from the group consisting of: allergy, asthma, rheumatoid arthritis, autoimmune diseases, and pruritus.

24. A method for modulating histamine $H_4$ receptor activity, comprising exposing histamine $H_4$ receptor to an effective amount of at least one chemical entity selected from compounds of Formula (I)

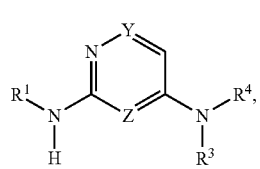

Formula (I)

wherein
Z is CH;
Y is N;
$R^1$ is:
a) —$(CH_2)_2OCH_3$, —$(CH_2)_2SCH_3$, or $C_{1-8}$alkyl, each independently unsubstituted or substituted with —OH or —$CF_3$;
b) —$(CH_2)_{0-2}$—$Ar^1$, —$CHR^2$—$Ar^1$, —$(CH_2)_{0-2}$—$Ar^2$, each of said $Ar^1$ and $Ar^2$ independently unsubstituted or substituted with halo, —$CH_3$, —$OCH_3$,
$Ar^1$ is a 6-membered aromatic carbocyclic ring,
$Ar^2$ is a 5 to 6-membered heteroaromatic ring containing N, S or O; or
c) cycloalkyl, —$(CH_2)$-(monocyclic cycloalkyl), —$(CH_2)$-(bridged polycyclic cycloalkyl)$_{0-1}$, —(CHR²)-(monocyclic cycloalkyl), —(CH₂)-(fused cycloalkyl), —(CH₂)-(bridged monocyclic cycloalkyl), —(CH₂)₀₋₁-tetrahydrofuranyl, or —(CH₂)₀₋₁-tetrahydropyranyl, each independently unsubstituted or substituted with one, two, or three $C_{1-4}$alkyl substituents;

R² is —$C_{1-4}$alkyl;

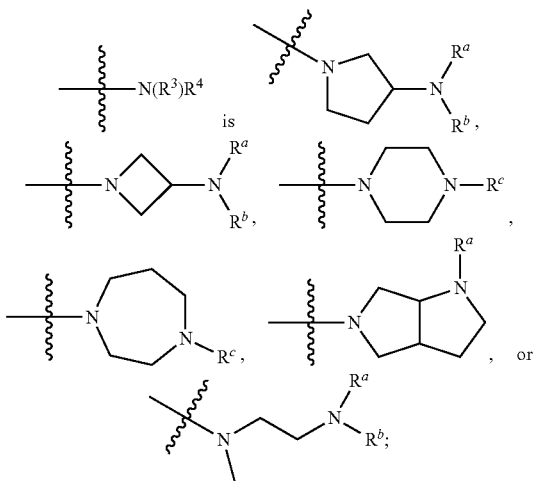

where $R^a$, $R^b$, and $R^c$ are each independently H or $C_{1-3}$alkyl; and pharmaceutically acceptable salts of compounds of Formula (I).

25. A method for modulating histamine H₄ receptor activity, comprising exposing histamine H₄ receptor to an effective amount of at least one chemical entity of claim 15.

26. A method as in claim 24, wherein said histamine H₄ receptor is in a human subject.

27. A method as in claim 26, wherein said human subject is suffering from or is diagnosed with a disease, disorder, or medical condition mediated by histamine H₄ receptor activity.

28. A method as in claim 27, wherein said disease, disorder, or medical condition is allergy, rheumatoid arthritis, asthma, autoimmune diseases, or pruritis.

29. A method as in claim 18, wherein said administration comprises a topical application.

30. A method as in claim 29, wherein said disorder or medical condition is inflammation.

31. A method as in claim 29, wherein said disorder or medical condition is at least one of pruritis, urticaria and atopic dermatitis.

\* \* \* \* \*

UNITED STATES PATENT AND TRADEMARK OFFICE
CERTIFICATE OF CORRECTION

PATENT NO. : 8,841,287 B2
APPLICATION NO. : 12/997567
DATED : September 23, 2014
INVENTOR(S) : Cai et al.

It is certified that error appears in the above-identified patent and that said Letters Patent is hereby corrected as shown below:

On Title page item 54, Column 1, lines 1-3, the Title should read:

DIAMINO-PYRIDINE, PYRIMIDINE, AND PYRIDAZINE MODULATORS OF THE HISTAMINE H4 RECEPTOR

In the claims

Column 193, line 66, claim 15 should read:

(S[[5]])-5-(3-(methylamino)pyrrolidin-1-yl)-N-(2-adamantyl)

Column 194, line 1, claim 15 should read:

(S[[5]])-5-(3-(methylamino)pyrrolidin-1-yl)-N-(1-adamantyl)

Signed and Sealed this
Tenth Day of November, 2015

Michelle K. Lee
*Director of the United States Patent and Trademark Office*